(12) United States Patent
Spindler

(10) Patent No.: US 6,406,853 B1
(45) Date of Patent: Jun. 18, 2002

(54) INTERVENTIONS TO MIMIC THE EFFECTS OF CALORIE RESTRICTION

(75) Inventor: Stephen R. Spindler, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/648,642

(22) Filed: Aug. 25, 2000

Related U.S. Application Data

(63) Continuation-in-part of application No. 09/471,225, filed on Dec. 23, 1999.

(51) Int. Cl.$^7$ .................................................. C12Q 1/68
(52) U.S. Cl. .............................. 435/6; 435/5; 435/91.1; 435/91.2; 514/693; 514/724; 119/15; 119/18; 119/34
(58) Field of Search ............................... 435/5, 6, 91.1, 435/91.2; 514/693, 724; 119/15, 18, 54

(56) References Cited

FOREIGN PATENT DOCUMENTS

WO    WO 01-12851    2/2001

OTHER PUBLICATIONS

Lee et al. Science, vol. 285, Aug. 1999, pp. 1390–1393.*
Lee et al., Gene Expression Profile of Aging and Its Retardation by Caloric Restriction, (1999) Science 285:1390.
Weindruch et al., Dietary Restriction in Mice Beginning at 1 Year of Age: Effect on Life–Span and Spontaneous Cancer Incidence, (1982) Science 215–1415.

* cited by examiner

*Primary Examiner*—W. Gary Jones
*Assistant Examiner*—Janell E. Taylor
(74) *Attorney, Agent, or Firm*—Townsend & Townsend & Crew LLP

(57) ABSTRACT

Long term calorie restriction has the benefit of increasing life span. Methods to screen interventions that mimic the effects of calorie restriction are disclosed. Extensive analysis of genes for which expression is statistically different between control and calorie restricted animals has demonstrated that specific genes are preferentially expressed during calorie restriction. Screening for interventions which produce the same expression profile will provide interventions that increase life span. In a further aspect, it has been discovered that test animals on a calorie restricted diet for a relatively short time have a similar gene expression profile to test animals which have been on a long term calorie restricted diet.

26 Claims, 13 Drawing Sheets

(3 of 13 Drawing Sheet(s) Filed in Color)

Average of Pairwise Comparison of the Global Gene Expression
Correlation Coefficient for Each Possible Pair of Mice

|  | Young CR | Young Control | STZ-Diabetic |
|---|---|---|---|
| Young CR | 0.64 ± 0.01 | -0.07 ± 0.02 | -0.16 ± 0.01 |
| Young Control |  | 0.15 ± 0.02 | 0.03 ± 0.02 |
| STZ-Diabetic |  |  | 0.38 ± 0.05 |

*All values calculated for average are Log (1+mRNA level)

Fig. 10

Average of Pairwise Comparison of the Global Gene Expression Correlation Coefficient for Each Possible Pair of Mice

|              | Old CR       | Old Control   | AG-Treated    |
|--------------|--------------|---------------|---------------|
| Old CR       | 0.72 ± 0.01  | -0.09 ± 0.02  | -0.17 ± 0.02  |
| Old Control  |              | 0.21 ± 0.07   | 0.05 ± 0.01   |
| AG-Treated   |              |               | 0.48 ± 0.02   |

*All values calculated for average are Log (1+mRNA level)

Fig. 12

INTERVENTIONS TO MIMIC THE EFFECTS OF CALORIE RESTRICTION

This application is a continuation in part of U.S. application Ser. No. 09/471,225, filed Dec. 23, 1999.

BACKGROUND OF THE INVENTION

1. Field of the Invention

For years, researchers have attempted to identify biomarkers of aging to facilitate the identification of interventions that might slow or reverse the aging process. Dietary calorie restriction (CR) is the only well-documented method for extending life span in homeothermic vertebrates, and is the most effective means known for reducing cancer incidence. Although many of the physiological consequences of CR were described 65 years ago, there is no consensus regarding its mode of action. Consequently, there has been no practical method of identifying interventions that might mimic such calorie-restriction effects. Rather, a researcher would have to wait the test animal's lifetime to determine whether a particular intervention impacted life-span and/or cancer incidence.

2. Description of the Related Art

Mammals seem to share a common set of genes, and yet they have widely differing life spans. It is impossible to know at present whether the differences in life spans are due to differences in the sequence of specific genes, or to differences in their expression. However, it is clear from many years of study in dozens of laboratories that long term reduction in dietary calorie consumption (CR) delays most age-related physiological changes, and extends life span in all species tested, provided malnutrition is avoided (Weindruch, et al. *The Retardation of Aging and Disease by Dietary Restriction* (Charles C. Thomas, Springfield, Ill., 1988)). These studies also have shown that CR is the most effective means now known for reducing cancer incidence and increasing the mean age of onset of age-related diseases and tumors in homeothermic vertebrates (Weindruch et al. (1982) Science 215: 1415). Thus, it seems clear that life spans can be extended through a relatively simple dietary regimen. However, there are no studies on the effects of short term calorie restriction on metabolism and gene expression.

One report has been published of gene expression profiling in muscle (Lee et al. (1999) Science 285: 1390) In these studies, many age related changes in muscle gene expression appeared to be prevented or reversed by CR. The expression profiles of 6500 genes were compared among old, long-term CR and control mice, and young control mice. Some age-related changes in muscle gene expression appeared to be wholly or partially prevented by CR.

SUMMARY OF THE INVENTION

The present invention contemplates a method of identifying interventions within a short time frame that mimic the effects of calorie restriction. Such interventions will lead to increased life span, reduce cancer incidence, and/or increase the age of onset of age-related diseases and tumors.

In a preferred embodiment a method of identifying an intervention that mimics the effects of caloric restriction in cells is disclosed, comprising the steps of:

obtaining a biological sample;

exposing said biological sample to an intervention;

waiting a specified period of time;

assessing changes in gene expression levels, levels of RNA, protein, or protein activity levels related to one or more biomarkers of aging; and identifying said intervention as one that mimics the effects of caloric restriction if one or more changes in said levels also occurs in caloric restriction.

The biological sample may be either in vitro or in vivo. In a preferred embodiment, the biological sample comprises cells. In a more preferred embodiment, the cells are obtained from a mammal. In an even more preferred embodiment, the mammal is a mouse.

In one embodiment, the change in gene expression levels, levels of RNA, protein, or protein activity levels corresponds to a change in gene expression for a gene encoding a chaperone protein. In a preferred embodiment, the chaperone protein is GRP78.

In one embodiment, said biomarker is apoptosis. In another preferred embodiment, said biomarker is aging. In another preferred embodiment, said biomarker of aging is a production of cancer cells.

In a preferred embodiment, the changes in said gene expression level, levels of RNA, protein, or protein activity levels related to one or more biomarkers of aging occur in 6 weeks or less. In a more preferred embodiment, the changes in said gene expression levels, levels of RNA, protein, or protein activity levels related to one or more biomarkers of aging occur in four weeks or less. In an even more preferred embodiment, the changes in said gene expression levels, levels of RNA, protein, or protein activity levels related to one or more biomarkers of aging occur in two weeks or less. In a most preferred embodiment, the changes in said gene expression levels, levels of RNA, protein, or protein activity levels related to one or more biomarkers of aging occur in about two days or less.

In a one embodiment, changes in gene expression are evaluated using a gene chip. In a preferred embodiment, the gene chip contains genes for immune system activation. In another preferred embodiment, the gene chip contains genes for DNA repair. In another preferred embodiment, the gene chip contains genes associated with apoptosis. In another preferred embodiment, the gene chip contains genes for the enteric nervous system.

In an alternate embodiment, the biological sample is a test animal. In a preferred embodiment the disclosed method additionally comprises determining changes in said levels in a reference animal having identifying characteristics of a long-term calorie-restricted animal wherein the reference animal has been on a calorie restricted diet for less than about 6 weeks and wherein said changes are used in said identifying said intervention as one that mimics the effects of calorie restriction. In a more preferred embodiment, the reference animal has been on a calorie restricted diet for less than about 4 weeks. In an even more preferred embodiment, the reference animal has been on a calorie restricted diet for less than about 2 weeks.

In a preferred embodiment, the test animal is a mouse. In a preferred embodiment, changes in gene expression are assessed in the test animal.

In a more preferred embodiment, the disclosed method further comprises:

obtaining a gene expression profile from a calorie-restricted reference animal;

comparing changes in gene expression for the test animal to the gene expression profile of the calorie-restricted reference animal; and identifyng said intervention as one that mimics the effects of calorie restriction if the gene expression profile of the test animal is statistically similar to the gene expression profile of the calorie restricted animal.

In a more preferred embodiment, the gene expression profile of the test animal is determined to be statistically similar to the gene expression of the calorie restricted animal by one-way ANOVA followed by Fisher's test (P<0.05).

In another aspect of the invention, a system is disclosed for identifying an intervention that mimics the effects of calorie restriction in a test animal comprising a test animal and a gene chip comprising genes known to have altered expression during calorie restriction. In a preferred embodiment, the gene chip comprises genes selected from the group consisting of genes for immune system activation, genes for DNA repair, genes associated with apoptosis and genes for the enteric nervous system.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

These and other feature of this invention will now be described with reference to the drawings of preferred embodiments which are intended to illustrate and not to limit the invention.

FIG. 10. Average of pairwise comparison of the global gene expression correlation coefficient for each possible pair of mice FIG. 11. The hepatic gene expression profiles of young CR, young control and streptozotocin (STZ)-treated mice. Levels of specific mRNA were determined using the Mu11KsubA and Mu11KsubB GeneChip arrays (Affymetrix, Santa Clara, Calif.) containing targets for approximately 12,000 known mouse genes and ESTs. The experiment tree function of GeneSpring 3.0 (Silicon Genetics, San Carlos, Calif.) was utilized to display the results. The horizontal axis represents the position of each gene assigned by the "gene tree" average-linkage hierarchical clustering algorithm of the program. Below the position assigned to each gene is a color-coded indication of its relative expression level, based on a continuous scale. Bright blue indicates no detectable expression, purple average expression, and bright red high expression. The average expression of each gene in each group is shown. The GeneSpring "experiment tree" clustering algorithm calculated an average-linkage hierarchical clustering dendrogram of the data for each group of mice, which is shown to the left of the expression profiles.

FIG. 12. Average of pairwise comparison of the global gene expression correlation coefficient for each possible pair of mice.

DETAILED DESCRIPTION OF THE PREFERRED EMBODIMENT

Figure 1:
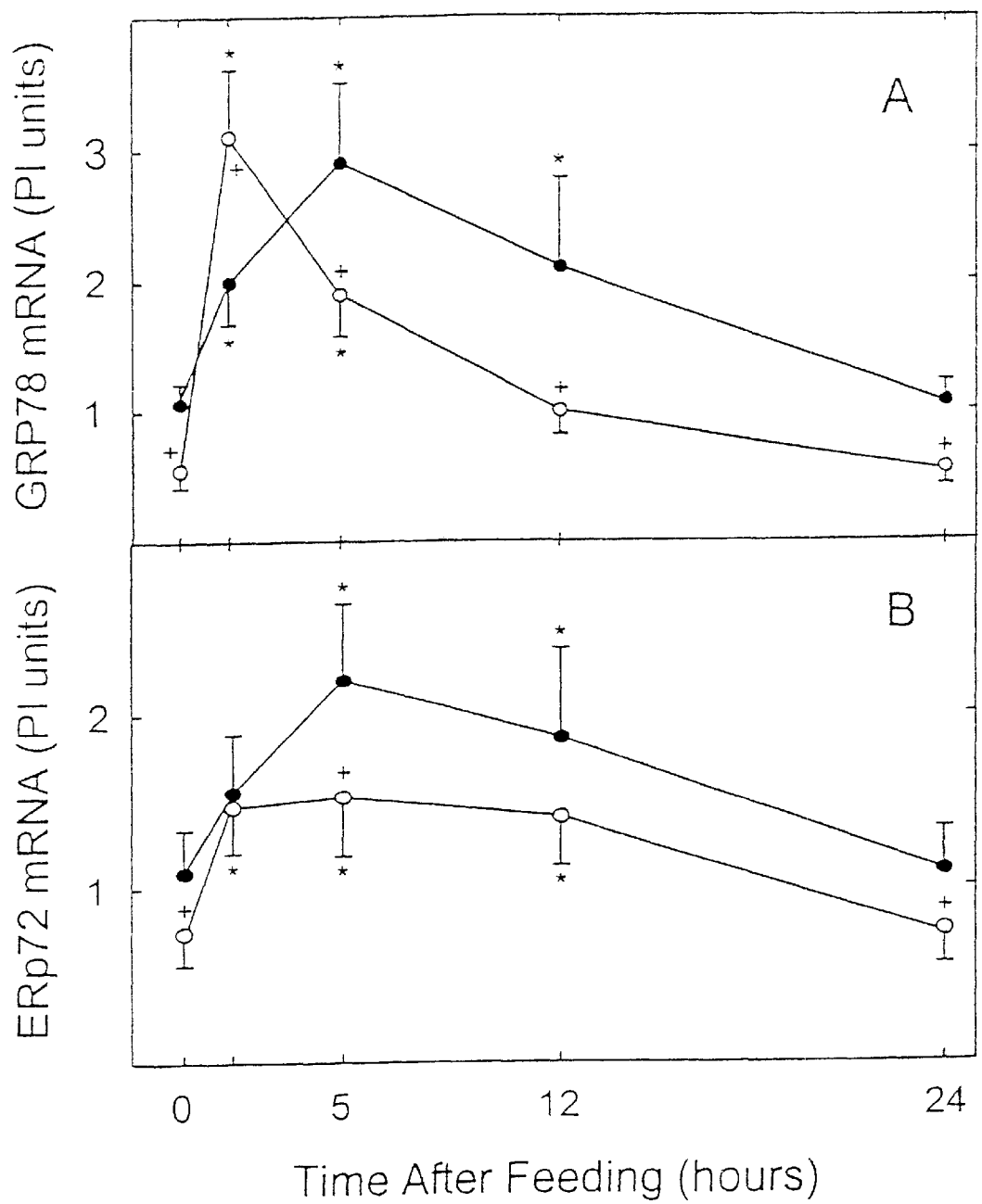
FIG. 1. Effects of feeding on hepatic GRP78 and ERp72 mRNA. At 0, 1.5, 5 and 12 h following feeding, 5 mice from each dietary group were killed. Their weights after 24 h of fasting were 22.96±1.49 for CR and 37.12±1.19 g for control mice. GRP78 mRNA (A) and ERp72 mRNA (B) from control (closed circle) and CR (open circle) mice were quantified using dot-blots. RNA loading and transfer were normalized using data obtained from serial probings for 18S ribosomal RNA and S-II mRNA. Similar results were obtained with both control probes. CR and control mice, fed once daily for 30 days, were fasted for 24 hours and killed (n=5, 0 time point) or refed and killed at the times specified (n=5 for each time point). + represents P<0.01 significance of difference between CR and control at each time point. * represents P<0.01 significance of difference from the 0 time point within each dietary group. The 0 and 24 hour times points are the same data set.

While the described embodiment represents the preferred embodiment of the present invention, it is to be understood that modifications will occur to those skilled in the art without departing from the spirit of the invention. The scope of the invention is therefore to be determined solely by the appended claims.

The effects of long term calorie restriction include increases in the rate of clearance of serum proteins, including glucose damaged serum proteins, from the blood as well as changes in gene expression. For example, long term calorie restriction down regulates the expression of certain chaperone genes, up regulates the expression of certain transcription factors and homeobox genes, increases expression of immune system genes, and increases genes enhancing genetic stability and apoptosis. These changes in gene expression correlate with an increase in apoptosis, reduced cancer incidence and increase the turnover of damaged and toxic serum proteins, reducing kidney and vascular damage with age or diabetes.

Molecular chaperones assist in the biosynthesis, folding, processing, and degradation of proteins. Many of the chaperone genes are stress inducible. Subsets of chaperones are induced by different physiological stressors. For example, the majority of the known endoplasmic chaperones are induced by stresses that produce malfolded or improperly glycosylated proteins in the ER. This unfolded protein response pathway also may adjust the level of protein trafficking through the ER to the level of ER chaperones. Other chaperones, such as the abundant cytoplasmic chaperone HSC70 are normally thought of as constitutively expressed. The present invention is based in part on the finding that certain chaperone genes are down regulated by calorie restriction (such regulation is thought to be mediated through the insulin and glucagon pathways). The expression of Erp72, Erp57, GRP 170, GRP78, GRP94, HSC70, Calnexin, and Calreticulin are particularly affected by calorie restriction.

The fasting mRNA and protein levels of nearly every ER chaperone studied were found to be significantly and consistently reduced in the livers of CR mice chronically fed a low calorie diet. In the case of GRP78, levels decreased by approximately 66%. Further, the reduction in chaperone mRNA levels was proportional to the reduction in calorie consumption. The fewer calories consumed, the lower the level of chaperone mRNA. We subsequently found that fasting chaperone mRNA levels changed over the course of 2 weeks in response to different levels of chronic calorie consumption. The more calories consumed per week, the higher the chaperone levels. Chaperone mRNA levels respond more rapidly to calorie consumption.

mRNA for most ER chaperones, and for the major cytoplasmic chaperone, HSC70, are dynamically responsive (within 1.5 h) to each meal, and to the number of calories consumed. Features of this induction distinguish it from the unfolded protein response. The feeding induction was observed in kidney and muscle tissue, as well as in the liver. Postprandial changes in glucagon, in conjunction with insulin, were found to be the key mediators of this induction.

Chaperone mRNA abundance responds within 1.5 h to caloric intake. Insulin and glucagon may be important for the response. This feeding response is rapid. By 1.5 hours after feeding, ER chaperone mRNAs were at or near their maximum level of induction. This feeding-related induction is not limited to one strain of mouse or to one species. Further, the response is found in tissues other than liver. Thus, it is a response which is generally important to the physiology of a variety of cell types in vivo.

Because many chaperones are relatively stable proteins, their protein levels change more slowly in response to caloric intake than their mnRNAs. For example, GRP78 protein has a half-life of over 24 hours in cultured cells. We found that GRP78 protein levels change only over a span of several days in response to changes in average daily calorie consumption. In this way, many chaperones may effectively integrate the rapid mRNA responses to feeding into longer term changes in chaperone protein levels. Long term differences in average calorie consumption do lead to differences in the hepatic levels of both ER and some cytoplasmic chaperones.

RNase protection assays indicate that GRP78 mRNA is transcriptionally regulated in response to feeding. Similar RNase protection results were obtained with hepatic RNA from chronically CR mice. Thus, both feeding and CR transcriptionally alter the expression of the chaperone genes.

Puromycin led to partial induction of GRP78 mRNA. It is unlikely that induction of the mRNA by cycloheximide is due to stabilization of the transcript by polysome aggregation. While cycloheximide protects some mRNAs from inactivation and degradation in this way, puromycin does not. Rather, it inhibits translation by polysome dissociation. Thus, maintenance of low hepatic GRP78 mRNA levels most likely requires the action of an unstable repressor of GRP78 gene expression in fasted mice. In the presence of inhibitors of translation, this repressor may decay, releasing the gene from repression.

Second, there was no augmentation of GRP78 mRNA induction when feeding and inhibition of translation were combined. While partial induction of the mRNA was found in puromycin treated mice, feeding induced the mRNA to the same level found in the absence of the inhibitor. Further, cycloheximide induced the mRNA to the same extent. Without being bound to any particular mechanism, it is suggested that the inhibitors and feeding may induce the gene through a common pathway.

Third, since feeding fully induced GRP78 mRNA in puromycin treated mice, de novo protein synthesis is not required for the feeding response. Preexisting signaling and regulatory factors mediate the response. Fourth, the feeding response cannot result from a postprandial increase in protein trafficking through the ER. Enhanced ER de novo protein trafficking can induce chaperone mRNA. However, no such increase could have occurred in the presence of puromycin.

Fifth, the unfolded protein and growth factor responses are not involved in the induction of chaperones by feeding. Cycloheximide blocks the unfolded protein and growth factor responses. We are aware of only one manipulation besides feeding capable of inducing ER chaperone mRNA in the presence of cycloheximide. GRP mRNAs are induced by cellular hypoxia in culture, and this induction is independent of cycloheximide treatment. Whether the feeding and hypoxia response share common molecular pathways is unknown at present.

Feeding is well-known to decrease glucagon and increase insulin levels. Both glucagon and dibutyryl-cAMP blunted the feeding induction of GRP78 mRNA. Thus, glucagon is a negative regulator of GRP78 expression in vivo. The feeding induction of GRP78 mRNA was significantly reduced in STZ-diabetic mice. Without being bound to any particular mechanism, this result and the absence of a feeding response in STZ-diabetic, dibutyryl-cAMP-treated mice indicate that the action of both hormones is required for the response.

Other effectors which are known to respond to feeding were also examined. Luminal stimuli can promote the release of gastrointestinal hormones. For this reason, we determined whether luminal filling with a non-digestible mixture of mineral oil and cellulose could stimulate chaperone expression. A small but significant response was found. However, insulin and glucagon have a much stronger effect on chaperone mRNAs, indicating they are the signals primarily responsible for the feeding response.

The feeding response was enhanced in adrenalectomized mice. These results suggest that other adrenal hormones, perhaps catecholamines, may partially blunt the chaperone mRNA response to feeding. However, the mechanism by which these hormones stimulate the feeding response is unknown at present.

Overall, feeding rapidly and strongly induced the mRNA for the major cytoplasmic chaperone, HSC70, and most ER chaperones examined. Feeding also induced BR chaperone mRNAs in at least three different tissues. Feeding and CR regulated chaperone mRNA abundance at the transcriptional level. Without being bound to any particular mechanism, feeding appeared to release chaperone gene expression from the effects of an unstable inhibitor. Insulin was required, and glucagon and cAMP mediated the feeding response. Postprandial changes in glucagon levels may be the primary mediator of the response. Gastrointestinal and adrenal hormones, but not glucocorticoids also have a role in the feeding response.

Surprisingly, changes in gene expression are also observed with short-term calorie restriction. These changes in gene expression are virtually identical to the changes observed in long-term CR. Short-term calorie restriction occurs when switching a mature test animal to a diet which is about 50% less than a control diet for about 2–6 weeks. In a preferred embodiment, the test animal is a mature mouse and the mature mouse is switched to a calorie-restricted diet at about 31 months. Preferably, an intermediate diet which is about 20–40% less than a control diet is employed for about two weeks before switching to a CR diet for an additional two weeks.

Both long term and short-term CR produces its profound effects on mammalian physiology by affecting the expression of genes. To identify as broadly as possible the effects of caloric restriction on global patterns of gene expression, gene chip technology was utilized to characterize the effects of long and short term CR on the expression of approximately 11,000 mouse genes in the liver.

Liver is an attractive organ for study, since it contains a number of cell types, allowing assessment of the effects of CR on hepatocytes, which are primarily responsible for the regulation of metabolism and blood sugar, neurons of the enteric nervous system, immune system cells in the blood, and vascular smooth muscle cells, among others. In liver, by far the predominant effect of caloric restriction is the activation of gene expression. In addition, after only four weeks of caloric restriction, the gene expression profile of old mature mice had been shifted from the profile characteristic of fully fed "normo-aging" mice to the gene expression profile of slow aging, long term CR mice. In both long and short-term CR mice, changes were observed in gene expression of immune system genes, genes enhancing genetic stability and apoptosis, genes of the enteric nervous system and liver specific genes.

The methods of the present invention include the identification of interventions that mimic the effects of calorie restriction. Particularly contemplated by the invention are methods of identifying interventions that have an effect on life span, aging, and/or the development of age-related diseases and cancer.

In certain embodiments, such methods comprise obtaining cells, exposing them to an intervention, and observing whether the intervention affects the gene expression profile, levels of RNA, protein, or protein activity related to one or more biomarkers of aging. Preferably, such changes in gene expression, RNA, protein, or protein activity levels would occur within four weeks of the intervention. More preferably, such changes would occur within two weeks of the intervention, and most preferably, such changes occur within two days of the intervention. Such methods permit the identification of pharmacological or other means of achieving a metabolic state similar to the profile observed with long and short-term CR.

The methods of the present invention include the use of in vitro assays (including gene chip assays) as well as animal assays. Preferably, however, the methods are carried out in live mammals. For example, transgenic mice having enhanced chaperone expression may be used to measure an intervention's ability to reduce cancer, apoptosis, and/or life span. Alternatively, the present methods may be used to identify interventions that mimic calorie restriction simply by measuring the intervention's ability to alter gene expression for a particular gene or set of genes in live mammals. Such methods allow identification of effective interventions in a short period of time. Interventions identified by the methods of the present invention may be pharmacological, surgical or otherwise. Combinatorial chemistry may also be used in order to screen a large number of pharmacological compounds. In general, the interventions identified by the present invention should be effective in the treatment of cancer, diabetes, age-related diseases and/or the extension of life span.

While the described embodiment represents the preferred embodiment of the present invention, it is to be understood that modifications will occur to those skilled in the art without departing from the spirit of the invention. The scope of the invention is therefore to be determined solely by the appended claims.

EXAMPLES

Example 1

Long Term Calorie Restricted (LTCR) Animals and Treatments for Chaperone Studies Female, 28-month old mice of the long-lived $F_1$ hybrid strain C3B10RF$_1$ have been described previously. Mice were weaned at 28 d, housed individually and subjected to one of two diets. The control diet consisted of casein (high protein), 207.0 g/kg, DL-methionine, 4.0 g/kg, dextrose monohydrate, 301.8 g/kg, corn starch, 290.0 g/kg, cellulose, 702. g/kg, brewer's yeast, 8.0 g/kg, Harlan Teklad Vitamin Mix #40060, 10.0 g/kg, Harlan Teklad AIN-76 Mineral Mix

170915, 35.0 g/kg, calcium carbonate ($CaCO_3$), 3.0 g/kg, magnesium oxide (MgO), 1.0 g/kg, sodium fluoride (NaF), 2.3 mg/kg, sodium molybdate ($Na2MoO.2H_2O$), 0.5 mg/kg. The 50% restricted diet consisted of casein (high protein), 362.0 g/kg, DL-methionine, 7.0 g/kg, dextrose monohydrate, 172.03 g/kg, corn starch, 153.1 g/kg, cellulose, 83.6 g/kg, brewer's yeast, 14.0 g/kg, Harlan Teklad Vitamin Mix #40060, 17.5 g/kg, harlan Teklad AIN-76 Mineral Mix #170915, 61.25 g/kg, calcium carbonate ($CaCO_3$), 5.25 g/kg, magnesium oxide (MgO), 1.75 g/kg, sodium fluoride (NaF), 3.0 mg/kg, sodium molybdate ($Na2MoO.2H_2O$), 0.9 mg/kg. From weaning, control mice were fed 4.8 g of the control diet on Monday through Thursday. On Friday they were fed 13.8 g of control diet. This feeding regimen provided 450 kJ/wk. From weaning, the 50% calorie restricted (CR) mice were fed 4.6 g of the restricted diet on Monday and Wednesday, and 6.9 g on Friday. This regimen provided 225 kJ/wk. Each dietary group received approximately equal amounts of protein, corn oil, minerals and vitamins per gram body weight. The amount of carbohydrates consumed varied between groups. Beginning 30 d before these studies, the control mice were fed 4.1 g (54.44 kJ) control diet daily at 0900 h. The 50% restricted mice were fed 2.3 g of restricted diet (32 kJ) daily at 0900 h. During this 30 d period, the control and restricted mice received approximately 15% and 50% less dietary energy than normally thought to be required for a typical mouse {Subcommittee on Laboratory Animal Nutrition & Committee on Animal Nutrition 1978 ID: 5480} All food was routinely consumed within 30 min.

Retired male Swiss-Webster breeder mice were purchased from Jackson Laboratories. Beginning 30 days before the studies, the mice were fed Monday and Wednesday 11 g and Friday 16.6 g of the control diet daily at 0900 h. In fasting-feeding studies, mice were deprived of food for 48 h, fed 5.5 g of the control diet at 0900 h, and killed 90 min later. The food was consumed within 30 min. Diabetes was induced by three weekly intraperitoneal injections of streptozotocin [10 mg/100 g body weight (b.w.)] in 50 mM sodium citrate, pH 4.5. Mice were diabetic one week after the last injection. Only mice with blood glucose level higher than 3 mg/ml were used. Mice injected with equivalent volumes of sodium citrate served as controls for the STZ-diabetic mice. Adrenalectomized and sham-operated mice were purchased from Jackson Laboratories. Dibutyryl cAMP (Sigma; 18 mg.100 g b.w.), and theophylline (Sigma; 3 mg/100 g b.w), glucagon (Sigma; 300 $\mu$g/100 g b.w.), dexamethasone (Sigma; 125 $\mu$g/100 g b.w), cycloheximide (Sigma; 4 mg.100 g b.w.), and puromycin (Sigma; 10 mg.100 g b.w.), were administered intraperitonealy to mice as specified in the figure legends. Mice received two doses of each drug or drug combination. The first injection was administered 30 min before feeding, and the second injection was administered 30 min after feeding. Mice were killed 1.5 h after the start of feeding. Drug-injected mice consumed similar amounts of food as control animals during the feeding period. All animal use protocols were approved by the institutional animal use committee of the University of California, Riverside.

Example 2

RNA Isolation and Quantification for Chaperone Studies

Mice were killed and the livers, kidneys, and muscle were removed. Muscle from the hind legs and back was removed and pooled for each animal. Tissues were flash frozen in liquid nitrogen. Approximately 0.2 g of frozen tissue was homogenized for 40 s in 4 ml of TRI Reagent (Molecular Research Center, Cincinnati, Ohio) using a Tekmar Tissuemizer (Tekmar, Cincinnait, Ohio) at a setting of 55. RNA was isolated as described by the TRI Reagent supplier. RNA was resuspended in FORMAzol (Molecular Research Center) and Northern and dot blots were performed using 20 and 10 $\mu$g of RNA respectively. The RNA was analyzed using Northern blots to verify its integrity. Dot blots were used to quantify mRNA levels (24; 27). Specific mRNA levels were normalized to the level of total RNA and/or mRNA present in each sample using hybridization with radiolabeled complementary DNA to 18S rRNA and/or transcription factor S-II, as indicated in the figure legends (12; 27). The murine ERp72 2.5 kb cDNA was excised with BamHI from pcD72-1 (19). The 1235 bp murine GRP75 coding fragment was excised with HindIII from pG7z-PBP1.8 (6). A 1.5 kb coding fragment of GRP78 cDNA was produced by digestion of p3C5 with EcoRI and PstI (15). A 1.4 kb hamster GRP94 coding fragment was produced by EcoRI and Sa/K digestion of p4A3 (15). A 664 bp coding fragment of rat calreticulin (nucleotides 148 to 812) was produced by PCR from GT10.U1 (23). The entire 2.4 kb cDNA of murine PDI was excised from pGEM59.4 with SacI and BamHII (19). A 1 kb coding fragment of hamster GRP170 cDNA was excised with EcoRI and XhoI from pCRtmII (16). The 1.9 kb cDNA of murine ERp57 was excised with HindIII and SstI from pERp61 (18). The 1 kb cDNA of murine HSC70 was excised with PstI from phsc1.5 (9). The 1.3 kb PEPCK coding fragment was produced by SphI followed by SalI digestions of pGEM5ZEP (a gift from Dr. Ganner D. K. Vanderbilt University School of Medicine, Nashville, Tenn.). The fragments were isolated by agarose gel electrophoresis and radioactively labeled using a $^{77}$QuickPrime Kit (Pharmacia) according to the manufacturer's instructions.

Example 3

RNase Protection Assays for Chaperone Studies

A 223 base pair (bp) DNA fragment made up of 110 bases of intron 3 and all 113 bases of exon 4 of the mouse GRP78 gene was synthesized by PCR using genomic DNA as template and inserted into pT7/T3 (Ambion, Austin, Texas). Two probes of the junction region of intron 7 and exon 7 of the GRP78 gene were produced by PCR using mouse genomic DNA as template. A 257-base fragment including all of exon 7 and the first 113 bases of intron 7 was produced. A 200-base fragment including all of exon 7 and the first 56 bases of intron 7 also was produced. The T7 RNA polymerase promoter was ligated to these PCR fragments using a Lig'nScribe kit as described by the supplier (Ambion). These constructs were used as template for the synthesis of [$^{32}$P]-labeled antisense RNA probes using a MAXIScript kit as described by the supplier (Ambion). RNase protection assays were performed using an RPA II kit as described by the supplier (Ambion). Hybridization of the 257-base RNA probe with GRP78 pre-mRNA protected all 257-bases corresponding to exon 7 and the first 113 bases of intron 7. Hybridization of the 200-base RNA probe to pre-mRNA protected 200-bases corresponding to all of exon 7 and the first 56 bases of intron 7. Hybridization of either probe to GRP78 mRNA protects the 143-bases complementary to exon 7. A 185- and a 277-bp cDNA fragment of S-II cDNA was synthesized and subcloned into pT7/T3 (12). [$^{32}$P]-labeled RNA probes for the sense and antisense transcripts were synthesized in vitro and RNase protection assays performed. Hybridization with S-II mRNA protected the entire 185- or 277-base region of the probes. Protection of only the sense strand probes was detected. Quantitation of the hybridized fragments was determined with ImageQuaNT (Molecular Dynamics, Sunnyvale, Calif.).

Example 4

Plasma Glucose and Insulin for Chaperone Studies

Plasma glucose, insulin, and glucagon concentrations were determined using Glucose [HK] 10 (Sigma, St. Louis, Mo.), Rat Insulin RIA and Glucagon RIA kits (Linco Research, St. Charles, Mo.), as described by the suppliers.

Example 5

Statistical Analysis for Chaperone Studies

The data shown in FIG. 1 are expressed as means±SD for 5 mice at each time point. The effects of food deprivation and subsequent feeding on mice of each dietary group were analyzed using a one-way ANOVA followed by Fisher's test. The analysis determined whether individual time point means differed from time 0 means within each dietary group. It also determined the differences between the means of the control and CR groups at each time point. Differences of $P<0.05$ were considered significant. Values are expressed as means±SD. Significance was determined with either Student's unpaired t-test ($P<0.95$) or a one-way ANOVA followed by Fisher's or Tukey's tests ($P<0.01$). All statistical analyses were performed with Minitab Statistical Software (Minitab, State College, Pa.).

Example 6

Chronic and Acute Effects of Calorie Consumption on Hepatic Chaperone mRNA

Feeding of the fasted mice rapidly induced the abundance of GRP78 and ERp72 mRNA (FIGS. 1A and 1B). A large increase in chaperone mRNA was detected by 1.5 h after feeding, the first time point studied. The 24-h fasting levels (0 time) of GRP78 and ERp72 mRNA were lower in the CR mice. The response to feeding was kinetically different in control and CR mice. Thus, the amount of food consumed affects the kinetics of the response. The integrated level of GRP78 and ERp72 mRNA over the entire 24-hour period was also less in the CR than in control mice. Similar results were obtained when the effects of feeding on HSC70, ERp57, and calreticulin mRNA were determined (data not shown). Thus, this represents a common response of chaperone gene expression to feeding.

Example 7

Fasting-Feeding Induced Multiple Chaperone mRNAs in Multiple Tissues

Figure 2:
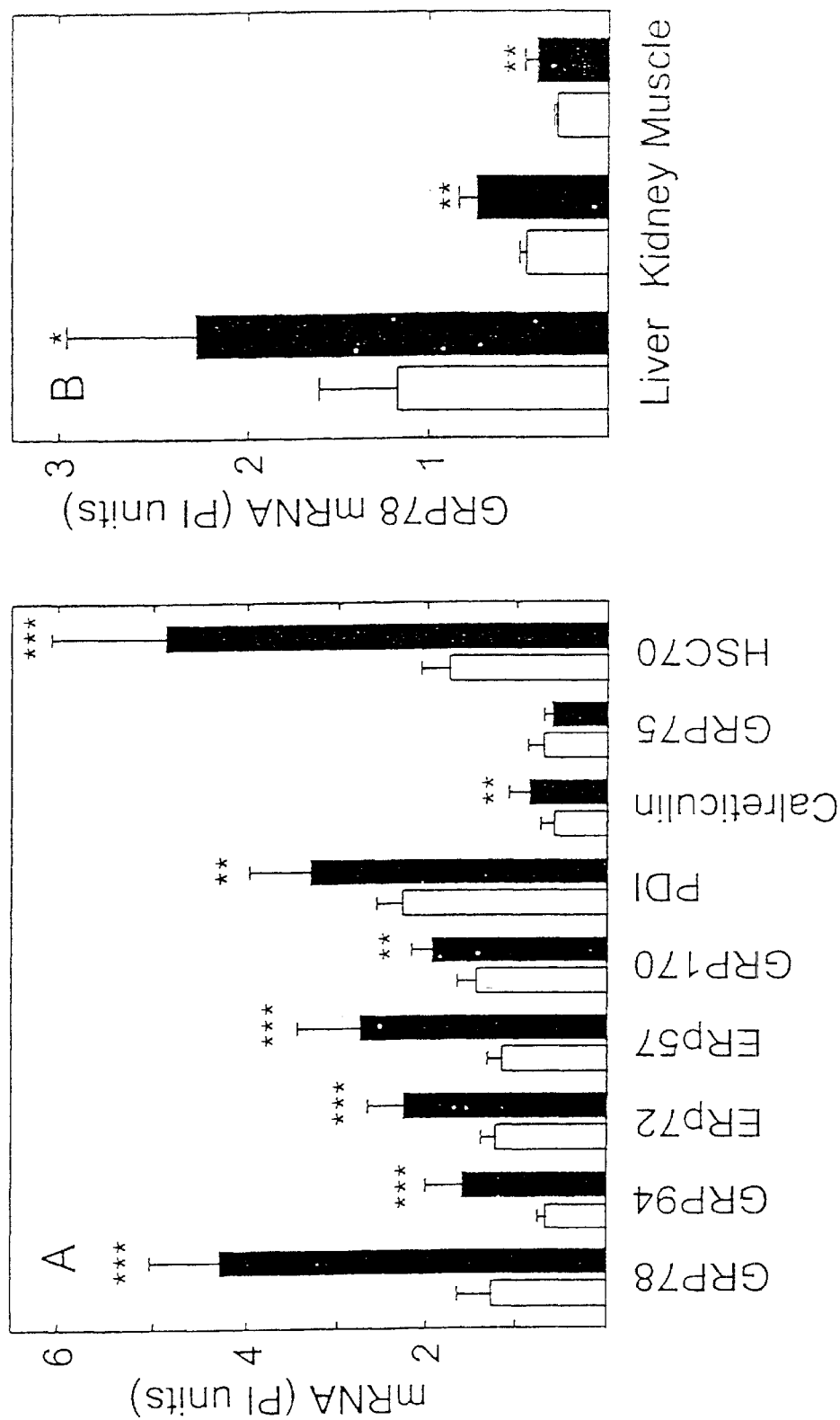
FIG. 2. The gene and tissue specificity of the chaperone feeding response. A, The domain of chaperone genes responsive to feeding was determined by quantifying hepatic chaperone mRNA abundance using RNA from mice fasted for 48 hours (n=6; open bars) or from mice fasted 48 hours, refed and killed 1.5 h later (n=6; filled bars). The mRNAs were quantified by dot-blotting and Northern blotting. There was no significant difference in the results obtained with either technique. The dot-blotting results are shown. B, Liver, kidney, and muscle GRP78 mRNA from 24-hour fasted mice (n=4), and from 24-hour fasted mice 1.5 hours after feeding (n=5). These data were from different mice than used in panel A. The statistical significance of the results are indicated (*, P<0.05; , P<0.01; *, P<0.001).

Mice were fasted for 48 hours and refed for 1.5 hours. Hepatic GRP78 mRNA was induced approximately 3-fold after this time (FIG. 2A). The mRNA for the other ER chaperones investigated, ERp57, ERp72, GRP94, GRP170, PDI, and calreticulin, and for the most abundant cytoplasmic chaperone, HSC70, also were induced by feeding (FIG. 2A). HSC70 was induced by nearly 3-fold. No changes in the mitochondrial chaperone GRP75 was detected in this study. By examining chaperone levels in other tissues of fasted and fed mice, we found that the feeding-related chaperone induction extends to at least kidney and muscle (FIG. 2B). GRP78 mRNA induction is shown in the figure (FIG. 2B).

HSC70 mRNA was also induced in these tissues (data not shown). In studies not shown, we have found that a similar induction of hepatic chaperone mRNAs occurs in rat. Thus, the response is shared by other species.

Example 8

CR Reduces the Abundance of the GRP78 Primary Transcript

Figure 3:
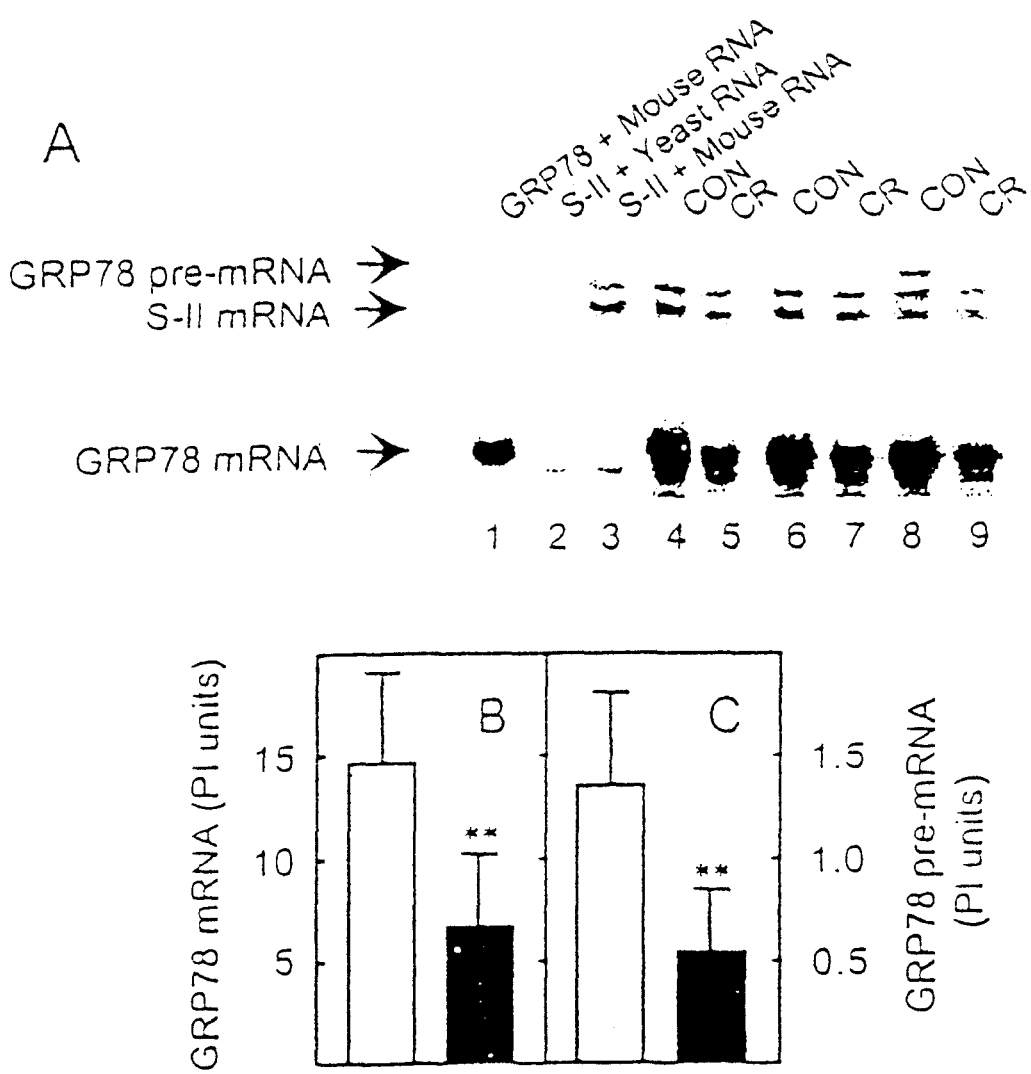
FIG. 3. Effects of CR on hepatic pre-mRNA and GRP78 mRNA abundance. A, RNase protection of pre-mRNA and mRNA in CR and control mice. Hepatic RNA was purified from control and CR mice and hybridized with an RNA probe for transcripts spanning the third intron and fourth exon boundary of the GRP78 gene. The precursor mRNA protected a 223 base region of the probe, labeled GRP78 pre-mRNA, while the GRP78 mRNA protected a 113 base fragment, so labeled in the figure. A probe for S-II mRNA coding sequences was included in each reaction as an internal control. It protected a 185 base fragment labeled S-II mRNA in the figure. Lane 1 shows the protected fragments produced by the GRP78 probe and mouse liver RNA. Lane 2 shows the fragments produced by the S-II probe hybridized to yeast total RNA. Lane 3 shows the results produced by the S-II probe hybridized to mouse liver RNA. Lanes 4, 6, and 8 show the results produced by hepatic RNA from control mice. Lanes 5, 7, and 9 show the results with RNA from CR mice. Quantification of the abundance of the protected fragments representing the GRP78 mRNA (B) and pre-mRNA (C). Studies such as those shown above were conducted using hepatic RNA from 6 CR and 6 control mice. The intensity of the protected fragments was quantified with a phosphorimager. The intensities of the pre-mRNA and mRNA fragments were normalized to the intensity of the protected fragment representing S-II mRNA. Statistical significance is indicated as in the legend to FIG. 2.

RNase protection studies were used to investigate the responsiveness of the GRP78 mRNA and primary transcript to chronic differences in dietary calorie consumption. A probe was utilized for these studies designed so that the GRP78 primary transcript protected a 223 base RNA fragment representing the third intron-fourth exon boundary of the transcript (FIG. 3A lane 1, upper band). The mRNA protected a 113 base fragment of the probe which represents the fourth exon of the gene (FIG. 3A, lane 1, lower band). Much less of the 223 and 113 base GRP78 precursor and mRNA probes were protected by RNA from CR mice (FIG. 3A, lanes 4–9). A probe for 185 bases of S-II mRNA was included in each sample as an internal control (FIG. 3A, lane 3). S-II mRNA is unresponsive to CR or fasting-feeding (25). The unlabeled bands in FIG. 3 represent RNase-resistant artifacts of the S-II probe (FIG. 3A, lane 2).

When the amount of protected probe was quantified and normalized to the signal obtained from the S-II probe, it became clear that the abundance of the chaperone precursor and mRNA were decreased to the same extent in the CR mice (FIG. 3B). The same conclusion was reached using a probe for the boundary regions of intron 7 and exon 7. Consequently, CR decreases either the rate of GRP78 gene transcription or the stability of the GRP78 primary transcript. The data are not consistent with blocked or paused GRP78 gene transcription or changes in the stability of the mRNA in CR mice.

Example 9

Fasting-feeding Induction of the GRP78 Primary Transcript

Figure 4:
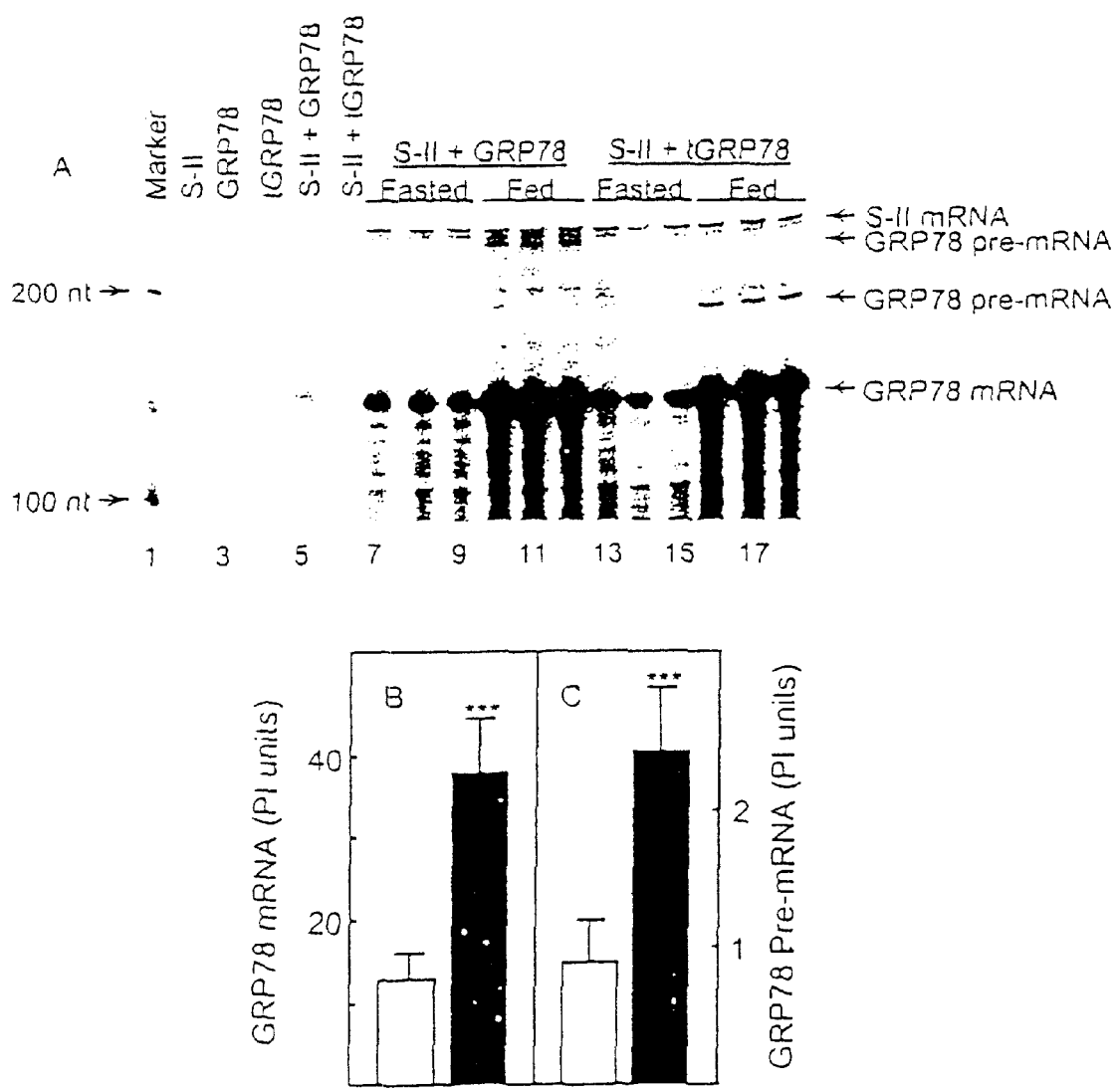
FIG. 4. Effects of feeding on hepatic GRP78 mRNA and pre-mRNA abundance. A, RNase protection of probes for hepatic GRP78 pre-mRNA and mRNA in mice after 48 hours of fasting (n=5), or 1.5 h after feeding of 48-hour fasted mice (n=5). RNA purified from liver was hybridized either to a probe for primary transcripts containing the exon 7 and intron 7 boundary of the GRP78 gene which produced a 257 base protected fragment (labeled S-II+GRP78; lanes 7–12), or to a probe for primary transcripts spanning the exon 7 and intron 7 boundary, which protected a 200 nucleotide fragment (labeled S-II+tGRP78, lanes 13–18), as indicated in the figure. GRP78 mRNA produced a 143 nucleotide fragment representing GRP78 mRNA, as indicated in the figure. A probe for S-II mRNA coding sequences was included in each reaction as an internal control. With this probe, S-II mRNA protected a 277 nucleotide fragment, labeled S-II mRNA in the figure. Lane 1, RNA markers. Lanes 2–6, hybridization of the indicated probes with yeast tRNA. Lanes 7–12, hybridization of the GRP78 and S-II probes with RNA from fasted (lanes 7–9) and refed (lanes 10–12) mice. Lanes 13–18, hybridization of tGRP78 and S-II probes with RNA from fasted (lanes 13–15) and refed (lanes 16–18) mice. Quantification of the abundance of the protected fragments representing the GRP78 mRNA (B) and pre-mRNA (C). Studies such as those shown above were conducted using hepatic RNA from 6 CR and 6 control mice. The intensity of the protected fragments was quantified and normalized as described in FIG. 3 above. Statistical significance is indicated as in the legend to FIG. 2.

RNase protection studies also were used to investigate the fasting-feeding response. RNA isolated 1.5 h after feeding protected much more of a 257 base fragment representing the exon 7-intron 7 boundary of the primary transcript than RNA isolated from fasted mice (compare FIG. 4A, lanes 10–12 to lanes 7–9). Similar results were obtained with a probe in which 200 bases representing the exon 7-intron 7 boundary were protected (compare FIG. 4A, lanes 16–18 to lanes 13–15). In each case, RNA from refed mice also protected more of the 143 base fragment representing the exon 7 region of the mRNA (FIG. 4A). A probe for 277 bp of the S-II mRNA was present in each assay for use as an internal control.

Quantification of these data, and normalization of the S-II internal control demonstrated that the mRNA and the precursor RNA were induced by feeding to essentially the same extent (FIGS. 4B and 4C). Similar results were obtained using the probe described earlier for the third intron-fourth exon boundary of the gene (data not shown). Without being bound to a specific mechanism, these data suggest the same molecular step is responsible for regulating the genetic responsiveness of chaperones to both acute and chronic changes in calorie consumption. This mechanism appears to involve changes in either the transcription or the stability of the primary transcript.

Example 10

Inhibitors of Protein Synthesis

Figure 5:
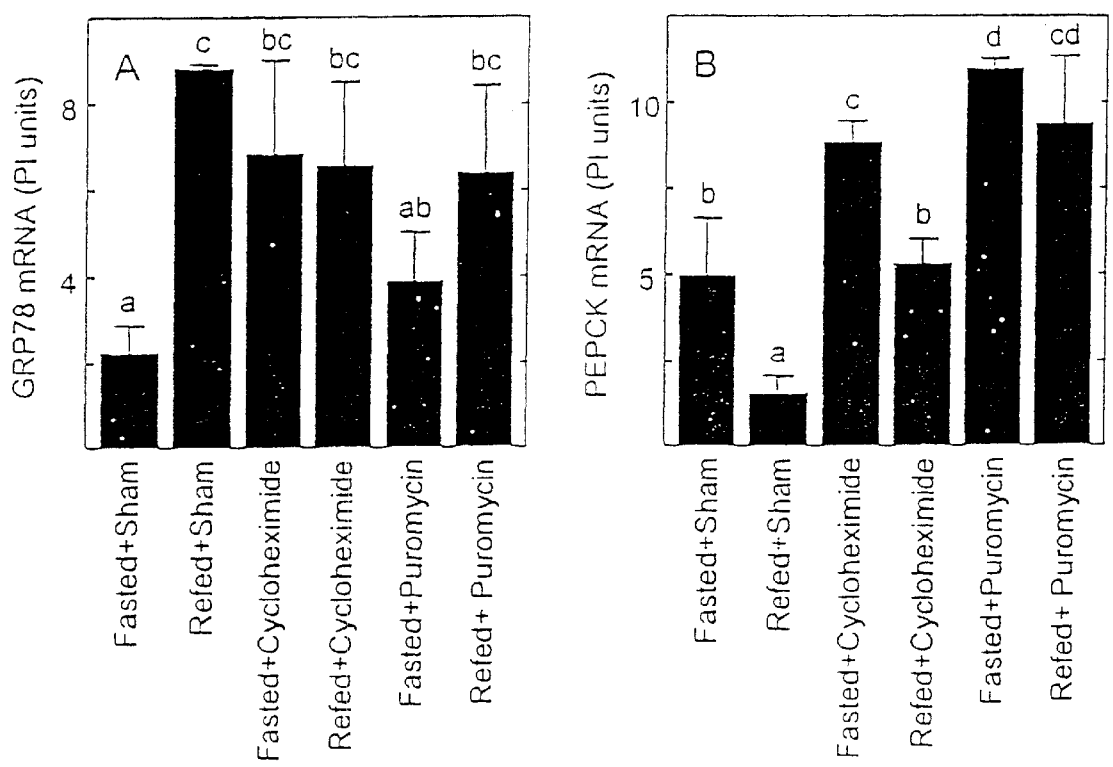
FIG. 5. Effects of protein synthesis inhibitors on the feeding response of GRP78 (A) and PEPCK (B) mRNA. Mice fasted for 48 h were injected i.p. with vehicle and after 1 hour injected a second time i.p with vehicle (Refed+Sham; n=6). Mice fasted for 48 hours were injected i.p. with vehicle 30 min before and 30 min after feeding (Refed+ Sham, n=6). Mice fasted for 48 h were injected i.p. with cycloheximide and after 1 hour injected a second time i.p with cycloheximide (Fasted+Cycloheximide; n=6). Mice fasted for 48 h were injected i.p. with cycloheximide 30 min before and 30 min after feeding (Refed+Cycloheximide; n=6). Mice fasted for 48 h were injected i.p. with puromycin and after 1 hour injected a second time i.p with puromycin (Fasted+Puromycin; n=6). Mice fasted for 48 h were injected i.p. with puromycin 30 min before and 30 min after feeding (Refed+Puromycin; n=6). GRP78 and PEPCK mRNA abundance were determined using purified hepatic RNA. Bars without common superscripts are significantly different ($P<0.005$).

To investigate the physiological basis for the fasting-feeding response, studies were performed using inhibitors of protein synthesis. Fasted mice were treated with a dose of cycloheximide or puromycin sufficient to inhibit greater than 95% of protein synthesis in the liver. Treatment with cycloheximide strongly induced GRP78 mRNA in fasted mice (FIG. 5A). GRP78 mRNA also was strongly induced in cycloheximide-treated, refed mice. Puromycin treatment modestly induced GRP78 mRNA in fasted mice (FIG. 5A). Feeding of puromycin treated mice fully induced the mRNA. Thus, induction by feeding does not appear to require de novo protein synthesis. Further, these results suggest that the lower chaperone mRNA levels in fasted mice may involve the action of a rapidly turning over factor.

The effects of the protein synthesis inhibitors on PEPCK mRNA also was determined as a positive control. The effects of fasting-feeding and cycloheximide treatment on this mRNA are well known. Fasting induced, and feeding repressed PEPCK mRNA, as expected (FIG. 5B). Also, as expected from published data, cycloheximide increased PEPCK mRNA in both fasted and refed mice through its effects on PEPCK mRNA stability. The effects of the inhibitors on PEPCK mRNA levels indicate the inhibitors were efficacious in these studies.

Example 11

Pancreatic Hormones and Glucose

Figure 6:
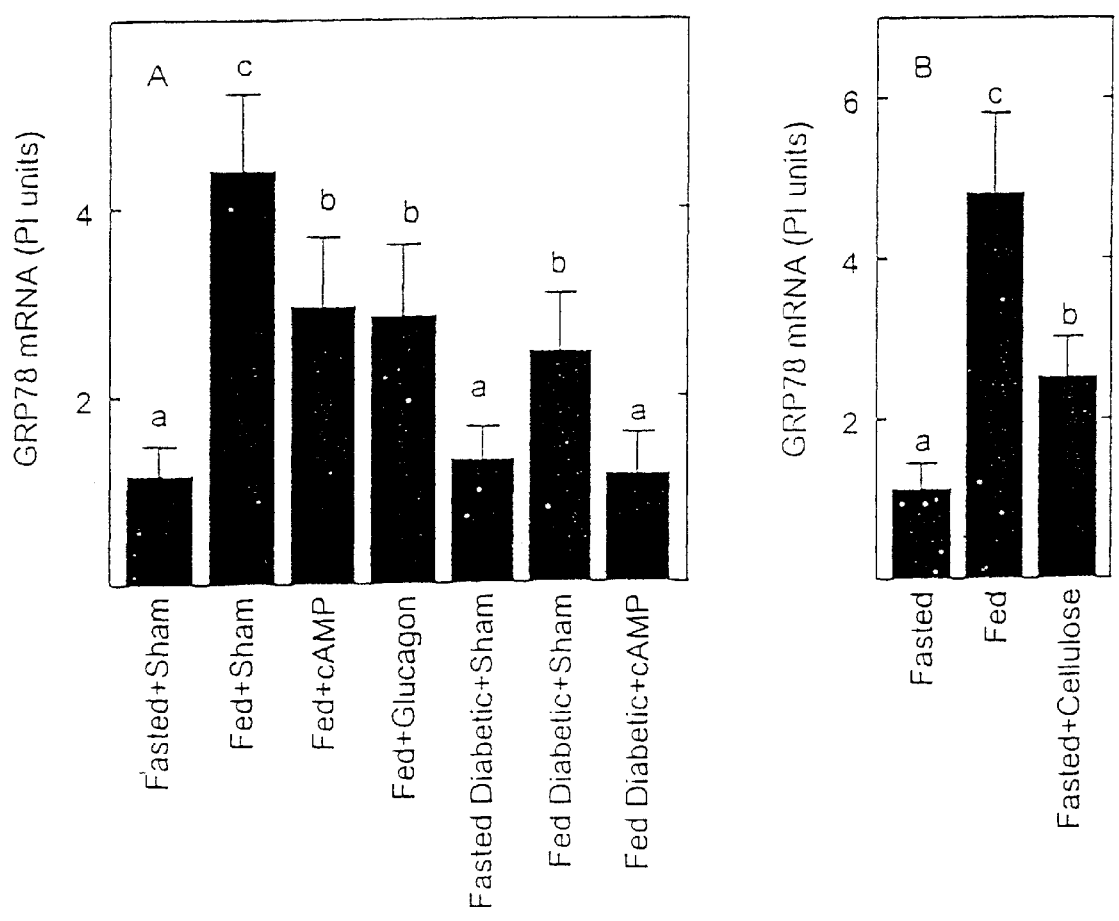
FIG. 6. Regulation of the fasting-feeding response by insulin, dibutyryl-cAMP, glucagon, and ingestion of mineral oil and cellulose. A, Groups of six mice were fasted for 48 h and treated as follows: Fasted+Sham mice were injected with vehicle and 1 h later vehicle injected a second time; Fed+Sham mice were sham injected with vehicle 30 min before and 30 min after feeding; Fed+cAMP mice were injected with dibutyryl-cAMP and theophylline 30 min before and 30 min after feeding; Fed+glucagon mice were injected with glucagon 30 min before and 30 min after feeding; Fasted Diabetic+Sham mice, previously rendered diabetic with STZ, were vehicle injected and 1 h later vehicle injected a second time; Fed Diabetic+Sham, STZ-diabetic mice were sham injected with vehicle 30 min before and 30 min after feeding; Fed Diabetic+cAMP, diabetic mice were injected with dibutyryl-cAMP and theophylline 30 min before and 30 min after feeding. All mice were killed 1 h after their last injection. Total RNA was isolated from the liver and subjected to dot-blot analysis. Bars with no common superscripts are significantly different ($P<0.005$). B, Effects of mineral oil and cellulose ingestion on liver GRP78 mRNA abundance. Groups of six mice were fasted for 48 h and treated as follows: Fasted, mice were fasted for 48 h and killed; Fed, mice were fasted for 48 h, fed, and killed 1.5 h later; Fasted+cellulose, mice fasted for 48 h were fed a mixture of cellulose and mineral oil, and killed 1.5 h later. Significance is indicated as in the legend to FIG. 5.

The physiological hallmarks of the fasting-feeding transition are increased circulating insulin and decreased circulating glucagon. In the studies shown in FIG. 6, fasted and refed sham-injected mice had serum glucose concentrations of 84.4±5.1 and 121.1±8.0 mg/dl, serum insulin concentrations of 0.491±0.203 and 1.3±0.256 pmol/ml, and serum glucagon concentrations of 143±22.4 and 81.4±13.2 pg/ml, respectively.

To investigate whether these hormones are involved in the postprandial induction of GRP78 mRNA, the effects of cAMP, glucagon, and STZ-induced diabetes on the response were examined. Administration of either dibutyryl cAMP or glucagon reduced the response of GRP78 mRNA to feeding (FIG. 6A). Vehicle alone had no effect. Likewise, STZ-induced diabetes resulted in a blunted response to feeding although it did not modify the fasting level of GRP78 mRNA. When STZ-induced diabetes was combined with cAMP administration, the postprandial induction of GRP78 mRNA was obliterated. The mRNA remained at fasting levels Without being bound to any particular mechanism, these results suggest that glucagon, acting to increase intracellular cAMP levels, suppresses chaperone gene transcription, or possibly GRP78 pre-RNA stability. Further, they suggest that insulin is required for full responsiveness of the chaperone genes to decreased intracellular cAMP.

Example 12

Luminal Filling

Luminal filling can lead to the release of some gastrointestinal polypeptides. For this reason, we investigated the role of luminal stimuli on the chaperone mRNA response. Fasted mice were refed a nonnutritive paste of cellulose (a normal component of their regular diet) and mineral oil. The mice initially consumed the mixture enthusiastically. Stomach filling was confirmed for each mouse by postmortem examination. Cellulose-mineral oil consumption produced a minor but significant increase in GRP78 mRNA (FIG. 6B), without producing a change in plasma glucose, insulin, or glucagon concentrations.

Example 13

Adrenal Hormones

Figure 7:
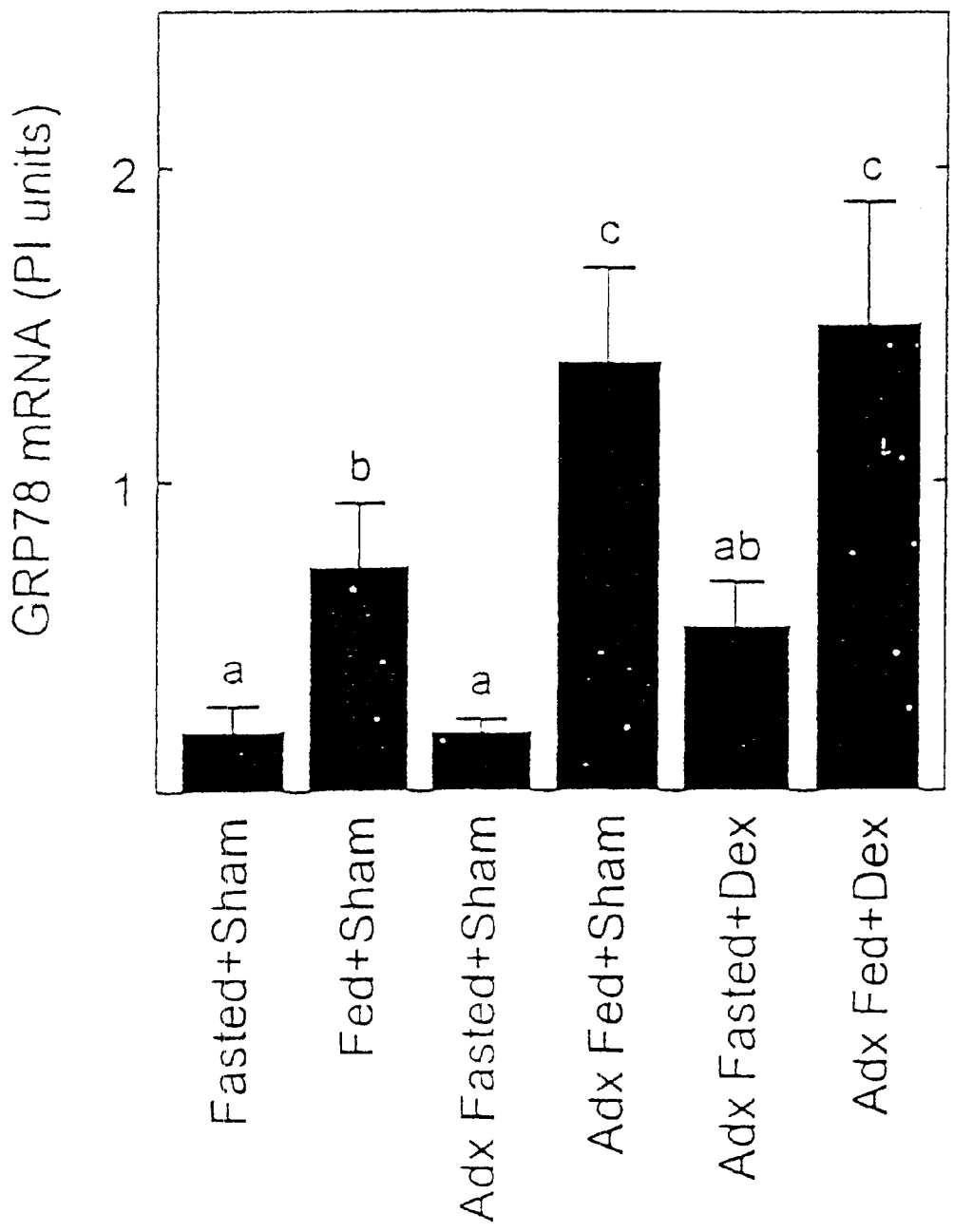
FIG. 7. Effects of adrenalectomy and dexamethasone administration on the expression and regulation of hepatic GRP78 mRNA. Groups of six mice were fasted for 48 h and treated as follows: Fasted+Sham, sham-operated mice were injected with vehicle IP 7.5 h and 1.5 h before they were killed; Fed+Sham, sham-operated mice were injected with vehicle IP 6 hours before and 30 min after feeding, and mice were killed 1 h after the last injection; Adx Fasted+Sham, adrenalectomized mice were injected with vehicle IP 7.5 h and 1.5 h before they were killed; Adx Fed+Sham, adrenalectomized mice were injected with vehicle IP 6 hours before and 30 min after feeding, and the mice killed 1 h later; Adx Fasted+Dex, adrenalectomized mice were injected IP with dexamethasone 7.5 h and 1.5 h before they were killed; Adx Fed+Dex, adrenalectomized mice were injected IP with dexamethasone 6 hours before and 30 min after feeding, and killed 1 h later. Significance is indicated as in the legend to FIG. 5.

To investigate the role of adrenal hormones in the postprandial induction of GRP78 mRNA, we examined the effects of feeding in adrenalectomized mice (FIG. 7). Neither adrenalectomy nor sham surgery had any effect on the fasting levels of GRP78 mRNA. However, adrenalectomy increased the magnitude of the postprandial induction of the mRNA by approximately 2-fold over that found in refed, sham-operated mice. The feeding response of GRP94, ERp72, and GRP170 were also enhanced in the adrenalectomized mice (data not shown). Thus, the increase is a generalized ER chaperone response. Administration of dexamethasone to adrenalectomized mice increased the basal level of GRP78 mRNA during starvation, although not significantly (FIG. 7). However, dexamethasone administration had no effect on the feeding induction of the gene, suggesting its absence from adrenalectomized mice is not responsible for the enhancement of the feeding response.

Example 14

Preparation of Test Groups for Short-term CR Studies

Three groups of 30 month old mice were utilized for these studies. Male $B6C3F_1$ mice were maintained as described (Dhahbi et al. (1998) J. Gerontol 53A: B180). Mice were weaned at 28 days and housed individually. The composition of the defined diets used have been described. They are formulated so that only the amount of carbohydrate consumed varied between the CR and control mice. A group of control mice was fed a purified, semi-defined diet from 6 weeks of age. Control mice consumed approximately 105 kcal per week from weaning. This is approximately 10% less than the amount of food thought to support optimal growth, fertility and fecundity in mice {Subcommittee on Laboratory Animal Nutrition & Committee on Animal Nutrition 1978 ID: 5480}. Subjectively, these mice appeared neither fat or lean. A group of calorically restricted mice (CR mice) were fed a diet reduced in dietary carbohydrate such that the mice consumed approximately 40% fewer calories than control mice. The long term CR mice consumed approximately 55 kcal per week from weaning. The short term CR mice were fed 105 kcal until the age of 29 months. They were then fed 80 kcal of control diet for 2 weeks, followed by 55 kcal of CR diet for two weeks. The mice were fed daily at 0900 hours. They had free access to water. For the studies, mice were fed a normal allotment of food Monday morning, and all the food was eaten within 45 minutes. They were fasted for 24 hours, and killed on Tuesday morning. At the time of use, the long term CR, short term CR and control mice weighed 22.8±1.4, 25.2±0.3 and 37.2±2.4 g, respectively. The mice were approximately 30 months old when killed.

Mice were killed by cervical dislocation and the liver rapidly removed and flash frozen in liquid nitrogen. Approximately 0.2 g of frozen liver was homogenized for 40 s in 4 ml of TRI Reagent (Molecular Research Center, Inc., Cincinnati, Ohio) using a Tekinar Tissuemizer (Tekmar Co., Cincinnati, Ohio) at a setting of 55. RNA was isolated as described by the supplier.

GeneChip oligonucleotide-based high-density array RNA expression assays were performed according to the standard Affrymetrix protocol. The biotinylated, fragmented cRNA was hybridized to the Mu11KsubA and Mu11KsubB Gene-Chip arrays (Affymetrix, Santa Clara, Calif.), which contain targets for more than 11,000 known mouse genes and ESTs. The arrays were washed, stained and scanned. Scanned image analysis and data quantification were performed using the Affymetrix GeneChip analysis suite v3.2 at default parameter settings. Resultant data were normalized by global scaling.

Data analysis. Data sets were normalized furher using GeneSpring 3.0 (Silicon Genetics, San Carlos, Calif.). Negative expression levels were forced to zero, and the expression data for each animal divided by the median of all experimental values for that chip above an expression level of 10. This step reduced cliip-to-chip signal variation. Fold change in expression was calculated by dividing the mean of the expression levels in the CR groups by the mean of the expression levels in the control group.

Statistical analysis. To test for significance of the effect of diet on gene expression, one-way ANOVA was followed by Fisher's test ($P<0.05$). Genes were placed in expression pattern groups (Table 2) for which they passed both tests. All statistical analyses were performed using Minitab Statistical Software.

Another aspect of this representation of the data was of interest. Significantly larger areas of blue were found in the expression profile of the control mice. These areas represent genes for which expression was not detectable. In both groups of CR mice, many of these regions were red, indicating higher levels of expression. Thus, a major effect of CR was the activation of specific gene expression.

To quantify the similarities in gene expression among groups of mice, a global expression correlation coefficient was calculated for each possible pair of mice. Table 1 shows the nine by nine matrix of these pairwise comparisons. The values are a measure of the similarities in gene expression between pairs of mice. Because the mice were genetically identical, the intra-group values provide a measure of the maximum correlations attainable. The inter-group correlations of the short- and long-term CR mice were similar to their intra-group correlations, indicating that gene expression in all CR mice was similar. In contrast, the control mice have little correlation with the mice in either CR group. This analysis suggests that short- and long-term CR had highly similar effects on overall patterns of specific gene expression.

TABLE 1

Pairwise comparisons of the global gene expression correlation coefficient calculated for each possible pair of mice.

|  | CR | | | CONTROL | | | SWITCHED | | |
|---|---|---|---|---|---|---|---|---|---|
| CR | 1.00* | 0.25 | 0.32 | 0.01 | 0.04 | −0.04 | 0.16 | 0.17 | 0.18 |
|  |  | 1.0 | 0.27 | −0.03 | 0.03 | −0.01 | 0.13 | 0.12 | 0.18 |
|  |  |  | 1.00 | 0.02 | 0.02 | −0.02 | 0.18 | 0.14 | 0.21 |
| CONTROL |  |  |  | 1.00 | 0.29 | 0.42 | 0.0 | 0.03 | 0.07 |
|  |  |  |  |  | 1.00 | 0.28 | 0.07 | 0.10 | 0.01 |
|  |  |  |  |  |  | 1.00 | −0.02 | 0.02 | 0.05 |
| SWITCHED |  |  |  |  |  |  | 1.00 | 0.24 | 0.18 |
|  |  |  |  |  |  |  |  | 1.0 | 0.16 |
|  |  |  |  |  |  |  |  |  | 1.00 |

Example 15

Gene Expression in Long and Short Term CR Mice

Figure 8:
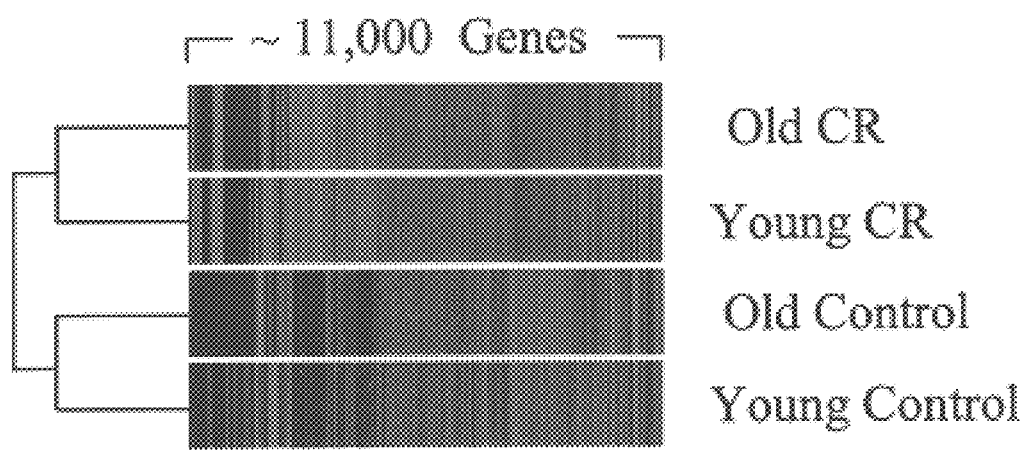
FIG. 8. The hepatic gene expression profiles of old control, old CR, young control, and young CR mice. The mice weighed 37.2+1.9 g, 22.8+1.2 g, 26.0+2.8 g, and 19.4+1.6 g, respectively. The CR groups consumed approximately 50% fewer calories than their control counterparts post-weaning, as described. Levels of specific mRNA were determined using the Mu11KsubA and Mu11KsubB GeneChip arrays (Affymetrix, Santa Clara, Calif.) containing targets for approximately 12,000 known mouse genes and ESTs. The experiment tree function of GeneSpring 3.0 (Silicon Genetics, San Carlos, Calif.) was utilized to display the results. The horizontal axis represents the position of each gene assigned by the "gene tree" average-linkage hierarchical clustering algorithmn of the program. Below the position assigned to each gene is a color-coded indication of its relative expression level, based on a continuous scale. Bright blue indicates no detectable expression, purple average expression, and bright red high expression. The average expression of each gene in each group is shown. The GeneSpring "experiment tree" clustering algorithm calculated an average- linkage hierarchical clustering dendrogram of the data for each group of mice, which is shown to the left of the expression profiles.

The global patterns of hepatic gene expression in the three groups of mice as displayed by GeneSpring 3.0, are shown in FIG. 8. The 11,000 genes assayed in the study are grouped according to both structure and function by the GeneSpring gene clustering algorithm across the horizontal axes of the figure. While this representation of the data cannot be subjected to statistical tests, subjective examination of this color coded representation of the data obtained immediately suggests that striking similarities exist in the gene expression profile of long and short term CR mice. Likewise, examination of the figure suggests that both CR expression profiles are very different than the profile of control mice. An average-linkage hierarchical clustering dendrogram calculated from the data by the GeneSpring clustering algorithm is shown to the left of the expression profiles. The dendrogram shows that the algorithm clustered the short- and long-term CR groups together, separated from the control group. This analysis agrees with our subjective interpretation of the expression profile.

Example 16

Long- and Short-term CR Induced Expression of the Same Genes

The pseudogene function of GeneSpring 3.0, and statistical analysis of the data were utilized to sort the genes into one of seven possible categories of relative gene expression. These groups were: expression not different among groups; expression high in long-term CR, low in control, and high in short-term CR (termed, high-low-high) (Appendix A); expression low in long-term CR, high in control, and low in short-term CR (low-high-low) (Appendix B); expression low in long-term CR and control, but high in short-term CR (low-low-high) (Appendix C); expression high in long-term CR and control, and low in short-term CR (high-high-low) (Appendix D); expression high in long-term CR, and low in control and short-term CR (high-low-low) (Appendix E); and expression low in long-term CR and high in control and short-term CR (low-high-high) (Appendix F). The vast majority of the genes were not different among groups, and will not be discussed further.

Table 2 shows the number of genes and expressed sequence tags (ESTs) in each of the other groups. Ninety percent of these genes and ESTs were in the high-low-high and low-high-low groups. In these groups, the short- and long-term CR expression patterns are most similar. The other 4 groups accounted for only 10% of the remaining genes and ESTs. These data indicate that short- and long-term CR produced remarkably similar effects on the expression of more than 11,000 hepatic genes and ESTs. A complete listing of the expression data for the genes and ESTs in each group is available (http://www.biochemistry.ucr.edu/faculty/spindler.htrml/GeneChipData) (This URL will be activated upon allowance of this application).

By far the most common response to short- and long-term CR was the high-low-high expression pattern. It accounted for nearly 86% of the genes and ESTs in the groups. Thus, the most common effect of short- and long-term CR was the activation of gene expression. To determine whether short- and long-term CR induced expression to the same degree in the high-low-high group, we tabulated the number of known genes for which expression was statistically the same in the two groups. In high-low-high, 303 of 340 known genes (89%) were expressed at the same level in the short- and long-term CR groups. For 26 of these genes (8%), expression in the long-term CR mice was statistically greater. For 11 genes (3%), expression was greater in the short-term CR group. Thus, short- and long-term CR induced the expression of the vast majority of these genes to the same levels.

Of the genes in the high-low-high group, 146 of 340 genes were activated from undetectable levels in the control mice to much higher, but very similar levels in both CR groups. Expression of these genes averaged 1.25±0.25 and 1.23±0.23, in the short- and long-term CR groups, respectively. These observations reinforce the idea that short- and long-term CR have highly homologous effects on the expression of genes.

To further understand the genomnic effects of CR, we identified the genes in the high-low-high group described above.

TABLE 2

GENES WHICH DIFFER FROM CONTROL IN RESPONSE TO CR

| LT CR* | CONTROL | ST CR** | GENES | EST's | PERCENT |
|---|---|---|---|---|---|
| High | Low | High | 340 | 860 | 85.7 |
| Low | High | Low | 23 | 37 | 4.3 |
| High | High | Low | 4 | 9 | 0.9 |
| Low | Low | High | 13 | 19 | 2.3 |

TABLE 2-continued

GENES WHICH DIFFER FROM CONTROL IN RESPONSE TO CR

| LT CR* | CONTROL | ST CR** | GENES | EST's | PERCENT |
|---|---|---|---|---|---|
| High | Low | Low | 26 | 55 | 5.8 |
| Low | High | High | 9 | 6 | 1.1 |

*Long-term CR
**Short-term CR

Example 17

Immune System Activation: The Immune Theory of Aging

Many of the genes which were induced by CR in the long and short term CR group were genes involved with immune system activation. Without being limited to any specific mechanism, this result provides support for the theory that the immune system plays a central role in the rate and many of the pathologies of aging. Slightly more than 130 T-cell receptor, IgG, IgA, IgD, IgK, and IgM, genes were present in the high-low-high group. The average fold relative expression of these mRNAs in the long and short term CR groups was 1.24±0.86 and 1.23±0.25, verses 0.16±0.16 in the control group. Thus, CR increased immunoglobulin and T-cell receptor expression more than 10-fold. It is highly unlikely that this increase was due to an increase in the amount of blood in the CR livers. The level of globin mRNA found in these mRNA samples was actually reduced by about 20% in the long and short term CR groups. No statistically significant difference was found in the globin mRNA concentration in the blood of these animals.

Other changes in gene expression indicate that CR activates the immune system (Table 3). As can be seen in the table, both long and short term CR induced the expression of hemopoietic and lymphopoetic cytokines, hormones, signal transduction proteins, protein kinase modulators of the cell cycle and signal transduction, cell-surface receptors, and transcription factors. Not shown are a group of 20 immune cell specific genes known to be involved in endocytosis, cell adhesion, phagocytosis, potassium channels, lymphocyte activation, VDJ recombination, and immune cell activation which were strongly and significantly induced by CR (3- to 40-fold; $P \geq 0.037$). Together, these data evidence that CR enhances the activity of the immune system.

TABLE 3

Immune system genes activated by short- and long-term CR

| LTCR* | STCR* | P | GENE |
|---|---|---|---|
| | | | Hormones / Cytokines / Chemokines |
| 4 | 4 | 0.003 | Antigen, B cell receptor; L43567 |
| 53 | 55 | <0.001 | Calcium/calmodulin-dependent protein kinase IV (Camk4); multifunctional serine-threonine protein kinase; T cells; X58995 |
| >100 | >100 | <0.001 | Chemokine (C-C) receptor 1 (Cmkbr1); growth inhibitory effects; liver and spleen; U28404 |
| 13 | 17 | <0.001 | Chemokine (C-C) receptor 5 (Cmkbr5); induces mobilization of intercellular calcium; beta-chemokine; leucocyte chemoattractant; liver, thymus, spleen, elsewhere; ET62976 |
| >100 | >100 | 0.003 | Chemokine (C-X-C) receptor 4 (Cmkbr4); integral membrane G-protein-coupled receptor; chemotaxis and calcium flux; directs |

TABLE 3-continued

Immune system genes activated by short- and long-term CR

| LTCR* | STCR* | P | GENE |
|---|---|---|---|
| | | | monocytes and lymphocytes to their target tissues; thymus, T cells, and monocytes; ET62920 |
| 19 | 21 | 0.002 | Colony stimulating factor 1 (macrophage) (Csf1); receptor; liver; X06368 |
| 10 | 8 | 0.016 | Complement receptor 2 (Cr2); Late pre-B cells; M35684 |
| 3 | 2 | 0.015 | Interferon beta type 1; growth factor; T helper cell differentiation factor; antiviral; modulates immune response to foreign and self-antigens; immune system cells, others; V00755 |
| 11 | 10 | <0.001 | Interferon-related developmental regulator (Ifrd1); T cells; V00756 |
| 9 | 6 | 0.044 | Interleukin 2 (Il2); stimulates proliferation of activated T lymphocytes; M16762 |
| >100 | >100 | 0.015 | Interleukin 2 receptor (Il2r); T cells; M26271 |
| 2 | 2 | 0.014 | Interleukin 6 (Il6); promotes B cell maturation to Ig-secreting cells; activation of T cells; some helper T cells and macrophages; X54542 |
| 5 | 6 | 0.004 | Interleukin 7 (Il7); growth factor; B cell progenitors; X07962 |
| 4 | 3 | 0.046 | Killer cell lectin-like receptor, subfamily A, member 3 (Klra3); Ly-49C; involved in graft rejection; subpopulation of natural killer cell; U49866 |
| >100 | >100 | 0.034 | Killer cell lectin-like receptor, subfamily A, member 6 (Klra6); Ly-49F; NK cell surface antigen; determinant of IL-2-activated NK cell specificity; inhibitory receptor for interaction with MHC class I proteins; NK cells; U10092 |
| 13 | 11 | <0.001 | Lymphocyte antigen 84 (Ly84); signal transduction protein 2; T cells; D13695 |
| 5 | 6 | 0.007 | Mast cell protease 7 (Mcpt7); released when mast cells are activated; mast cells; ET61471 |
| 3 | 2 | 0.037 | Myc box dependent interacting protein 1 (Bin1); endocytosis and signal transduction; recycling synaptic vesicle components; macrophages, neurons, endocrine cells; U86405 |
| >100 | >100 | <0.001 | Paired-Ig-like receptor A1 (Pira1); activates B lymphocytes, dendritic and myeloid-linage cells; ET62839 |
| 5 | 4 | 0.027 | Paired-Ig-like-receptor A6 (Pira6); appears to activate immunoglobulin-related receptor; B lymphocytes, myeloid lineage cells; ET62844 |
| 3 | 4 | 0.038 | Preprosomatostatin (Smst); regulates T cell IFN-gamma production; macrophages, nervous system; X51468 |
| >100 | >100 | <0.001 | Protein tyrosine phosphatase, receptor type E (Ptpre); transmembranal, receptor-like form and a cytoplasmic, non-receptor form; hematopoietic tissues; ET61424 |
| 23 | 41 | 0.010 | Proviral integration site (Pim2); serine/threonine kinase 2; cell proliferation; mitogen stimulated; long-term potentiation in hippocampus; immune and epithelial cells, CNS; L41495 |
| | | | Receptors / Signal Transduction Proteins |
| 11 | 8 | 0.001 | Small inducible cytokine subfamily, member 2 (Scyb2); small inducible cytokine; macrophages; X53798 |
| 8 | 8 | 0.002 | Son of sevenless 1, homologue 1 (Drosophila) (Sos1); Ras-specific exchange factor; T cells; Z11574 |
| >100 | >100 | <0.001 | Son of sevenless 2 homologue 2 (Drosophila) (Sos2); Ras-specific exchange factor; T cells; Z11664 |
| >100 | >100 | 0.002 | Spleen protein kinase (Syk); signal transduction; lymphopoietic and haematopoietic cells, platelets, macrophages and neutrophils; ET61263 |
| >100 | >100 | 0.048 | Tbcl; domains homologous to tre-2 oncogene and yeast mitosis regulators BUB2 and cdc16; nuclear localization; B lymphocytes; dendritic cells, myeloid-linage cells; U33005 |
| 2 | 2 | 0.044 | Thrombin receptor; transmembrane G-protein-coupled receptor; activated by serine protease cleavage; mitogen and apoptosis inducer following vessel injury; platelets, monocytes, endothelial cells, neuronal and glial cells; U36757 |
| >100 | >100 | 0.002 | Wee1 homologue (S. pombe) (Wee1); inhibits entry into mitosis by phosphorylation of the Cdc2 kinase; lymphocytes; D30743 |
| | | | Transcription Factors |
| 38 | 35 | <0.001 | Abelson murine leukemia oncogene (Abl); nonreceptor tyrosine kinase; role in cell cycle progression, cell proliferation and differentiation; liver, B cells, others; X07540 |
| >100 | >100 | 0.047 | Homeo box A4 (Hoxa4); transcription factor; embryonic spinal cord and adult testis; X13538 |
| 4 | 7 | 0.026 | Homeo box B4 (Hoxb4); transcription factor; embryonic development; haematopoiesis; NK cells; M36654 |
| 6 | 10 | 0.029 | Homeo box B7 (Hoxb7); transcription factor; embryonic development; haematopoiesis; developing embryo; blood, bone marrow, natural killer cells; X06762 |

TABLE 3-continued

Immune system genes activated by short- and long-term CR

| LTCR* | STCR* | P | GENE |
|---|---|---|---|
| 8 | 9 | <0.001 | Homeo box C6 (Hoxc6); transcription factor; embryogenesis; haematopoiesis; liver and many other tissues; X16510 |
| 40 | 36 | 0.001 | Homeo box D1 (Hoxd1); transcription factor; neurogenesis; developing CNS and forelimb bud; X60034 |
| >100 | >100 | <0.001 | Nuclear factor of activated T cells, cytoplasmic 2 (Nfatc2); T cell transcription factor isoform B; T cells; U36575 |
| 5 | 5 | 0.001 | SRY-box containing gene 4 (Sox4); Sox gene family transcription factor; thymus, bone marrow, gonads; ET62444 |
| 2 | 2 | 0.012 | Zinc finger protein 79 (Zfp79); Kruppel type zinc finger putative transcriptional repressor; associates with RB in vitro; hematopoietic cells, perhaps others; U29513 |
| | | | Primary Response Genes |
| >100 | >100 | 0.005 | Fos-like antigen-1 (Fosl1); spleenocytes; U34245 |
| >100 | >100 | <0.001 | Immunity associated protein, 38 kDa (Jmap38); spleenocytes; Y08026 |
| >100 | >100 | <0.001 | Immunoresponsive gene 1(Irg1); activated by bacterial LPS treatment; macrophages; L38281 |
| >100 | >100 | <0.001 | Prostaglandin-endoperoxide synthase (Ptgs2); putative mediator of inflammation; induced by growth factors and cytokines; monocytes and fibroblasts; M88242 |
| 388 | 353 | 0.001 | T-cell acute lymphocytic leukemia 2 (Ta12); putative basic helix-loop-helix transcription factor activated in T-cell acute lymphoblastic leukemia; T cells; M81077 |
| >100 | >100 | <0.001 | Tumor necrosis factor induced protein 3 (Tnfip3); putative helix-loop-helix transcription factor activated in T-cell acute lymphoblastic leukemia; lymphocytes; U19463 |
| | | | Cell Adhesion / Membrane Components |
| >100 | >100 | 0.002 | ADP-ribosyltransferase 2a (Art2a); homologue of the rat T cell differentiation marker RT6; cell-cell signaling; cytotoxic T lymphocytes; X52991 |
| 9 | 9 | 0.013 | Cadherin 9 (Cdh9); calcium-binding membrane glycoprotein; cell adhesion molecule; thymocytes; U69136 |
| 6 | 5 | 0.015 | CD22 antigen (Cd22); mediates B cell interactions with endothelial cells; B cells; L16928 |
| 7 | 7 | 0.002 | CD53 antigen (Cd53); pan-leukocyte antigen; cell membrane glycoprotein; thymocytes; X97227 |
| 40 | 36 | <0.001 | Erythrocyte protein band 7.2 (Epb7.2); involved in Na+/K+ permeability of cells; spleen, lung, testis; X91043 |
| 8 | 8 | 0.006 | Integrin alpha 4 (Itga4); cell adhesion; lymphocytes; X53176 |
| >100 | >100 | <0.001 | Mannose receptor, C type 2 (Mrc2); cell adhesion; antigen presentation; widespread tissue distribution, fetal liver; U56734 |
| | | | Immune Cell Function |
| 38 | 44 | <0.001 | Cytochrome b-245, beta polypeptide (Cybb); gp91phox; flavocytochrome mediating electron transfer from NADPH to molecular oxygen in the respiratory burst oxidase; phagocytes; U43384 |
| 8 | 8 | <0.001 | Cytotoxic T lymphocyte-associated protein 2 beta (Ctla2b); homologue of cysteine protease proregion, T cells; X15592 |
| >100 | >100 | <0.001 | GranzymeG (Gzmg); CTL serine protease 3; may play a role in cytolytic lymphocyte activation; T lymphocytes; X14092 |
| >100 | >100 | 0.007 | Helicase, lymphoid specific (Hells); replication, repair, recombination and transcription; T and B cells; U25691 |
| >100 | >100 | 0.001 | Mast cell protease 4 (Mcpt4); secretory granule serine protease; peritoneal and most connective tissue mast cells; M55617 |
| 5 | 6 | 0.007 | Mast cell protease 7 (Mcpt7); released when mast cells are activated; mast cells; ET61471 |
| 8 | 8 | 0.005 | Potassium voltage gated channel, shaker related subfamily, member 2 (Kcna2); T cells, myelinating Schwann cells; M30440 |
| 3 | 3 | 0.003 | Terminal deoxynucleotidyl transferase (Tdt); VDJ assembly; recombination; earliest stage B and T cells; X04123 |

*Fold of control

Further support for this view was found in the liver specific genes which were strongly induced in expression by CR (Table 4). Long and short-term CR significantly enhanced the expression of the CD44 hyaluronan receptor gene, which has a role in lymphocyte homing and activation. Likewise, CR activated the mRNA abundance of the chemokine receptor 4, which is also involved in stimulating growth of pre-B cells; the mannnose receptor, C type 2, which is involved in antigen presentation; colony stimulating factor 1, which is a macrophage growth factor; and proteaseome 3, which enhances the generation of class I binding peptides.

TABLE 4

Liver specific and ubiquitous genes

| LTCR* | STCR* | P | GENE |
|---|---|---|---|
| | | | Cytokines / Growth Factors |
| 12 | 7 | 0.003 | C-Fos induced growth factor (Figf); secreted growth factor; mitogenic and morphogenic activity; endothelial cells of liver during embryonic development; X99572 |
| 2 | 2 | 0.002 | Fibroblast growth factor 2 (Fgf2); mitogen, differentiation and survival factor, angiogenic factor; stimulates hepatocyte proliferation and migration; hepatocytes, other cells; M30644 |
| >100 | >100 | 0.001 | Fibroblast growth factor 3 (Ffg3); liver epithelial cells; Y00848 |
| 3 | 3 | 0.012 | Fibroblast growth factor 7 (Fgf7); liver epithelial cells; ET62118 |
| >100 | >100 | 0.001 | Follistatin (Fst); binds and inactivates activin; control of the inflammatory cascade; liver; Z29532 |
| >100 | >100 | 0.005 | Inhibin beta B (Inhbb); transforming growth factor beta (TGF-beta) superfamily member; liver and elsewhere; X69620 |
| >100 | >100 | 0.001 | Inhibin beta E (Inhbe); transforming growth factor beta (TGF-beta) superfamily member; liver and elsewhere; U96386 |
| 13 | 9 | 0.000 | Interferon alpha gene family leukocyte (Infa); inhibition of cell proliferation; ubiquitous; M28587 |
| 3 | 2 | 0.015 | Interferon beta type 1; growth factor; T helper cell differentiation factor; antiviral; modulates immune responses to foreign and self-antigens; ubiquitous; V00755 |
| 11 | 11 | 0.001 | Interferon-beta (Ifnb); inhibitor of inflammation; liver and other cells; J00424 |
| 13 | 13 | <0.001 | Neurotrophin 3 (Ntf3); secreted protein; binds high affinity receptor trk C; may be involved in postnatal development; liver parenchymal cells, cerebellum, thymus, other; X53257 |
| 4 | 5 | 0.003 | Preproendothelin 1 (Edn1); activates p38 MAP kinase and JNK; portal vein constriction; hepatic stellate cells, liver and arterial smooth muscle cell, others; U07982 |
| 10 | 15 | 0.003 | Transforming growth factor beta 2 (Tgfb2); cell proliferation; liver stellate cells; X57413 |
| | | | Cell Surface Receptors |
| >100 | >100 | 0.020 | Bradykinin receptor beta (Bdkrb); G-protein-coupled membrane bound; T-kininogen modulation during acute phase protein synthesis; liver (ubiquitous); ET61559 |
| 2 | 2 | 0.017 | CD44 antigen (Cd44); receptor for hyaluronan; cell surface glycoprotein; hyaluronan clearance from the blood; lymphocyte homing and activation; liver, CNS, other; U57612 |
| >100 | >100 | <0.001 | Chemokine (C-C) receptor 1 (Cmkbr1); mediates growth inhibitory effects of the chemokine; liver and spleen; U28404 |
| 12 | 8 | 0.013 | Chemokine (C-X-C) receptor 4 (Cmkar4); primary receptor stromal cell-derived factor/pre-B growth stimulating factor; seven transmembrane domain receptor; liver and bone marrow; X99581 |
| >100 | >100 | <0.001 | Fibroblast growth factor receptor 2 (Fgfr2); membrane-spanning tyrosine kinase; activated by three members of the FGF family; liver development; liver parenchymal cells and others; M86441 |
| 4 | 3 | 0.001 | Leptin receptor (Lepr); transmembrane receptor; liver, lung, muscle, brain, other; ET61693 |
| 4 | 3 | 0.027 | Melanocortin 5 receptor (Mc5r); G-protein-coupled receptor; stimulates adenylyl cyclase; widely expressed; X76295 |
| 3 | 4 | 0.029 | Pancreatic polypeptide receptor 1 (Ppyr1); neuropeptide Y; peptide YY receptor; G-protein-coupled; liver; U40189 |
| >100 | >100 | <0.001 | Proteaseome 3 (Psme3): Ki antigen; cell proliferation; enhances generation of class I binding peptides; liver, broad tissue distribution; U60330 |
| >100 | >100 | <0.001 | Purinergic receptor P2X, ligand-gated ion channel 1 (P2rx1); mediate Ca(2+) influx; liver, ubiquitous; X84896 |
| 64 | 68 | 0.001 | Ryanodine receptor 2 (Ryr2); endoplasmic reticulum membrane Ca2+ channels; controls cytosolic calcium levels; liver, cardiac muscle, neurons, most excitable cells; X83933 |
| >100 | >100 | 0.003 | Transferrin receptor (Trfr); cell surface glycoprotein; cell growth; iron uptake; liver; X57349 |
| | | | Signal Transduction / Cell Cycle / Cell Growth |
| 38 | 35 | <0.001 | Abelson murine leukemia oncogene (Abl); nonreceptor tyrosine kinase; role in cell proliferation and differentiation; liver, B cells; X07540 |
| >100 | >100 | 0.006 | Cyclin-dependent kinase inhibitor 1B (P27) (Cdkn1b); cell cycle; ubiquitous; U10440 |
| 35 | 40 | 0.003 | Guanine nucleotide binding protein, alpha inhibiting 1 (Gnail); liver, cerebral cortex, others; U38501 |
| >100 | >100 | 0.013 | Guanine nucleotide binding protein beta 4 (Gnb4); liver, brain, blood cell; M63658 |

TABLE 4-continued

Liver specific and ubiquitous genes

| LTCR* | STCR* | P | GENE |
|---|---|---|---|
| >100 | >100 | 0.001 | Histamine receptor H1(Hrh1); coupled to phosphoinositide turnover-calcium mobilization signaling pathway; regulates IGF-I expression and cell proliferation; regulates thyroxine transport into hepatocytes; liver, brain, spleen (ubiquitous); D50095 |
| >100 | >100 | 0.002 | Interferon-activated gene 204 (Ifi204); mediates antimicrobial, immunomodulary and cell growth-regulatory activities of interferons; nucleoli; M31419 |
| 4 | 4 | 0.004 | Kinase interacting with leukemia-associated gene (Kis); cytosolic phosphoprotein; integration of intracellular proliferation and differentiation signaling; ubiquitous; X82320 |
| 9 | 8 | 0.004 | MAD homologue 5 (Madh5); downstream component in the TGF-beta family signaling cascade; liver development angiogenesis; liver; ET62570 |
| >100 | >100 | 0.002 | MAP kinase kinase kinase (Map3k1), serine-threonine kinase; regulates sequential protein phosphorylation pathways involving mitogen-activated protein kinases (MAPKs); ubiquitous; ET61257 |
| >100 | >100 | 0.002 | Mitogen activated protein kinase 1 (Mapk1); signal transduction; cell proliferation, differentiation, and apoptosis; liver, ubiquitous; U85608 |
| >100 | >100 | 0.004 | NIMA-related expressed kinase (Nek1); ubiquitous; S45828 |
| 3 | 3 | 0.041 | Neuroblastoma ras oncogene (Nras); key component of growth signaling pathways; liver, wide tissue distribution; X13664 |
| >100 | >100 | <0.001 | Phosphatidylinositol 3-kinase regulatory subunit, polypeptide 1 (p85alpha) (Pik3r1); role in cell growth, differentiation, survival, and vesicular transport; liver; ET61628 |
| >100 | >100 | 0.003 | Phospholipase C, gamma 1 (Plcg1); produces second messengers of signal transduction pathways related to cell proliferation; ubiquitous; ET63005 |
| >100 | >100 | <0.001 | Proteaseome 3 (Psme3); Ki antigen; cell proliferation; enhances the generation of class I binding peptides by altering the cleavage pattern of the proteosome; liver, neurons, broad tissue distribution; U60330 |
| 3 | 2 | 0.002 | Protein tyrosine phosphatase, non-receptor type 16 (Ptpn16); growth factor-induced immediate early gene; dephosphorylates MAP kinase; liver parenchymal and vascular smooth muscle cells, others; X61940 |
| 11 | 12 | 0.001 | Ras-GTPase-activating protein SH3-domain binding protein 2 (G3bp2-pending); essential for Ras signaling; ubiquitous; U65313 |
| 2 | 2 | 0.001 | Rhodopsin kinase (Rhok); small GTPase and serine/threonine protein kinase; regulates actin cytoskeletal reorganization; enhances secretion; ubiquitous except for brain and muscle; U58513 |
| 15 | 14 | 0.018 | Ros 1 proto-oncogene (Ros1); embryonic development; tyrosine kinase catalytic domains; expressed in neoplastic and fetal tissues; neoplastic and fetal tissues; U15443 |
| 6 | 4 | 0.010 | SUMO-1 activating enzyme subunit 1; conjugates SUMO-1 (a small ubiquitin-like protein) to other proteins; modification of I Kappa B alpha blocks NF kappa B-dependent transcriptional activation; ubiquitous; AA162130 |
| >100 | >100 | <0.001 | Wingless related MMTV integration site 10b (Wnt10b); developmental regulation of cell growth and differentiation; ET62229 |
| | | | Nuclear Receptors |
| 19 | 17 | 0.016 | Thyroid hormone receptor alpha (Thra); energy balance, thermoregulation, substrate uptake; liver; X07751 |
| 10 | 9 | 0.003 | Glucocorticoid receptor 1 (Grl1); energy balance; substrate uptake; liver; X04435 |
| 45 | 42 | <0.001 | Nuclear receptor subfamily 2, group F member 1 (Nr2f1); COUP-TF1; orphan steroid hormone receptor, transcription factor; liver; X74134 |
| >100 | >100 | 0.010 | Nuclear receptor subfamily 2, group F member 2 (Nr2f2); apolipoprotein regulatory protein 1; member of the COUP-family of steroid hormone orphan receptors; liver, lung, kidney; X76653 |
| | | | Transcription Factors |
| 4 | 3 | 0.016 | Sine oculis-related homeobox 1 homologue (Drosophila) (Six1); AREC3; expressed in many cell-types during development; ET61028 |
| 9 | 7 | 0.003 | cAMP responsive element binding protein 1 (Creb1); a mediator of cAMP responsive transcriptional regulation; ubiquitous; X67719 |

TABLE 4-continued

Liver specific and ubiquitous genes

| LTCR* | STCR* | P | GENE |
|---|---|---|---|
| >100 | >100 | <0.001 | Reticuloendotheliosis (Rel); c-rel: member of the Rel/nuclear factor (NF)-kappaB family of transcriptional factors; ubiquitous; X15842 |
| >100 | >100 | <0.001 | E4F transcription factor 1 (E4f1); DNA binding transcription factor; ubiquitous; X76858 |
| 4 | 4 | 0.026 | Forkhead box C2 (Foxc2); transcription factor; hepatocytes; X74040 |
| 11 | 11 | 0.001 | Homeo box A9 (Hoxa9); transcription factor; embryogenesis; M28449 |
| >100 | >100 | 0.003 | Homeo box msh-like 1 (Msx1); transcription factor; early stage of eye developmental regulation in embryo; embryogenesis; X59251 |
| 2 | 3 | 0.003 | Inhibitor of DNA binding 4 (Idb4); dominant negative regulator of bHLH transcription factors; myogenesis, neurogenesis D83 and haematopoiesis; liver and elsewhere; X75018 |
| >100 | >100 | 0.010 | Myogen factor 5 (Myf5); transcription factor; embryonic liver and heart; X56182 |
| 6 | 8 | 0.003 | Nuclear transcription factor-Y alpha (Nfya); CAAT-box DNA binding protein subunit A; involved in activation of many hepatic genes; ubiquitous; X55315 |
| 3 | 3 | 0.018 | Paired box gene 2 (Pax2); Pax2 transcription factor; developing embryo excretory and CNS; X55781 |
| 12 | 13 | 0.003 | RE1-silencing transcription factor (Rest); transcription factor; represses expression of neuronal genes; many nonneuronal cells and tissues; U13878 |
| >100 | >100 | 0.002 | Sine oculis-related homeobox 1 homolog (Drosophila) (Six1); homeobox; development of limb tendons; skeletal and smooth muscle cells; X80339 |
| >100 | >100 | 0.005 | SRY-box containing gene 12 (Sox12); transcription factor; Sox family plays important role in development; developing embryos; ET62446 |
| 2 | 3 | 0.032 | T-box 4 (Tbx4); DNA binding domain putative transcription factor; putative roll in inductive interactions during embryogenesis; embryonic development; ET62078 |
| >100 | >100 | 0.009 | Trans-acting transcription factor 1 (Sp1); transcription factor; component of some hepatic glucose response elements, ubiquitous; X60136 |
| >100 | >100 | 0.024 | Transcription elongation factor A 1(Tceal); transcription elongation factor; liver; D00925 |
| 14 | 12 | <0.001 | Yes-associated protein, 65 kDa (Yap); transcription activator; ubiquitous; X80508 |
| 10 | 10 | <0.001 | Zinc finger protein 37 (Zfp37); putative transcription factor; peroxisome proliferator responsive; liver; X89264 |
| >100 | >100 | 0.009 | Zinc finger protein 61 (Zfp61); putative transcription factor; liver, elsewhere; L28167 |

Translation / Splicing / RNA Processing Factors

| LTCR* | STCR* | P | GENE |
|---|---|---|---|
| 7 | 7 | 0.001 | Cytoplasmic polyadenylation element binding protein (Cpeb); RNA binding protein that promotes polyadenylation and translational activation; ubiquitous; Y08260 |
| 4 | 4 | 0.011 | Eukaryotic translation initiation factor 1A (Eif1a); ubiquitous; U28419 |
| >100 | >100 | <0.001 | Ribosomal protein L32, pseudogene (Rpl32-ps); ubiquitous; K02060 |
| >100 | >100 | 0.000 | Ribosomal protein L7 (Rpl7); incorporated into 60 S subunit; ubiquitous; X57960 |
| 18 | 13 | 0.001 | Signal recognition particle 9 kDa (Srp9); synthesis and translocation of membrane and secreted proteins into the endoplasmic reticulum; ubiquitous; X78304 |
| >100 | >100 | 0.004 | Splicing factor arginine/serine-rich 3 (Sfrs3); splicing factor belonging to the highly conserved family of SR proteins; regulation of constitutive and alternative splicing; ubiquitous; X91656 |

Chromatin Structure

| LTCR* | STCR* | P | GENE |
|---|---|---|---|
| 4 | 5 | 0.009 | Chromobox homologue (Drosophila HP1beta) (Cbx); modifs chromatin heritably activating or silencing genes; ubiquitous during development; X56690 |
| >100 | >100 | 0.028 | Histone H1 subtype e (H1e); chromatin structure; ubiquitous; L04141 |
| >100 | >100 | <0.001 | Histone H1; chromatin structure; ubiquitous; J03482 |
| 109 | 70 | <0.001 | Histone H1b; chromatin structure; ubiquitous; ET62262 |
| >100 | >100 | 0.024 | Histone H2A; chromatin structure; ubiquitous; X16495 |
| 4 | 3 | 0.030 | Histone H2B; chromatin structure; ubiquitous; ET62908 |
| 7 | 8 | 0.006 | Histone H3. 1-D (H3-D) and histone H4-D (H4-D); chromatin structure; ubiquitous; U62672 |

TABLE 4-continued

Liver specific and ubiquitous genes

| LTCR* | STCR* | P | GENE |
|---|---|---|---|
| >100 | >100 | <0.001 | Histone H3.2-F (H3-F), histone H2a.1-F (H2a-F), histone H2b-F (H2b-F); chromatin structure; ubiquitous; U62669 |
| 4 | 4 | 0.034 | HpaII tiny fragmnents locus 9c (Htf9c); structural similarity with yeast nucleic acid-modifying enzymes; activated at the G1/S transition, and S phase; down-regulated in growth arrested cells; liver (ubiquitous); X56044 |

*Fold of control

Example 18

CR Stimulates the Expression of Genes Enhancing Genetic Stability and Apoptosis The accumulation of genetic damage has been postulated to be a cause of aging. Without being limited to any specific mechanism, CR has been postulated to either reduce the rate of accumulation of genetic damage, or to enhance its rate of repair. Both long and short term CR enhanced the expression of numerous genes associated with DNA repair (Table 5). These genes included Xpa, which is involved in nucleotide excision DNA repair; and the Brca2 gene, which is important in DNA double-strand break repair and DNA damage-induced cell-cycle checkpoint activation.

A theory of aging closely related to the DNA damage theory proposes that the reduction of apoptosis with age, and its restoration with CR plays and important role in aging. This hypothesis proposes that the accumulation of damaged cells with age contributes to aging itself and to the onset of the diseases of aging. Long and short term CR greatly enhanced the expression of a number of genes which choreograph the progression of a cell through the apoptotic pathway (Table 5). These genes included Casp1, Casp3, Bax, and Bcl2 which code for key components of the apoptotic pathway.

TABLE 5

Genetic stability and apoptosis

| LTCR* | STCR* | P | GENE |
|---|---|---|---|
| | | | DNA Replication / Repair |
| 9 | 8 | <0.001 | Antigenic determinant of rec-A protein (Kin); Kin17; DNA-binding nuclear protein upregulated in response to UV and ionizing radiation; accumulated in the nucleus of proliferating cells; ubiquitous; X58472 |
| >100 | >100 | 0.001 | Breast cancer 2 (Brca2); DNA double-strand break repair and DNA damage-induced cell-cycle checkpoint activation; ubiquitous; ET62746 |
| 3 | 3 | 0.029 | DNA primase p49 subunit (Prim); DNA replication; liver (ubiquitdus); X74351 |
| 6 | 5 | 0.009 | Mut L homologue 1 (*E. Coli*) (Mlh1); transcription-coupled nucleotide excision repair; cell cycle checkpoint control; ubiquitous; ET63479 |
| 3 | 3 | 0.025 | Xeroderma pigmentosum complementation group A (Xpa); nucleotide excision DNA repair; ubiquitous; X7435 |
| | | | Apoptosis |
| >100 | >100 | 0.001 | B-cell leukemia/lymphoma 2 (Bcl2); suppresses apoptosis by controlling mitochondrial membrane permeability; many cells and tissues; L31532 |
| >100 | >100 | <0.001 | Bcl2-associated X protein (Bax); pro-apoptotic activity; can form channels in lipid membranes; many cells and tissues; LZ2472 |
| 5 | 4 | 0.033 | Caspase 1 (Casp1); cysteine protease mediator of apoptosis; ubiquitous; U04269 |
| 2 | 3 | 0.000 | Caspase 3 (Casp3); cysteine protease mediator of apoptosis; ubiquitous; ET63241 |
| 3 | 4 | 0.005 | Cyclin G (Ccng); augments apoptosis; target gene of P53; liver, elsewhere; Z37110 |
| >100 | >100 | <0.001 | Fused toes (Fts); a gene related to ubiquitin-conjugating enzymes; suggested role in apoptosis during development; expression distribution poorly defined; X71978 |
| 22 | 21 | <0.001 | P53 specific ubiquitin ligase 2 (Mdm2); promotes ubiquitination and proteaesome degradation of p53; inactivation by stress causes cell cycle arrest and apoptosis; liver, elsewhere; X58876 |
| >100 | >100 | <0.001 | RNA-dependent EIF-2 alpha kinase; double-stranded RNA-dependent protein kinase; key mediator of antiviral effects of interferon; ubiquitous; ET61211 |
| >100 | >100 | 0.009 | Tumor necrosis factor (Tnf); Proapoptotic factor in liver; X02611 |

*Fold of control

Example 19

CR Activation of Genes of the Enteric Nervous System

The liver is a highly innervated organ. This innervation includes elements of the enteric nervous system, as well as sympathetic innervation in the small arteries of the hepatic mesentery. This nervous innervation is essential to the activity of the liver. Nervous innervation has a role in the release of glucose by hepatocytes in response to insulin. As shown in Table 6, long and short term CR activated the expression of a large number of genes associated with the membrane receptor signaling, including membrane receptors for protein and small molecule neurotransmitters, and for cell growth and maintenance factors. CR induced the expression of genes for both phosphatases and kinases involved in signaling by these receptors. CR also induced the expression of four neuronal tissue specific transcription factors (Table 6).

CR enhanced the ability of liver neurons to transduce and respond to nervous system signaling. Eight genes for membrane channels were induced, including genes for sodium, potassium, and water channels (Table 6). Also induced were a number of integral membrane proteins such as proteolipid protein and cadherin 8, as well as the products of 5 genes for molecular motors which are probably involved in neural plasticity and remodeling. These proteins included 4 members of the dynein, axon, heavy chain family. Our results are consistent with the idea that CR increases the remodeling and activity of hepatic nerves after only 4 weeks.

TABLE 6

Neuronal Cell Specific Genes

| LTCR* | STCR* | P | GENE |
|---|---|---|---|
| | | | Signal Transduction |
| 19 | 18 | 0.001 | 5-hydroxytryptamine (serotonin) receptor 1E beta (Htr1eb); G-protein-coupled receptor; CNS; Z14224 |
| >100 | >100 | <0.001 | Activin A receptor, type 1B (Acvr1b); limb development; embryo brain, dorsal root ganglia, spinal cord, vibrissae, elsewhere; Z31663 |
| 5 | 5 | 0.005 | Ankyrin 3 (Ank3); implicated in Na(+) channel clustering and activity; neuronal axons, wide distribution; ET62740 |
| 3 | 3 | 0.022 | Bone morphogenetic protein receptor, type 1B (Bmpr1b); activin receptor-like kinase-6; serine-threonine kinase; CNS, muscle, blood vessels, others; Z23143 |
| 5 | 6 | 0.004 | Discs, large homologue 1 (Drosophila) (Dlgh1); role in localization and function of glutamate receptors and K(+) channels; neurons, epithelial cells; ET61665 |
| 67 | 70 | 0.001 | Eph receptor A7 (Epa7); developmental kinase 1; member of receptor tyrosine kinase family; brain, testes and spleen; X79082 |
| >100 | >100 | 0.001 | Fibroblast growth factor 9 (Fgf9); autocrine/paracrine growth factor; embryonic neural cell differentiation; adult and developing neuronal cells, epithelial cells, others; U33535 |
| 14 | 15 | <0.001 | Fibroblast growth factor homologous factor 1 (Fgf1); nervous system development and function; highest in brain and skeletal muscle; U66201 |
| 17 | 19 | 0.003 | G-protein-coupled receptor, family C, group 1, member H (Gprc1h); glutamate receptor, metabotropic 8; CNS, glial cells, retina, olfactory bulb, stellate/basket cells; U17252 |
| 28 | 29 | <0.001 | Gamma-aminobutyric acid (GABA-A) receptor, subunit beta 3 (Gabrb3); links binding of GABA to inhibitory chloride flux; CNS; U14420 |
| 12 | 11 | <0.001 | Glutamate receptor, ionotropic, kainate 1 (Grik1); CNS; X66118 |
| >100 | >100 | 0.007 | Gonadotropin releasing hormone receptor (Gnrhr); G-protein-coupled receptor; activates MAPK cascades; brain, anterior pituitary, reproductive organs; L28756 |
| 4 | 3 | 0.018 | H6 homeo box 2 (Hmx2); specification of neuronal cells; developing CNS; S80989 |
| >100 | >100 | 0.001 | Histamine receptor H1 (Hrh1); coupled to phosphoinositide turnover-calcium mobilization signaling; regulates IGF-I expression, cell proliferation, neural function; neurons, liver, elsewhere; D50095 |
| 64 | 73 | <0.001 | Neuropeptide Y receptor Y6 (Npy6r); regulates energy balance through its orexigenic, antithermogenic, and insulin secretagogue actions; neurons, vascular smooth muscle cells; U58367 |
| >100 | >100 | <0.001 | Paired-Ig-like receptor A1 (Pira1); activating receptor on B lymphocytes, dendritic and myeloid-linage cells; ET62839 |
| 4 | 4 | 0.003 | Preproglucagon (Gcg); glucagon-like peptides I and II; neuropeptide; CNS, pancreatic alpha cells, ileum, Z46845 |
| >100 | >100 | 0.013 | Protein kinase, cGMP-dependent, type II (Prkg2); signal transduction; brain, kidney, small intestine, colon; L12460 |
| >100 | >100 | 0.001 | Protein tyrosine phosphatase, receptor type, M (Ptprm);. expressed in capillaries in developing neural tissue, lung; X58287 |
| >100 | >100 | <0.001 | Relaxin precursor (Rln); insulin gene family; remodeling of collagen; brain, uterus, prostate, pancreas and kidney; Z27088 |
| >100 | >100 | <0.001 | Ryanodine receptor 3 (Ryr3); intracellular Ca2+ channels; neurons, skeletal and smooth muscle; ET61090 |

TABLE 6-continued

Neuronal Cell Specific Genes

| LTCR* | STCR* | P | GENE |
|---|---|---|---|
| | | | Neuronal Tissue Specific Transcription Factors |
| >100 | >100 | <0.001 | Atonal homologue 5 (Drosophila) (Atoh 5); neurogenin 3; transcription factor; neuroD-related bHLH protein; CNS; U76208 |
| 19 | 18 | 0.003 | Embigin (Emb); DNA-binding transcription factor; class VI POU domain; CNS; D13801 |
| >100 | >100 | 0.026 | Paired box gene 6 (Pax6); transcription factor; development of CNS, eye; X63963 |
| >100 | >100 | <0.001 | Zinc finger protein 2 (Zfp2); Mkr-2; differentiation and/or maintenance of neurons; central and peripheral neurons; Y00850 |
| | | | Channels |
| 4 | 3 | 0.007 | Aquaporin 4 (Aqp4); allows water and small solutes through plasma membrane; brain and other tissues; U48397 |
| 5 | 6 | 0.004 | Discs, large homologue 1 (Drosophila) (Dlgh1); localization and function of glutamate receptors and K(+) channels; neural synapses; ET61665 |
| 22 | 25 | 0.001 | Gap junction membrane channel protein beta 6 (Gjb6); connexin 30; forms transmembranous gap junction channels between adjacent cells; brain, skin; ET63385 |
| 11 | 11 | 0.001 | K+ channel beta-subunit, ion channel; brain and kidney; X97281 |
| 14 | 16 | 0.001 | Potassium inwardly-rectifying channel, subfamily J, member 6 (Kcnj6); neurons; ET61642 |
| 8 | 8 | 0.005 | Potassium, voltage gated channel, shaker related subfamily, member 2 (Kcna2); T cells, myelinating Schwann cells; M30440 |
| 27 | 28 | <0.001 | Sodium channel 27; brain; L22340 |
| 11 | 11 | <0.001 | Sodium channel, type X, alpha polypeptide (Scn10a); brain, unmyelinated axons; Y09108 |
| | | | Molecular Motors |
| 2 | 2 | 0.004 | Dilute lethal-20J; Class-V myosin; vesicular membrane trafficking; transport of endoplasmic reticulum vesicles in neurons; M33467 |
| 7 | 8 | 0.001 | Dynein, axon, heavy chain 1 (Dnahc1); dyneins are molecular motors that drive the beating of cilia and flagella; brain, trachea, testis; ET63395 |
| >100 | >100 | <0.001 | Dynein, axon, heavy chain 3 (Dnahc3); brain, trachea, testis; ET63399 |
| 5 | 6 | 0.013 | Dynein, axon, heavy chain 6 (Dnahc6); brain, trachea, testis; ET63402 |
| 4 | 5 | 0.002 | Dynein, axon, heavy chain 9 (Dnahc9); brain, trachea, testis; ET63405 |
| | | | Cell Surface and Secreted Proteins |
| >100 | >100 | 0.001 | Cadherin 8 (Cdh8); adhesion molecule; subdivisions of the early CNS and thymus; ET63017 |
| 37 | 36 | <0.001 | Glutamic acid decarboxylase, 67 kD; responsible for gamma-aminobutyric acid synthesis; brain, islets; Y12257 |
| 2 | 2 | 0.011 | Glypican 4 (Gpc4); cell surface heparin sulfate proteoglycan; role in regulation of neural cell transition from proliferation to differentiation; neurons; X83577 |
| 19 | 20 | <0.001 | Neurexophilin 2 (Nxph2); neuronal glycoprotein; binds to alpha-neurexins; brain; U56650 |
| 13 | 13 | <0.001 | Neurotrophin 3 (Ntf3); secreted protein; maintenance and plasticity of neurons; enteric neurons, others; X53257 |
| 43 | 41 | 0.001 | Proteolipid protein (Plp), main integral protein of myelin; CNS; X07215 |
| 4 | 4 | 0.043 | Sema domain, immunbglobulin domain (Ig), short basic domain, secreted, (semaphorin) 3E (Sema3e); glycoprotein involved in embryonic development; developing neural tubes, lungs, skeletal elements; ET63410 |
| >100 | >100 | <0.001 | Sema domain, seven thrombospondin repeats (type 1 and type 1-like) (Sema5a); axonal guidance; early embryogenesis; X97817 |
| | | | Other Genes |
| 6 | 7 | 0.015 | Disabled homolog 1 (Drosophila) (Dab1); adaptor molecule in neural development; neuronal and hematopoietic cells; ET63156 |
| 23 | 24 | <0.001 | Galanin (Gal); neuropeptide; enhances hepatic glucose production; hepatic nerves and elsewhere; L38580 |
| 3 | 4 | 0.006 | Netrin 1 (Ntn1); axon outgrowth-promoting protein; guidance molecule; guides growing axons in development; CNS; U65418 |
| 127 | 129 | <0.001 | Nucleosome assembly protein 1-like 2 (Napl12); Bpx; brain; X92352 |

TABLE 6-continued

Neuronal Cell Specific Genes

| LTCR* | STCR* | P | GENE |
|---|---|---|---|
| >100 | >100 | <0.001 | Proteaseome 3 (Psme3); Ki antigen; cell proliferation; enhances generation of class I binding peptides; liver, neurons, elsewhere; U60330 |
| 58 | 58 | <0.001 | UDP-glucuronosyltransferase 8 (Ugt8); cerebroside and sulfatide biosynthesis; CNS and peripheral nervous system; X92122 |

*Fold of control

Example 20

Induction of Other Liver Specific Genes by CR

Of the approximately 200 genes reported to be expressed either liver specifically or ubiquitously, 13 code for cytokines or growth factors; 12 for cell surface receptors; 21 for signal transduction, cell cycle or cell growth related proteins; 4 for nuclear receptors, 20 for transcription factors; 6 for translation, splicing, or RNA processing related factors; and 9 for chromatin structure related genes (Table 4). The overall pattern of genes induced in this group of genes suggests that CR stimulates the growth, remodeling and responsiveness of liver cells to signaling systems. These results are consistent with those found for neuronal genes, discussed above.

Both long and short term CR induced the expression of the cell growth factors Tgfb2, Fgf1, Fgf2, Fgf3, Fgf7, Fgf9, Figf, Inhbb, Inhbe, and 3 interferon-related genes. Likewise, a large number of genes coding for cell cycle regulation were induced by CR. These genes included Ptpn16, Nek1, Plcg1, Map3k1, Mapk1, Madh5, Wnt10b, Abl, and others. Without being limited to any specific mechanism, the hypothesis that CR induces cell remodeling and growth of liver cells is further supported by the observation that both long and short term CR very strongly induced the expression of 7 histone genes. In 6 cases, these mRNA levels were induced from undetectable, or nearly undetectable levels. Two other genes which appear to be associated with chromatin structural modification were also strongly induced by CR (Htf9c and homologous to Drosophila Hp1; Table 4). Further evidence that CR enhances cell division and remodeling is the up regulation of the mRNA for the transferrin receptor, which mediates cellular iron uptake, a process essential for cell growth and division.

Three receptor mRNAs associated with energy balance were induced by CR. Two of these were for neuropeptide Y receptor Y6 (Table 6) and pancreatic polypeptide receptor 1, and one was for the leptin receptor (Table 4).

Example 21

Global Hepatic Gene Expression Profile

We have tested the hypotheses that CR produces similar effects on gene expression early and late in life by examining the effects of aging and caloric intake on the expression of approximately 12,000 genes and ESTs in the liver of old (27-month-old) and young (7-month-old), control and CR mice, using GeneChip microarrays. We found that CR produced a massive reprogramming of gene expression early and late in life. The patterns of expression induced by CR in young and old mice were highly homologous. Comparison of gene expression in the groups of mice indicated that CR only prevented age-related changes in the expression of a few genes. Examination of the genes involved does not support the idea that they have a principle role in the age-retarding effects of CR. Together, the results do not support the idea that CR acts principally to prevent deleterious age-related changes in gene expression. Instead, CR induces a highly-homologous, major reprogramming of gene expression in animals of all ages.

The average global hepatic gene expression profile for each group of mice, displayed using GeneSpring 3.0 (Silicon Genetics, San Carlos, Calif.), is shown in FIG. 8. The GeneSpring experiment tree algorithm clustered gene expression in the young and old CR mice together, and separately clustered expression in the young and old control mice together. These results indicate that that the effects of the CR diet on gene expression was significantly greater than the effect of age. Further, these data indicate that CR produced homologous effects on gene expression in the young and old mice.

TABLE 7

Pairwise comparisons of the global gene expression correlation coefficients for each possible pair of mice.

| | Old-CR | Old-Control | Young-CR | Young-Control |
|---|---|---|---|---|
| Old-CR | 0.53 ± 0.02* | −0.09 ± 0.02 | 0.41 ± 0.04 | −0.10 ± 0.03 |
| Old-Control | | 0.28 ± 0.06 | −0.11 ± 0.03 | 0.23 ± 0.02 |
| Young-CR | | | 0.41 ± 0.01 | −0.08 ± 0.02 |
| Young-Control | | | | 0.22 ± 0.02 |

*All values average values, ± SD are calculated as the Log (1+ the mRNA level)

These conclusions are supported by comparison of the correlation coefficients calculated from the expression data for each possible pair of mice in the study (Table 7). Because the mice were genetically identical, intra-group values provide a measure of the maximum correlations attainable. Inter-group values measure the similarity between groups. Inter-group comparisons between young and old CR and control mice indicated that gene expression in all CR mice was highly homologous, regardless of the age of the animals. Likewise, regardless of age, the intra-group expression patterns of the control mice were highly homologous. In contrast, there was no intra-group correlation between mice in different dietary groups, regardless of age. These data indicate that the number of calories consumed, but not age was the major influence in determining the global patterns of gene expression in these mice. This novel result is fuirther supported by the analysis described below.

The patterns of gene expression in the mice were further evaluated by successive application of the Venn Diagram Function of GeneSpring 3.0, one-way ANOVA, and Fisher's test ($P<0.05$) to the levels of expression of each gene and expressed sequence tag (EST) in the 4 groups of mice. These operations sorted the genes and ESTs into one of 9 possible categories (Tables 8A and B). Only statistically significant differences of 2-fold or more are shown. The expression of most genes and ESTs were not affected by either CR (~80% unchanged) or aging (95% unchanged). Of the genes and ESTs which did changed expression among the groups, 5-times as many genes and ESTs changed expression level in response to CR (2456) as changed in response to age (561). Of the genes and ESTs responsive to CR, most (40%) were upregulated in both young and old mice. Two other groups of genes and ESTs were upregulated either in old mice only (28% of the genes that changed expression), or in young mice only (19% of the genes that changed expression). An even smaller number of genes and ESTs were down regulated by the CR diet in young or old mice (13% of the genes that changed expression).

TABLE 8

The effects of age and diet on gene expression a. Diet Effect

| Young (CR/Control)* | Old (CR/Control)* | | | |
|---|---|---|---|---|
| | Up** | Unchanged | Down** | Total |
| Up** | 975 (8.1%***) | 473 (3.9%) | 0 | 1448 |
| Unchanged | 685 (5.7%) | 9587 (79.6%) | 172 (1.4%) | |
| Down** | 0 | 105 (0.9%) | 46 (0.4%) | 151 |
| Total | 1660 | | 218 | | b. Age Effect

| Control (Old/Young)* | CR (Old/Young)* | | | |
|---|---|---|---|---|
| | Up** | Unchanged | Down** | Total |
| Up** | 6 (0.05%***) | 136 (1.1%) | 2 (0%) | 144 |
| Unchanged | 186 (1.5%) | 11482 (95%) | 112 (0.9%) | |
| Down** | 1 (0%) | 113 (0.9%) | 5 (0.4%) | 119 |
| Total | 193 | | 119 | |

*Fold change of average mRNA levels of Old/Young mice
**Fold change of 2-fold or greater
***Percent of total genes and ESTs measured in study Example 22

208 Genes Greater in CR in Both Young and Old

Three novel conclusions can be drawn from these data. First, CR induced a substantial age-independent reprogramming of gene expression. A large number of genes and ESTs (975) were up regulated by CR in both young and old mice (Table 8A). In this group, 208 were known genes (See Appendix G) All of these known genes were among the group of 340 genes induced in 30 month old mice by both long-term CR (LT-CR; life-long) and short-term CR (ST-CR; only 4 weeks of CR). This highly reproducible, age-independent, responsiveness to CR suggests to us that these genes and ESTs are likely to mediate the life- and health-span extending effects of CR. At a minimum, the dietary responsiveness of these genes can be used as a gauge of the effectiveness of other treatments in reproducing the effects of CR on global patterns of gene expression. Further, because 90% of the genes and ESTs induced by lifelong CR (which includes the age-independent and age-dependent genes and ESTs) can be induced after only 4 weeks of CR, the vast majority of the genetic reprogramming induced by CR can be reproduced rapidly.

Example 23

142 Genes Up in Young CR But Not in Old CR

There is a second novel conclusion which can be drawn from the results in Table 8A. CR produced some "age-dependent" reprogramming of gene expression in both young and old mice. Of the 473 genes and ESTs induced by CR only in young mice, 142 are known genes (Appendix H) These results indicate that this subset of genes was also CR responsive in old mice, but not to sufficient levels that they were distinguished statistically from control expression levels in these studies. Thus, Table 8A overestimates the number of young-specific induced genes by approximately 25%. Of the young-specific genes, 8% are involved in transcriptional regulation; 5% are growth factors, cytokines or hormones; 18% are involved in signal transduction or cell cycle regulation; 14% are involved in embryogenesis and development; 14% are involved in cellular adhesion, or are components of the extracellular matrix or membrane; 7% are channels or ion pumps; 3% are involved in extracellular transport or secretion; 3% are involved in metabolism; 3% in DNA replication, repair or apoptosis; 3% in chromatin structure; 9% in immune function or in the primary response; and 15% are involved in other functions.

Example 24

200 Known Genes Greater in Old CR But Not in Young CR

Of the 685 genes and ESTs induced by CR in old mice, the identity of 200 are known (Table 8A); (Appendix I). Of these, 122 (61%) previously were shown to be induced by ST-CR in old mice. Thus, the majority are rapidly responsive to CR. Of the remaining 78 genes, approximately 12% are transcriptional regulators; 8% are growth factor, cytokines or hormones; 13% are involved in signal transduction or cell cycle regulation; 11% are involved in embryogenesis and development; 10% are involved in cellular adhesion, or are components of the extracellular matrix or membrane; 4% are channels or ion pumps; 4% are involved in extracellular transport or secretion; 3% are involved in metabolism; 3% in DNA replication, repair or apoptosis; 2% in chromatin structure; 3% in immune function or in the primary response; 2% in translation, splicing or RNA processing; 2% are cell surface receptors; and 23% are involved in other functions.

The proportion of genes involved in each functional category above are remarkably similar. Further, many of the genes induced by CR in young mice were members of similar gene families or were structurally or functionally related to genes induced only in old mice. These similarities suggest that CR has highly homologous age-specific effects. It is less likely that the relative proportion of genes falling into each category, and the identity of these genes is an artifact of the probes present on the chip. Firstly, all of the results are statistically significant. Second, the genomic profiles produced in several drug studies were strikingly different from those found here as to the identity of the genes affected, and their functional categories (data not shown). Together, these results indicate that CR has a robust, pervasive, and highly homologous effect in both young and old mice. It induced the expression of a substantial group of genes involved in a wide variety of cellular functions.

A commonly expressed view in the literature of CR and aging assumes tacitly or explicitly that CR acts by preventing deleterious, age-related changes in gene expression. This view is shown schematically in FIG. 9. This hypothesis assumes that prevention of age related changes in gene expression underlies the health- and life-span extending effects of CR. During aging, some genes become over expressed or under-expressed relative to their levels in young animals (lower and upper lines, FIG. 9). Some of these deviations are assumed to be deleterious. Preferably, no changes would change with time, and aging would either not occur or occur more slowly (center line, FIG. 9). In this view, CR should wholly or partially return over- or under-expressed genes to their youthful levels (arrows, FIG. 9). Although the reasoning is circular, some have said that if CR changes the expression of a gene toward the center line in the figure, it restored youthful levels of expression. We have analyzed the results of the studies reported here to evaluate this hypothesis further.

Figure 9:
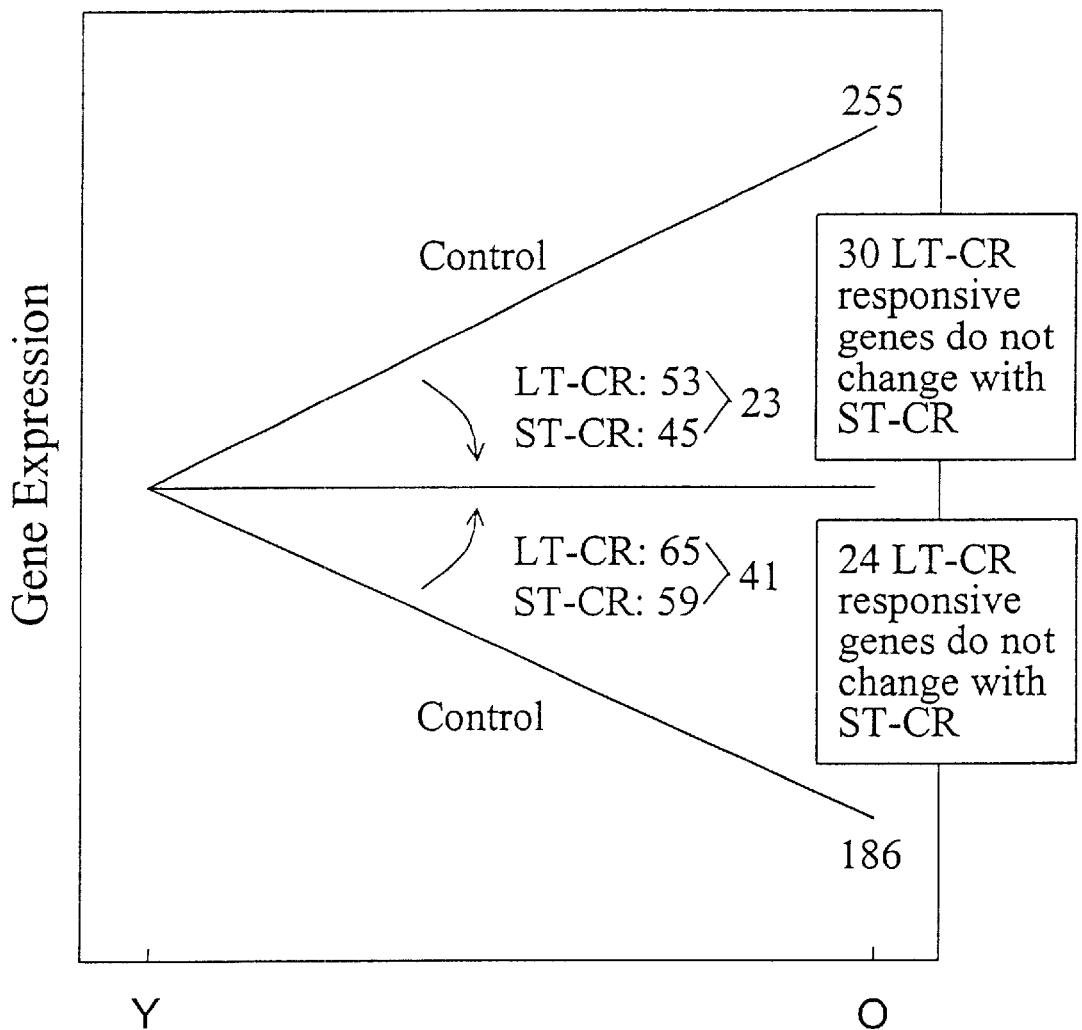
FIG. 9. Schematic representation of the hypothesis that CR acts by preventing age-related changes in gene expression. During aging, some genes become over expressed or under-expressed relative to their levels in young aninals (lower and upper lines). Unchanged expression with age is represented by the horizontal line. These deviations are assumed to be deleterious. The important genes effected by CR, in this hypothesis, are the over- or under-expressed genes returned to youthful levels of expression (arrows). The numbers of genes and ESTs in each category are shown at the ends of the lower and upper lines. The number of known genes in each category returned to baseline expression by LT- and ST-CR are given after the colons. Long-term and short-term CR both acted to reverse or prevent 23 of the increases and 41 of the decreases. Thus, long-term LT-CR actually prevented the increased expression of only 30 genes and ESTs and the decreased expression of only 24 genes and ESTs.

Of the approximately 12,000 genes and ESTs examined, aging of control mice increased the expression of 257 genes and ESTs, and decreased expression of 191 genes and ESTs (FIG. 9). Long-term CR wholly or partially, reversed or prevented 55 of the increases and 70 of the decreases. Short-term CR reversed 45 of the increases and 59 of the decreases in gene expression. Long-term and short-term CR both acted to reverse or prevent 23 of the increases and 41 of the decreases. Thus, long-term CR actually prevented the increased expression of only 32 genes and ESTs and the decreased expression of only 29 genes and ESTs. It is likely that the number of ESTs in each class overestimates the number of authentic genes in each category. First, the genes and ESTs which responded to CR in only 4 weeks are likely a subset of the genes and ESTs which respond acutely to CR. We have not yet examined longer times on the domain of genes responsive to acute CR. Some genes may be "slow changers" in response to acute CR. Second, we have found that many of the known genes present on these chips are redundant (e.g., multiple immunoglobulin genes of each class and T cell receptor genes, cloned chromosome breakpoints representing parts of two genes, uncharacterized chromosome regions, uninvestigated, unpublished cDNA sequences, etc.). For example, of the 23 genes and ESTs reduced to baseline expression levels only by LT-CR, 12 were known genes (Table 9). Of the 27 genes and ESTs which were decreased in expression by age and returned to baseline expression only by LT-CR, only 13 were from known genes (Table 10).

Of the 12 genes prevented from increasing with age by CR, few are involved in signal transduction. Rather, 6 are involved in immune system function, particularly in macrophage differentiation, proliferation, apoptosis, and activity. Of these, platelet-activating factor acetylhydrolase activity reduces plasma platelet activating factor mRNA levels. Platelet activating factor is a potent pro-inflammatory autacoid with diverse physiological and pathological actions. It does not seem likely that the return of these genes to baseline expression levels is due to a general reduction in inflammation, stress, or immune activity. In a previous study, we found that 61 immune system genes, including 6 primary response genes, and an additional 9 apoptotic genes were up regulated by both LT- and ST-CR in the liver of mice. Similar considerations apply to the other 6 genes in this group, and to the genes prevented from decreasing with age (Table 10). One can speculate about why reduction in the expression of the relatively few immune system specific, acute phase response genes and other genes listed in Table 9, or enhanced expression of the 13 immune system, and neuron or liver specific genes in Table 10 might be important in reducing the rate of aging. However, with few exceptions, very similar genes, and in some cases closely related family members of the genes in these lists are present in the group of 340 known genes induced by both LT- and ST-CR. Thus, it seems intuitively and statistically much more likely that the massive reprogramming of gene expression induced by CR (Tables 9 and 10) is responsible for the increase in life- and health-span induced by CR. The genes prevented from increasing and decreasing with age (Tables 9 and 10) seem much more likely to be the result, rather than the cause of these effects.

In summary, the studies presented here show that a major effect of CR is to massively (more than 10% of the genes and ESTs investigated) reprogram gene expression to a new pattern associated with slower aging and delayed onset of age-related diseases. This reprogramming includes age-independent induction of a relatively large group of genes and ESTs, as well as induction of smaller groups of genes age-dependently. Further, we found that age-related changes in gene expression are relatively rare. Even rarer are instances in which life-long CR prevents these changes. The rarity of such genes, and their identity suggest to us that they do not play a major role in the physiological effects of CR. The large and rapid response induced by CR on total liver gene expression suggests that major, systemic regulators of gene expression are altered by CR. Study of the regulation of a number of these genes should yield the identity of the regulators, and reveal how they are influenced by CR.

TABLE 9 mRNAs increased by age and returned to control levels by LT-CR

| GenBank | Phenotype |
|---|---|
| | Immune System |
| AF018268 | Apoptosis inhibitory 6 (Api6); a member of macrophage scavenger receptor cysteine-rich domain superfamily; inhibits apoptosis of a variety of cell types; secreted specifically by macrophages |
| M13018 | Cysteine rich intestinal protein (Crip); double zinc finger protein; expression changes with acute liver injury (cellular damage); may function in cell proliferation, differentiation or turnover; high expression in innnune cells, low in liver |
| J04596 | GRO1 oncogene (Gro1); encodes a cytokine; mediator of inflammatory and immune responses; also called melanoma growth-stimulatory activity; cell cycle regulator; platelets |
| L20315 | Macrophage expressed gene 1 (Mpeg1 or Mpg-1); increased when murine fetal liver hematopoietic progenitor cells induced to differentiate into macrophages; high levels in macrophages, moderate levels in certain myelomonocytic cell lines |

TABLE 9-continued mRNAs increased by age and returned to control levels by LT-CR

| GenBank | Phenotype |
|---|---|
| U34277 | Phospholipase A2 group VII, platelet-activating factor acetylhydrolase, plasma (Pla2g7); secreted phospholipase A2 which modifies the pro-inflammatory platelet-activating factor (PAF) to yield the biologically inactive lyso-PAF; regulates baseline circulating PAF levels and may be critical in resolving inflammation; high PAF is a predictor of heart disease; liver macrophages |
| L27990 | Sjogren syndrome antigen A1 (Ssa1); Ro52; stress response gene; ribonucleoprotein; macrophages |
| | Ubiquitous |
| D86729 | Heterogeneous nuclear ribonucleoprotein A1 (Hnrpa1); ribonucleoprotein, RNA processing; early down-regulation of this gene contributes to the cytotoxicity of the topoisomerase inhibitors that induce DNA cleavage; ubiquitous |
| U50850 | Retinoblastoma-like 2 (Rbl2); p130; transcriptional cell cycle repression through G1 phase (controls cyclin A, cdc 25G and cdc2 genes); tumor suppressor gene; expressed independently of retinoblastoma gene; expressed in embryo and ubiquitously in adult |
| U34042 | Tolloid-like (Tll), an alternatively spliced product of the bone morphogenic protein-1 gene; metalloprotease purified from extracts capable of inducing ectopic bone formation; ubiquitous |
| | Liver Specific |
| U60438 | Serum amyloid A protein isoform 2 (Saa2); encodes an acute-phase reactant serum protein; liver |
| | Not Reported in Liver |
| M27501 | Protamine 2 (Prm2); compacting chromatin; expressed in postmitotic male germ cells during late stages of spermatogenesis |
| U52433 | Tubby (Tub); mutation in the tub gene causes maturity-onset obesity; adipocyte fat storage increased by 5–6 fold, insulin resistance; mutant mice have retinal and cochlear degeneration; gene function unknown; brain, hypothalamus, cochlea, retina |

TABLE 10 mRNAs decreased by age and returned to control levels by LT-CR

| GenBank | Phenotype |
|---|---|
| | Immune System |
| M30903 | B lymphocyte kinase (Blk); src-family protein tyrosine kinase; plays important role in B-cell development/activation and immune responses; B-lineage cells |
| U43384 | Cytochrome b-245, beta polypeptide (Cybb, cytochrome b558); integral component of the microbicidal oxidase electron transport chain of phagocytic cells, respiratory burst oxidase; phagocytes |
| U10871 | Mitogen activated protein kinase 14 (Mapk14); signal transduction, stimulate phosphorylation of transcription factors; major upstream activator of MAPKAP kinas 2; hematopoietic stem cells |
| Z22649 | Myeloproliferative leukemia virus oncogene (Mp1); Member of hematopoietic cytokine receptor family, cell cycle regulator, induces proliferation and differentiation of hematopoietic cell lines; hematopoietic precursor cells, platelets and megakaryocytes |
| Y07521 | Potassium voltage gated channel, Shaw-related subfamily member 1 (Kcnc1) potassium channels with properties of delayed rectifiers; nervous system, skeletal system, T lymphocytes |
| U87456 | Flavin-containing monooxygenase 1 (Fmo1); xenobiotic metabolism; highly expressed in liver, lung, kidney, lower expressed in heart, spleen, testis, brain |
| U40189 | Pancreatic polypeptide receptor 1 (Ppyr1), neuropeptide Y receptor, peptide Y receptor; G-protein-coupled receptor; liver, gastrointestinal tract, prostate, neurons endocrine cells |
| | Neuron Specific |
| U16297 | Cytochrome b-561 (Cyb561); electron transfer protein unique to neuroendocrine secretory vesicles; vectoral transmembrane electron transport; brain |
| D50032 | Trans-golgi network protein 2 (Ttgn2); integral membrane protein localized to the trans-Golgi network; involved in the budding of exocytic transport vesicles; brain neurons |
| | Liver Specific/Ubiquitous |
| D82019 | Basigin (Bsg), CD147, neurothelin; membrane glycoprotein, immunoglobulin superfamily, homology to MHCs, acts as an adhesion molecule or a receptor, neural network formation and tumor progression; embryo, liver and other organs |

TABLE 10-continued mRNAs decreased by age and returned to control levels by LT-CR

| GenBank | Phenotype |
|---|---|
| L38990 | Glucokinase (Gk), key glycolytic enzyme; liver |
| U50631 | Heat-responsive protein 12 (Hrsp12); heat-responsive, phosphorylated protein sequence simularity to Hsp70; liver, kidney |
| U39818 | Tuberous sclerosis 2 (Tsc2); mutationally inactivated in some families with tuberous sclerosis; encodes a large, membrane-associated GTPase activating protein (GAP tuberlin); may have a key role in the regulation of cellular growth; ubiquitous |

Gene Expression in STZ-diabetic Mice

Streptozotocin (STZ) induces diabetes. Mice receiving three treatments with STZ were diabetic for about 4 weeks. Diabetes reduces insulin levels to almost zero. CR has a similar effect in that it lowers insulin levels, although not as low as in STZ-treated animals. Also, while CR lengthens life span, STZ has the opposite effect and shortens life span.

Figure 11:
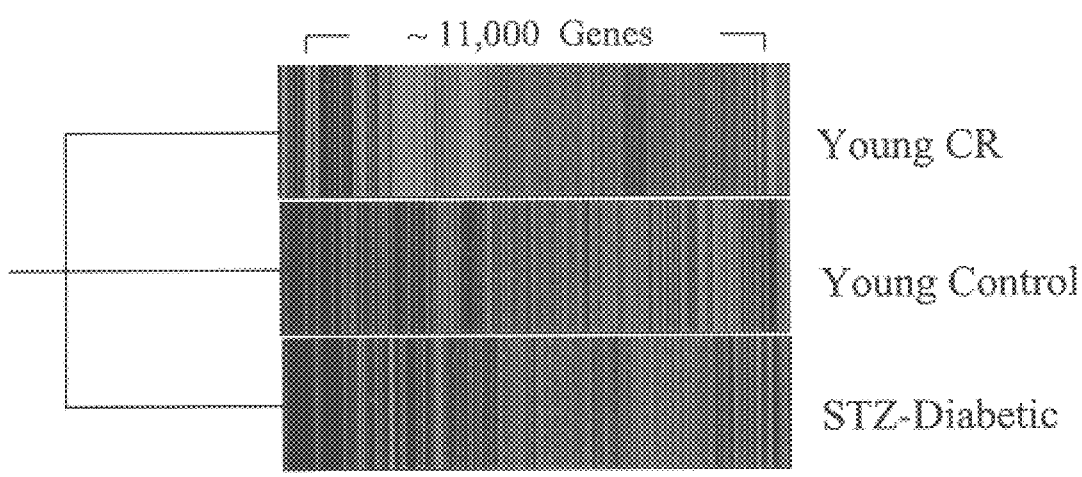

FIG. 10 shows pairwise comparison of global gene expression correlation coefficients for each possible mouse pair. The results indicate that hepatic gene expression is very different between young CR, young control and STZ-diabetic mice. FIG. 11 presents a visual profile which shows that the pattern of gene expression in the three groups is dissimilar. In conclusion, lowering insulin in the pathological way found in serious diabetes is insufficient to produce the gene expression profile or the life-span effects observed with CR.

Example 26

Gene Expression in Aminoguanidine Treated Mice

Figure 13:
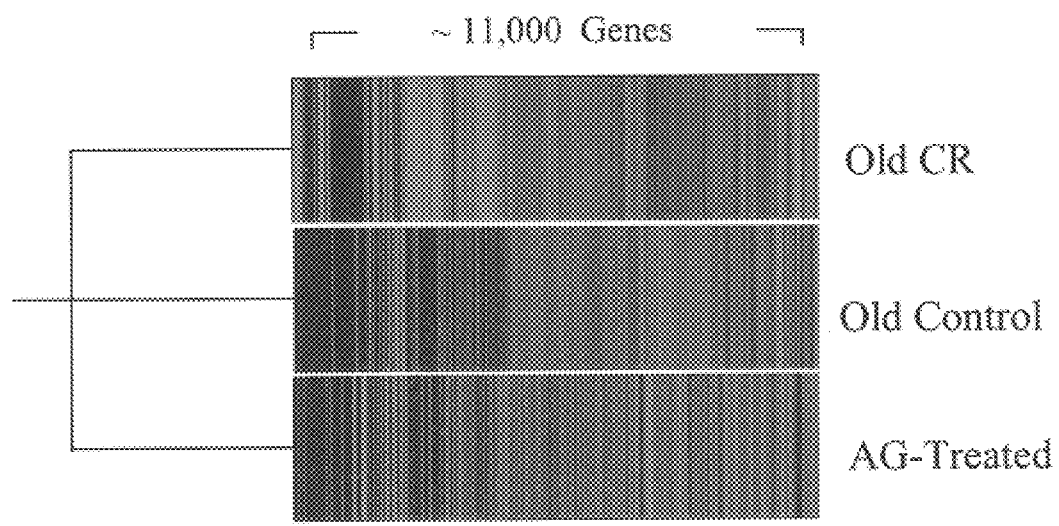
FIG. 13. The hepatic gene expression profiles of old CR, old control and aminoguanidine (AG)-treated mice. Levels of specific mRNA were determined using the Mu11KsubA and Mu11KsubB GeneChip arrays (Affymetrix, Santa Clara, Calif.) containing targets for approximately 12,000 known mouse genes and ESTs. The experiment tree function of GeneSpring 3.0 (Silicon Genetics, San Carlos, Calif.) was utilized to display the results. The horizontal axis represents the position of each gene assigned by the "gene tree" average-linkage hierarchical clustering algorithm of the program. Below the position assigned to each gene is a color-coded indication of its relative expression level, based on a continuous scale. Bright blue indicates no detectable expression, purple average expression, and bright red high expression. The average expression of each gene in each group is shown. The GeneSpring "experiment tree" clustering algorithm calculated an average-linkage hierarchical clustering dendrogram of the data for each group of mice, which is shown to the left of the expression profiles.

Aminoguanidine is believed to retard aging by preventing cross-linking of protein initiated by the aldehyde form of glucose. However, mice fed aminoguanidine exhibited little or no effect on life span. However, a large effect on gene expression was observed (FIG. 12). Gene expression for aminoguanidine-treated mice did not correlate with either old CR or old control. A visual representation of this finding is shown in FIG. 13. In conclusion, although aminoguanidine has little effect on aging in mice, major differences in gene expression are observed. These effects are not like those of CR, and this is consistent with the absence of a strong effect on the life-span of mice.

Example 27

To determine whether certain interventions mimic calorie restriction in mice, the following groups of mice are prepared.

Group 1: Controls

Group 2: Troglitazone (synthetic proposed calorie restriction mimetic drug that lowers insulin levels in rats and mice, lowers blood pressure and triglycerides, inhibits free radicals, increases mitochondrial mass, and doesn't seem to change food intake in rodents): treatment starts at 10 months Group 3: IGF-1 (natural proposed calorie restriction mimetic hormone that lowers both insulin and glucose levels and which may be directly involved in the basic mechanisms of aging; has rejuvenating effects on immune, muscular, and other systems): treatment starts at 12 months Group 4: ALT-711 (or other AGE breaking agent: proposed calorie restriction mimetic that acts by reversing the effects of elevated glucose levels as they occur or after they occur, rather than by reducing glucose levels): treatment starts at 18 months.

Animals in all groups will receive the same, known amount of food throughout the study.

Troglitazone and IGF-1 doses will be chosen to set glucose and insulin levels in the range for young or preferably calorie-restricted animals. Glucose and insulin will be measured but not controlled in the control and ALT-711 groups. Troglitazone will be supplied at a dose of ~0.2% of the diet (standard for troglitazone studies for other purposes). Similarly, ALT-711 will be incorporated into the diet. A low (non-toxic) level of ALT-711 is used that will remain constant over time.

It is assumed that IGF-1 will be supplied by injection (3 times per week, minimum) unless a continuous delivery method can be arranged. The preferred dosage method is implantation of non-dividing IGF-1-secreting cells, to attain steady IGF-1 levels, and if possible, this will be done. If this is not possible, IGF-1 will be obtained as a gift from Genentech or another manufacturer. Other possible alternatives to injection are: osmotic minipump; injection of IGF-1 into subcutaneous slow-release reservoirs; inflsion by means of minipumps used by Celtrix; use of skin patches that allow slow-release to the body.

There will be 60 animals in each longevity-testing group (LTG). Each LTG will be accompanied by another set of, on average, 40 similarly-treated animals, which will be set aside for sacrifice to permit biochemical assays and histological documentation of the condition of the animals at fixed ages (sacrifice group, SG). In the case of the IGF-1 and troglitazone groups, some animals will be earmarked for pilot dose-finding experiments in a manner that will allow the average SG size to remain at 40, as described below. The groups earmarked for dose-verification will be referred to as the pilot dose groups, or PDGs.

For troglitazone, about a 2-month supply of each of three troglitazone diets (containing 0.1%, 0.2%, or 0.3% troglitazone) will be initially ordered. The main 0.2% troglitazone dose will be tested on a small pilot mouse population before committing the troglitazone group proper to this dose. If 0.2% troglitazone is not found to yield the expected changes in circulating insulin after 2 weeks on the 0.2% troglitazone, the diet will be changed to the more appropriate dose diet at that time and verified on a second small pilot mouse population.

Similarly, some animals will be used for IGF-1 injection pilot experiments to determine the proper starting dose.

At age 12 months: Sacrifice 3 animals/SG to obtain common baseline group of 12 animals to be compared to all subsequent results. This is the middle-aged universal control group. All subsequent data can be compared to the results for this pooled group.

At age 12.5 months: Begin the IGF-1 PDG with 7 mice given the best estimated dose of IGF-1. Sacrifice two weeks later for determination of insulin and glucose levels. Begin a verification/second trial dose of IGF-1 at 13 months, 1 week of age, and sacrifice this second PDG at 13 months, 3 weeks of age. Assuming the assays for insulin and glucose can be completed in 1 week, this regimen will allow the final dose for the LTG to be determined prior to age 14 months. Similarly, at 12.5 months, place 7 mice on the 0.2% troglitazone diet. Two weeks later, sacrifice and assay for insulin and glucose. Begin adjusted-dose or verification dose group at 13 months, 1 week and sacrifice after two weeks.

At age 14 months: Begin troglitazone and IGF-1 at the experimentally-determined or estimated optimal doses for each.

At age 15 months: Sacrifice six animals from the IGF-1 and troglitazone SGs for determinations of glucose, insulin, and all other endpoints involved in the study. If necessary, adjust the IGF-1 dose again (both in the LTG and the untapped portion of the IGF-1 SG) and/or order diet with a modified troglitazone content. Sacrifice three animals each from the SGs for the controls and the ALT-11 groups and pool to create a common group of six animals for comparison to the IGF-1 and troglitazone groups.

At age 18 months: same as at 15 months, but use 7 mice/SG for IGF-1 and troglitazone and 4 mice/SG for the control and for the ALT-711 group. Begin the ALT-711 groups on ALT-711 immediately after this sampling.

At around 27 months (~24–30 months): Sample all remaining surviving SG mice.

If the total initial numbers of mice in the sacrifice groups for treatments 1, 2, 3, and 4 are 30, 50, 50, and 30, respectively, then if there were no mortality in any of these groups, there would be 20 animals left in each SG at the time of final sampling. But if we assume that only ⅓ of this number will be alive, then about 7 animals will remain to be sampled at the final sample time, or about the minimum required for statistical significance. If the mean survival rate at 27 month is over 73%, the 27 month end point may be postponed to a greater age.

In addition to other biochemical markers, assays may include:

heart and thymus volume and histology;
autoantibody titer;
T and B cell characteristics;
protein or albumin concentration in bladder urine at sacrifice;
molecular glycation indices;
protein carbonyl content or other free radical/oxidation indices; and
incidence of neoplasia, esp. of prostate and breast.

APPENDIX A

| P | CR | std | CON | std | SW | std | GenBank | Description | Location |
|---|----|----|-----|-----|-----|-----|---------|-------------|----------|
| | | | | | | | | | NOT REPORTED IN LIVER; NERVOUS TISSUE |
| 0.046 | 0.88 | 0.79 | 0.00 | 0.00 | 1.20 | 0.18 | L34676 | X11 protein gene; X11 protein binds amyloid precursor protein; receptor trafficking; +1543 may regulate the processing of amyloid precursor protein to the amyloid beta peptide | Neurons |
| 0.006 | 0.95 | 0.27 | 0.28 | 0.27 | 1.23 | 0.11 | U65418 | Netrin-1; axon outgrowth-promoting protein; guidance molecule; guides growing axons in development | CNS |
| <0.001 | 1.10 | 0.02 | 0.00 | 0.00 | 1.09 | 0.19 | X97817 | Semaphorin F; involved in axonal guidance | Early embryogenesis |
| <0.001 | 1.02 | 0.01 | 0.04 | 0.08 | 1.06 | 0.09 | L38580 | Galanin; a neuropeptide; enhances hepatic glucose production; present in hepatic nerves | Released by hepatic nerves; CNS and peripheral organs including pituitary, adrenal gland, lung, tongue, testes, ovary-fallopian tubes, and uterus; not detectable in heart, liver, kidney, urinary bladder or skeletal muscle |
| <0.001 | 1.14 | 0.16 | 0.02 | 0.03 | 1.14 | 0.16 | X92122 | UDP-galactose ceramide galactosyl transferase; key enzyme in cerebroside sulfatide glycosphingolipids; abundant in myelin | tissue distribution and characterized biosynthesis; most |
| <0.001 | 1.10 | 0.10 | 0.06 | 0.10 | 1.16 | 0.18 | U56650 | Neurexophilin 2 (Nxph-2); neuronal glycoprotein; binds to alpha-neurexins | +120 Brain |
| <0.001 | 0.99 | 0.22 | 0.04 | 0.06 | 1.04 | 0.06 | L42340 | Sodium channel 27 | Brain; tissue distribution and protein poorly characterized |
| <0.001 | 1.16 | 0.27 | 0.03 | 0.06 | 1.11 | 0.11 | X61449 | Brain expressed anonymous cDNA | Brain; expression poorly characterized |
| <0.001 | 1.13 | 0.17 | 0.01 | 0.02 | 1.15 | 0.20 | X92352 | Bpx, strong homology to genes encoding nucleosome assembly proteins; poorly characterized | Brain; tissue distribution poorly characterized |

-63-

| P | CR | std | CON | std | SW | std | GenBank | Description Location |
|---|---|---|---|---|---|---|---|---|
| 0.001 | 1.29 | 0.29 | 0.03 | 0.05 | 1.22 | 0.22 | X07215 | PLP; proteolipid protein, main CNS integral protein of the myelin |
| <0.001 | 1.17 | 0.19 | 0.03 | 0.06 | 1.16 | 0.25 | Y12257 | Glutamic acid decarboxylase_67 Brain, islets; isozyme of liver form kD. |
| 0.001 | 1.36 | 0.15 | 0.00 | 0.00 | 1.09 | 0.35 | ET63017 | Cadherin-8, adhesion molecule MCad8 expression is restricted to particular subdivisions of the early central nervous system (CNS) and to the thymus |
| 0.001 | 1.19 | 0.35 | 0.09 | 0.15 | 1.43 | 0.12 | ET61642 | Inward rectifier potassium channel 2 (GIRK2) Neurons |
| 0.001 | 1.18 | 0.25 | 0.11 | 0.19 | 1.16 | 0.21 | X97281 | K+ channel beta-subunit, ion Brain and Kidney channel |
| <0.001 | 1.06 | 0.07 | 0.10 | 0.12 | 1.08 | 0.08 | Y09108 | SNS-TTXi sodium channel, ion Brain channel; small-diameter sensory neurons associated with unmyelinated axons express a tetrodotoxin-insensitive (TTXi) voltage-gated sodium channel (VGSC); may play an important role in the transmission of nociceptive information to the spinal cord |
| 0.005 | 1.26 | 0.03 | 0.15 | 0.26 | 1.16 | 0.39 | M30440 | Potassium channel gene (MK2); T cells; myelinating Schwann cells Shaker subfamily |
| 0.018 | 1.78 | 0.50 | 0.40 | 0.46 | 1.10 | 0.21 | S80989 | NK-related homeobox gene (Nkx- Developing CNS and ear in E13.5 5.2); cell type specification of embryos; cell type specification of neuronal cells |
| 0.011 | 1.00 | 0.21 | 0.50 | 0.24 | 1.22 | 0.13 | X83577 | K-glypican; cell surface heparin In embryo major sites are tubular and sulfate proteoglycan; suggested epithelial cells in kidney and role in regulating cell cycle proliferating neuroepithelial cells in progression during the transition brain; neurons of neural cells from proliferation to differentiation. |
| 0.044 | 1.12 | 0.26 | 0.61 | 0.27 | 1.32 | 0.28 | U36757 | Thrombin receptor (PAR-1); Blood, platelets, monocytes; transmembrane G-protein coupled endothelial cells; cardiomyocytes; receptor; activated by serine neuronal and glial cells protease cleavage; thrombin is a |

-64-

| P | CR | std | CON | std | SW | std | GenBank | Description | Location |
|---|---|---|---|---|---|---|---|---|---|
| 0.004 | 1.02 | 0.02 | 0.53 | 0.17 | 1.02 | 0.12 | M33467 | serine protease generated by the activation of the blood coagulation cascade following vessel injury; thrombin acts as a mitogen, apoptosis inducer and regulator of inflammation | |
| 0.000 | 1.31 | 0.06 | 0.00 | 0.00 | 0.98 | 0.06 | ET62839 | Dilute lethal-20J; Class-V myosin; unique type of myosin motor; role in membrane traffic through actin rich regions of the cytoplasm; transport endoplasmic reticulum vesicles in neurons and pigment granules in melanocytes | Adult germ line cells; early embryo; oocyte during oogenesis; enriched in vesicular brain; neurons; melanocytes |
| 0.015 | 1.14 | 0.15 | 0.20 | 0.20 | 1.36 | 0.55 | ET63156 | Immunoglobulin-like receptor (PIRA1); activating receptor on myeloid-linage cells. | B lymphocytes; dendritic cells, murine B lymphocytes; dendritic cells; myeloid-linage cells. |
| 0.001 | 1.21 | 0.21 | 0.05 | 0.09 | 1.37 | 0.36 | ET63385 | Mouse homolog of the Drosophila Disabled (Dab) protein; MDab217; an adaptor molecule functioning in neural development. | Neuronal and hematopoietic cell lines; growing nerves of embryonic mice |
| 0.043 | 1.44 | 0.43 | 0.33 | 0.56 | 1.40 | 0.38 | ET63410 | Connexin30 (CX30); gap junction protein that forms transmembranous gap junction channels that connect adjacent cells | Brain; skin |
| <0.001 | 1.12 | 0.04 | 0.09 | 0.15 | 1.12 | 0.21 | X53257 | Semaphorin Hv; a novel member of semaphorin gene family; secreted glycoprotein involved in embryonic development Neurotrophin-3 (NT-3); secreted protein; binds high affinity receptor trk C | Developing lungs; skeletal elements; neural tubes Liver parenchymal cells olfactory bulb cerebellum; septum and hippocampus; thymus, heart, diaphragm, pancreas, spleen, kidney, adrenal gland |

| P | CR | std | CON | std | SW | std | GenBank | Description Location |
|---|---|---|---|---|---|---|---|---|
| 0.004 | 1.16 | 0.28 | 0.22 | 0.26 | 1.22 | 0.19 | ET61665 | Discs-large tumor suppressor Localized to synapse; epithelial cells homologue (dlgh1); important role in the localization and function of glutamate receptors and K(+) channels; member of the MAGUK (membrane associated guanylate kinase homologue) family of proteins |
| 0.001 | 1.05 | 0.20 | 0.16 | 0.27 | 1.32 | 0.15 | ET63395 | Axonemal dynein heavy chain Brain, trachea, testis (mdhc1); axonemal dyneins are molecular motors that drive the beating of cilia and flagella; heavy chains are main components of multisubunit motor ATPase complexes called dyneins |
| 0 | 1.21 | 0.17 | 0.00 | 0.00 | 0.95 | 0.09 | ET63399 | Axonemal dynein heavy chain Brain, trachea, testis (mdhc3); axonemal dyneins are molecular motors that drive the beating of cilia and flagella; heavy chains are main components of multisubunit motor ATPase complexes called dyneins |
| 0.013 | 1.09 | 0.08 | 0.21 | 0.36 | 1.30 | 0.42 | ET63402 | Axonemal dynein heavy chain Brain, trachea, testis (mdhc6); axonemal dyneins are molecular motors that drive the beating of cilia and flagella; heavy chains are main components of multisubunit motor ATPase complexes called dyneins |
| 0.002 | 1.07 | 0.09 | 0.24 | 0.21 | 1.14 | 0.23 | ET63405 | Axonemal dynein heavy chain Brain, trachea, testis (mdhc9); axonemal dyneins are molecular motors that drive the beating of cilia and flagella; heavy chains are main |

| P | CR | std | CON | std | SW | std | GenBank | Description Location |
|---|---|---|---|---|---|---|---|---|
| 0 | 1.02 | 0.08 | 0.05 | 0.09 | 1.14 | 0.08 | Y08485 | Synaptonemal complex protein 3; Testis; synaptonemal complex part of the lateral element of the protein 1 is also expressed in synaptonemal complex; a embryonic ovary, adult brain and meiosis-specific protein structure testis essential for synapsis of homologous chromosomes |
| 0.007 | 1.20 | 0.53 | 0.00 | 0.00 | 1.28 | 0.30 | L28756 | Gonadotropin-releasing hormone Anterior pituitary, brain and receptor; G-protein-coupled reproductive organs as well as many receptor; GnRH activates all four steroid-dependent tumor tissues MAPK cascades by a PKC-dependent mechanism. |
| 0.003 | 1.18 | 0.24 | 0.29 | 0.23 | 1.09 | 0.10 | Z46845 | Preproglucagon; glucagon-like Pancreatic alpha cells, ileum+K41, peptide I and II; member of CNS vasoactive intestinal peptide (VIP)/secretin/glucagon/GHRH family of neuropeptides |
| <0.001 | 1.09 | 0.15 | 0.08 | 0.11 | 1.10 | 0.15 | U66201 | Fibroblast growth factor Highest expression in brain and homologous factor 1 (FGF-1); skeletal muscle nervous system development and function |
| <0.001 | 1.13 | 0.15 | 0.00 | 0.00 | 0.99 | 0.18 | Z27088 | Relaxin precursor (rlx); relaxin; Brain, uterus, prostate gland, member of insulin gene family; pancreas and kidney, with other remodeling of collagen and tissues giving weak signals uterine contractility |
| 0.005 | 1.20 | 0.24 | 0.25 | 0.22 | 1.23 | 0.29 | ET62740 | Ankyrin-3 (Ank3); also called Widely distributed, especially in ankyrin(G); skeletal protein epithelial tissues, muscle, and implicated in Na(+) channel neuronal axons clustering; essential for clustering NaCh and neurofascin at axon initial segments and is required for physiological levels of sodium channel activity |
| 0.007 | 1.37 | 0.08 | 0.34 | 0.35 | 1.05 | 0.25 | U48397 | Mercurial-insensitive water Brain, eye, lung, kidney, heart, channel 1 (mMIWC1); allows muscle |

| p | CR | std | CON | std | SW | std | GenBank | Description Location |
|---|---|---|---|---|---|---|---|---|
| 0.004 | 1.16 | 0.28 | 0.22 | 0.26 | 1.22 | 0.19 | ET61665 | Discs-large tumor suppressor homologue (dlgh1) gene; important role in the localization and function of glutamate receptors and K(+) channels; member of the MAGUK (membrane associated guanylate kinase homologue ues) family of proteins Localized to synapse; epithelial cells |
| 0.005 | 1.26 | 0.03 | 0.15 | 0.26 | 1.16 | 0.39 | M30440 | Potassium channel gene (MK2); T cells; myelinating Schwann cells shaker subfamily |
| 0 | 1.00 | 0.15 | 0.02 | 0.03 | 1.15 | 0.10 | U58367 | Neuropeptide Y receptor Y5/Y6/Y2b (referred to as both Y5 and Y2b, has now been designated as Y6 in literature); neuropeptide Y is an important regulator of energy balance in mammals through its orexigenic, antithermogenic, and insulin secretagogue actions; expressed abundantly in the central nervous system; NPY receptors mediate a variety of physiological responses including feeding and vasoconstriction Neurons, vascular smooth muscle |
| 0.000 | 1.06 | 0.15 | 0.00 | 0.00 | 1.56 | 0.37 | ET61090 | Ryanodine receptor type-3; intracellular Ca2+ channels Skeletal and smooth muscle, CNS |
| 0.006 | 0.96 | 0.24 | 0.18 | 0.32 | 1.10 | 0.10 | ET62978 | Neosin/lark; RNA-binding protein; Drosophila homologue encodes an element of the clock output pathway regulating adult eclosion (circadian rhythm) Uncharacterized, probably neuronal |
| 0.001 | 1.24 | 0.31 | 0.00 | 0.00 | 1.18 | 0.27 | D50095 | Histamine H1 receptor; GTP-binding protein-coupled receptor; coupled to phosphoinositide turnover-calcium mobilization Liver, brain, spleen (ubiquitous) |

| P | CR | std | CON | std | SW | std | GenBank | Description Location |
|---|---|---|---|---|---|---|---|---|
| 0 | 1.09 | 0.16 | 0.00 | 0.00 | 1.15 | 0.13 | U60330 | signaling pathway; regulates insulin-like growth factor I expression and cell proliferation; modulates IL-6 action; regulates physiological functions in neurons; regulates transport of thyroxine into hepatocytes Ki antigen (PA28 gamma); cell Liver, neurons, broad tissue proliferation; the interferon- distribution gamma (IFN-gamma)-inducible PA 28 activator complex enhances the generation of class I binding peptides by altering the cleavage pattern of the proteosome |
| 0 | 1.09 | 0.16 | 0.00 | 0.00 | 1.18 | 0.18 | Z31663 | Activin type IB receptor; limb Embryo: brain, some ganglia, development; expressed vibrissae, lungs, body wall, stomach, coincidently with the formation gonads, ribs, limbs, shoulders, of the last phalanx of each digit olfactory region, eye, tooth primordium, esophagus, mesonephros, dorsal root ganglia and is strongly expressed in the spinal cord. |
| 0.001 | 1.02 | 0.35 | 0.00 | 0.00 | 1.31 | 0.16 | U33535 | Fibroblast growth factor 9 (FGF-Adult and developing CNS: neurons, 9); autocrine and paracrine astrocytes, oligodendrocytes, glial growth factor; prevents cell cells, epithelial cells, brain, kidney, death in cultured motoneurons; prostate (stromal cells); in plays a role in embryonic neural embryogenesis expressed in many cell differentiation; areas including intermediate thrombopoietic activity (acts on mesoderm the in vivo proliferation of megakaryocytes) |

NOT REPORT IN LIVER: MUSCLE

| P | CR | std | CON | std | SW | std | GenBank | Description Location |
|---|---|---|---|---|---|---|---|---|
| 0.008 | 1.27 | 0.33 | 0.27 | 0.27 | 1.04 | 0.13 | X04405 | Myoglobin gene; small globular Muscle heme protein; binds gaseous ligands such as O2, CO and NO |
| 0.002 | 1.32 | 0.20 | 0.00 | 0.00 | 0.80 | 0.39 | X92523 | Skeletal muscle-specific calpain Skeletal muscle; differentially spliced (canp3); intracellular calcium- variants in smooth muscles during |

-69-

| P | CR | std | CON | std | SW | std | GenBank | Description | Location |
|---|---|---|---|---|---|---|---|---|---|
| 0.001 | 1.14 | 0.15 | 0.15 | 0.27 | 1.17 | 0.15 | M92416 | dependant cysteine proteinase; fetal period tissue specific myofibrogenesis, modifies ryanodine receptor Ca2+ release channel Fibroblast growth factor (Fgf6); Fgf6 is the only known member of the FGF family whose expression is restricted to the muscle cell lineage during development | Skeletal muscle |
| 0.012 | 1.33 | 0.35 | 0.00 | 0.00 | 1.45 | 0.67 | M14537 | Nicotinic acetylcholine receptor beta subunit | Skeletal muscle |
| 0.003 | 1.09 | 0.12 | 0.14 | 0.24 | 1.11 | 0.31 | X55718 | Nicotinic acetylcholine receptor e subunit; embryonic | Skeletal muscle |
| 0.003 | 1.08 | 0.04 | 0.00 | 0.00 | 1.19 | 0.47 | Z67747 | ZT3 zinc finger factor | Skeletal, cardiac muscle, and spleen in adult |
| 0.01 | 1.15 | 0.12 | 0.02 | 0.04 | 1.29 | 0.62 | U37353 | Protein phosphatase 2A regulatory subunit | Skeletal and heart muscle |
| 0.005 | 0.93 | 0.18 | 0.00 | 0.00 | 1.14 | 0.14 | ET62103 | Nebulin; a family of giant myofibrillar proteins | Skeletal muscle |
| 0.002 | 1.18 | 0.18 | 0.24 | 0.21 | 1.14 | 0.22 | ET62883 | Skeletal muscle chloride channel | Skeletal muscle |
| 0.023 | 1.45 | 0.58 | 0.00 | 0.00 | 1.16 | 0.61 | ET63019 | Skeletal muscle ryanodine receptor; calcium release channel | Skeletal muscle |
| 0 | 1.02 | 0.07 | 0.00 | 0.00 | 1.27 | 0.23 | ET62998 | Dystrobrevin:postsynaptic protein; important in the formation and maintenance of the mammalian neuromuscular junctions. | Skeletal muscle |
| 0.001 | 1.19 | 0.25 | 0.25 | 0.05 | 1.21 | 0.20 | ET62865 | Alpha 4 integrin; a leukocyte glycoprotein involved in both cell-extracellular matrix and cell-cell interaction | Skeletal muscle |
| 0 | 0.98 | 0.21 | 0.00 | 0.00 | 1.25 | 0.05 | U49393 | Sarcoendoplasmic reticulum Ca2+ ATPase; ion pump | Skeletal, smooth, and cardiac muscle |
| 0.005 | 1.20 | 0.24 | 0.25 | 0.22 | 1.23 | 0.29 | ET62740 | Ankyrin-3 (Ank3); also called ankyrin(G); skeletal protein implicated in Na(+) neuronal axons | Widely distributed, especially in muscle epithelial tissues, muscle, and |

-70-

| P | CR | std | CON | std | SW | std | GenBank | Description Location |
|---|---|---|---|---|---|---|---|---|
| 0.007 | 1.37 | 0.08 | 0.34 | 0.35 | 1.05 | 0.25 | U48397 | channel clustering; essential for clustering NaCh and neurofascin at axon initial segments and is required for physiological levels of sodium channel activity. |
| 0.000 | 1.06 | 0.15 | 0.00 | 0.00 | 1.56 | 0.37 | ET61090 | Mercurial-insensitive water Brain, eye, lung, kidney, heart, channel 1 (mMIWC1); allows muscle water and small solutes to pass |
| 0.005 | 1.17 | 0.23 | 0.43 | 0.16 | 1.24 | 0.23 | X83932 | Ryanodine receptor type-3; Skeletal and smooth muscle, CNS intracellular Ca2+ channels |
| 0.004 | 1.25 | 0.48 | 0.00 | 0.00 | 1.28 | 0.24 | X80417 | Ryanodine receptor type 1 (RYR1 Skeletal muscle gene); intracellular calcium channel |
|  |  |  |  |  |  |  |  | MB-IRK2 (second class of inward Heart, kidney, and skeletal muscle rectifier potassium channels); ion channel |

VASCULAR SMOOTH MUSCLE

| P | CR | std | CON | std | SW | std | GenBank | Description Location |
|---|---|---|---|---|---|---|---|---|
| 0 | 1.00 | 0.15 | 0.02 | 0.03 | 1.15 | 0.10 | U58367 | Neuropeptide Y receptor Neurons, vascular smooth muscle Y5/Y6/Y2b (referred to as both cells Y5 and Y2b, has now been designated as Y6 in literature); (NPY-Y6); neuropeptide Y is an important regulator of energy balance in mammals through its orexigenic, antithermogenic, and insulin secretagogue actions; expressed abundantly in the central nervous system; NPY receptors mediate a variety of physiological responses including feeding and vasoconstriction |
| 0.021 | 1.40 | 0.24 | 0.00 | 0.00 | 0.79 | 0.71 | J03293 | Phosphorylase kinase, gamma Heart, skeletal and cardiac muscle subunit; phosphorylates and (not in liver and the liver gamma activates glycogen subunit does not cross-hybridize with phosphorylase, the enzyme that the skeletal muscle gamma subunit initiates the catabolism of cDNA) glycogen in skeletal muscle |

| P | CR | std | CON | std | SW | std | GenBank | Description | Location |
|---|---|---|---|---|---|---|---|---|---|
| 0.044 | 1.12 | 0.26 | 0.61 | 0.27 | 1.32 | 0.28 | U36757 | Thrombin receptor (PAR-1); Transmembrane G-protein coupled receptor; activated by serine protease cleavage; thrombin is a serine protease generated by the activation of the blood coagulation cascade following vessel injury; thrombin acts as a mitogen and apoptosis inducer | Blood, platelets, monocytes; endothelial cells; cardiomyocytes; neuronal and glial cells |
| 0.000 | 1.06 | 0.15 | 0.00 | 0.00 | 1.56 | 0.37 | ET61090 | Ryanodine receptor type-3; intracellular Ca2+ channels | Skeletal and smooth muscle, CNS |

NOT REPORTED IN LIVER: SIGNAL TRANSDUCTION

| P | CR | std | CON | std | SW | std | GenBank | Description | Location |
|---|---|---|---|---|---|---|---|---|---|
| 0.013 | 0.77 | 0.51 | 0.00 | 0.00 | 1.10 | 0.15 | L12460 | Mouse cyclic GMP-dependent protein kinase II; signal transduction | Brain, kidney, small intestine, colon |
| 0.000 | 0.96 | 0.15 | 0.00 | 0.00 | 1.48 | 0.12 | Y00850 | Mouse Kruppel-like gene (MKr2); Restricted to central and peripheral differentiation and/or phenotypic maintenance of neurons | neurons of adults |
| 0.022 | 1.13 | 0.08 | 0.24 | 0.40 | 1.04 | 0.35 | Z23143 | Activin receptor-like kinase-6; receptors for morphogenic proteins; serine-threonine kinase | Developing mesenchyme, muscle, blood vessels, CNS, ear, eye, epithelium |
| 0.044 | 1.26 | 0.38 | 0.39 | 0.44 | 1.12 | 0.12 | X66983 | Rck gene; protein kinase | Photoreceptors, olfactory receptors, respiratory and choroid plexus epithelial cells, germ cells |
| 0.048 | 1.79 | 1.06 | 0.00 | 0.00 | 1.18 | 0.54 | U33005 | Tbc1; domains homologous to tre-2 oncogene and yeast mitosis regulators BUB2 and cdc16; nuclear localization | Not well-characterized; hematopoietic cells, testis and kidney |
| <0.001 | 0.98 | 0.18 | 0.03 | 0.03 | 1.08 | 0.11 | Y12293 | LUN transcription factor; forkhead domain identical to the HFH8 gene; C-terminal region similar to the HFH8 gene | Lung bronchiolar epithelium and type II pneumocytes; tissue distribution not well characterized |
| <0.001 | 1.18 | 0.20 | 0.00 | 0.00 | 1.04 | 0.15 | U48721 | Zinc finger protein 60 (ZFP60); Kruppel associated boxes | Expressed transiently during in vitro muscle differentiation |
| 0.003 | 1.43 | 0.41 | 0.07 | 0.12 | 1.33 | 0.34 | D13801 | DNA-binding transcription factor CNS; (Emb); class VI POU domain | tissue distribution not well characterized |

-72-

| P | CR | std | CON | std | SW | std | GenBank | Description | Location |
|---|---|---|---|---|---|---|---|---|---|
| 0.026 | 1.07 | 0.69 | 0.00 | 0.00 | 1.06 | 0.09 | X63963 | Paired box protein transcription factor | (Pax-6); Development of eye and CNS |
| <0.001 | 1.07 | 0.02 | 0.00 | 0.00 | 1.07 | 0.19 | U76208 | Neurogenin 3 transcription factor; related bHLHprotein | (Ngn3); CNS and early precursors of neuroD- pancreatic endocrine cells (embryogenesis) |
| 0.003 | 1.15 | 0.31 | 0.07 | 0.12 | 1.28 | 0.32 | U17252 | Metabotropic glutamate receptor 8; G-protein coupled | CNS, glial cells; retina and olfactory bulb; stellate/basket cells |
| <0.001 | 1.02 | 0.02 | 0.04 | 0.06 | 1.06 | 0.17 | U14420 | GABA-benzodiazepine receptor beta-3 subunit; link binding of GABA (gamma-aminobutyric acid) to inhibitory chloride flux | CNS |
| <0.001 | 1.11 | 0.22 | 0.09 | 0.16 | 1.07 | 0.07 | X66118 | Glutamate receptor subunit GluR5-2c. | Brain |
| 0.001 | 1.11 | 0.33 | 0.06 | 0.10 | 1.05 | 0.04 | Z14224 | 5HT1E beta serotonin receptor; G protein-coupled receptor | Brain; tissue distribution not well characterized |
| 0.001 | 1.21 | 0.29 | 0.02 | 0.03 | 1.26 | 0.29 | X79082 | MDK1 (mouse developmental kinase 1); member of receptor tyrosine kinase family | Brain, testes and spleen |
| <0.001 | 1.20 | 0.22 | 0.01 | 0.01 | 1.30 | 0.27 | Z48757 | Intestinal tyrosine kinase; protein tyrosine kinase | Mammary gland and intestine |
| 0.001 | 1.11 | 0.16 | 0.00 | 0.00 | 1.19 | 0.37 | X58287 | MR-PTPmu; receptor-like protein tyrosine phosphatase | Lung, brain, heart |
| <0.001 | 1.11 | 0.17 | 0.00 | 0.00 | 1.14 | 0.14 | M61000 | Bombesin/gastrin-releasing peptide receptor; member of the G protein-coupled receptor family | Fibroblasts |
| 0.001 | 1.20 | 0.18 | 0.09 | 0.16 | 1.00 | 0.25 | ET61461 | G-protein coupled receptor; poorly characterized | Unknown |
| 0.009 | 1.14 | 0.10 | 0.50 | 0.18 | 0.96 | 0.20 | ET63226 | Nude gene (Whn) winged helix transcription factor family; modulates growth factor production by differentiating epithelial cells including keratinocytes; also controls development of the immune system in thymus. | In adult thymus and skin; embryonic nails, nasal passages, tongue, palate and teeth |
| NOT REPORTED IN LIVER HORMONE / GROWTH FACTOR | | | | | | | | | |
| 0.007 | 1.09 | 0.08 | 0.39 | 0.27 | 1.11 | 0.20 | M22740 | Thyrotropin beta-subunit | (TSH- Pituitary |

| p | CR | std | CON | std | SW | std | GenBank | Description | Location |
|---|---|---|---|---|---|---|---|---|---|
| 0.007 | 1.00 | 0.11 | 0.39 | 0.27 | 1.11 | 0.12 | U12932 | Follicle stimulating hormone beta (FSH-beta, gonadotropin); pituitary stimulates development of follicle and spermatogenesis | Gonadotropes of the anterior pituitary |
| 0.004 | 0.91 | 0.33 | 0.21 | 0.34 | 1.46 | 0.09 | U25145 | Lutenizing hormone beta subunit; Gonadotropes regulation of reproduction | Gonadotropes of the anterior pituitary |

NOT REPORTED IN LIVER; EMBRYONIC DIFFERENTIATION TRANSCRIPTION FACTORS

| p | CR | std | CON | std | SW | std | GenBank | Description | Location |
|---|---|---|---|---|---|---|---|---|---|
| 0.001 | 1.06 | 0.09 | 0.00 | 0.00 | 0.98 | 0.33 | X51683 | T gene (Brachyury gene); T-box family; sequence specific DNA-binding protein that functions as a transcription activator; required for morphogenesis of mesoderm-derived structures, control of gastrulation; development of the heart; perhaps limb formation | Early embryogenesis; mesoderm formation; heart and limb morphogenesis |
| 0.001 | 1.09 | 0.10 | 0.00 | 0.00 | 1.17 | 0.37 | Z15103 | Mox-1; homeobox gene; marker of epithelial-mesenchymal transformation | Early embryogenesis; mesodermal patterning in mouse embryos |
| 0.001 | 1.08 | 0.08 | 0.22 | 0.18 | 0.91 | 0.21 | X86368 | Fkh-2; a forkhead/winged helix transcription factor | Numerous tissues of embryo, including paraxial mesoderm, somites, branchial arches, vibrissae, central nervous system and kidney |
| <0.001 | 1.10 | 0.02 | 0.00 | 0.00 | 1.09 | 0.19 | X97817 | Semaphorin F; involved in axonal guidance | Early embryogenesis |
| 0.018 | 1.78 | 0.50 | 0.40 | 0.46 | 1.10 | 0.21 | S80989 | NK-related homeobox gene (Nkx-5.2); cell type specification of neuronal cells | Developing CNS and ear in E13.5 embryos; cell type specification of neuronal cells |
| 0.011 | 1.00 | 0.21 | 0.50 | 0.24 | 1.22 | 0.13 | X83577 | K-glypican; cell surface heparin sulfate proteoglycan; suggested role in regulating cell cycle progression during the transition of neural cells from proliferation to differentiation. | In embryo major sites are tubular epithelial cells in kidney and proliferating neuroepithelial cells in the brain; neurons |
| 0 | 1.03 | 0.03 | 0.11 | 0.10 | 1.08 | 0.21 | M34094 | Retinoic acid-responsive protein (MK); growth differentiation factor | Mid-gestation mouse embryogenesis; not reported in normal adult liver |

| P | CR | std | CON | std | SW | std | GenBank | Description Location |
|---|---|---|---|---|---|---|---|---|
| 0 | 1.11 | 0.09 | 0.00 | 0.00 | 1.03 | 0.15 | M93128 | Homeobox transcription factor Embryo (EVX2); limb development |
| 0 | 1.04 | 0.15 | 0.13 | 0.12 | 1.16 | 0.10 | X16510 | Hox 3.3; homeobox transcription Spleen, bone marrow factor; embryogenesis; haematopoiesis |
| 0 | 1.09 | 0.16 | 0.00 | 0.00 | 1.18 | 0.18 | Z31663 | Activin type IB receptor; limb Embryo: brain, some ganglia, development; expressed vibrissae, lungs, body wall, stomach, coincidently with the formation gonads, ribs, limbs, shoulders, of the last phalanx of each digit olfactory region, eye, tooth primordium, esophagus, mesonephros, dorsal root ganglia and is strongly expressed in the spinal cord. |
| 0 | 0.99 | 0.06 | 0.12 | 0.20 | 1.10 | 0.13 | D78175 | Atrial natriuretic peptide Epithelial and endothelial cells; lung clearance receptor (ANP-CR or (smooth muscle cells), heart (aortic NPRC); membrane protein; smooth muscle cells), placenta modulates availability of natriuretic peptides at target organs; activation of G protein-coupled signaling system; may modulate endothelial permeability; inhibition of vascular endothelial cell growth factor; modulates activity of mitogen-activated protein kinase (MAPK, regulation of cell proliferation) |

NOT REPORTED IN LIVER Other

| P | CR | std | CON | std | SW | std | GenBank | Description Location |
|---|---|---|---|---|---|---|---|---|
| 0.000 | 1.43 | 0.07 | 0.18 | 0.21 | 1.05 | 0.22 | Z38118 | Synaptonemal complex protein 1 Testis (SCP1); pairing of chromosomes during meiosis |
| 0.003 | 0.86 | 0.29 | 0.11 | 0.19 | 1.21 | 0.19 | U61085 | Thiazide-sensitive sodium and Kidney chloride cotransporter; transmembrane protein |
| 0.024 | 1.20 | 0.36 | 0.34 | 0.30 | 1.46 | 0.44 | X95226 | Dystrobrevin; formation and CNS maintenance of mammalian |

-75-

| P | CR | std | CON | std | SW | std | GenBank | Description | Location |
|---|---|---|---|---|---|---|---|---|---|
| 0.000 | 1.38 | 0.32 | 0.00 | 0.00 | 0.96 | 0.10 | U73915 | Membrane metalloendopeptidase homologue (Pex); mineralization of extracellular matrix by osteoclasts | neuromuscular junction Kidney, bone |
| 0.011 | 1.10 | 0.10 | 0.35 | 0.38 | 1.13 | 0.13 | M10114 | Kappa-casein; milk protein | Mammary glands |
| 0.037 | 1.32 | 0.29 | 0.14 | 0.24 | 0.90 | 0.63 | X99251 | Repetin; similar to intermediate filament-associated proteins profilaggrin and trichohyalin; expression during late epidermal differentiation | Epithelia of forestomach and tongue |
| 0.006 | 1.26 | 0.18 | 0.30 | 0.22 | 0.98 | 0.29 | U66204 | Fibroblast growth factor homologous factor 4 (FHF-4); involved in nervous system development and function | CNS |
| 0.004 | 1.06 | 0.10 | 0.36 | 0.27 | 1.10 | 0.10 | M36516 | Zinc finger proteins (mkr3,4,5) | Whole embryo, testes in adult |
| 0.034 | 0.96 | 0.30 | 0.32 | 0.40 | 1.14 | 0.12 | X86000 | N-glycan alpha 2,8-sialyltransferase (STSia IV) | Lung, heart, spleen, brain |
| 0.025 | 1.21 | 0.11 | 0.40 | 0.36 | 1.12 | 0.33 | M25513 | Rod transducin alpha subunit (Tr-alpha); couples photolysis of rhodopsin to activation of cGMP phosphodiesterase; visual signal cascade | Retina, not reported in liver, kidney, of heart |
| 0.008 | 1.18 | 0.51 | 0.23 | 0.40 | 1.82 | 0.25 | X12875 | Neural cell adhesion molecule L1 (N-CAM L1); involved in Ca2+ independent neural adhesion | Nerve cells |
| 0.049 | 1.44 | 0.41 | 0.49 | 0.38 | 1.12 | 0.30 | Y00500 | Glandular kallikrein mGK-5; serine protease | Salivary glands; possible crosshybridization with liver kallikreins |
| 0.030 | 1.18 | 0.07 | 0.29 | 0.45 | 0.85 | 0.25 | X63100 | Connexin45; gap junction protein; ion exchange channels | Lung, brain, heart, intestine; embryonic brain, skin, and kidney |
| 0.036 | 1.30 | 0.18 | 0.41 | 0.45 | 1.06 | 0.28 | ET62673 | Hyaluronan synthase 3; polymerizes hyaluron, (extracellular) glycosaminoglycan; can be hallmark of tissue remodeling; reduces cell motility; hyaluron found throughout the | Eyes, kidney, chondrocytes |

| P | CR | std | CON | std | SW | std | GenBank | Description Location |
|---|---|---|---|---|---|---|---|---|
| 0.017 | 1.81 | 0.92 | 0.00 | 0.00 | 1.12 | 0.11 | D87471 | extracellular matrix, especially in soft connective tissue Actin capping protein; germ cell Haploid germ cells of testis gene 3 (gsg3); homologue of somatic cell type actin capping protein alpha (ACP alpha) |
| 0.019 | 1.16 | 0.14 | 0.48 | 0.30 | 1.26 | 0.29 | J04847 | PL10; ATP-dependent RNA Testis (not reported in liver) helicase; suggested role in spermatogenesis; protein homologous to eIF-4A |
| <0.001 | 1.09 | 0.14 | 0.01 | 0.02 | 1.19 | 0.29 | Z46299 | Sp17 gene for sperm specific Mammalian testis; sperm-specific protein; calmodulin binding protein |
| <0.001 | 1.05 | 0.05 | 0.14 | 0.23 | 1.08 | 0.09 | X72697 | Meiosis-specific XMR; Testis; lymphoid cell lineages; nuclei transcriptional activator function? of spermatocytes, early in the prophase of the first meiotic division, and later becomes concentrated in the XY nuclear subregion |
| <0.001 | 1.20 | 0.18 | 0.02 | 0.02 | 1.07 | 0.26 | M19413 | Testicular alpha tubulin Testis |
| <0.001 | 1.17 | 0.20 | 0.08 | 0.14 | 1.01 | 0.01 | X96606 | Ott, mouse X-linked multigene Expressed during meiosis family |
| 0.002 | 1.14 | 0.31 | 0.13 | 0.22 | 1.23 | 0.10 | D13664 | Osteoblast specific factor 2 Osteoblastic cells (OSF-2); extracellular matrix? |
| 0.006 | 1.33 | 0.43 | 0.09 | 0.15 | 1.40 | 0.39 | X15830 | Neuroendocrine protein 7B2; Widely distributed neuroendocrine secretory protein present in protein; neurons, endocrine cells; serum; proteolytic conversion and pituitary, cells producing insulin and activation of proprotein glucagon; melanosomes convertases 2 in the endoplasmic reticulum |
| 0.440 | 1.10 | 0.80 | 0.53 | 0.59 | 1.27 | 0.67 | D38162 | Alpha1(XI) collagen (COL11a1); Embryo cartilaginous tissue, brain, structural integrity: essential for heart, tongue, intestine, and otic normal cartilage development vesicles |
| 0.002 | 1.01 | 0.03 | 0.43 | 0.37 | 1.56 | 0.04 | M35732 | Seminal vesicle secretory protein Seminal vesicles IV (SVS IV); major secretory protein of seminal vesicles; regulation of the immune response, blood coagulation; |

-77-

| P | CR | std | CON | std | SW | std | GenBank | Description | Location |
|---|---|---|---|---|---|---|---|---|---|
| 0.043 | 1.87 | 0.72 | 0.00 | 0.00 | 0.97 | 0.95 | X05260 | inflammatory reaction; reproduction Y chromosome RNA transcript expressed in testis (pY353/B); protein product uncharacterized; sex determination factor? | Testis (reported not present in adult liver) |
| 0.046 | 2.86 | 0.65 | 0.00 | 0.00 | 1.46 | 1.74 | U96701 | Intracellular serine proteinase inhibitor (mBM2A); serine proteinase inhibitors (serpins) are regulators of extracellular proteolysis | Predominantly in testis |
| 0.019 | 1.42 | 0.39 | 0.58 | 0.06 | 1.11 | 0.20 | ET63122 | Beta-Tectorin; extracellular matrix protein | Inner ear; expressed by cells in and surrounding the mechanosensory epithelia in embryo and adult |
| 0.005 | 1.00 | 0.05 | 0.25 | 0.31 | 1.15 | 0.21 | X04724 | Preproinsulin gene II | Pancreas and islets |
| 0.004 | 1.21 | 0.39 | 0.06 | 0.11 | 1.63 | 0.46 | X04725 | Preproinsulin gene I | Pancreas and islets |
| 0.002 | 1.51 | 0.44 | 0.00 | 0.00 | 1.20 | 0.32 | ET63205 | Odorant binding protein Ib | Nasal epithelium. |
| 0 | 1.18 | 0.33 | 0.00 | 0.00 | 1.51 | 0.21 | ET63408 | Capping protein beta 3 subunit; a novel isoform of actin-binding protein; a component of the cytoskeletal calyx of the mammalian sperm head. | Spermiogenesis |
| 0.045 | 1.24 | 0.21 | 0.00 | 0.00 | 0.93 | 0.81 | X58169 | T-complex responder (Tcp-10); Tcp-10 gene has been established as a molecular candidate for the T complex responder locus which plays a central role in the transmission ratio distortion phenotype expressed by males heterozygous for a T haplotype.. | Male germ line |
| 0.011 | 1.45 | 0.81 | 0.00 | 0.00 | 1.72 | 0.25 | ET61364 | Meprin beta subunit isoform (Mep-1beta); meprins are membrane-bound oligomeric metalloendopeptidases, contain alpha and/or beta subunit | Kidney, intestine, not reported in liver |
| 0.008 | 1.19 | 0.16 | 0.22 | 0.19 | 1.37 | 0.47 | ET62832 | Perforatorial protein (PERF 15); a | Testis |

-78-

| P | CR | std | CON | std | SW | std | GenBank | Description | Location |
|---|---|---|---|---|---|---|---|---|---|
| 0.016 | 1.29 | 0.33 | 0.24 | 0.26 | 1.17 | 0.40 | ET62968 | novel testicular protein; sequence similarities to a family of lipid binding proteins; major component of the rat sperm perinuclear theca. | Olfactory and testicular cells |
| 0.003 | 0.94 | 0.45 | 0.02 | 0.04 | 1.21 | 0.02 | ET63528 | Odorant receptor 23 (OR23) A-myb; a conserved member of the Myb proto-oncogene family, cell differentiation); encodes a sequence-specific DNA binding protein (A-Myb) that binds to and transactivates myb-promoters containing myb-binding sites | Abundant expression in testis (germ low level expression in ovary, spleen (B lymphocytes) and brain; CNS in embryos |
| 0.005 | 1.44 | 0.46 | 0.00 | 0.00 | 1.14 | 0.39 | ET63177 | Pax-4; a paired-box transcription factor that plays an important role in the development of pancreatic beta/delta cells; role in endocrine cell development | Pancreatic islet endocrine progenitor cells |
| 0.001 | 1.06 | 0.22 | 0.04 | 0.07 | 1.37 | 0.33 | M20567 | Heat-shock-like protein (HSP70.2); not induced by heat shock; developmentally regulated in spermatogenic cells; critical role in spermatogenesis | 70-2 Male germ cells |
| 0.001 | 1.30 | 0.05 | 0.00 | 0.00 | 1.10 | 0.38 | ET61399 | G protein alpha olfactory subunit; sensory transduction | Olfactory epithelium |
| 0.015 | 1.07 | 0.08 | 0.09 | 0.15 | 1.16 | 0.57 | L28819 | Involucrin; a glycine-, serine- and cysteine-rich protein expressed late in differentiation of granular layers in normal epidermis | Epidermis |
| 0.005 | 1.45 | 0.52 | 0.05 | 0.09 | 1.17 | 0.26 | ET62336 | DNA ligase III-beta; DNA ligase III Alpha exists as two distinct isoforms beta denoted alpha and beta | Alpha is expressed in most tissues; beta is expressed in testes and during spermatogenesis |
| 0 | 0.95 | 0.18 | 0.07 | 0.12 | 1.13 | 0.11 | D49438 | 25-hydroxyvitamin D3 hydroxylase; metabolism and regulation of vitamin D3 | 24- Kidney and intestine. |
| 0.011 | 1.27 | 0.28 | 0.00 | 0.00 | 1.22 | 0.59 | M26940 | Beta-casein gene | Mammary glands |

-79-

| P | CR | std | CON | std | SW | std | GenBank | Description | Location |
|---|---|---|---|---|---|---|---|---|---|
| 0.001 | 1.03 | 0.29 | 0.05 | 0.05 | 1.12 | 0.10 | V00740 | Epsilon-casein | Mammary glands |
| 0 | 1.01 | 0.08 | 0.02 | 0.04 | 1.07 | 0.07 | V00428 | Lysozyme; signaling molecule for Macrophages, paneth cells (located mast cells which respond with in duodenal crypts) histamine secretion | |
| BLOOD-NOT IgG | | | | | | | | | |
| 0.037 | 1.24 | 0.26 | 0.45 | 0.42 | 1.09 | 0.16 | U86405 | Amphiphysin II; endocytosis and Macrophages, neurons, germ cells, signal transduction (recycling endocrine tissues synaptic vesicle components) | |
| 0.013 | 1.02 | 0.02 | 0.11 | 0.19 | 0.94 | 0.44 | U69136 | T1-cadherin, calcium-binding Thymocytes membrane glycoprotein acting as cell adhesion molecule (CAMs). | |
| 0.006 | 1.31 | 0.40 | 0.16 | 0.20 | 1.32 | 0.30 | X53176 | Integrin alpha-4; cell adhesion Lymphocytes | |
| <0.001 | 1.27 | 0.15 | 0.03 | 0.05 | 1.14 | 0.24 | X91043 | Erythrocyte band 7 integral Spleen, lung, testis, not reported in membrane protein; protein 7.2b; liver stomatin | |
| <0.001 | 1.06 | 0.06 | 0.14 | 0.12 | 1.12 | 0.15 | X15592 | CTLA-2-beta; homologue to T cells cysteine protease proregion | |
| 0.002 | 1.11 | 0.15 | 0.15 | 0.26 | 1.12 | 0.20 | X97227 | Cell surface glycoprotein CD53; Thymocytes pan-leukocyte antigen; cell membrane glycoprotein | |
| <0.001 | 1.10 | 0.20 | 0.03 | 0.05 | 1.27 | 0.19 | U43384 | Gp91phox (Cybb); phagocyte Phagocyte cytochrome b558; heterodimer comprised of gp91phox and p22phox; a flavocytochrome that mediates the transfer of electrons from NADPH to molecular oxygen in the respiratory burst oxidase | |
| 0.005 | 1.26 | 0.03 | 0.15 | 0.26 | 1.16 | 0.39 | M30440 | Potassium channel gene (MK2); T cells; myelinating Schwann cells shaker subfamily | |
| 0.002 | 0.99 | 0.29 | 0.00 | 0.00 | 1.35 | 0.35 | X52991 | Homologue of the rat T cell Cytotoxic T lymphocytes differentiation marker RT6; cell-cell signaling | |
| 0.000 | 1.37 | 0.11 | 0.00 | 0.00 | 0.97 | 0.11 | X14092 | MCSP-1 CTL serine protease 1; T lymphocytes may play a role in cytolytic lymphocyte activation | |
| 0.033 | 1.36 | 0.33 | 0.29 | 0.50 | 1.07 | 0.30 | U04269 | Interleukin-1 beta converting Monocytes and macrophages | |

-80-

| P | CR | std | CON | std | SW | std | GenBank | Description | Location |
|---|---|---|---|---|---|---|---|---|---|
| 0.015 | 1.47 | 0.47 | 0.24 | 0.41 | 1.07 | 0.06 | L16928 | enzyme (ICE); may mediate endotoxin-induced cholestatic effect of decreased hepatocellular bile salt uptake; IL-1DOWN in CR | |
| 0.027 | 1.20 | 0.13 | 0.24 | 0.34 | 0.94 | 0.44 | ET62844 | Differentiation antigen (CD22); B cells mediates B cell interactions with endothelial cells | receptor B lymphocytes, myeloid lineage cells |
| 0.046 | 1.31 | 0.39 | 0.31 | 0.50 | 0.98 | 0.18 | U49866 | Immunoglobulin-like PIRA6 (12M1); appears to activate immunoglobulin-related receptor | |
| 0.003 | 1.07 | 0.07 | 0.38 | 0.21 | 1.05 | 0.17 | X04123 | Class I recognizing receptors Subpopulation of natural killer cell involved in ability of F1 hybrid mice to reject parental H-2d bone marrow cell grafts | |
| 0.007 | 1.53 | 0.51 | 0.00 | 0.00 | 1.51 | 0.54 | U25691 | Terminal deoxynucleotidyltransferase; template-independent DNA polymerase; VDJ assembly; recombination | Earliest stage B and T cells |
| 0.005 | 1.07 | 0.45 | 0.00 | 0.00 | 1.93 | 0.62 | M23501 | Lymphocyte specific helicase; T and B cells at both the immature putative role in replication, repair, and mature stage; not in heart, liver, recombination and transcription lung, muscle, brain or kidney | |
| 0.007 | 1.08 | 0.13 | 0.20 | 0.34 | 1.11 | 0.23 | ET61471 | P500/TCA3; SIS-epsilon; small, T cells, myeloid and lymphoid cells secreted, and inducible protein; expressed more abundantly in activated mouse helper T cells than by resting T cells | |
| 0.001 | 1.10 | 0.31 | 0.00 | 0.00 | 1.41 | 0.33 | M55617 | Mast cell protease 7 (mMCP-7); Mast cells mouse mast cell tryptase 2; released when mast cells are activated | |
| | | | | | | | | Mast cell protease-4 | |

BLOOD/HORMONE/CYTOKINE/CHEMOKINE/SIGNAL TRANSDUCTION/RECEPTOR

| P | CR | std | CON | std | SW | std | GenBank | Description | Location |
|---|---|---|---|---|---|---|---|---|---|
| 0.038 | 1.06 | 0.10 | 0.30 | 0.53 | 1.15 | 0.21 | X51468 | Preprosomatostatin; precurser Macrophages; nervous system peptide cleaved to release | Peritoneal and most connective tissue |

| P | CR | std | CON | std | SW | std | GenBank | Description Location |
|---|---|---|---|---|---|---|---|---|
| 0.044 | 1.53 | 0.46 | 0.17 | 0.30 | 1.03 | 0.69 | M16762 | somatostatin which regulates T cell IFN-gamma production |
| 0.014 | 1.06 | 0.06 | 0.54 | 0.18 | 1.30 | 0.34 | X54542 | Interleukin 2 (IL-2); stimulates Helper T cells proliferation of activated T lymphocytes |
| 0.004 | 1.00 | 0.08 | 0.22 | 0.38 | 1.40 | 0.24 | X07962 | Interleukin-6; promotes B cell Some helper T cells and maturation to Ig- secreting cells; macrophages |
| 0.000 | 1.52 | 0.10 | 0.00 | 0.00 | 0.97 | 0.19 | U28404 | Interleukin 7 (IL-7); growth factor B cell progenitors helps activate T cells |
| 0.001 | 1.38 | 0.28 | 0.12 | 0.21 | 1.00 | 0.17 | X53798 | Macrophage inflammatory MIP-1alpha RL2 in liver and spleen protein-1 alpha receptor; mediates growth inhibitory effects of the chemokine |
| <0.001 | 0.99 | 0.11 | 0.07 | 0.13 | 1.25 | 0.22 | ET62976 | Macrophage inflammatory Macrophages protein-2 (MIP2); small inducible cytokine subfamily member |
| 0.015 | 1.31 | 0.23 | 0.44 | 0.35 | 1.04 | 0.13 | V00755 | Macrophage inflammatory protein Thymus, heart, spleen, and liver; to receptor 1-alpha 2; Induces lesser extent in the lung and brain mobilization of intercellular calcium; beta-chemokine; leucocyte chemoattractant |
| <0.001 | 1.21 | 0.19 | 0.11 | 0.19 | 1.10 | 0.11 | V00756 | Interferon beta (type 1); growth Ubiquitous factor; T helper cell differentiation factor; antiviral; modulates immune responses to foreign and self-antigens |
| 0.015 | 1.31 | 0.52 | 0.00 | 0.00 | 1.19 | 0.50 | M26271 | Interleukin 2 receptor; cytokine T cells receptor |
| 0.016 | 1.47 | 0.65 | 0.14 | 0.21 | 1.08 | 0.10 | M35684 | Complement receptor type 2 Late pre-B cells (CR2) |
| 0.010 | 1.22 | 0.69 | 0.05 | 0.09 | 2.15 | 0.64 | L41495 | Protein-serine/threonine kinase Blood, epithelial and CNS embryonic (pim-2); cell proliferation; highly development expressed in mitogenically stimulated (cytokines) hematopoietic cells; evokes long-term potentiation in hippocampus |

-82-

| P | CR | std | CON | std | SW | std | GenBank | Description | Location |
|---|---|---|---|---|---|---|---|---|---|
| 0.002 | 2.00 | 0.36 | 0.00 | 0.00 | 1.17 | 0.55 | ET61263 | Cytosolic tyrosine protein kinase SYK; signal transduction | Lymphopoiesis; haematopoietic cells, platelets, macrophages and neutrophils |
| <0.001 | 1.07 | 0.11 | 0.02 | 0.03 | 1.11 | 0.10 | X58995 | Calmodulin-dependent protein kinase IV; multifunctional, serine-threonine protein kinase | T cells |
| 0.002 | 1.22 | 0.42 | 0.00 | 0.00 | 1.14 | 0.13 | D30743 | Wee1 kinase; inhibits entry into mitosis by phosphorylation of the Cdc2 kinase | Lymphocytes |
| 0.044 | 1.12 | 0.26 | 0.61 | 0.27 | 1.32 | 0.28 | U36757 | Thrombin receptor (PAR-1); transmembrane G-protein coupled receptor; activated by protease cleavage; thrombin is a serine protease generated by the activation of the blood coagulation cascade following vessel injury; thrombin acts as a mitogen and apoptosis inducer. | Blood, platelets, monocytes; endothelial cells; cardiomyocytes; serine neuronal and glial cells |
| <0.001 | 1.15 | 0.13 | 0.00 | 0.00 | 1.05 | 0.17 | U36575 | T cell transcription factor NFAT1 isoform B | T cells |
| <0.001 | 1.02 | 0.16 | 0.00 | 0.00 | 1.13 | 0.15 | Z11664 | Son of sevenless 2; Ras-specific exchange factors | T cells |
| 0.002 | 1.18 | 0.17 | 0.16 | 0.27 | 1.22 | 0.25 | Z11574 | Son of sevenless 1; Ras-specific exchange factors | T cells |
| 0.026 | 0.82 | 0.47 | 0.19 | 0.34 | 1.43 | 0.39 | M36654 | Homeobox gene 2.6 (Hox-2.6) transcription factor; haematopoiesis development; | Whole embryo; in adult: blood cells, embryonic stem cells and low levels in somatic and spermatogenic cells |
| 0.034 | 1.30 | 0.84 | 0.00 | 0.00 | 1.22 | 0.24 | U10092 | Ly-49F-GE antigen; NK cell suface molecule; determinant of IL-2-activated NK cell specificity; inhibitory receptor for interaction with MHC class I | NK cell NK cells |
| 0.003 | 1.15 | 0.23 | 0.27 | 0.12 | 1.17 | 0.24 | L43567 | Antigen, B cell receptor | Blood |
| 0.007 | 1.08 | 0.13 | 0.20 | 0.34 | 1.11 | 0.23 | ET61471 | Mast cell protease 7 (mMCP-7); mast cell tryptase 2; released when mast cells are activated | Mast cells |
| 0 | 1.14 | 0.05 | 0.00 | 0.00 | 0.96 | 0.26 | ET61424 | Protein-tyrosine phosphatase | Hematopoietic tissues |

| P | CR | std | CON | std | SW | std | GenBank | Description Location |
|---|---|---|---|---|---|---|---|---|
| 0.003 | 1.31 | 0.57 | 0.00 | 0.00 | 1.63 | 0.18 | ET62920 | CC Chemokine Receptor-4; Thymus, T cells, and monocytes epsilon precursor; the protein tyrosine phosphatase epsilon (PTPepsilon) gene gives rise to two proteins: a transmembranal, receptor-like form and a cytoplasmic, non-receptor form |
| 0 | 1.04 | 0.15 | 0.13 | 0.12 | 1.16 | 0.10 | X16510 | CC Chemokine Receptor-4; Thymus, T cells, and monocytes integral membrane protein; G-protein coupled receptor; signals involve chemotaxis and calcium flux; directs cell movement in thymus; directs monocytes and lymphocytes to their target tissues |
| 0.044 | 1.12 | 0.26 | 0.61 | 0.27 | 1.32 | 0.28 | U36757 | Hox 3.3; homeobox transcription Spleen, bone marrow factor; embryogenesis; haematopoiesis |
| 0.000 | 1.31 | 0.06 | 0.00 | 0.00 | 0.98 | 0.06 | ET62839 | Thrombin receptor (PAR-1); Blood, platelets, monocytes; transmembrane G-protein coupled endothelial cells; cardiomyocytes; receptor; activated by serine neuronal and glial cells protease cleavage; thrombin is a serine protease generated by the activation of the blood coagulation cascade following vessel injury; Thrombin acts as a mitogen and apoptosis inducer. |

BLOOD: TRANSCRIPTION FACTOR

| P | CR | std | CON | std | SW | std | GenBank | Description Location |
|---|---|---|---|---|---|---|---|---|
| 0.029 | 1.07 | 0.25 | 0.18 | 0.31 | 1.77 | 0.83 | X06762 | Immunoglobulin-like receptor B lymphocytes; dendritic cells, PIRA1; activating receptor on myeloid-linage cells. murine B lymphocytes, dendritic cells, and myeloid-linage cells Hox2.3; homeobox gene; embryo Whole developing embryo; blood; development; haematopoiesis bone marrow cells; natural killer cells |
| 0.012 | 1.10 | 0.20 | 0.46 | 0.27 | 1.11 | 0.11 | U29513 | KRAB-zinc finger protein 79; Hematopoietic cells; others? Kruppel type zinc finger putative transcriptional repressor; associates with RB in vitro |

| P | CR | std | CON | std | SW | std | GenBank | Description | Location |
|---|---|---|---|---|---|---|---|---|---|
| 0.001 | 1.03 | 0.03 | 0.21 | 0.14 | 1.04 | 0.25 | ET62444 | Sox4; transcription factor in the Sox gene family with separable DNA-binding and transactivation domains | Thymus, bone marrow, and gonads |
| PRIMARY RESPONSE GENES - LIVER | | | | | | | | | |
| 0.002 | 0.91 | 0.20 | 0.22 | 0.20 | 1.15 | 0.14 | L24118 | TNF-inducible; primary response gene B94 | Liver (during development) and monocytes (postnatally) |
| 0.002 | 1.19 | 0.32 | 0.00 | 0.00 | 1.27 | 0.33 | X83601 | PTX3, entraxins; include reactive protein (CRP) and serum amyloid P component (SAP) which are prototypic acute phase reactants that serve as indicators of inflammatory reactions. | Liver, skeletal muscle and heart |
| 0.002 | 1.09 | 0.31 | 0.00 | 0.00 | 1.39 | 0.39 | M31419 | Interferon-activatable gene (204); Nucleoi mediates antimicrobial, immunomodulary and cell growth-regulatory activities of interferons; increased up to 75-fold by alpha-interferon treatment | |
| PRIMARY RESPONSE GENES - OTHER TISSUES | | | | | | | | | |
| <0.001 | 1.11 | 0.17 | 0.09 | 0.15 | 1.00 | 0.17 | D13695 | ST2L, primary response gene; specifically induced by growth stimulation; highly similar to IL1 receptor type 1 | T cells |
| 0.005 | 1.28 | 0.46 | 0.00 | 0.00 | 1.40 | 0.39 | U34245 | Fos-related antigen-1 (Fra-1) | Spleen |
| <0.001 | 1.04 | 0.04 | 0.00 | 0.00 | 1.14 | 0.21 | Y08026 | Immunity associated protein 38; inducible by malaria | Spleen |
| 0.001 | 1.35 | 0.36 | 0.01 | 0.00 | 1.23 | 0.20 | M81077 | TAL2 | T cells |
| <0.001 | 1.03 | 0.14 | 0.00 | 0.00 | 1.10 | 0.09 | U19463 | Zinc finger protein A20; activated by T cell acute lymphoblastic leukemia; helix-loop-helix DNA binding protein | Lymphocytes |
| 0.1 | 1.27 | 0.24 | 0.00 | 0.00 | 1.40 | 1.23 | L15435 | 4-1BB ligand, inflammatory response; member of the TNF | T cells |

| P | CR | std | CON | std | SW | std | GenBank | Description | Location |
|---|---|---|---|---|---|---|---|---|---|
| <0.001 | 1.18 | 0.18 | 0.00 | 0.00 | 1.03 | 0.16 | M88242 | Glucocortoid-regulated inflammatory cyclooxygenase; prostaglandin G/H synthase, putative mediator of inflammation; mRNA and protein rise dramatically in response to growth factors, cytokines, and oncogene activation; suppressed by glucocorticoid hormone | Fibroblasts and human monocytes family; important for the generation of antiviral CD8 T cell responses |
| <0.001 | 1.07 | 0.12 | 0.00 | 0.00 | 1.16 | 0.09 | L38281 | Immune-responsive gene 1 (Irg1); activated by bacterial LPS treatment | Macrophages |
| 0.001 | 1.15 | 0.32 | 0.02 | 0.03 | 1.31 | 0.28 | K02785 | Gene induced by PDGF with some homology to c-fos | Unknown |
| INTRACELLULAR TURNOVER | | | | | | | | | |
| 0.002 | 0.95 | 0.10 | 0.43 | 0.27 | 1.37 | 0.11 | X92664 | Ubiquitin-conjugating enzyme UbcM2 (E2); nonlysosomal protein degradation system; histone ubiquitination alters chromatin structure | Liver, skeletal muscle (ubiquitous) |
| 0 | 1.11 | 0.11 | 0.00 | 0.00 | 1.02 | 0.10 | X71978 | Ft1, a novel gene related to ubiquitin-conjugating enzymes; deletion leads to partial syndactyly of the limbs and thymic hyperplasia, suggesting impaired programmed cell death | |
| CHROMATIN STRUCTURE | | | | | | | | | |
| 0.028 | 1.33 | 0.95 | 0.00 | 0.00 | 1.79 | 0.49 | L04141 | Histone H1 subtype (H1e); chromatin structure | Liver (ubiquitous) |
| 0.000 | 1.74 | 0.30 | 0.00 | 0.00 | 1.08 | 0.24 | J03482 | Histone H1b; chromatin structure | Ubiquitous |
| 0.000 | 1.69 | 0.18 | 0.02 | 0.03 | 1.09 | 0.27 | ET62262 | Histone H2B; chromatin structure | Ubiquitous |
| 0.030 | 1.41 | 0.26 | 0.34 | 0.53 | 1.10 | 0.24 | ET62908 | Histone H3.2-616, and histone H2b-616; chromatin structure | Liver (ubiquitous) |
| 0.038 | 1.20 | 0.27 | 0.00 | 0.00 | 0.79 | 0.70 | U62675 | Histone H3.1-D (H3-D) and histone H4-D (H4-D) genes; chromatin structure | Liver |
| 0.006 | 1.08 | 0.12 | 0.15 | 0.18 | 1.12 | 0.40 | U62672 | | Ubiquitous |

| P | CR | std | CON | std | SW | std | GenBank | Description Location |
|---|---|---|---|---|---|---|---|---|
| 0.024 | 1.22 | 0.82 | 0.00 | 0.00 | 1.36 | 0.11 | X16495 | Histone H2A; chromatin Ubiquitous structure |
| <0.001 | 1.07 | 0.13 | 0.00 | 0.00 | 1.19 | 0.13 | U62669 | Histone H3.2-F (H3-F), histone Ubiquitous H2a.1-F (H2a-F), histone H2b-F (H2b-F); chromatin structure |
| 0.034 | 1.11 | 0.15 | 0.30 | 0.52 | 1.16 | 0.21 | X56044 | Htf9-c; structrural similarity with Liver (ubiquitous) yeast and bacterial nucleic acid-modifying enzymes; activated at the G1/S transition, maximum and S phase; down in growth arrested cells |
| 0.009 | 1.06 | 0.11 | 0.28 | 0.48 | 1.44 | 0.21 | X56690 | Homologous to Drosophila HP1 Ubiquitous during development gene; modifs chromatin, rendering heritable changes in gene expression; activates or silences genes |
| 0.025 | 1.51 | 0.35 | 0.27 | 0.47 | 0.99 | 0.36 | X92842 | SURF-6; involved in a nucleolar Nucleolus (ubiquitous) ribosome maturation; housekeeping |

CELL CYCLE / CELL DIVISION

| P | CR | std | CON | std | SW | std | GenBank | Description Location |
|---|---|---|---|---|---|---|---|---|
| 0.022 | 1.11 | 0.17 | 0.00 | 0.00 | 0.82 | 0.60 | X66285 | HC1 gene; mouse gene homologous to the E5 ORF from bovine papillomavirus type 1; transforms immortalized rodent cells. |
| 0.000 | 1.09 | 0.27 | 0.00 | 0.00 | 1.54 | 0.14 | ET62229 | Wnt10b; developmental Developing limbs, face and skin of regulation of cell growth and embryos and in adult differentiation in certain adult mammalian tissues |
| 0.003 | 1.66 | 0.58 | 0.00 | 0.00 | 1.11 | 0.22 | ET61747 | Citron; Rho (controls actin Ubiquitous structures) target protein; role in cytokinesis |
| 0.001 | 1.93 | 0.38 | 0.00 | 0.01 | 1.12 | 0.45 | Y00848 | Int-2 (FGF-3); expressed in Early embryogenesis; discrete embryonic development regions during development; not reported in adult |
| 0.002 | 1.46 | 0.17 | 0.47 | 0.20 | 1.08 | 0.17 | X61940 | Mitogen-activated protein kinase Liver parenchymal cells, vascular phosphatase (MKP- smooth muscle, others 1/3CH134/ERP1); serum growth factor-induced immediate early |

-87-

| P | CR | std | CON | std | SW | std | GenBank | Description Location |
|---|---|---|---|---|---|---|---|---|
| <0.001 | 1.08 | 0.07 | 0.00 | 0.00 | 1.05 | 0.20 | Z72000 | BTG3; negative control of cell Fibroblast, brain cycle gene; dephosphorylates MAP kinase |
| <0.001 | 1.13 | 0.11 | 0.03 | 0.05 | 1.04 | 0.16 | X07540 | C-Abl; c-Abl; a nonreceptor Liver, B cells tyrosine kinase; appears to play a role in cell cycle progression, cell proliferation and differentiation |
| 0.006 | 1.02 | 0.02 | 0.00 | 0.00 | 0.92 | 0.45 | U10440 | G1 cyclin-Cdk protein kinase Ubiquitous inhibitor p27, cell cycle; cyclin-dependent kinase inhibitor p27 (Kip1) |
| 0 | 1.08 | 0.17 | 0.00 | 0.00 | 1.29 | 0.21 | ET61628 | Phosphoinositide 3-kinase Liver (regulatory subunit p85alpha); plays critical roles in cell growth, differentiation, survival, and vesicular transport |
| 0.002 | 1.48 | 0.47 | 0.00 | 0.00 | 1.26 | 0.23 | ET61257 | Map Kinase Kinase Kinase (MEKK Ubiquitous 1) ; MEK kinases (MEKKs) are serine-threonine kinases that regulate sequential protein phosphorylation pathways involving mitogen-activated protein kinases (MAPKs), including members of the Jun kinase (JNK) family. |
| 0.002 | 1.10 | 0.41 | 0.00 | 0.00 | 1.25 | 0.22 | U85608 (was U11548) | Mitogen-activated protein kinase Liver (15 times higher in fetal than (MAPK); signal transduction; adult); ubiquitous important in cell proliferation, differentiation, and apoptosis; induced by epidermal growth factor; activation of MAPK induces c-Fos and c-Jun; CR reduces the age related decline in MAPK activation |
| 0.002 | 1.09 | 0.31 | 0.00 | 0.00 | 1.39 | 0.39 | M31419 | Interferon-activatable gene (204); Nucleoi mediates antimicrobial, |

-88-

| P | CR | std | CON | std | SW | std | GenBank | Description | Location |
|---|---|---|---|---|---|---|---|---|---|
| | | | | | | | | immunomodulary and cell growth-regulatory activities of interferons; increased up to 75-fold by alpha-interferon treatment | |
| DNA REPLICATION / REPAIR | | | | | | | | | |
| 0.029 | 1.36 | 0.37 | 0.48 | 0.34 | 1.27 | 0.24 | D13544 | Primase small (p49) subunit; cell proliferation; DNA replication | Liver (ubiquitous) |
| 0.025 | 1.24 | 0.37 | 0.45 | 0.16 | 1.14 | 0.25 | X74351 | XPAC (Xeroderma Pigmentosum group A Correcting protein); nucleotide excision DNA repair | Ubiquitous |
| 0.001 | 1.03 | 0.29 | 0.00 | 0.00 | 1.27 | 0.30 | ET62746 | Brca2 gene; familial breast cancer susceptibility gene; important in DNA double-strand break repair (DSBR) and DNA damage-induced cell-cycle checkpoint activation | Ubiquitous |
| <0.001 | 1.17 | 0.13 | 0.13 | 0.14 | 1.07 | 0.19 | X58472 | KIN17, DNA-binding, nuclear protein, upregulated in response to UV and ionizing radiation; accumulated in the nucleus of proliferating fibroblasts; overexpression inhibits progression into S phase | Ubiquitous |
| 0.009 | 1.02 | 0.03 | 0.17 | 0.14 | 0.85 | 0.37 | ET63479 | MLH1; DNA mismatch repair gene; function in mutation avoidance; cell cycle checkpoint control; cytotoxicity of various DNA-damaging agents; transcription-coupled nucleotide excision repair. | Ubiquitous |
| APOPTOSIS | | | | | | | | | |
| 0.005 | 1.07 | 0.19 | 0.33 | 0.30 | 1.36 | 0.23 | Z37110 | Cyclin G; augments apoptosis; target gene of P53 | Liver |
| 0.000 | 1.00 | 0.09 | 0.42 | 0.05 | 1.12 | 0.04 | ET63241 | Apopain precursor (LICE; YAMA protein); caspase-3; cysteine protease; mediator of | Liver, neurons, lung, kidney, spleen, lymphocytes |

-89-

| P | CR | std | CON | std | SW | std | GenBank | Description | Location |
|---|---|---|---|---|---|---|---|---|---|
| <0.001 | 1.14 | 0.13 | 0.05 | 0.09 | 1.06 | 0.11 | X58876 | Mdm2 is a P53 specific ubiquitin ligase; promotes the ubiquitination and proteasome-dependent degradation of p53; immediately after cellular stress, MDM2 ability to bind to p53 is blocked, preventing MDM2-mediated degradation, P53 levels rise causing cell cycle arrest or apoptosis | Liver |
| <0.001 | 1.12 | 0.15 | 0.00 | 0.00 | 1.08 | 0.24 | L22472 | Bax alpha; Bcl-2-family protein with pro-apoptotic activity; can form channels in lipid membranes | Liver |
| 0.001 | 1.21 | 0.28 | 0.00 | 0.00 | 1.16 | 0.22 | L31532 | Bcl-2-beta; suppresses programmed cell death | Liver |
| 0.050 | 1.25 | 0.15 | 0.47 | 0.50 | 1.01 | 0.07 | U48804 | Zn-finger protein Pw1/Peg3; activates NFkappaB; regulator of TNF response; induced during p53/c-myc-mediated apoptosis; Pw1/Peg3 with Siah1a induces apoptosis independently of p53; inhibiting Pw1/Peg3 activity blocks p53-induced apoptosis | Ubiquitous |
| 0 | 0.91 | 0.19 | 0.00 | 0.00 | 1.08 | 0.06 | ET61211 | RNA-dependent EIF-2 alpha kinase; double-stranded (ds) RNA-dependent protein kinase (PKR); key mediator of antiviral effects of interferon (IFN); active player in apoptosis | Ubiquitous |
| 0 | 1.11 | 0.11 | 0.00 | 0.00 | 1.02 | 0.10 | X71978 | Ft1, a novel gene related to ubiquitin-conjugating enzymes; deletion leads to partial syndactyly of the limbs and thymic hyperplasia, suggesting impaired programmed cell death | |

SERUM PROTEINS/SECRETED PROTEINS

| P | CR | std | CON | std | SW | std | GenBank | Description | Location |
|---|---|---|---|---|---|---|---|---|---|
| 0.000 | 1.28 | 0.19 | 0.11 | 0.19 | 0.95 | 0.09 | V00743 | Alpha-fetoprotein (AFP); main component of mammalian fetal | Liver (fetal & adult) |

| P | CR | std | CON | std | SW | std | GenBank | Description | Location |
|---|---|---|---|---|---|---|---|---|---|
| <0.001 | 1.10 | 0.09 | 0.07 | 0.12 | 1.07 | 0.16 | M16395 | Alpha-fetoprotein (AFP); main component of mammalian fetal serum; synthesized by visceral endoderm of the yolk sac and by fetal liver; blood level decreases after birth; synthesis reactivated in liver tumors | Liver (fetal & adult) |
| 0.018 | 1.14 | 0.13 | 0.38 | 0.42 | 1.30 | 0.26 | X03479 | Serum amyloid A (Saa) 3; serum protein; major acute phase protein | Liver |
| 0.049 | 1.15 | 0.64 | 0.57 | 0.18 | 1.71 | 0.35 | ET63455 | Serum amyloid A-4 protein (Saa4); a minor, normal high-density lipoprotein (HDL, apolipoprotein); acute-phase apolipoprotein; induced by trauma and inflammation; normally rapidly catabolized; degraded by secreted or cell-associated neutral proteases generated by macrophages | Epithelial cells in a variety of tissues |
| 0.008 | 1.57 | 0.50 | 0.14 | 0.25 | 1.00 | 0.25 | V00829 | Kallikrein; serine protease; generates proinflammatory kinins; processes peptides | Liver |
| 0.002 | 1.27 | 0.40 | 0.00 | 0.00 | 1.35 | 0.31 | X61597 | Kallikrein-binding protein; tissue kallikrein regulation; serine proteinase inhibitor superfamily | Liver, lung, thymus |

EXTRACELLULAR MATRIX / CELL ADHESION

| P | CR | std | CON | std | SW | std | GenBank | Description | Location |
|---|---|---|---|---|---|---|---|---|---|
| 0.002 | 1.60 | 0.32 | 0.03 | 0.05 | 1.17 | 0.41 | Z50147 | Cell adhesion regulator; extracellular matrix protein | Liver |
| 0.000 | 1.34 | 0.27 | 0.05 | 0.08 | 0.95 | 0.11 | X06115 | E-cadherin; cell-cell adhesion; cell surface glycoprotein; transmembrane protein | Liver (epithelial cells) |

| P | CR | std | CON | std | SW | std | GenBank | Description Location |
|---|---|---|---|---|---|---|---|---|
| 0.001 | 0.94 | 0.16 | 0.42 | 0.06 | 1.26 | 0.14 | ET62381 | K-cadherin/cadherin-6; present at Cerebral cortex in neonatal mice; external cell surface at cell-cell newly formed epithelium of the renal contact sites; calcium-dependent vesicle; proximal renal tubules; cell adhesion molecules CD4+ CD8+ thymocytes |
| 0.006 | 1.05 | 0.09 | 0.35 | 0.31 | 1.06 | 0.05 | U69137 | T2-cadherin; calcium-binding Thymocytes; developing testis and membrane glycoprotein; cell retina adhesion molecule |
| 0.003 | 1.08 | 0.13 | 0.09 | 0.15 | 0.99 | 0.34 | X77557 | cadherin 11(cad11); calcium- Mesoderm surrounding organs; dependent mesenchymal cell Developing somites; adhesion molecule |
| 0.004 | 1.56 | 0.22 | 0.25 | 0.29 | 1.17 | 0.34 | X67783 | Vascular cell adhesion molecule-1 Liver (VCAM-1); immunoglobulin gene superfamily; transmembrane |
| <0.001 | 1.29 | 0.29 | 0.01 | 0.03 | 1.22 | 0.19 | X66976 | Collagen alpha 1 type VIII; Epithelial,endothelial, and extracellular matrix; component mesenchymal cells in newborn of basal laminae mouse tissue |
| 0.004 | 1.37 | 0.47 | 0.00 | 0.00 | 1.32 | 0.34 | Z35166 | Collagen IV alpha 3 chain; Liver extracellular matrix; component of basal laminae |
| 0.012 | 1.08 | 0.18 | 0.30 | 0.42 | 1.51 | 0.36 | Z35168 | Collagen IV alpha 5 chain; Liver collagen; extracellular matrix |
| 0.006 | 1.11 | 0.45 | 0.00 | 0.00 | 1.42 | 0.39 | L02918 | Procollagen type V alpha 2 Liver |
| 0.001 | 0.97 | 0.11 | 0.14 | 0.25 | 1.48 | 0.29 | X66402 | Stromelysin 1; extracellular Liver, stromal cells matrix-degrading metalloproteinase |
| 0.009 | 1.30 | 0.57 | 0.00 | 0.00 | 1.46 | 0.43 | U08210 | Tropoelastin; elastic fibers in Vessel vessel walls and other tissues consist of cross-linked tropoelastin in association with several microfibrillar protein |
| <0.001 | 1.12 | 0.16 | 0.00 | 0.00 | 1.15 | 0.13 | X16490 | Plasminogen activator inhibitor 2; Liver; mainly expressed in the skin, serine protease inhibitor; bone-marrow, spleen, lung, thymus, inactivates urokinase-type and urinary bladder plasminogen activator and regulates degradation of the extracellular matrix; one form is cytoplasmic the other is |

| P | CR | std | CON | std | SW | std | GenBank | Description | Location |
|---|---|---|---|---|---|---|---|---|---|
| 0.010 | 1.21 | 0.41 | 0.32 | 0.29 | 2.11 | 0.63 | D13509 | translocated into the endoplasmic reticulum, glycosylated and secreted Pancreatitis-associated protein (PAP); C-type lectin; adhesion protein; binds laminin; may be important in liver cell differentiation/proliferation; adhesion molecule for hepatocytes | Liver (ductular cells), pancreas, small intestine |
| 0.014 | 1.31 | 0.46 | 0.13 | 0.23 | 1.66 | 0.59 | ET63188 | Fibroblast activation protein; cell-surface glycoprotein; member of the serine protease family; expressed at sites of tissue remodelling. | Fibroblasts |
| 0.017 | 1.61 | 0.70 | 0.00 | 0.00 | 1.45 | 0.59 | X75636 | Iduronato-2-sulfatase (IDS); degrades heparin sulfate and dermatan sulfate in lysosomes; deficiency causes fatal lysosomal storage disorder, mucopolysaccharidosis type II (the glycosaminoglycans heparin sulfate and dermatan sulfate accumulate); part of proteoglycans which bind, help package and store secretory molecules; function in cell adhesion and basal lamina formation | Ubiquitous |

TRANSPORT / SECRETION

| P | CR | std | CON | std | SW | std | GenBank | Description | Location |
|---|---|---|---|---|---|---|---|---|---|
| 0.010 | 1.15 | 0.14 | 0.31 | 0.37 | 1.09 | 0.16 | ET63248 | RAN binding protein 1 (RANBP1); RAN-specific GTPase-activating protein; required for nucleocytoplasmic transport of many types of cargo | Ubiquitous |
| 0.013 | 0.99 | 0.16 | 0.25 | 0.41 | 1.15 | 0.15 | D87900 | ARF3; ADP-ribosylation factor; involved in formation of coated | Ubiquitous |

-93-

| p | CR | std | CON | std | SW | std | GenBank | Description | Location |
|---|---|---|---|---|---|---|---|---|---|
| 0.001 | 1.04 | 0.07 | 0.38 | 0.16 | 1.12 | 0.12 | U19521 | Vesicle transport protein (munc-18c) | Ubiquitous vesicles |
| 0.001 | 1.12 | 0.15 | 0.43 | 0.09 | 1.06 | 0.13 | X14972 | Alpha-adaptin; adaptor complex components; link clathrin to coated vesicle receptors | Liver and brain |
| <0.001 | 1.05 | 0.07 | 0.00 | 0.01 | 1.04 | 0.17 | Z22821 | Rab23; Ras-related small GTPase; protein trafficking; regulatory elements of intracellular transport machinery; regulate vesicle docking and fusion, organelle dynamics | Liver regeneration leads to central differential regulation of some Rabs; the other cells |
| 0.003 | 1.23 | 0.28 | 0.00 | 0.00 | 1.28 | 0.45 | D29797 | Syntaxin 3A, IER transport, membrane fusion | vesicular Liver |
| <0.001 | 1.08 | 0.09 | 0.01 | 0.02 | 1.13 | 0.11 | X66449 | Calcyclin, also called S100A6; calcium binding protein; mucus secretion. | Epithelial cells and fibroblasts of liver; breast, heart, intestine, kidney, ovary, placenta, stomach, thymus, and uterus; high levels of expression in epithelial lining the gastrointestinal, respiratory and urinary tracts |
| 0.001 | 1.21 | 0.18 | 0.00 | 0.00 | 1.12 | 0.29 | U96700 | Serine proteinase inhibitor 6 (SPI6); not secreted, remains in the endoplasmic reticulum; intracellular function unclear | Lymphocytes; endothelial cells in epithelial cells; platelets |
| 0.013 | 1.10 | 0.15 | 0.00 | 0.00 | 1.05 | 0.58 | L39373 | N-acetylglucosaminyltransferase III (Mgat3); transfers the bisecting GlcNAc to the core of complex, N-linked carbohydrates | Liver |
| 0.001 | 0.97 | 0.15 | 0.48 | 0.11 | 1.08 | 0.07 | U58513 | Rho kinase (p160, ROCK-2); is a small GTPase; serine/threonine coiled-coil-forming protein kinase; downstream targets include LIM-kinase 1, which phosphorylates cofilin, an actin-depolymerizing factor; regulates actin | Rho Ubiquitously expressed except in the brain and muscle |

-94-

| P | CR | std | CON | std | SW | std | GenBank | Description | Location |
|---|---|---|---|---|---|---|---|---|---|
| 0.009 | 2.03 | 0.56 | 0.24 | 0.41 | 1.11 | 0.39 | U96724 | Phosphatidylinositol transfer protein alpha (Pitpn); cytosolic protein binds phosphatidylinositol and transfers it between membranes; mutant in this gene (the mouse vibrator mutation) causes an early-onset progressive action tremor, degeneration of brain stem and spinal cord neurons, and juvenile death. | Ubiquitous cytoskeletal reorganization; Rho activity enhances secretion; phosphorylation of myosin light chain and moesin may prevent pathologic platelet activation during atherogenesis. |
| 0.001 | 1.27 | 0.13 | 0.07 | 0.12 | 0.94 | 0.31 | X78304 | Signal recognition particle ribonucleoprotein; synthesis and translocation of secreted proteins (SRP9); | Ubiquitous cytoplasmic |
| 0.001 | 1.01 | 0.08 | 0.15 | 0.25 | 1.22 | 0.18 | ET62525 | Polypeptide N-acetylgalactosaminyltransferase-T4 (polypeptide GalNAc transferase-T4; ppGaNTase-T4; fourth member of the mammalian UDP-GalNAc; localization; transferase controls the initiation of mucin-type O-linked protein glycosylation, in which N-acetylgalactosamine is transferred to serine and threonine amino acid residues | Wide expression pattern; detected in embryonic tissues, as well as adult sublingual gland, stomach, colon, small intestine, lung, cervix, and lower levels detected in Golgi-like kidney, liver, heart, brain, spleen, 4 GalNAc and ovary |
| 0.017 | 1.07 | 0.06 | 0.25 | 0.44 | 0.97 | 0.11 | X14926 | Calreticulin; endoplasmic reticulum chaperone; also functions in calcium storage and signaling, and cell attachment; nuclear matrix component | Ubiquitous |
| 0.017 | 1.61 | 0.70 | 0.00 | 0.00 | 1.45 | 0.59 | X75636 | Iduronato-2-sulfatase (IDS); | Ubiquitous |

-95-

| P | CR | std | CON | std | SW | std | GenBank | Description | Location |
|---|---|---|---|---|---|---|---|---|---|
| TRANSLATION | | | | | | | | | |
| 0.011 | 1.04 | 0.05 | 0.29 | 0.28 | 1.12 | 0.31 | U28419 | Translation initiation factor eif-4C homologue | Ubiquitous |
| 0.000 | 1.48 | 0.24 | 0.00 | 0.00 | 1.05 | 0.08 | X57960 | Ribosomal protein L7; incorporated into 60 S subunit | Ubiquitous |
| 0.013 | 1.17 | 0.22 | 0.37 | 0.29 | 1.04 | 0.18 | M29015 | Ribosomal protein L7 (rpL7); incorporated into 60 S subunit | Ubiquitous |
| <0.001 | 1.06 | 0.05 | 0.00 | 0.00 | 1.18 | 0.25 | K02060 | Ribosomal protein L32 | Ubiquitous |
| 0.001 | 1.27 | 0.13 | 0.07 | 0.12 | 0.94 | 0.31 | X78304 | Signal recognition particle (SRP9); ribonucleoprotein; synthesis and translocation of secreted proteins | Ubiquitous cytoplasmic |
| TRANSCRIPTION | | | | | | | | | |
| 0.026 | 1.20 | 0.18 | 0.34 | 0.35 | 1.36 | 0.48 | X74040 | Mesenchyme fork head-1 (MFH-1) transcription factor | H+J509 hepatocytes |
| 0.016 | 1.32 | 0.28 | 0.31 | 0.26 | 1.08 | 0.37 | ET61028 | ARE Binding Protein (AREC3) | Many cell-types during development; muscle in adult |
| 0.005 | 1.16 | 0.04 | 0.00 | 0.00 | 0.77 | 0.46 | ET62446 | Sox12; transcription factor; Sox family plays important role in development | Developing embryos |
| 0.018 | 1.19 | 0.27 | 0.39 | 0.32 | 1.14 | 0.18 | X55781 | Pax2 transcription factor; paired box family (homologous to Drosophila segmentation genes) | Developing embryo excretory and to CNS |
| 0.032 | 1.16 | 0.18 | 0.50 | 0.35 | 1.26 | 0.09 | ET62078 | Putative transcription factor | Many locations in embryo during |

| P | CR | std | CON | std | SW | std | GenBank | Description Location |
|---|---|---|---|---|---|---|---|---|
| 0.003 | 1.06 | 0.13 | 0.48 | 0.25 | 1.31 | 0.11 | X75018 | Id4; CD44; dominant negative Embryogenesis, up-regulated regulators of bHLH transcription between day 9.5 and 13.5 of factors; differentiation in cellular gestation; adult highest expression systems including myogenesis, testis, brain and kidney; also in liver; neurogenesis and adipocytes, astrocytes, muscle cells haematopoiesis; adipocyte and others differentiation |
| 0.009 | 1.56 | 0.64 | 0.00 | 0.00 | 1.47 | 0.44 | L28167 | Zinc finger protein, the Kruppel- Liver, lens, heart, kidney, spleen, associated box (KRAB); similar brain of newborn mice to profilaggrin (expressed in differentiating epidermal cells) |
| 0.003 | 1.17 | 0.37 | 0.10 | 0.16 | 1.21 | 0.18 | U13878 | Neural-restrictive silencer factor Many nonneuronal cells and tissues (NRSF/REST); transcription factor; represses expression of neuronal genes including mAChR, SCG-10 and type II sodium channel genes; recruits mSin3 and histone deacetylase |
| <0.001 | 1.09 | 0.12 | 0.11 | 0.13 | 1.09 | 0.09 | X89264 | Zinc-finger protein Zfp-37; Liver transcription factor (putative); peroxisome proliferator responsive; contains Kruppel-associated box |
| 0.018 | 1.18 | 0.62 | 0.08 | 0.07 | 1.06 | 0.08 | U15443 | C-ros (c-ros); embryonic Neoplastic and fetal tissues development; tyrosine kinase catalytic domains; expressed in neoplastic and fetal tissues |
| 0.003 | 1.24 | 0.40 | 0.00 | 0.00 | 1.25 | 0.32 | X59251 | Hox-7; transcription factor; early Embryogenesis stage of eye developmental regulation in embryo |
| 0.001 | 1.12 | 0.27 | 0.10 | 0.18 | 1.17 | 0.12 | M28449 | Hox-1.7; homeobox; transcription Embryogenesis factor |
| 0.01 | 1.53 | 0.65 | 0.00 | 0.00 | 1.50 | 0.46 | X56182 | Myf-5; myogen factor 5; Embryonic liver and heart |

-97-

| P | CR | std | CON | std | SW | std | GenBank | Description | Location |
|---|---|---|---|---|---|---|---|---|---|
| 0.047 | 1.45 | 0.81 | 0.00 | 0.00 | 1.42 | 0.72 | X13538 | transcription factor; helix-loop-helix family | |
| 0.001 | 1.23 | 0.23 | 0.03 | 0.05 | 1.11 | 0.26 | X60034 | Hox-1.4; transcription factor | Embryonic spinal cord and adult testis |
| 0.002 | 1.27 | 0.23 | 0.00 | 0.00 | 1.14 | 0.38 | X80339 | Hox-4.9; homeobox; transcription factor | Neurogenesis |
| 0.024 | 1.56 | 0.52 | 0.00 | 0.00 | 1.49 | 0.83 | D00925 | Six1; homeobox; development of limb tendons | Skeletal and smooth muscle |
| 0.003 | 1.17 | 0.15 | 0.13 | 0.22 | 0.88 | 0.27 | X67719 | Transcription factor S-II-related protein; transcription elongation factor | Liver |
| 0.009 | 1.50 | 0.67 | 0.00 | 0.00 | 1.34 | 0.29 | X60136 | CREBcAMP-responsive-element binding protein | Ubiquitous |
| <0.001 | 1.16 | 0.03 | 0.09 | 0.15 | 1.02 | 0.07 | X80508 | Sp1; transcription factor; zinc finger protein | Ubiquitous |
| <0.001 | 1.07 | 0.06 | 0.00 | 0.00 | 0.95 | 0.13 | X76858 | Yes-associated protein (YAP65); transcription activator | Ubiquitous |
| 0.002 | 1.99 | 0.65 | 0.00 | 0.00 | 1.08 | 0.19 | Y12783 | Phi AP3, nuclear factor; DNA binding transcription factor; inactivates adjacent enhancer function; GLI-Kruppel related; cell-cycle regulated | Ubiquitous |
| | | | | | | | | Ring1B; interacts directly with the repressor domain of M33; M33 is a transcription factor implicated in mesoderm patterning in the mouse; in Drosophila, homologue genes maintain transcriptional repression of developmental genes including homeotic genes | Expression distribution not reported |
| 0.003 | 1.08 | 0.17 | 0.17 | 0.29 | 1.41 | 0.32 | X55315 | CAAT-box DNA binding protein subunit A (NF-YA) | Ubiquitous |
| 0 | 1.36 | 0.25 | 0.00 | 0.00 | 1.02 | 0.04 | X15842 | C-rel; encodes a member of the Rel/nuclear factor (NF)-kappaB family of transcriptional factors | Ubiquitous |

RNA SPLICING / PROCESSING

| P | CR | std | CON | std | SW | std | GenBank | Description | Location |
|---|---|---|---|---|---|---|---|---|---|
| 0.011 | 1.06 | 0.08 | 0.38 | 0.33 | 1.04 | 0.10 | ET63161 | Alternative splicing factor (ASF); recruits basal splicing factors during spliceosome assembly | Ubiquitous (?) |
| 0.001 | 1.04 | 0.12 | 0.15 | 0.26 | 1.07 | 0.07 | Y08260 | CPEB protein; RNA binding protein that interacts with the cytoplasmic maturation-type polyadenylation element to promote polyadenylation and translational activation | Ubiquitous |
| 0.004 | 1.14 | 0.19 | 0.00 | 0.00 | 1.02 | 0.44 | X91656 | Srp20 gene; splicing factor belonging to the highly conserved family of SR proteins; multiple roles in the regulation of constitutive and alternative splicing | Ubiquitous |
| MEMBRANE PROTEIN | | | | | | | | | |
| 0.003 | 1.08 | 0.17 | 0.00 | 0.00 | 1.47 | 0.51 | M17376 | Alpha-1-acid glycoprotein I (AGP-1); membrane protein | Liver |
| 0.001 | 1.48 | 0.19 | 0.00 | 0.00 | 0.97 | 0.37 | M75875 | MHC class I T3-d gene; H-2-d haplotype; beta-2-microglobulin associated protein; cell surface glycoprotein; class I antigen | Unknown |
| 0.036 | 1.09 | 0.10 | 0.44 | 0.38 | 1.09 | 0.23 | J03298 | Major histocompatibility complex DO beta gene | Ubiquitous |
| 0.001 | 1.76 | 0.14 | 0.01 | 0.01 | 1.02 | 0.47 | D90146 | MHC gene Q8/9d Qa-2,3 class I antigen | Ubiquitous |
| 0.001 | 1.12 | 0.29 | 0.00 | 0.00 | 1.16 | 0.18 | U06662 | 59-kd oncofetal antigen; Fetal antigen; not reported in adult antigens present on the surface tissues of all major classes of rodent tumors | |
| 0.008 | 1.07 | 0.73 | 0.00 | 0.00 | 1.73 | 0.16 | X61576 | Connexin 43; gap junction proteins; contain ion exchange channels that generate signals throughout the tissue | Liver, heart, bone, skin, etc.; Mol Carcinog 1996 Aug;16(4):203-12 |
| 0.024 | 1.41 | 0.69 | 0.00 | 0.00 | 1.45 | 0.61 | M91243 | Connexin family of gap junction (cell-to-cell channels) proteins (Cx50); likely IS lens fiber protein | Ubiquitous |

| P | CR | std | CON | std | SW | std | GenBank | Description | Location |
|---|---|---|---|---|---|---|---|---|---|
| 0.023 | 1.38 | 0.74 | 0.00 | 0.00 | 1.30 | 0.40 | X54424 | MP70 Gamma adaptin; component of adaptor; the protein complex links clathrin to transmembrane proteins in coated pits and vesicles | major Liver (ER) |
| 0.005 | 1.43 | 0.52 | 0.00 | 0.00 | 1.37 | 0.38 | U49185 | Occludin; occludin is a transmembrane protein located at tight junctions and is known to interact with other tight junction proteins | Liver |
| 0.027 | 1.28 | 0.32 | 0.60 | 0.13 | 1.43 | 0.37 | M81591 | CD10 neutral endopeptidase 24.11 (CD10/NEP); cell surface metalloproteinase; activation marker for mononuclear cells; peptide mediated signal transduction; inactivates numerous endogenous peptides in the brain, kidney, and lung in vivo | Ubiquitous |
| 0.009 | 1.06 | 0.75 | 0.00 | 0.00 | 1.93 | 0.43 | Z22216 | Apolipoprotein C2 (APOC2); required for lipolysis of triglycerides by lipoprotein lipase | Fetal liver, adult liver, intestine and peritoneal macrophages |
| 0.026 | 1.09 | 0.03 | 0.50 | 0.19 | 0.93 | 0.27 | V00834 | MHC class II H2-IE-alpha | B cells, IgE |
| 0.003 | 1.16 | 0.07 | 0.46 | 0.13 | 0.90 | 0.21 | X68061 | Beta-2-microglobulin; membrane protein; 45,000 MW HLA antigen | Liver (hepatocytes) |
| 0.002 | 0.99 | 0.29 | 0.00 | 0.00 | 1.38 | 0.36 | M23383 | Glucose transporter 2 | Liver |
| 0.038 | 1.24 | 0.60 | 0.22 | 0.28 | 1.08 | 0.12 | ET63259 | Cea14 gene (carcinoembryonic antigen family members); unknown function; member of the immunoglobulin superfamily | Many cea genes expressed in fetal liver |
| 0 | 1.08 | 0.15 | 0.18 | 0.17 | 1.32 | 0.16 | ET63260 | Cea15 gen (carcinoembryonic antigen family members); unknown function; member of the immunoglobulin superfamily | Many cea genes expressed in fetal liver |
| 0.001 | 1.04 | 0.04 | 0.22 | 0.12 | 1.16 | 0.28 | ET63261 | Cea16 gene (carcinoembryonic antigen family members); liver | Many cea genes expressed in fetal liver |

| P | CR | std | CON | std | SW | std | GenBank | Description | Location |
|---|---|---|---|---|---|---|---|---|---|
| METABOLISM/ENERGY GENERATION | | | | | | | | | |
| 0.003 | 0.97 | 0.05 | 0.18 | 0.26 | 1.34 | 0.33 | U00932 | Glutamine; fructose-6-phosphate amidotransferase (GFAT); rate-limiting enzyme in hexosamine synthesis | Liver |
| 0.016 | 1.10 | 0.16 | 0.33 | 0.41 | 1.24 | 0.21 | D21826 | CMP-N-acetylneuraminic acid hydroxylase; ganglioside expression | Liver |
| 0.001 | 1.08 | 0.31 | 0.00 | 0.00 | 1.58 | 0.32 | X98792 | Prostaglandin synthase cyclooxygenase Down in CR | Liver |
| 0.002 | 1.23 | 0.28 | 0.01 | 0.02 | 1.42 | 0.41 | M29395 | Orotidine-5'-monophosphate decarboxylase; conversion of orotidine 5'-monophosphate to UMP; UMP biosynthetic pathway. | Liver |
| <0.001 | 1.01 | 0.03 | 0.01 | 0.01 | 1.11 | 0.10 | X72959 | Nat3 gene for N-acetyltransferase | Liver |
| 0.001 | 1.10 | 0.13 | 0.06 | 0.10 | 1.20 | 0.30 | J04947 | ACE; angiotensin-converting enzyme | Liver |
| <0.001 | 1.16 | 0.02 | 0.04 | 0.08 | 1.02 | 0.13 | L09105 | Glucose phosphate isomerase | Ubiquitous |
| 0.039 | 1.39 | 0.70 | 0.00 | 0.00 | 1.56 | 0.80 | X14489 | Thymidylate synthase (TS) | Ubiquitous (all proliferating cells) |
| 0.005 | 1.37 | 0.42 | 0.00 | 0.00 | 1.54 | 0.51 | U34071 | Alpha-galactosidase A; lysosomal enzyme | Ubiquitous (most cases) |
| 0.004 | 1.08 | 0.20 | 0.51 | 0.17 | 1.11 | 0.03 | J00355 | Alpha-amylase-1 (Amy-1A); glycogen digestion and mobilization | Liver and salivary glands |
| 0 | 1.10 | 0.09 | 0.29 | 0.05 | 1.20 | 0.19 | X07888 | 3-hydroxy-3-methylglutaryl coenzyme A reductase; key regulatory enzyme for cholesterol biosynthesis. | Liver |
| ION CHANNELS / PUMP | | | | | | | | | |
| 0.000 | 1.42 | 0.20 | 0.00 | 0.00 | 0.95 | 0.14 | ET61677 | Epithelial sodium channel alpha subunit | Liver |
| 0.044 | 1.33 | 0.44 | 0.35 | 0.34 | 1.07 | 0.33 | U03723 | AKR voltage-gated potassium-channel (KCNA4) | Ubiquitous |
| 0.039 | 1.24 | 0.23 | 0.45 | 0.34 | 1.09 | 0.31 | M30441 | Potassium channel gene (MK3) | Ubiquitous |
| 0 | 1.27 | 0.05 | 0.13 | 0.13 | 1.07 | 0.13 | ET61590 | Putative capacitative calcium | Brain, kidney, heart and lung, no trp |

| P | CR | std | CON | std | SW | std | GenBank | Description | Location |
|---|---|---|---|---|---|---|---|---|---|
| | | | | | | | | entry channel (Trp6); involved in calcium entry secondary to activation of receptors coupled by the Gq class of G protein. | message detected in liver |
| 0.002 | 1.19 | 0.35 | 0.06 | 0.10 | 1.43 | 0.34 | ET61440 | Trp-related protein 3; cation channel; essential for agonist-activated capacitative Ca2+ entry; putative subunits of CCE channels | Endothelium |
| NUCLEAR RECEPTORS | | | | | | | | | |
| 0.016 | 1.38 | 0.67 | 0.07 | 0.13 | 1.28 | 0.26 | X07751 | Thyroid hormone receptors | Liver |
| 0.003 | 1.24 | 0.31 | 0.13 | 0.16 | 1.23 | 0.26 | X04435 | Glucocorticoid receptor | Liver |
| <0.001 | 1.20 | 0.23 | 0.03 | 0.05 | 1.11 | 0.15 | X74134 | COUP-TF1; steroid hormone receptor; transcription factor | Liver |
| 0.01 | 1.13 | 0.12 | 0.00 | 0.00 | 1.21 | 0.61 | X76653 | Apolipoprotein regulatory protein1 (ARP-1); member of the COUP-family of steroid hormone orphan receptors | Liver, lung, kidney |
| 0.049 | 0.90 | 0.55 | 0.35 | 0.04 | 1.40 | 0.43 | X59411 | Androgen receptor | Sex glands, liver, brain, pituitary, heart, kidney, bone |
| CYTOKINE/GROWTH FACTOR | | | | | | | | | |
| 0.003 | 1.10 | 0.23 | 0.11 | 0.18 | 1.61 | 0.45 | X57413 | Transforming growth factor-beta2 (TGFbeta2); cell proliferation | Liver stellate cells |
| 0.012 | 1.11 | 0.23 | 0.35 | 0.32 | 1.05 | 0.06 | ET62118 | Keratinocyte growth factor/fibroblast growth factor-7 precursor (mKGF) | Liver epithelial cells |
| 0.001 | 1.38 | 0.08 | 0.00 | 0.00 | 0.94 | 0.40 | Z29532 | Follistatin; binds and inactivates activin; up-regulated by mediators of inflammation; control of the inflammatory cascade | Liver |
| 0.000 | 1.41 | 0.13 | 0.11 | 0.17 | 0.94 | 0.25 | M28587 | Alpha leukocyte interferon (MuIFN-alpha A); inhibition of cell proliferation | Ubiquitous |
| 0.015 | 1.31 | 0.23 | 0.44 | 0.35 | 1.04 | 0.13 | V00755 | Interferon beta (type 1); growth factor; T helper cell | Ubiquitous |

-102-

| P | CR | std | CON | std | SW | std | GenBank | Description Location |
|---|---|---|---|---|---|---|---|---|
| 0.002 | 1.10 | 0.10 | 0.48 | 0.17 | 1.15 | 0.16 | M30644 | Basic fibroblast growth factor Endothelial cells (vascular); pituitary; (Fgfb; FGF-2); potent trophic peritoneal mesothelial cells; effects on neurons, glia and astrocytes; leukocytes endothelial cells; mitogen, differentiation and survival factors, angiogenic factor; levels are markedly elevated after liver injury; stimulates hepatocyte proliferation and migration at the wound front; differentiation factor; antiviral; modulates immune responses to foreign and self-antigens |
| <0.001 | 1.12 | 0.04 | 0.09 | 0.15 | 1.12 | 0.21 | X53257 | NT-3 gene for neurotrophin-3; Liver parenchymal cells, olfactory secreted protein; binds high bulb, cerebellum, septum, affinity receptor trk C; postnatal hippocampus; thymus, heart, development? diaphragm, pancreas, spleen, kidney, adrenal |
| 0.001 | 1.07 | 0.07 | 0.10 | 0.17 | 1.13 | 0.23 | J00424 | Interferon-beta Liver |
| 0.001 | 1.10 | 0.11 | 0.02 | 0.02 | 1.18 | 0.38 | U96386 | Activin beta E subunit, member Liver of TGF-beta superfamily |
| 0.005 | 1.24 | 0.41 | 0.00 | 0.00 | 1.28 | 0.39 | X69620 | Inhibin beta-B subunit; activins Liver are dimeric proteins, members of the transforming growth factor beta (TGF-beta) gene superfamily, consisting of beta-subunits of inhibin (betaA and betaB) |
| 0.003 | 2.25 | 0.40 | 0.18 | 0.32 | 1.19 | 0.55 | X99572 | C-fos-induced growth factor Endothelial cells, expressed in many (FIGF); secreted dimeric protein tissues (including liver) during member of the platelet-derived embryonic development growth factor/vascular endothelial growth factor (PDGF/VEGF) family; mitogenic and morphogenic activity on fibroblasts. |
| 0.003 | 1.11 | 0.10 | 0.26 | 0.26 | 1.17 | 0.22 | U07982 | Preproendothelin-1; induces Vascular wall (endothelial cells. |

-103-

SIGNAL TRANSDUCTION

| P | CR | std | CON | std | SW | std | GenBank | Description | Location |
|---|---|---|---|---|---|---|---|---|---|
| 0.004 | 1.30 | 0.21 | 0.30 | 0.29 | 1.09 | 0.19 | | smooth muscle alpha-actin arterial smooth muscle cells, select expression; induced in stellate epithelial cells); kidney, lung, and endothelial cells of liver after trachea; liver (nonparenchymal cells, injury predominately in sinusoidal endothelial cells) | |
| 0.041 | 1.19 | 0.25 | 0.41 | 0.28 | 1.13 | 0.40 | X82320 | Stathmin; phosphoprotein participating in relay and integration of intracellular signaling pathways involved in control of cell proliferation, differentiation, and other activities | cytosolic Ubiquitous |
| 0.002 | 1.46 | 0.17 | 0.47 | 0.20 | 1.08 | 0.17 | X13664 | N-ras; key component of growth signaling pathways; transmits membrane receptor kinase signals; GTP-binding switch protein | Liver, wide tissue distribution |
| 0.004 | 1.17 | 0.48 | 0.00 | 0.00 | 1.09 | 0.15 | X61940 | Mitogen-activated protein kinase phosphatase 1/3CH134/ERP1); serum growth factor-induced immediate early gene; dephosphorylates MAP kinase | Liver parenchymal cells, vascular (MKP- smooth muscle, others |
| 0.001 | 1.09 | 0.27 | 0.10 | 0.15 | 1.23 | 0.22 | S45828 | Serine/threonine/tyrosine protein kinase (Nek1); related to the NIMA (a protein kinase which controls initiation of mitosis in Aspergillus nidulans) | All organs examined |
| 0.013 | 1.02 | 0.03 | 0.00 | 0.00 | 1.02 | 0.57 | U65313 | Ras-GTPase-activating domain binding protein (G3BP); essential for Ras signaling | SH3- Ubiquitous |
| 0.003 | 1.09 | 0.11 | 0.03 | 0.05 | 1.25 | 0.45 | M63658 U38501 | G protein beta-subunit G protein alpha i1 subunit | Brain, liver, blood cell Liver; cerebral cortex; pancreatic acinar cells; white adipose tissue; others |
| 0.010 | 1.32 | 0.28 | 0.24 | 0.41 | 1.06 | 0.11 | AA162130 | SUMO-1 activating enzyme | Ubiquitous |

-104-

| P | CR | std | CON | std | SW | std | GenBank | Description Location |
|---|---|---|---|---|---|---|---|---|
| 0.003 | 1.11 | 0.50 | 0.00 | 0.00 | 2.16 | 0.55 | ET63005 | subunit 1 (SAE1); one subunit of a dimer that conjugates SUMO-1 (a small ubiquitin-like protein) to other proteins; SUMO-1 modification of I Kappa B alpha takes place on the same residues used for ubiquitination; blocks NF kappa B-dependent transcriptional activation |
| 0.001 | 0.97 | 0.15 | 0.48 | 0.11 | 1.08 | 0.07 | U58513 | Phospholipase C gamma 1; Ubiquitous; hepatocytes; hepatic substrate of many growth factor stellate cells; vascular smooth receptor and nonreceptor tyrosine muscle; vascular endothelial cells kinases; produces second messenger molecules that are elements of signal transduction pathways related to cell proliferation. Rho kinase (p160, ROCK-2); Rho Ubiquitously expressed except in the is a small GTPase; brain and muscle serine/threonine coiled-coil-forming protein kinase; downstream targets include LIM-kinase 1, which phosphorylates cofilin, an actin-depolymerizing factor; regulates actin cytoskeletal reorganization; Rho activity enhances secretion; phosphorylation of myosin light chain and moesin may prevent pathologic platelet activation during atherogenesis. |
| 0.002 | 1.48 | 0.47 | 0.00 | 0.00 | 1.26 | 0.23 | ET61257 | Map kinase kinase kinase (MEKK 1); serine-threonine kinase; regulates sequential protein phosphorylation pathways involving mitogen-activated protein kinases (MAPKs), including some Jun kinases |
| 0.002 | 1.10 | 0.41 | 0.00 | 0.00 | 1.25 | 0.22 | U85608 (was | Mitogen-activated protein kinase Liver (15 times higher in fetal than (MAPK); signal transduction; adult); ubiquitous |

-105-

| P | CR | std | CON | std | SW | std | GenBank | Description Location |
|---|---|---|---|---|---|---|---|---|
| 0.004 | 1.09 | 0.08 | 0.12 | 0.20 | 0.89 | 0.32 | U11548 | important in cell proliferation, differentiation, and apoptosis; induced by epidermal growth factor; activation of MAPK induces c-Fos and c-Jun; CR reduces the age related decline in MAPK activation |
| | | | | | | | ET62570 | Mad homologue Smad5; Liver downstream component in the TGF-beta family signaling cascade, transduces signals from the cell surface to the nucleus; participates in regulation of gene expression; essential in left/right isomerism and liver development; essential for angiogenesis |
| 0.001 | 1.24 | 0.31 | 0.00 | 0.00 | 1.18 | 0.27 | D50095 | Histamine H1 receptor; GTP-binding protein-coupled receptor; coupled to phosphoinositide turnover-calcium mobilization signaling pathway; regulates insulin-like growth factor I expression and cell proliferation; modulates IL-6 action; regulates physiological functions in neurons; regulates transport of thyroxine into hepatocytes Liver, brain, spleen (ubiquitous) |
| 0 | 1.09 | 0.16 | 0.00 | 0.00 | 1.15 | 0.13 | U60330 | Ki antigen (PA28 gamma); cell Liver, neurons, broad tissue proliferation; the interferon-distribution gamma (IFN-gamma)-inducible PA 28 activator complex enhances the generation of class I binding peptides by altering the cleavage pattern of the proteosome |
| 0.002 | 1.09 | 0.31 | 0.00 | 0.00 | 1.39 | 0.39 | M31419 | Interferon-activatable gene (204); Nucleoi mediates antimicrobial, |

-106-

| P | CR | std | CON | std | SW | std | GenBank | Description | Location |
|---|---|---|---|---|---|---|---|---|---|
| MEMBRANE RECEPTORS | | | | | | | | | |
| 0.029 | 1.11 | 0.15 | 0.33 | 0.38 | 1.39 | 0.49 | U40189 | Pancreatic polypeptide/neuropeptide Y/peptide YY receptor (NPYR-D); G protein-coupled immunomodulary and cell growth-regulatory activities of interferons; increased up to 75-fold by alpha-interferon treatment | Liver |
| 0 | 1.00 | 0.15 | 0.02 | 0.03 | 1.15 | 0.10 | U58367 | Neuropeptide Y receptor Y5/Y6/Y2b (referred to as both Y5 and Y6 in literature); designated as Y6 in literature); (NPY-Y6); (neuropeptide Y is an important regulator of energy balance in mammals through its orexigenic, antithermogenic, and insulin secretagogue actions; expressed abundantly in the central nervous system); NPY receptors mediate a variety of physiological responses including feeding and vasoconstriction | Neurons, vascular smooth muscle |
| 0.027 | 1.12 | 0.15 | 0.31 | 0.34 | 0.95 | 0.32 | X76295 | Melanocortin 5 receptor; G- protein-coupled receptor; stimulates adenylyl cyclase | Widely expressed |
| 0.020 | 1.89 | 0.60 | 0.00 | 0.00 | 1.29 | 0.82 | ET61559 | Bradykinin B1 subtype receptor; G protein-coupled membrane bound; T-kininogen modulation during acute phase protein synthesis | Liver (ubiquitous) |
| 0.013 | 2.14 | 0.64 | 0.17 | 0.16 | 1.38 | 0.69 | X99581 | Chemokine receptor; stromal cell-derived factor/pre-B growth stimulating factor; seven transmembrane domain receptor | primary Liver and bone marrow |
| 0.001 | 1.46 | 0.18 | 0.38 | 0.22 | 0.98 | 0.10 | ET61693 | Leptin receptor (OB-R); | Lung, liver, muscle, brain; |

-107-

| P | CR | std | CON | std | SW | std | GenBank | Description | Location |
|---|---|---|---|---|---|---|---|---|---|
| | | | | | | | | transmembrane receptor | developing bone, mesenchyme, notochord and liver (Am J Clin Nutr 1999 Jan;69(1):18-21) |
| 0.000 | 1.52 | 0.10 | 0.00 | 0.00 | 0.97 | 0.19 | U28404 | Macrophage inflammatory protein-1 alpha receptor; mediates growth inhibitory effects of the chemokine | MIP-1alpha RL2 in liver and spleen |
| 0.017 | 1.10 | 0.20 | 0.48 | 0.29 | 1.12 | 0.12 | U57612 | CD44; receptor for hyaluronan; cell surface glycoprotein; hyaluronan clearance from the blood; involved in lymphocyte homing and activation; | Liver, central nervous system, lung, liver epidermis, and pancreas |
| <0.001 | 1.24 | 0.25 | 0.00 | 0.00 | 1.28 | 0.24 | M86441 | BEK fibroblast growth factor receptor (BEK FGF receptor, FGF-2), membrane-spanning tyrosine kinase; activated by three members of the FGF family; activation causes the foregut endoderm to develop into the liver | Li+ J520 liver parenchymal cells and others |
| <0.001 | 1.04 | 0.05 | 0.00 | 0.00 | 1.13 | 0.20 | U56734 | Member of the macrophage mannose receptor type C (calcium dependent) lectin family; critical for processes ranging from cell adhesion to antigen presentation; gene family includes macrophage mannose, the phospholipase A2, and the DEC 205 receptors; | Widespread tissue distribution; fetal liver; chondrocytes in cartilaginous regions of the embryo endothelialized sites; |
| 0.002 | 1.17 | 0.15 | 0.06 | 0.11 | 1.27 | 0.38 | X06368 | Macrophage colony-stimulating factor-1 (CSF-1) receptor | Liver |
| 0.001 | 1.13 | 0.15 | 0.02 | 0.03 | 1.21 | 0.34 | X83933 | Ryanodine receptor type 2; form ER; Ca2+ channels in the membrane of the ER; intracellular calcium release channels controlling cytosolic calcium levels. | cardiac muscle; neurons; most excitable cells; liver |
| 0.003 | 1.19 | 0.38 | 0.00 | 0.00 | 1.23 | 0.31 | x57349 | Transferrin receptor; cell surface | Liver |

-108-

| P | CR | std | CON | std | SW | std | GenBank | Description Location |
|---|---|---|---|---|---|---|---|---|
| <0.001 | 0.98 | 0.26 | 0.00 | 0.00 | 1.10 | 0.03 | X84896 | glycoprotein; cell growth; binds the major serum iron-transport protein, transferrin, and mediates cellular iron uptake |
| | | | | | | | | P2X purinergic receptor (P2XR) Liver; ubiquitous channels bind extraacellular ATP and mediate Ca(2+) influx |
| 0 | 1.09 | 0.16 | 0.00 | 0.00 | 1.15 | 0.13 | U60330 | Ki antigen (PA28 gamma); cell Liver, neurons, broad tissue proliferation; the interferon-distribution gamma (IFN-gamma)-inducible PA 28 activator complex enhances the generation of class I binding peptides by altering the cleavage pattern of the proteosome |

CYTOSKELETON

| P | CR | std | CON | std | SW | std | GenBank | Description Location |
|---|---|---|---|---|---|---|---|---|
| 0.022 | 2.47 | 0.20 | 0.00 | 0.00 | 1.60 | 1.35 | X05640 | NF-M gene for middle-molecular- Epithelial cells (mainly liver and brain) mass neurofilaments (like keratins) |
| 0.006 | 1.07 | 0.19 | 0.40 | 0.23 | 1.09 | 0.10 | ET62211 | Formin; reorganization of the Ubiquitous cytoskeleton, cytokinesis, stress fiber formation, and transcriptional activation of the serum response factor |
| 0.033 | 1.42 | 0.83 | 0.00 | 0.00 | 1.41 | 0.51 | X57377 | Myosin heavy chain gene; novel CNS, cephalic ganglia, and spinal ganglia; IId skeletal myosin heavy chain gene expressed in fat-storing cells (FSC, lipocytes, or Ito cells) of regenerating liver |
| 0.012 | 1.06 | 0.07 | 0.38 | 0.26 | 1.22 | 0.32 | ET61336 | Nonmuscle myosin heavy chain CNS; IId skeletal myosin heavy chain IIB; cell motility gene expressed in fat-storing cells (FSC, lipocytes, or Ito cells) of regenerating liver |
| 0.001 | 1.62 | 0.35 | 0.00 | 0.00 | 1.12 | 0.31 | M91602 | Myosin light chain 2; contractile fat-storing cells (FSC, lipocytes, or protein Ito cells) of regenerating liver; muscle |
| 0.000 | 1.90 | 0.15 | 0.00 | 0.00 | 0.97 | 0.35 | V00830 | Epidermal keratin subunit; Liver (bile duct epthelium, epithelial |

-109-

| P | CR | std | CON | std | SW | std | GenBank | Description Location |
|---|---|---|---|---|---|---|---|---|
| 0.001 | 0.97 | 0.15 | 0.48 | 0.11 | 1.08 | 0.07 | U58513 | intermediate filament protein; cells) maintenance of epidermal cell shape and resistance to mechanical trauma Rho kinase (ROCK-2); (Rho is a Ubiquitously expressed except in the small GTPase; serine/threonine brain and muscle protein kinase); Rho activity enhances secretion; phosphorylation of myosin light chain |
| 0.038 | 0.97 | 0.47 | 0.49 | 0.02 | 1.32 | 0.20 | ET61218 | Microtubule-associated protein 4 Most cell types including liver (MAP4); co-localizes with microtubules; expressed during developmental; likely involved in differentation |

TUMOR SUPRESSORS/ANTI-TUMOR FACTORS

| P | CR | std | CON | std | SW | std | GenBank | Description Location |
|---|---|---|---|---|---|---|---|---|
| 0.006 | 1.12 | 0.23 | 0.35 | 0.30 | 1.33 | 0.19 | X97719 | Friend-virus-susceptibility-1 gene (Fv1); prevents or delays spontaneous or experimentally induced viral tumors |
| 0.029 | 1.77 | 1.69 | 0.00 | 0.00 | 3.00 | 0.39 | X74671 | Neurofibromatosis type 2 gene; Ubiquitous tumor supressor gene; cytoskeleton-membrane linker; mutant leads to CNS tumors |
| 0 | 0.91 | 0.19 | 0.00 | 0.00 | 1.08 | 0.06 | ET61211 | RNA-dependent EIF-2 alpha Ubiquitous kinase; double-stranded (ds) RNA-dependent protein kinase (PKR); key mediator of antiviral effects of interferon (IFN); active player in apoptosis |

FUNCTION UNKNOWN

| P | CR | std | CON | std | SW | std | GenBank | Description Location |
|---|---|---|---|---|---|---|---|---|
| 0 | 1.23 | 0.24 | 0.00 | 0.00 | 1.13 | 0.16 | X96737 | Synaptobrevin-like gene (SYBL1); Ubiquitous housekeeping gene; X-linked; inactivated on one X in every female cell, and also inactive on the Y of male cells |
| 0.007 | 1.35 | 0.59 | 0.00 | 0.00 | 1.21 | 0.22 | ET62791 | WW domain binding protein 6; Uncharacterized WW domain is a globular protein |

-110-

| P | CR | std | CON | std | SW | std | GenBank | Description | Location |
|---|----|----|----|----|----|----|---------|-------------|----------|
| | | | | | | | | domain that is involved in mediating protein-protein interaction and that ultimately participates in various intracellular signaling events; WW domain mediates protein-protein interaction by binding proline-rich modules in ligands. | |

APPENDIX B

| Low-Hi-Low p value | CR-ave. | std | Cont-ave | std | Sw-ave | std | GenBank | Name/Description | Tissue |
|---|---|---|---|---|---|---|---|---|---|
| 0.001 | 0.77 | 0.20 | 1.84 | 0.06 | 0.73 | 0.28 | M95599 | Homeobox-containing protein (Hox-1.11) | Most abundant in 12-day-old embryos and progressively decreases during further embryonic development. |
| 0.001 | 0.54 | 0.04 | 1.85 | 0.27 | 0.91 | 0.28 | X58196 | Mouse H19 gene: The H19 gene produces an abundant stage of developmentally regulated transcript in normal tissues of embryos. It is subject to transcriptional regulation by parental imprinting, which results in the maternally inherited gene being expressed and the paternally inherited gene being repressed. | It is expressed at the blastocyst of development, and accumulates to high levels in endodermal and mesodermal origin After birth the gene is expressed in all tissues except skeletal muscle. A muscle specific isoform has also been cloned |
| 0.002 | 0.89 | 0.23 | 2.14 | 0.46 | 0.79 | 0.05 | X99807 | Selenoprotein P: covalently bound 8-12 selenocysteine residue. Its concentration is sensitive to the selenium status of the animal. Its function is unknown. | Liver, testis, brain, gut, and hematopoietic cells |
| 0.005 | 1.17 | 1.26 | 4.28 | 0.80 | 0.75 | 0.16 | J04953 | Gelsolin: a Ca2+- and polyphosphoinositide 4,5-bisphosphate (PIP2)1-regulated actin filament severing and capping protein that is implicated in actin remodeling in growing and in apoptotic cells | Ubiquitous |
| 0.044 | 0.68 | 0.78 | 1.96 | 0.53 | 0.33 | 0.58 | L23971 | Fragile X mental retardation syndrome protein (Fmr1) (mouse homologue): Fragile X Mental Retardation Syndrome is the most common form of hereditary mental retardation, and is caused by defects in the FMR1 gene. FMR1 is an RNA-binding protein and the syndrome results from lack of | Brain |

-112-

| Low-Hi-Low p value | CR-ave. | std | Cont-ave | std | Sw-ave | std | GenBank | Name/Description Tissue |
|---|---|---|---|---|---|---|---|---|
| | | | | | | | | expression of FMR1 or expression of a mutant protein that is impaired in RNA binding. The specific function of FMR1 is not known |
| Not reported in liver, muscle, brain, blood: | | | | | | | | |
| 0.032 | 0.18 | 0.31 | 11.84 | 8.02 | 0.00 | 0.00 | L02241 | Mouse protein kinase inhibitor Testis specific (testicular isoform): inhibitor protein of the cAMP-dependent protein kinase. This isoform of PKI is reported found only in testis |
| 0.017 | 1.24 | 1.37 | 4.54 | 1.85 | 0.16 | 0.26 | D89901 | High-glycine tyrosine keratin type Hair II.3 |
| Blood, T and B cells | | | | | | | | |
| 0 | 0.77 | 0.12 | 2.89 | 0.34 | 1.23 | 0.42 | X14061 | Beta-globin complex DNA for γ, Blood bh0, bh1, b1 and b2 genes, bh2 and bh3 pseudogenes: |
| 0.004 | 0.29 | 0.27 | 3.06 | 1.00 | 0.98 | 0.37 | X53247 | EN-7: [has 100% seq homology T, B and myeloid hemopoietic with RAS-related C3 botulinum cells substrate 2 (Rac2)]: a member of the ras gene superfamily. mRNA expression is restricted to the cells of hemopoietic lineages, mRNA levels increase with the terminal differentiation of hemopoietic cells into granulocytes. |
| 0.008 | 0.79 | 0.13 | 2.15 | 0.61 | 0.94 | 0.18 | U09010 | Mannose-binding protein A (Mbl1):a Blood serum protein, a member of a family of collagenous lectins (collectins), that activates the complement system after binding to glycoconjugates found on the surface of microorganism |
| 0.022 | 0.72 | 0.05 | 2.55 | 0.95 | 1.21 | 0.38 | M22531 | Mouse complement C1q B chain: Macrophages Mouse complement component C1q |

-113-

| p value | Low-Hi-Low CR-ave. | std | Cont-ave | std | Sw-ave | std | GenBank | Name/Description | Tissue |
|---|---|---|---|---|---|---|---|---|---|
| | | | | | | | | is a serum glycoprotein which consists of six A chains, six B chains and six C chains. | |
| Energy Metabolism / Biosynthesis | | | | | | | | | |
| 0.006 | 0.85 | 0.15 | 2.57 | 0.75 | 0.90 | 0.26 | Y00309 | Lactate dehydrogenase-A (LDH-A) | Liver, muscle |
| 0.018 | 0.97 | 0.15 | 2.87 | 1.18 | 0.73 | 0.24 | X02520 | Lactate dehydrogenase A4 isoenzyme | Liver, muscle |
| 0.008 | 0.92 | 0.13 | 2.22 | 0.64 | 0.84 | 0.14 | J05277 | Hexokinase(HK): catalyzes the first step in glucose metabolism, that is, the conversion of glucose to glucose-6-phosphate (G6P) | Liver, muscle |
| 0.047 | 0.92 | 0.07 | 2.10 | 0.88 | 0.79 | 0.33 | X58426 | Hepatic triglyceride lipase: an important enzyme that is involved in the metabolism of chylomicrons, intermediate density lipoproteins, and high density lipoproteins | Liver |
| 0.001 | 0.00 | 0.00 | 43.66 | 12.59 | 1.17 | 1.77 | U84207 | CTP:phosphocholine cytidylyltransferase: Phosphatidylcholine (PC) is the most abundant eukaryotic phospholipid and serves critical structural and cell-signaling functions. CTP:phosphocholine cytidylyltransferase (CT) is the rate-limiting enzyme in the CDP-choline pathway of PC biosynthesis, which is utilized by all tissues and is the sole or major PC biosynthetic pathway in all non-hepatic cells | Ubiquitous |
| Extracellular Matrix | | | | | | | | | |
| 0.009 | 0.83 | 0.17 | 2.32 | 0.67 | 1.02 | 0.22 | M18194 | Fibronectin (FN): an extracellular matrix protein, is involved in the adhesion and migration of hematopoietic cells, found in many | Ubiquitous ? |

-114-

| Low-Hi-Low p value | CR-ave. std | Cont-ave std | Sw-ave std | GenBank | Name/Description | Tissue |
|---|---|---|---|---|---|---|
| *Protein Turn-Over / Transport / Processing* | | | | | | |
| 0 | 0.83 | 0.02 3.40 | 0.25 1.13 | 0.38 | | extracellular matrices as well as being abundant plasma proteins. The plasma isoforms of fibronectin, which are synthesized in the adult by liver hepatocytes, differ from those derived from most other cells and tissues due to alternative mRNA splicing | |
| 0 | 0.73 | 0.12 2.11 | 0.33 0.98 | 0.06 | ET61037 | Polyubiquitin: Ubiquitin is an omnipresent protein found in all eukaryotes so far analysed. It is involved in several important processes, including protein turnover, chromosome structure and stress response | Ubiquitous |
| 0.001 | 0.00 | 0.00 16.01 | 3.18 2.78 | 3.98 | X70303 | Proteasome subunit MC3 (alpha type): The proteasome is a multisubunit 20 S proteinase complex involved in ubiquitin-dependent and -independent intracellular protein metabolism. | Ubiquitous |
| | | | | | D87899 | ADP-ribosylation factor 2 (ARF2) ADP-ribosylation factors (ARFs) are a family of small GTP-binding proteins that are involved in the formation of coated transport vesicles for protein secretion through the endoplasmic reticulum and Golgi vesicular trafficking system | Ubiquitous? |
| 0.063 | 0.81 | 0.17 3.06 | 1.71 1.01 | 0.29 | D78645 | Glucose-regulated protein 78 | Liver, adipose, brain, heart, kidney, lung, spleen, muscle, small intestine. |

| Low-Hi-Low p value | CR-ave. std | Cont-ave std | Sw-ave std | GenBank | Name/Description | Tissue |
|---|---|---|---|---|---|---|
| Signal Transduction | | | | | | |
| 0.004 | 1.05 0.32 | 2.48 0.57 | 0.83 0.09 | M13964 | Stimulatory G protein of adenylate cyclase, alpha chain: component signal transduction systems. | Ubiquitous |
| Transcription Factor | | | | | | |
| 0.037 | 0.94 0.10 | 2.14 0.85 | 0.82 0.24 | X57638 | Peroxisome proliferator activated receptor alpha: is activated by a diverse class of rodent hepatocarcinogens that causes proliferation of peroxisomes | Liver |

APPENDIX C

| Low-Low-Hi p value | CR-ave | std | Cont-ave | std | SW-ave | std | GenBank | Name/Description | Tissue |
|---|---|---|---|---|---|---|---|---|---|
| 0.013 | 5.61 | 9.71 | 5.11 | 4.87 | 40.81 | 18.89 | X04591 | Brain creatine kinase B: The creatine brain kinase-B (CKB) enzyme is proposed to have a pivotal role in the regeneration of ATP in the nervous system. | brain |
| 0.013 | 1.48 | 1.77 | 1.09 | 0.94 | 4.52 | 1.34 | M61705 | Intestinal alkaline phosphatase (IAP); a membrane-bound metalloenzyme catalysing cleavage of inorganic phosphate nonspecifically from a wide variety of phosphate esters. | intestine, (kidney) |
| 0.015 | 0.00 | 0.00 | 0.01 | 0.01 | 15.52 | 8.36 | D78353 | Eosinophil peroxidase; is one of the blood (eosinophils) granule enzymes in the eosinophil-specific granules and is distinct from myeloperoxidase. | |
| 0.001 | 1.12 | 1.18 | 0.77 | 0.66 | 6.74 | 1.50 | M12930 | Erythropoietin; The glycoprotein produced in the kidney or hormone erythropoietin regulates the liver of adult and the liver level of oxygen in the blood by of fetal or neonatal modulating the number of circulating mammals erythrocytes. | |
| 0 | 0.17 | 0.29 | 0.15 | 0.14 | 9.80 | 2.34 | J05149 | Insulin receptor (IR) | ubiquitous |
| 0.009 | 0.00 | 0.00 | 0.00 | 0.01 | 7.52 | 3.82 | U65586 | Telomeric protein mTRF1; a telomere repeat binding factor packages the long tandem arrays of the double-stranded TTAGGG sequence motif in mammalian telomeres. | ubiquitous |
| 0.016 | 0.00 | 0.00 | 0.01 | 0.01 | 34.54 | 20.11 | X14897 | Fos B; a nuclear protein of 338 amino acids presenting a 70% homology with c-fos, whose expression is activated during G0/G1 transition. Similar to c-fos, fos B protein plays a role in control of gene expression. | ubiquitous |

| Low-Low-Hi p value | CR-ave | std | Cont-ave | std | SW-ave | std | GenBank | Name/Description Tissue |
|---|---|---|---|---|---|---|---|---|
| 0.005 | 0.98 | 0.98 | 0.66 | 0.56 | 3.62 | 1.12 | X66225 | Retinoid X receptor-gamma (mRXR- ubiquitous (one isoform in gammal); a kind of nuclear receptors adrenals, kidney, and of retinoids which play a liver; another in brain and fundamental role in regulating normal lungs; both are expressed cell proliferation and differentiation. strongly in brain and The retinoid X receptors (RXRs) muscle) regulate gene expression by forming transcriptionally active heterodimeric RAR(the retinoic acid receptors)/RXR or homodimeric RXR/RXR complexes on DNA. |
| 0.023 | 2.31 | 3.18 | 1.84 | 1.63 | 16.67 | 9.38 | X54239 | Evx1 protein; A murine even-skipped embryos (eve) homologue. During embryogenesis, Evx 1 shows a biphasic expression pattern. The early and late transcription pattern is compatible with a role of Evx 1 in specifying posterior positional information along the embryonic axis and in specifying neuronal cell fates within the differentiating neural tube. |
| 0.006 | 0.00 | 0.00 | 0.00 | 0.00 | 55.35 | 24.84 | X70800 | Wnt-11 protein; The Wnt gene family embryos (truncus encodes a set of signalling arteriosus, somites at the molecules, thought to play an medial junction of the important role in key processes of dermatome and the embryonic development. WNT11 has myotome, and limb bud possible roles in the development of mesenchyme) skeleton, kidney and lung. |
| 0.039 | 1.10 | 0.18 | 0.44 | 0.57 | 4.73 | 3.06 | X99796 | Tsx; a gene of unknown function tetis that was shown to be expressed specifically in the testis. It locates 3' form the Xist gene which involves in the X inactivation. |

| Low-Low-Hi p value | CR-ave | std | Cont-ave | std | SW-ave | std | GenBank | Name/Description | Tissue |
|---|---|---|---|---|---|---|---|---|---|
| 0.043 | 0.00 | 0.00 | 0.01 | 0.02 | 15.23 | 11.16 | X14770 | Rds protein/peripherin; photoreceptor disc membrane-associated glycoprotein involved in retinal degeneration slow. It is 92.5% identical to the sequence of the bovine photoreceptor-cell protein peripherin. It may function as an adhesion molecule for stabilization of the outer segment discs. | a eye? |
| 0 | 0.99 | 1.04 | 0.68 | 0.59 | 15.29 | 2.39 | X57302 | Hepatitis virus MHV-A59 defective interfering (DI) RNA; RNA of defective-interfering virus formed earlier in infection, can mediate homologous interference. | ? |

APPENDIX D

| Hi-Hi-Low p value | CR-ave | std | CONT-ave | std | Swiched-ave | std | GenBank | Name/Description tissue |
|---|---|---|---|---|---|---|---|---|
| 0 | 1.42 | 0.20 | 1.17 | 0.30 | 0.04 | 0.07 | AF009414 | SOX11; Sox genes, which encode ubiquitous transcription factors related by a DNA-binding motif termed the HMG box, are known to have diverse roles in vertebrate differentiation and development. SOX11 was suggested a role in neuronal maturation and an additional role in tissue modelling during development. |
| 0.041 | 1.01 | 0.43 | 1.21 | 0.25 | 0.38 | 0.23 | L40156 | surfactant protein D (Sftp4); Surfactant protein-D (SP-D) is a collectin found also in heart, stomach, associated with surfactant in the lung, and kidney but not in brain SP-D has also been functionally characterized as an opsonin for diverse microorganisms and a chemoattractant for phagocytic cells. |
| 0.013 | 1.02 | 0.10 | 1.26 | 0.17 | 0.54 | 0.29 | D86176 | Phosphatidylinositol 4-phosphate 5-highly expressed in the kinase-alpha; the type I brain and testis, but barely phosphatidylinositol- 4-phosphate 5-detectable in the liver and kinase (PI4P5K) have been identified as skeletal muscle one of the cytosolic components required for ATP-dependent, Ca2+-activated secretion. |
| 0.032 | 1.16 | 0.33 | 1.31 | 0.27 | 0.61 | 0.07 | Z36293 | Sialoadhesin; Sialoadhesin is a expressed strongly by macrophage-restricted adhesion macrophages in lymphoid molecule of 185 kDa that mediates sialic and haemopoietic tissues acid-dependent binding to cells. |

APPENDIX E

| Hi-Low-Low p value | CR-ave | std | CONT-ave | std | Switched-ave | std | GenBank | Name/Description | Tissue |
|---|---|---|---|---|---|---|---|---|---|
| 0.001 | 3.65 | 0.92 | 0.32 | 0.10 | 1.10 | 0.33 | D83262 | Neuronal glutamate transporter EAAT4: induces high-affinity uptake of L-glutamate that is dependent on external Na+. | Brain (neurons) |
| 0.014 | 2.73 | 0.31 | 0.63 | 1.09 | 0.42 | 0.52 | X90778 | Histone H2B | testis-specific |
| 0.017 | 2.25 | 0.34 | 0.79 | 0.74 | 0.51 | 0.50 | M96760 | rod outer segment membrane protein 1 (Rom1): Rom-1 and peripherin are related retina-specific integral membrane protein localized to the photoreceptor disk rim, where they may act jointly in the photoreceptor disk biogenesis. | eye? |
| 0.018 | 7.93 | 4.23 | 0.00 | 0.00 | 1.16 | 1.25 | X14971 | alpha-adaptin (A): Adaptins are components of the adaptor complexes which link clathrin to receptors in coated vesicles. The alpha-adaptins, which are found exclusively in endocytic coated vesicles | brain and liver |
| 0.02 | 7.76 | 4.74 | 0.00 | 0.00 | 0.00 | 0.00 | D49429 | PW29: calcium binding protein with strongly oligoproline motif, a mouse homolog of Mcd1pS.c./Rad21S.p., has been implicated in sister chromatid cohesion. | expressed in the testis, brain, kidney and heart |
| 0.022 | 10.70 | 6.08 | 0.00 | 0.00 | 1.38 | 1.61 | M55617 | mast cell protease-4: a secretory granule serine protease of the peritoneal connective tissue mast cells (CTMC). | connective tissue |
| 0.023 | 1.78 | 0.51 | 0.84 | 0.63 | 0.21 | 0.31 | AF013253 | preprocortistatin (Cort): Cortistatin is a 14-residue putative neuropeptide with structural similarity to somatostatin and is expressed predominantly in cortical GABAergic interneurons. Administration of cortistatin into the brain ventricles specifically enhances slow-wave sleep, presumably by antagonizing the effects of acetylcholine on cortical excitability. | brain (cerebral cortex and hippocampus) |

| Hi-Low-Low p value | CR-ave | std | CONT-ave | std | Switched-ave | std | GenBank | Name/Description | Tissue |
|---|---|---|---|---|---|---|---|---|---|
| 0.032 | 2.12 | 0.81 | 0.73 | 0.61 | 0.37 | 0.39 | U02982 | secretogranin III (SgIII): an acidic chromogranin/secretogranin-like protein of pituitary-specific unknown function that is present in the storage vesicles of many neuroendocrine cells. | brain- and pituitary-specific |
| 0.033 | 1.70 | 0.28 | 0.70 | 0.52 | 0.54 | 0.45 | U39818 | tuberin (TSC2): the tuberous sclerosis 2 (TSC2) gene product, which contains an activity that specifically stimulates the intrinsic GTPase activity of Rap1a and may acts as a presumed tumor-suppressor. | ubiquitous |
| 0.037 | 21.18 | 14.98 | 0.00 | 0.00 | 0.00 | 0.00 | D17407 | U2af1-rs1(SP2); encodes a protein with significant similarity to U2 small nuclear ribonucleoprotein auxiliary factor small subunits, an essential mammalian splicing factor; an endogenous imprinted gene on the proximal region of chromosome 11. This gene is transcribed exclusively from the unmethylated paternal allele, while the methylated maternal allele is silent. | Ubiquitous |
| 0.038 | 16.26 | 11.58 | 0.00 | 0.00 | 0.00 | 0.00 | X72862 | Beta-3-adrenergic receptor; a member of the super-family of G protein-coupled receptors; in mouse plays a role in the control of cAMP accumulation and may be involved in the control of energy expenditure in fat tissue. | mainly expressed in mouse brown and white adipose tissues |
| Transcription Factor | | | | | | | | | |
| 0.007 | 2.57 | 0.46 | 0.70 | 0.71 | 0.41 | 0.52 | L10409 | Fork head related protein (HNF-3 beta): in addition to its known functions as transcriptional activators in adult liver, play a role in body axis formation, neural tube plate and gut patterning and definitive endoderm formation during gastrulation. | Adult liver, embyonic node, floor |

| Hi-Low-Low p value | CR-ave | std | CONT-ave | std | Switched-ave | std | GenBank | Name/Description | Tissue |
|---|---|---|---|---|---|---|---|---|---|
| 0.007 | 36.94 | 12.40 | 0.00 | 0.00 | 6.27 | 10.87 | X86368 | Transcription factor FKH-2: a member of the "winged helix" or "forkhead" transcription factor family; expression patterns of the fkh-2 gene and HNF-3 beta, are overlapping in early stages of gestation. | Expressed in embryos and becomes restricted to the midbrain |
| 0 | 12.24 | 3.07 | 0.00 | 0.00 | 0.80 | 1.39 | X61754 | Heat shock transcripton factor 2; binds to the heat shock element (HSE). | Ubiquitous |
| 0.001 | 4.43 | 0.96 | 0.00 | 0.00 | 1.05 | 0.77 | L77247 | Zinc finger protein (kid-1); a putative renal transcription factor; regulation during ontogeny and in response to ischemia and toxic injury | Kidney and eye |
| 0.024 | 16.08 | 10.27 | 0.00 | 0.00 | 0.00 | 0.00 | X92592 | Fkh-5 (also known as Mf3 and TWH); a member of the 'winged helix' or 'forkhead' transcription factor gene family | Specifically expressed in the developing central nervous system |
| 0.007 | 36.92 | 17.87 | 0.13 | 0.22 | 0.00 | 0.00 | U66620 | SWI/SNF complex 60 KDa subunit (BAF60a); mammalian homologue of yeast SWI/SNF complex; also referred to as BRG1-associated factors (BAFs); facilitates the function of transcriptional activators by opposing chromatin-dependent repression of transcription, and (in mamals) is likely dedicated to developmentally distinct functions. | Ubiquitous |
| 0.005 | 1.95 | 0.59 | 0.87 | 0.26 | 0.22 | 0.17 | U83148 | NFIL3/E4BP4 transcription factor; nuclear factor regulated by IL-3/adenovirus E4 promoter binding protein in a distinct growth factor-regulated signaling pathway that is responsible for the survival of early B-cell progenitors | Blood |

Cell Growth/Cycle

| Hi-Low-Low p value | CR-ave | std | CONT-ave | std | Switched-ave | std | GenBank | Name/Description | Tissue |
|---|---|---|---|---|---|---|---|---|---|
| 0 | 14.42 | 3.83 | 0.00 | 0.00 | 0.00 | 0.00 | L25602 | Bone morphogenetic protein 2 (BMP-2); pleiotropic functions range from extraskeletal and skeletal organogenesis to bone generation and regeneration; structurally related to transforming growth facto-beta s, activins, and inhibins | Ubiquitous |
| 0.004 | 2.97 | 0.78 | 0.34 | 0.60 | 0.33 | 0.58 | D89080 | Fibroblast growth factor 10 (FGF10): has expressed important roles in mediating mesenchymal-epithelial cell interactions during embryogenesis. In particular, Fgf10 is predicted to function as a regulator of brain, lung and limb development, prostatic growth and development and so on. | relatively abundantly in embryos and the lung, and at much lower levels in brain and heart |
| 0.002 | 14.09 | 4.67 | 1.12 | 1.93 | 0.00 | 0.00 | M30903 | B lymphocyte kinase (blk); a Src family tyrosine kinase specific to B lymphoid cells | Blood (specifically expressed in the B cell lineage) |
| 0.007 | 4.14 | 1.40 | 0.00 | 0.00 | 1.09 | 1.14 | X59398 | Tyrosine kinase receptor of the PDGFR/CSF1R family (Flt-3); involved in development and function of various cell lineages; unidentified ligand in placenta, gonads and hematopoietic and nervous systems. | various adult tissues including gonads and brain, and in hematopoietic cells |
| 0.008 | 1.64 | 0.34 | 0.00 | 0.00 | 0.71 | 0.62 | U22399 | Cdk-inhibitor p57KIP2 (KIP2); a potent, tight-binding inhibitor of several G1 cyclin/Cdk complexes; and is suggested to be involved in decisions to exit the cell cycle during development and differentiation.. | High-Cdk expression level in skeletal muscle, heart, brain, lungs, and eye |
| Extracellular Matrix | | | | | | | | | |
| 0.023 | 24.61 | 5.47 | 0.00 | 0.00 | 7.30 | 12.64 | M32136 | alpha-1 type IX collagen (COL9A1); structural component of the extracellular matrix of connective tissues | a ubiquitous |

| Hi-Low-Low p value | CR-ave | std | CONT-ave | std | Switched-ave | std | GenBank | Name/Description | Tissue |
|---|---|---|---|---|---|---|---|---|---|
| 0.035 | 2.93 | 1.06 | 0.64 | 1.10 | 0.81 | 0.21 | U43541 | s-laminin (also called laminin beta 2): a muscle homologue of the B1 (beta 1) chain of the widely distributed basal lamina (BL) glycoprotein, laminin. It may affect postsynaptic differentiation. | |
| DNA respair | | | | | | | | | |
| 0.039 | 14.29 | 8.65 | 0.00 | 0.00 | 2.67 | 3.79 | L26320 | FLap endonuclease-1 (FEN-1): an enzyme which functions in double-strand break repair flap resolution; it specifically cleaves DNA flap strands that terminate with a 5' single-stranded end; in addition to endonuclease activity, FEN-1 has a 5'-3' exonuclease activity which is specific for double-stranded DNA. | Ubiquitous |

APPENDIX F

| Low-Hi-Hi p value | CR-ave | CR-std | Cont-ave | Cont-std | SW-ave | SW-std | GenBank | Name/Description | Tissue |
|---|---|---|---|---|---|---|---|---|---|
| 0.005 | 0.46 | 0.08 | 1.07 | 0.27 | 1.22 | 0.14 | L11333 | Mouse carboxyesterase; serine-dependent enzymes | Predominantly in male livers |
| 0.049 | 0.51 | 0.45 | 1.18 | 0.06 | 1.06 | 0.14 | M74149 | Creatine kinase B; plays an important role in buffering ATP and ADP levels in tissues which have intermittently high and fluctuating energy demands | liver, brain, skeletal muscle, heart, intestines |
| 0.014 | 0.56 | 0.06 | 1.16 | 0.25 | 1.27 | 0.27 | M17122 | Complement 4b-binding protein (C4b-binding protein);an abundant oligomeric plasma glycoprotein which controls the activation of the complement cascade through the classical pathway | Liver |
| 0.02 | 0.30 | 0.39 | 1.16 | 0.32 | 1.38 | 0.34 | U36393 | TFEB; a member of the microphthalmia-TFE (MiT) subfamily of basic helix-loop-helix leucine zipper (bHLH-ZIP) transcription factors. | the Liver, brain, skeletal muscle, heart, spleen, lung, kidney, testis |
| 0.025 | 0.58 | 0.11 | 1.09 | 0.31 | 1.28 | 0.25 | D70849 | Zic3; encodes a zinc finger protein, is expressed in the developing matured central nervous system in a highly restricted manner.It's the vertebrate homologue of Drosophila odd-paired, which may play an essential role in parasegmental subdivision and in visceral mesoderm development. | Restricted in the cerebellum at or the adult stage. |
| 0.046 | 0.50 | 0.21 | 1.37 | 0.35 | 1.49 | 0.57 | D37837 | 65-kDa macrophage protein; is phosphorylated specifically in LPS-stimulated murine macrophages. a murine homologue of human L-plastin, recently identified as a novel transformation-induced polypeptide of neoplastic human cells. Its function is implicated in macrophage activation by LPS. | cytosolic Hemopoietic cells |

-126-

| Low-Hi-Hi p value | CR-ave | CR-std | Cont-ave | Cont-std | SW-ave | SW-std | GenBank | Name/Description | Tissue |
|---|---|---|---|---|---|---|---|---|---|
| 0.01 | 0.27 | 0.13 | 1.55 | 0.51 | 1.39 | 0.35 | U04268 | Mouse stem cell antigen Sca-2 precursor; a member of the Ly-6 family, a group of small cysteine-rich cell surface proteins that are anchored in the membrane by a glycosyl-phosphatidylinositol moiety. | Early thymic precursor and mature peripheral B cells (not mature thymocytes and peripheral T cells) |
| 0.018 | 0.51 | 0.05 | 1.20 | 0.24 | 1.37 | 0.40 | D38580 | Vomeronasal secretory protein (VNSP I);secretory protein, member of the lipocalin superfamily | Specifically expressed in vomeronasal and posterior glands of the nasal septum, the ducts of which open into the lumen of the vomeronasal organ |
| 0.024 | 0.27 | 0.08 | 1.03 | 0.07 | 1.48 | 0.67 | M27501 | Protamine 2: the predominant nuclear proteins of mammalian spermatozoa, is regulated during germ cell development | Testis-specific |

APPENDIX G 208 known genes: 2-fold or greater in CR vs. Cont at old and young age

| GenBank | Description | Location |
|---|---|---|
| Transcription Factor / Nuclear Receptor | | |
| Y00850 | Zinc finger protein 2 (Zfp2); Mkr-2; differentiation and/or maintenance of neurons | Brain (Central and peripheral neurons) |
| X63963 | Paired box protein (Pax-6); transcription factor | Developing CNS |
| X06762 | Homeo box B7 (Hoxb7); transcription factor; embryonic development; haematopoiesis; | Developing embryo; blood; bone marrow cells; natural killer cells |
| X74040 | Homeo box A9 (Hoxa9); transcription factor | Embryogenesis |
| X59251 | Homeo box msh-like 1 (Msx1); transcription factor; early stage of eye developmental regulation in embryo | Embryogenesis |
| Z67747 | Zinc finger protein 62 (Zfp62); a member of a multigene family encoding Zn mediated nucleic acid binding proteins | Embryonic development and Skeletal, cardiac muscle, and spleen in adult |
| M36516 | Zinc finger protein 28 (Zfp28); a member of a multigene family encoding Zn mediated nucleic acid binding proteins | Embryonic development, testes in adult |
| U48721 | Zinc finger protein 60 (Zfp60); a member of a multigene family encoding Zn mediated nucleic acid binding proteins; Kruppel associated boxes; associated with transcriptional control | Expressed transiently during muscle differentiation |
| X04435 | Glucocorticoid receptor 1 (Grl1); energy balance; substrate uptake; liver | Liver |
| X74134 | Nuclear receptor subfamily 2, group F member 1 (Nr2f1); COUP-TF1; orphan steroid hormone receptor; transcription factor | Liver |
| D00925 | Transcription elongation factor A 1(Tcea1); transcription elongation factor | Liver |
| X89264 | Zinc finger protein 37 (Zfp37); putative transcription factor; peroxisome proliferator responsive | Liver |
| X56182 | Myogen factor 5 (Myf5); transcription factor | Liver and heart (embrionic) |

208 known genes: 2-fold or greater in CR vs. Cont at old and young age

| GenBank | Description | Location |
|---|---|---|
| X76653 | Nuclear receptor subfamily 2, group F member 2 (Nr-2f2); apolipoprotein regulatory protein 1; member of the COUP-family of steroid hormone orphan receptors | Liver, lung, kidney |
| L24118 | Tumor necrosis factor induced protein 2 (Tnfip2); putative transcription factor | Liver; monocytes |
| U36575 | Nuclear factor of activated T cells, cytoplasmic 2 (Nfatc2); T cell transcription factor isoform | Lymphocytes |
| U19463 | Tumor necrosis factor induced protein 3 (Tnfip3); putative helix-loop-helix transcription factor activated in T-cell acute lymphoblastic leukemia | Lymphocytes |
| U19463 | Tumor necrosis factor induced protein 3 (Tnfip3); putative helix-loop-helix transcription factor activated in T-cell acute lymphoblastic leukemia | Lymphocytes |
| ET61028 | Sine oculis-related homeobox 1 homologue (Drosophila) (Six1); AREC3 | Many cell-types during development |
| U13878 | RE1-silencing transcription factor (Rest); transcription factor; represses expression of neuronal genes; | Many nonneuronal cells and tissues |
| Y12293 | Forkhead box F2 (Foxf2); transcription factor; a developmental regulator in embryonic development | Mesodermal tissues and embryonic: central nervous system, eye, ear, and limb bud |
| X60034 | Homeo box D1 (Hoxd1); transcription factor; neurogenesis | Neurogenesis |
| ET63177 | Pax-4 (Pax4); a paired-box transcription factor that plays an important role in the development of pancreatic beta/delta cells; role in endocrine cell development | Pancreatic islet endocrine progenitor cells |
| M81077 | T-cell acute lymphocytic leukemia 2 (Tal2); putative basic helix-loop-helix transcription factor activated in T-cell acute lymphoblastic leukemia | T cells |
| X72697 | Meiosis-specific XMR (Xmr); transcriptional activator function? | Testis; lymphoid cell lineages; nuclei of spermatocytes, early in the prophase of the first meiotic division, and later becomes concentrated in the XY nuclear subregion |
| X76858 | E4F transcription factor 1 (E4f1); DNA binding transcription factor | Ubiquitous |

208 known genes: 2-fold or greater in CR vs. Cont at old and young age

| GenBank | Description | Location |
|---|---|---|
| X15842 | Reticuloendotheliosis (Rel); c-rel: member of the Rel/nuclear factor (NF)-kappaB family of transcriptional factors | Ubiquitous |
| X60136 | Trans-acting transcription factor 1 (Sp1); transcription factor; component of some hepatic glucose response elements | Ubiquitous |
| X80508 | Yes-associated protein, 65 kDa (Yap); transcription activator | Ubiquitous |
| ET61461 | G-protein coupled receptor; poorly characterized | Unknown |

Translation / Splicing / RNA Processing Factors

| GenBank | Description | Location |
|---|---|---|
| Y08260 | Cytoplasmic polyadenylation element binding protein (Cpeb); RNA binding protein that promotes polyadenylation and translational activation | Ubiquitous |
| X91656 | Splicing factor arginine/serine-rich 3 (Sfrs3); splicing factor belonging to the highly conserved family of SR proteins; regulation of constitutive and alternative splicing | Ubiquitous |
| U28419 | Translation initiation factor eif-4C homologue | Ubiquitous |

*Signal Transduction / Cell Cycle and Growth*

| GenBank | Description | Location |
|---|---|---|
| L28756 | Gonadotropin releasing hormone receptor (Gnrhr); G-protein-coupled receptor; activates MAPK cascades | Brain (anterior pituitar), reproductive organs |
| Z31663 | Activin A receptor, type 1B (Acvr1b); serine/threonine kinase receptor; a downstream transducer of activin signals | Brain (cerebral cortex, olfactory tubercle, and hippocampus) |
| X66118 | Glutamate receptor, ionotropic, kainate 1 (Grik1) | Brain (CNS) |
| L41495 | Proviral integration site (Pim2); serine/threonine kinase 2; cell proliferation; mitogen stimulated; long-term potentiation in hippocampus | Brain (CNS), Immune and epithelial cells |
| Z72000 | B-cell translocation gene 3 (Btg3); negative control of cell cycle | Brain, fibroblast |

208 known genes: 2-fold or greater in CR vs. Cont at old and young age

| GenBank | Description | Location |
|---|---|---|
| X79082 | Eph receptor A7 (Epa7); developmental kinase 1; member of receptor tyrosine kinase family | Brain, testes and spleen |
| Z27088 | Relaxin (Rln); insulin gene family; remodeling of collagen | Brain, uterus, prostate gland, pancreas and kidney |
| X58287 | Protein tyrosine phosphatase, receptor-type, M (Ptprm) | Capillaries in developing neural tissue, lung; |
| ET61628 | Phosphatidylinositol 3-kinase regulatory subunit, polypeptide 1 (p85alpha) (Pik3r1); role in cell growth, differentiation, survival, and vesicular transport | Liver |
| V00829 | kallikrein 6 (Klk6); a member of multigene subfamily of serine protease that act on a diverse number of substrates,including several growth factors and extracellular matrix glycoproteins and proteinases; | Liver |
| Z22821 | Rab23; Ras-related small GTPase; protein trafficking; central regulatory elements of the intracellular transport machinery; regulate vesicle docking and fusion, organelle dynamics | Liver |
| M25513 | Guanine nucleotide binding protein, alpha transducing 1 (Gnat1) | Liver and others |
| M63658 | Guanine nucleotide binding protein beta 4 (Gnb4) | liver, brain, blood cell |
| U38501 | Guanine nucleotide binding protein, alpha inhibiting 1 (Gnai1) | Liver; cerebral cortex; pancreatic acinar cells; white adipose tissue; others |
| D30743 | Wee1 homologue (S. pombe) (Wee1); inhibits entry into mitosis by phosphorylation of the Cdc2 kinase | Lymphocytes |
| ET61263 | Spleen protein kinase (Syk); signal transduction | Lymphopoiesis; haematopoietic cells, platelets, macrophages and neutrophils |
| Z48757 | Intestinal tyrosine kinase; protein tyrosine kinase | Mammary gland and intestine |
| ET61665 | Discs-large tumor suppressor homologue (dlgh1); important role in the localization and function of glutamate receptors and K(+) channels | Neurons; epithelial cells |
| ET61399 | G protein alpha olfactory subunit; sensory transduction | Olfactory epithelium |
| M14537 | Acetylcholine receptor beta (Acrb) | Skeletal muscle |

208 known genes: 2-fold or greater in CR vs. Cont at old and young age

| GenBank | Description | Location |
|---|---|---|
| X92523 | Calpain 3 (Capn3); intracellular calcium-dependant cysteine proteinase; tissue specific myofibrogenesis, modifies ryanodine/receptor Ca2+ release channel | Skeletal muscle |
| Z11574 | Son of sevenless 1, homologue 1 (Drosophila) (Sos1); Ras-specific exchange factor | T cells |
| Z11664 | Son of sevenless 2 homologue 2 (Drosophila) (Sos2); Ras-specific exchange factor | T cells |
| U10440 | Cyclin-dependent kinase inhibitor 1B (P27) (Cdkn1b); cell cycle | Ubiquitous |
| ET61257 | MAP kinase kinase kinase (Map3k1); serine-threonine kinase; regulates sequential protein phosphorylation pathways involving mitogen-activated protein kinases (MAPKs) | Ubiquitous |
| S45828 | NIMA-related expressed kinase (Nek1) | Ubiquitous |
| U65313 | Ras-GTPase-activating protein SH3-domain binding protein 2(G3bp2-pending); essential for Ras signaling; | Ubiquitous |
| ET62740 | Ankyrin 3 (Ank3); implicated in Na(+) channel clustering and activity; neuronal axons | Wide distribution |

*Hormone/Growth Facotr/Cytokine/Chemokine*

| | | |
|---|---|---|
| X07962 | Interleukin 7 (IL-7); growth factor | B cell progenitors |
| U66201 | Fibroblast growth factor homologous factor 1 (FGF-1); nervous system development and function | Brain, skeletal muscle and other |
| U66204 | Fibroblast growth factor homologous factor 4 (FHF-4); involved in nervous system development and function | Brain (CNS) |
| X99572 | C-fos-induced growth factor (FIGF); secreted dimeric protein member of the platelet-derived growth factor/vascular endothelial growth factor (PDGF/VEGF) family; mitogenic and morphogenic activity on fibroblasts. | Endothelial cells, expressed in many tissues (including liver) during embryonic development |
| J00424 | Interferon-beta | Liver |
| X07751 | Thyroid hormone receptors | Liver |
| ET62118 | Keratinocyte growth factor/fibroblast growth factor-7 precursor (mKGF) | Liver epithelial cells |

-132-

208 known genes: 2-fold or greater in CR vs. Cont at old and young age

| GenBank | Description | Location |
|---|---|---|
| X57413 | Transforming growth factor-beta2 (TGFbeta2); cell proliferation | Liver stellate cells |
| ET62976 | Macrophage inflammatory protein receptor 1-alpha 2; Induces mobilization of intercellular calcium; beta-chemokine; leucocyte chemoattractant | Liver, brain, thymus, heart, spleen |
| X53798 | Small inducible cytokine subfamily, member 2 (Scyb2) | Macrophages |
| V00428 | Lysozyme; signaling molecule for mast cells which respond with histamine secretion | Macrophages, paneth cells (located in duodenal crypts) |
| ET61471 | Mast cell protease 7 (mMCP-7); mouse mast cell tryptase 2; released when mast cells are activated | Mast cells |
| U28404 | Macrophage inflammatory protein-1 alpha receptor; mediates growth inhibitory effects of the chemokine | MIP-1alpha RL2 in liver and spleen |
| U58367 | Neuropeptide Y receptor Y5/Y6/Y2b (referred to as both Y5 and Y2b, has now been designated as Y6 in literature); (NPY-Y6); neuropeptide Y is an important regulator of energy balance in mammals through its orexigenic, antithermogenic, and insulin secretago | Neurons, vascular smooth muscle cells |
| U10092 | Killer cell lectin-like receptor, subfamily A, member 6 (Klra6); Ly-49F; NK cell surface antigen; determinant of IL-2-activated NK cell specificity; inhibitory receptor for interaction with MHC class I proteins | NK cells |
| M31419 | Interferon-activatable gene (204); mediates antimicrobial, immunomodulary and cell growth-regulatory activities of interferons; increased up to 75-fold by alpha-interferon treatment | Nucleoi |
| X04725 | Preproinsulin gene I | Pancreas and islets |
| X04724 | Preproinsulin gene II | Pancreas and islets |
| M92416 | Fibroblast growth factor (Fgf6); Fgf6 is the only known member of the FGF family whose expression is restricted to the muscle cell lineage during development | Skeletal muscle |
| X58995 | Calmodulin-dependent protein kinase IV; multifunctional, serine-threonine protein kinase | T cells |
| V00756 | Interferon beta (type 2) | T cells |
| M26271 | Interleukin 2 receptor; cytokine receptor | T cells |

208 known genes: 2-fold or greater in CR vs. Cont at old and young age

| GenBank | Description | Location |
|---|---|---|
| D13695 | Lymphocyte antigen 84 (Ly84); signal transduction protein 2 | T cells |
| M28587 | Alpha leukocyte interferon (MuIFN-alpha A); inhibition of cell proliferation | Ubiquitous |
| U49866 | killer cell lectin-like receptor, subfamily A, member 3 (Klra3); interact with MHC class I (MHC-I) molecules on target cells | natural killer cell |

*DNA Replication / Repair / Apoptosis*

| | | |
|---|---|---|
| L31532 | Bcl-2-beta; suppresses programmed cell death | Liver |
| Z37110 | Cyclin G; augments apoptosis; target gene of P53 | Liver |
| U25691 | Lymphocyte specific helicase; putative role in replication, repair, recombination and transcription | T and B cells |
| L15435 | Tumor necrosis factor (ligand) superfamily, member 9 (Tnfsf9), a member of the TNF family; proapoptosis facotor | T cells |
| ET62746 | Brca2 gene; familial breast cancer susceptibility gene; important in DNA double-strand break repair (DSBR) and DNA damage-induced cell-cycle checkpoint activation | Ubiquitous |
| U04269 | Caspase 1 (Casp1); cysteine protease mediator of apoptosis | Ubiquitous |
| X58472 | KIN17, DNA-binding, nuclear protein, upregulated in response to UV and ionizing radiation; accumulated in the nucleus of proliferating fibroblasts; overexpression inhibits progression into S phase | Ubiquitous |
| ET63479 | MLH1; DNA mismatch repair gene; function in mutation avoidance; cell cycle checkpoint control; cytotoxicity of various DNA-damaging agents; transcription-coupled nucleotide excision repair. | Ubiquitous |
| ET61211 | RNA-dependent EIF-2 alpha kinase; double-stranded (ds) RNA-dependent protein kinase (PKR); key mediator of antiviral effects of interferon (IFN); active player in apoptosis | Ubiquitous |

208 known genes: 2-fold or greater in CR vs. Cont at old and young age

| GenBank | Description | Location |
|---|---|---|
| X74351 | XPAC (Xeroderma Pigmentosum group A Correcting protein); nucleotide excision DNA repair | Ubiquitous |
| X71978 | Ft1, a novel gene related to ubiquitin-conjugating enzymes; deletion leads to partial syndactyly of the limbs and thymic hyperplasia, suggesting impaired programmed cell death | |

Transporter / Channel / Pumps

| GenBank | Description | Location |
|---|---|---|
| Y09108 | sodium channel, type X, alpha polypeptide (Scn10a); ion channel; small-diameter sensory neurons associated with unmyelinated axons express a tetrodotoxin-insensitive (TTXi) voltage-gated sodium channel (VGSC); may play an important role in the transmission of nociceptive informatio | Brain |
| U14420 | gamma-aminobutyric acid (GABA-A) receptor, subunit beta 3 (Gabrb3); link binding of GABA (gamma-aminobutyric acid) to inhibitory chloride flux | Brain (CNS) |
| U48397 | Mercurial-insensitive water channel 1 (mMIWC1); allows water and small solutes to pass | Brain, eye, lung, kidney, heart, muscle |
| X97281 | K+ channel beta-subunit, ion channel | Brain, Kidney |
| ET61590 | Putative capacitative calcium entry channel (Trp6); involved in calcium entry secondary to activation of receptors coupled by the Gq class of G protein. | Brain, kidney, heart and lung |
| X63100 | Gap junction membrane channel protein alpha 7 (Gja7); connexin45; gap junction protein; ion exchange channel | Brain, lung, brain, heart, intestine, kidney |
| ET63385 | Gap junction membrane channel protein beta 6 (Gjb6); connexin 30; forms transmembranous gap junction channels between adjacent cells | Brain; skin |
| L42340 | Sodium channel 27 | Brain; tissue distribution and protein poorly characterized |
| ET61440 | Trp-related protein 3; cation channel; essential for agonist-activated capacitative Ca2+ entry; putative subunits of CCE channels | Endothelium |
| M23383 | Glucose transporter 2 | Liver |
| D29797 | Syntaxin 3A, IER vesicular transport, membrane fusion | Liver |

208 known genes: 2-fold or greater in CR vs. Cont at old and young age

| GenBank | Description | Location |
|---|---|---|
| X83933 | Ryanodine receptor type 2; form Ca2+ channels in the membrane of the ER; intracellular calcium release channels controlling cytosolic calcium levels. | Liver, neuron, cardiac muscle |
| ET62883 | Skeletal muscle chloride channel | Skeletal muscle |
| X80417 | MB-IRK2 (second class of inward rectifier potassium channels); ion channel | Skeletal muscle, heart, kidney |
| M30440 | Potassium channel gene (MK2); shaker subfamily | T cells; myelinating Schwann cells |
| U03723 | AKR voltage-gated potassium-channel (KCNA4) | Ubiquitous |
| U49393 | ATPase (Atp2a3); Ca++ transporting, ion pupmp | Ubiquitous |
| X84896 | Purinergic receptor P2X, ligand-gated ion channel 1 (P2rx1); mediate Ca(2+) influx; liver, ubiquitous; | ubiquitous |
| ET63248 | RAN binding protein 1 (RANBP1); RAN-specific GTPase-activating protein; required for nucleocytoplasmic transport of many types of cargo | Ubiquitous |
| U19521 | Vesicle transport protein (munc-18c) | Ubiquitous |

*Chromatic Structure*

| | | |
|---|---|---|
| J03482 | Histone H1; chromatin structure | Ubiquitous |
| ET62262 | Histone H1b; chromatin structure | Ubiquitous |
| X16495 | Histone H2A; chromatin structure | Ubiquitous |
| ET62908 | Histone H2B; chromatin structure | Ubiquitous |
| U62672 | Histone H3.1-D (H3-D) and histone H4-D (H4-D); chromatin structure | Ubiquitous |
| U62675 | Histone H3.2-616, and histone H2b-616; chromatin structure | Ubiquitous |
| U62669 | Histone H3.2-F (H3-F), histone H2a.1-F (H2a-F), histone H2b-F (H2b-F); chromatin structure | Ubiquitous |

*Biosynthesis and Metabolism*

| | | |
|---|---|---|
| X92122 | UDP-glucuronosyltransferase 8 (Ugt8); key enzyme in cerebroside and sulfatide biosynthesis; glycosphingolipids; most abundant in myelin | Brain (CNS and PNS); tissue distribution poorly characterized |

208 known genes: 2-fold or greater in CR vs. Cont at old and young age

| GenBank | Description | Location |
|---|---|---|
| Y12257 | Glutamic acid decarboxylase 67 kD; a rate-limiting enzyme in the biosynthesis of the neurotransmitter, gamma-aminobutyric acid (GABA) | Brain (CNS) |
| D49438 | 25-hydroxyvitamin D3 24-hydroxylase; metabolism and regulation of vitamin D3 | Kidney and intestine. |
| X07888 | 3-hydroxy-3-methylglutaryl coenzyme A reductase; key regulatory enzyme for cholesterol biosynthesis. | Liver |
| D21826 | Cytidine monophospho-N-acetylneuraminic acid hydroxylase; the key enzyme for the synthesis of N-glycolylneuraminic acid (NeuGc) | Liver |
| U00932 | Glutamine fructose-6-phosphate transaminase 1 (Gfpt1); rate-limiting enzyme in hexosamine synthesis | Liver |
| L39373 | Mannoside acetyl glucosaminyl transferase 3 (Mgat3); transfers the bisecting GlcNAc to the core of complex, N-linked carbohydrates | Liver |
| X72959 | N-acetyl transferase 3 (Nat3) | Liver |
| J00355 | Alpha-amylase-1; glycogen digestion and mobilization | Liver and salivary glands |
| J04947 | Angiotensin converting enzyme (Ace); dipeptidyl carboxypeptidase that converts angiotensin I into the potent vasoconstrictor angiotensin II | Liver, brain |
| L09105 | Glucose phosphate isomerase (GPI); a housekeeping gene expressed in all tissues and organisms that utilize glycolysis and gluconeogenesis. | Ubiquitous |
| ET62525 | Polypeptide N-acetylgalactosaminyltransferase-T4 (polypeptide GalNAc transferase-T4; ppGaNTase-T4); fourth member of the mammalian UDP-GalNAc; Golgi-like localization; 4 GalNAc-transferase controls the initiation of mucin-type O-linked protein glycosylation | Ubiquitous |
| X14489 | Thymidylate synthase (Tyms) | Ubiquitous (all proliferating cells) |
| U34071 | Galactosidase, alpha (Gla); carbohydrate metabolism | Ubiquitous (most cases) |

*Cellular Component ( cell adhesion / membrane components / extracelluar matrix)*

208 known genes: 2-fold or greater in CR vs. Cont at old and young age

| GenBank | Description | Location |
|---|---|---|
| ET62381 | K-cadherin/cadherin-6; present at external cell surface at cell-cell contact sites; calcium-dependent cell adhesion molecule | Brain (cerebral cortex in neonatal mice), thymocytes |
| X95226 | Dystrobrevin (Dtn); formation and maintenance of mammalian neuromuscular junction | Brain (CNS) |
| X07215 | Proteolipid protein (Plp), main integral protein of myelin | Brain (CNS) |
| ET61336 | Nonmuscle myosin heavy chain IIB; cell motility | Brain (CNS) |
| ET63017 | Cadherin 8 (Cdh8); adhesion molecule | Brain (subdivision of early CNS) and thymus |
| X57377 | Myosin Va (Myo5a); cytoskeleton | CNS, cephalic ganglia, and spinal ganglia; IId skeletal myosin heavy chain gene expressed in fat-storing cells (FSC, lipocytes, or Ito cells) of regenerating liver |
| X66976 | Procollagen, type VIII, alpha 1 (Col8a1); extracellular matrix: component of basal laminae | Epithelial, endothelial, and mesenchymal cells in newborn mouse tissue |
| M91602 | Myosin light chain, phosphorylatable, cardiac ventricles (Mylpcl); contractile protein, cytoskeleton | fat-storing cells (FSC, lipocytes, or Ito cells) of regenerating liver; muscle |
| ET63188 | Fibroblast activation protein; cell-surface glycoprotein; member of the serine protease family; expressed at sites of tissue remodelling. | Fibroblasts |
| M17376 | Alpha-1-acid glycoprotein I (AGP-1); membrane protein | Liver |
| U49185 | Occludin (Ocln); occludin is a transmembrane protein located at tight junctions and is known to interact with other tight junction proteins | Liver |
| L02918 | Procollagen type V alpha 2 | Liver |
| V00830 | Epidermal keratin subunit; intermediate filament protein; maintenance of epidermal cell shape and resistance to mechanical trauma | Liver (epithelial cells) |
| X53176 | Integrin alpha 4 (Itga4); cell adhesion | Lymphocytes |
| X91043 | Erythrocyte protein band 7.2 (Epb7.2); stomatin; involved in Na+/K+ permeability of cells | Spleen, lung, testis, not reported in liver |
| U69136 | Cadherin 9 (Cdh9); calcium-binding membrane glycoprotein; cell adhesion molecule | Thymocytes |
| X97227 | CD53 antigen (Cd53); pan-leukocyte antigen; cell membrane glycoprotein | Thymocytes |

208 known genes: 2-fold or greater in CR vs. Cont at old and young age

| GenBank | Description | Location |
|---|---|---|
| X75636 | Iduronato-2-sulfatase (Ids); degrades heparin sulfate and dermatan sulfate in lysosomes; deficiency causes fatal lysosomal storage disorder, mucopolysaccharidosis type II (the glycosaminoglycans heparin sulfate and dermatan sulfate accumulate); part of proteoglycans which bind, help package and store secretory molecules; function in cell adhesion and basal lamina formation | Ubiquitous |
| X66402 | Matrix metalloproteinase 3 (Mmp3); extracellular matrix-degrading metalloproteinase | Ubiquitous |
| U56734 | Mannose receptor, C type 2 (Mrc2); cell adhesion; antigen presentation | Wide tissue distribution |

*Cell surface receptor*

| GenBank | Description | Location |
|---|---|---|
| D78175 | Natriuretic peptide receptor 3 (Npr3); membrane protein; modulates availability of natriuretic peptides at target organs; activation of G protein-coupled signaling system; | Epithelial and endothelial cells; lung (smooth muscle cells), heart (aortic smooth muscle cells) |
| M61000 | Gastrin releasing peptide receptor (Grpr); member of the G protein-coupled receptor family | Fibroblasts |
| M35684 | Complement receptor 2 (Cr2) | Late pre-B cells |
| ET61559 | Bradykinin B1 subtype receptor; G protein-coupled membrane bound; T-kininogen modulation during acute phase protein synthesis | Liver (ubiquitous) |
| M86441 | Fibroblast growth factor receptor 2 (Fgfr2); membrane-spanning tyrosine kinase; activated by three members of the FGF family | Liver parenchymal cells and others |
| U57612 | CD44 antigen (Cd44); receptor for hyaluronan; cell surface glycoprotein; hyaluronan clearance from the blood; lymphocyte homing and activation | liver, CNS, other |
| ET61693 | Leptin receptor (OB-R); transmembrane receptor | Liver, Lung, muscle, brain; developing bone, mesenchyme |

208 known genes: 2-fold or greater in CR vs. Cont at old and young age

| GenBank | Description | Location |
|---|---|---|
| ET62920 | CC Chemokine Receptor-4; integral membrane protein; G-protein coupled receptor; signals involve chemotaxis and calcium flux; directs cell movement in thymus; directs monocytes and lymphocytes to their target tissues | Thymus, T cells, and monocytes |

*Molecular Motors:*

| | | |
|---|---|---|
| ET63395 | Axonemal dynein heavy chain (mdhc1); axonemal dyneins are molecular motors that drive the beating of cilia and flagella; heavy chains are main components of multisubunit motor ATPase complexes called dyneins | Brain, trachea, testis |
| ET63399 | Axonemal dynein heavy chain (mdhc3); axonemal dyneins are molecular motors that drive the beating of cilia and flagella; heavy chains are main components of multisubunit motor ATPase complexes called dyneins | Brain, trachea, testis |
| ET63402 | Axonemal dynein heavy chain (mdhc6); axonemal dyneins are molecular motors that drive the beating of cilia and flagella; heavy chains are main components of multisubunit motor ATPase complexes called dyneins | Brain, trachea, testis |
| ET63405 | Axonemal dynein heavy chain (mdhc9); axonemal dyneins are molecular motors that drive the beating of cilia and flagella; heavy chains are main components of multisubunit motor ATPase complexes called dyneins | Brain, trachea, testis |
| ET62103 | Nebulin; a family of giant myofibrillar proteins | |

*Serum Protein/Secreted Protein*

208 known genes: 2-fold or greater in CR vs. Cont at old and young age

| GenBank | Description | Location |
|---|---|---|
| V00743 | Alpha fetoprotein (Afp); main component of mammalian fetal serum; synthesized by visceral endoderm of the yolk sac and by fetal liver; blood level decreases after birth; synthesis reactivated in liver tumors | Liver (fetal & adult) |

*Immune Cell Function / Primary Response Genes*

| GenBank | Description | Location |
|---|---|---|
| M88242 | prostaglandin-endoperoxide synthase 2 (Ptgs2); putative mediator of inflammation; induced by growth factors and cytokines | Fibroblasts and monocytes |
| L38281 | Immunoresponsive gene 1(Irg1); activated by bacterial LPS treatment | Macrophages |
| U43384 | Cytochrome b-245, beta polypeptide (Cybb); a flavocytochrome that mediates the transfer of electrons from NADPH to molecular oxygen in the respiratory burst oxidase | Phagocyte |
| Y08026 | Immunity-associated protein, 38 kDa (Imap38) | Spleen |
| X15592 | Cytotoxic T lymphocyte-associated protein 2 beta (Ctla2b); homologue of cysteine protease proregion; | T cells |

*Others*

| GenBank | Description | Location |
|---|---|---|
| ET62336 | DNA ligase III-beta; DNA ligase III exists as two distinct isoforms denoted alpha and beta | Alpha is expressed in most tissues; beta is expressed in testes and during spermatogenesis |
| X61449 | nucleosome assembly protein 1-like 1 | Brain; expression poorly characterized |
| L28819 | Involucrin (Ivl); a glycine-,serine- and cysteine-rich protein expressed late in differentiation of grandular layers in normal epidermis | Epidermis |
| X99251 | Repetin (Rptn); calcium-binding; similar to intermediate filament-associated proteins profilaggrin and trichohyalin; expression during late epidermal differentiation | Epithelia of forestomach and tongue |

208 known genes: 2-fold or greater in CR vs. Cont at old and young age

| GenBank | Description | Location |
|---|---|---|
| ET61424 | Protein-tyrosine phosphatase epsilon precursor; the protein tyrosine phosphatase epsilon (PTPepsilon) gene gives rise to two proteins: a transmembranal, receptor-like form and a cytoplasmic, non-receptor form | Hematopoietic tissues |
| U73915 | Phosphate regulating neutral endopeptidases on the X chromosome (Phex); mineralization of extracellular matrix by osteoclasts | Kidney, bone |
| ET61364 | Meprin beta subunit isoform (Mep-1beta); meprins are membrane-bound oligomeric metalloendopeptidases, contain alpha and/or beta subunit | Kidney, intestine, not reported in liver |
| U60330 | Proteaseome 3 (Psme3); Ki antigen; cell proliferation; enhances generation of class I binding peptides; | Liver, neurons, broad tissue distribution |
| X16490 | Plasminogen activator inhibitor, type II (Planh2); serine protease inhibitor; inactivates urokinase-type plasminogen activator and regulates degradation of the extracellular matrix; one form is cytoplasmic the other is translocated into the endoplasmic reticulum | Liver; bone-marrow, spleen, lung, thymus, skin |
| X58169 | T-complex protein 10a (Tcp10a); Tcp-10 gene has been established as a molecular candidate for the T complex responder locus which plays a central role in the transmission ratio distortion phenotype expressed by males heterozygous for a T haplotype. | Male germ line |
| Z46299 | Sperm autoantigenic protein 17 (Sp17); sperm specific protein; calmodulin binding protein | Mammalian testis; sperm-specific |
| M26940 | Casein beta (Csnb); milk protein | Mammary glands |
| ET63259 | Cea14 gene (carcinoembryonic antigen family members); unknown function; member of the immunoglobulin superfamily | Many cea genes expressed in fetal liver |
| ET63260 | Cea15 gen (carcinoembryonic antigen family members); unknown function; member of the immunoglobulin superfamily | Many cea genes expressed in fetal liver |

208 known genes: 2-fold or greater in CR vs. Cont at old and young age

| GenBank | Description | Location |
|---|---|---|
| ET63261 | Cea16 gene (carcinoembryonic antigen family members); unknown function; member of the immunoglobulin superfamily | Many cea genes expressed in fetal liver |
| M20567 | Heat shock protein, 70 kDa 2 (Hsp70-2); not induced by heat shock; developmentally regulated in P60spermatogenic cells; critical role in spermatogenesis | Meiotic phase of spermatogenesis |
| X04405 | Myoglobin (Mb); small globular heme protein; oxygen-carrying | Muscle |
| ET63205 | Odorant binding protein Ib | Nasal epithelium. |
| ET63156 | Disabled homolog 1 (Drosophila) (Dab1); adaptor molecule in neural development | neuronal and hematopoietic cells |
| ET62968 | Odorant receptor 23 (OR23) | Olfactory and testicular cells |
| U96701 | Serine protease inhibitor 15 (Spi15); regulator of extracellular proteolysis | Predominantly in testis |
| ET63408 | Capping protein beta 3 subunit; a novel isoform of the actin-binding protein; a component of the cytoskeletal calyx of the mammalian sperm head. | Spermiogenesis |
| ET62832 | Perforatorial protein (PERF 15); a novel testicular protein; sequence similarities to a family of lipid binding proteins; major component of the rat sperm perinuclear theca. | Testis |
| Z38118 | Synaptonemal complex protein 1 (Sycp1); pairing of chromosomes during meiosis | Testis |
| M19413 | Tubulin alpha, related sequence 1 (Tuba-rs1) | Testis |
| Y08485 | Synaptonemal complex protein 3 (Sycp3); part of the lateral element of the synaptonemal complex; a meiosis-specific protein structure essential for synapsis of homologous chromosomes | Testis; synaptonemal complex protein 1 is also expressed in embryonic ovary, adult brain and testis |
| X96737 | Synaptobrevin like 1 (Sybl1); housekeeping gene; X-linked; inactivated on one X in every female cell, and also inactive on the Y of male cells | Ubiquitous |
| X92842 | Surfeit gene 6 (Surf6); involved in a nucleolar ribosome maturation; housekeeping | ubiquitous (nucleolus) |

208 known genes: 2-fold or greater in CR vs. Cont at old and young age

| GenBank | Description | Location |
|---|---|---|
| ET62791 | WW domain binding protein 6; WW domain is a globular protein domain that is involved in mediating protein-protein interaction and that ultimately participates in various intracellular signaling events; WW domain mediates protein-protein interaction by bin | Uncharacterized |
| ET62978 | Neosin/lark; RNA-binding protein; Drosophila homologue encodes an element of the clock output pathway regulating adult eclosion (circadian rhythm) | Uncharacterized, probably neuronal |

*** APPENDIX H 142 known genes: 2-fold up in young CR vs young Control and unchanged in old CR vs old Control

| t-test | ng t-test | Bank Bank | notype | ation |
|---|---|---|---|---|
| 0.083 | 0.001 | 854 | troglycan (Dag1); Dystrophin associated oprotein 1; acts as a receptor for ement membrane components | cle, epithelial cells (liver and others) |
| 0.010 | 0.000 | 664 | rin A5 (Efna5); Eph-related receptor sine kinase ligand 7; LERK-7; AL-1; S; essential for proper axon guidance and graphic mapping | ryo visual system, CNS and peripheral nervous system |
| 0.084 | 0.014 | 122 | assium inwardly-rectifying channel, family J, member 6 (Kcnj6) ; G protein-vated; play a role in resting potential and trolling excitability of the cell | rons |
| 0.425 | 0.008 | 135 and 861 | tin receptor (Lepr); Obr; leptin is a key ght control hormone; mutation of the leptin ptor causes obesity | r, ubiquitous, but not in thymus or pancreas |
| 0.346 | 0.008 | 701 | inoblastoma-like 1(p107) scriptional cell cycle repression; pressor gene; binds to myc gene | (Rbl1); hest in liver and heart embryo, lower in adult liver, CNS, tumor liferating cells, heart, lung, kidney, intestine |
| 0.117 | 0.0005603 | | aete-scute complex homolog-like sophila) (Ascl1); helix-loop-helix protein scriptional factor; controls a basic ration in development of neuronal enitors in distinct neural lineages | eloping CNS and peripheral nervous systems, in adult n only |
| 0.124 | 0.0074120 | | ivin receptor IIB (Acvr2b); receptor for vins, which play an important part in oderm induction | ryo, testis |
| 0.374 | 0.006 | 546 | -ribosylation-like 4 (Arl4); sylation factor like protein 4; involved in ation of transport vesicles; expressed in erentiating cells | ADP- pocytes, ubiquitous |

-145-

| | | | |
|---|---|---|---|
| 0.856 | 0.027 | 478 | binding protein 1 (Aebp1); transcriptional essor with carboxylpeptidase activity; no scription during adipocyte differential or oblast calcification | eoblasts and adipose tissue |
| 0.221 | 0.027 | 1705 | aline phosphatase 3, intestine, not Mn iring (Akp3); intestinal alkaline sphatase (IAP); a membrane-bound alloenzyme catalyzing cleavage of ganic phosphate nonspecifically from a e variety of phosphate esters. | stine, kidney |
| 0.592 | 0.009 | 361 and 1891 | ylase 2, pancreatic (Amy2); J00361 se alpha-amylase-like gene; glycogen stion and mobilization | creas, liver and many others |
| 0.125 | 0.001 | 676 | yloid beta (A4) precursor protein-binding, ily A, member 2 (Apba2); X11 protein e; X11 protein binds amyloid precursor ein; receptor trafficking; may regulate the essing of amyloid precursor protein to the loid beta peptide | rons |
| 0.071 | 0.006 | 216 | lipoprotein CII (Apoc2); required for lysis of triglycerides by lipoprotein lipase | l liver, adult liver, intestine and peritoneal macrophages |
| 0.371 | 0.006 | 573 | n derived neurotrophic factor (Bdnf); lates development and maintaince of the ous system | in, highest in hippocampus and cerebral cortex |
| 0.062 | 0.004 | 740 | ein delta (Csnd); epsilon-casein ein) | (milk mary glands |
| 0.324 | 0.016 | 526 | 8 antigen (Cd48); BCM-1; Blast-1; iates cell adhesion | face of leukocytes |
| 0.796 | 0.024 | 562 | division cycle 25 homolog C (S. visiae) (Cdc25c); encodes nine/tyrosine phosphatases that activate lin-dependent kinases; control of sitions between phases of cell division | n spleen and thymus |

| | | | |
|---|---|---|---|
| 0.101 | 0.039 | 715 | ular retinoic acid binding protein I; intracellular pipid binding protein bp1); a high affinity for retinoic acid | ely expressed during development also in thymus |
| 0.051 | 0.006 | 690 | omobox homolog 1 (Drosophila HP1 beta) x1); Homologous to Drosophila HP1 gene; if's chromatin, rendering heritable changes gene expression; activates or silences es | quitous during development |
| 0.541 | 0.002 | 032 | lin B2 (Ccnb2); regulator of transitions een phases of cell division | hest in pachytene spermatocytes, also in early ryogenesis |
| 0.343 | 0.002 | 771 | ochrome c, testis (Cyct); maintains tinous spermatogenesis | tis |
| 0.110 | 0.016 | 859 | D (aspartate-glutamate-alanine-aspartate) polypeptide 4 (Ddx4); DNA helicase; ortant role in determination events of cells | ryonic gonads and testicular germ cells |
| 0.059 | 0.034 | 3226 | ensin related sequence cryptdin peptide eth cells) ( Defcr-rs1); CRS1C; microbial peptide | eth cells of the small intestine; smooth muscle |
| 0.044 | 0.031 | 903 | a-like 1 homolog (Drosophila) (Dll1); cell- communication regulating the rmination of various cell fates during elopment | ryo, not in adult liver |
| 0.167 | 0.038 | 986 | mocollin 1 (Dsc1); a "skin-type" mosomal cadherin; formation of tinized epithelial structure during mouse elopment; cell to cell adhesion | ryo and skin |
| 0.475 | 0.002 | 963 | hanous homolog 1 (Drosophila) (Diap1); in regulation of cell morphology, adhesion cytokinesis; Rho regulates actin merization by targeting profilin via the hanous homolog 1 beneath specific ma membranes | oblasts (ubiquitous) |
| 0.174 | 0.027 | 925 | transcription factor 5 (E2f5); M.musculus mRNA for E2f5 protein. | |
| 0.899 | 0.000 | 328 | -like module containing, mucin-like, hormone receptor-like sequence 1 (Emr1); M.musculus mRNA for o. | |
| 0.177 | 0.010 | 2930 | hropoietin (Epo); M12930 Mouse erythropoietin gene, complete cds | |

-147-

| | | | |
|---|---|---|---|
| 0.143 | 0.023 | 325 | ogenital dysplasia homolog (Fgd1); U22325 Mus musculus faciogenital dysplasis (Fgd1) mRNA, plete cds |
| 0.993 | 0.047 | 1737 | specific gene 27 (Fsp27); M61737 M.musculus adipocyte-specific mRNA, partial cds |
| 0.062 | 0.046 | 535 | oblast growth factor 9 (Fgf9); U33535 Mus musculus fibroblast growth factor 9 (FGF-9) mRNA, plete cds |
| 0.993 | 0.003 | 853 | lin 1 (Fbln1); M.musculus (isolate Mk24) mRNA for the 3' end of MB-90/fibulin C form. |
| 0.358 | 0.006 | 854 | lin 1 (Fbln1); M.musculus (isolate Mk31) mRNA for MB-90/fibulin D form. |
| 0.150 | 0.002 | 099 | junction membrane channel protein beta 3 (Gjb3); connexin31. |
| 0.341 | 0.000 | 953 | olin (Gsn); J04953 Mouse gelsolin gene, complete cds |
| 0.956 | 0.001 | 265 | osaminyl (N-acetyl) transferase 1, core 2 (Gcnt1); U19265 Mus musculus core2-GlcNAc-transferase -GnT) mRNA, complete cds |
| 0.374 | 0.008 | 996 | th factor receptor bound protein 10 (Grb10); U18996 Mus musculus growth factor receptor-binding ein (Grb10) gene, complete cds |
| 0.145 | 0.041 | 0422 | one 4 protein (Hist4);J00422 Mouse histone H4 gene, complete cds |
| 0.724 | 0.000 | 071 | eo box C5 (Hoxc5); U28071 Mus musculus homeobox protein (Hoxc-5) gene, complete cds |
| 0.207 | 0.037 | 519 | roxysteroid dehydrogenase-5, delta <5>-3-beta (Hsd3b5); Mus musculus 3-ketosteroid reductase D3b5) mRNA, complete cds |
| 0.116 | 0.003 | 973 | rferon alpha family, gene 4 (Ifna4); X01973 Mouse gene for interferon alpha 4 (Mu IFN-alpha 4) |
| 0.095 | 0.007 | 599 | rferon gamma receptor 2 (Ifngr2); U69599 Mus musculus interferon gamma receptor second chain r2) gene |
| 0.008 | 0.015 | 542 | rleukin 6 (Il6); |
| 0.566 | 0.008 | 359 | 359 mouse alpha-amylase-2 gene |
| 0.086 | 0.009 | 761 | oncogene (Jun); Mouse mRNA for protein homologous to human c-JUN. |
| 0.785 | 0.046 | 08574 | voltage-gated channel, subfamily S, 2 (Kcns2)Mus musculus potassium channel alpha subunit 9.2) mRNA, complete cds. |
| 0.128 | 0.018 | 193 | tin complex 1, acidic, gene 10 (Krt1-10); L00193 Mouse epidermal keratin type I intermediate ent gene |
| 0.053 | 0.026 | 313 | tin complex 1, acidic, gene 15 (Krt1-15); cytoskeletal structural protein D16313 Mouse cytokeratin gene, complete cds |
| 0.071 | 0.002 | 889 | r cell lectin-like receptor, subfamily A, member 8 (Klra8); U12889 Mus musculus Ly49H mRNA, plete cds |
| 0.763 | 0.002 | 4398 | rin (Lor); M34398 Mouse loricrin mRNA, complete cds |
| 0.088 | 0.016 | 503 | phoid enhancer binding factor 1 (Lef1); D16503 Mouse mRNA for LEF-1S, complete cds |
| 0.079 | 0.001 | 3099 | usculus epidymal sperm gene. |
| 0.701 | 0.026 | 3121 | usculus mRNA for alpha tectorin. |
| 0.016 | 0.019 | 3404 | usculus mRNA for axonemal dynein heavy chain (partial, ID mdhc8). |
| 0.145 | 0.003 | 3397 | usculus mRNA for cytoplasmic dynein heavy chain (partial, ID mdhc11). |

| | | |
|---|---|---|
| 0.591 | 0.000 3151 | usculus mRNA for neural cell adhesion molecule. |
| 0.119 | 0.047 3209 | usculus mRNA for Nkx2-3 gene. |
| 0.225 | 0.040 3083 | usculus PR264 gene. |
| 0.208 | 0.034 595 | gen activated protein kinase kinase kinase 2 (Map4k2); U50595 Mus musculus Rab8-racting protein mRNA, complete cds |
| 0.139 | 0.000 3431 | se DNA for neurotrophic factor, exon 3 and complete cds. |
| 0.044 | 0.039 3429 | se DNA for vav-T, partial cds. |
| 0.392 | 0.032 997 | se mRNA for cytotoxic T-cell membrane glycoprotein Ly-3 3' flank. |
| 0.153 | 0.028 1015 | se NLRR-2 mRNA for leucine-rich-repeat protein, partial cds. |
| 0.427 | 0.015 210 | musculus (Notch2) mRNA, complete |
| 0.000 | 0.034 2373 | musculus ACF7 neural isoform 1 (mACF7) mRNA, partial cds. |
| 0.066 | 0.000 3257 | musculus cea12 gene. |
| 0.087 | 0.028 3255 | musculus cea9 gene. |
| 0.302 | 0.034 1200 | musculus complement recepter (CRY) mRNA, partial cds (spleen-specific). |
| 0.170 | 0.000 1528 | musculus CRE-BP1 transcription factor, novel spliced form, mRNA, partial cds. |
| 0.189 | 0.043 2694 | musculus glucose-6-phosphate dehydrogenase (G6PD) gene, nuclear gene encoding mitochondrial ein, exon 6 and partial cds. |
| 0.374 | 0.000 1692 | musculus implantin mRNA, partial cds. |
| 0.142 | 0.018 2692 | musculus laminin alpha 3B chain (Lama3B) mRNA, partial cds. |
| 0.346 | 0.005 2477 | musculus mena protein (Mena) mRNA, complete cds. |
| 0.155 | 0.000 1218 | musculus microtubule-associated protein 4 (MAP4) mRNA, partial cds. |
| 0.075 | 0.001 1544 | musculus P-glycoprotein (mdr2) gene, partial cds. |
| 0.084 | 0.040 2235 | musculus polyreactive autoantibody, immunoglobulin IgM heavy chain mRNA, partial cds. |
| 0.074 | 0.001 1683 | musculus potassium channel mKv3.2 mRNA, partial cds. |
| 0.043 | 0.019 1621 | musculus putative protein kinase MRK2 mRNA, partial cds. |
| 0.110 | 0.026 1556 | musculus rearranged T cell receptor (TCRV-alpha-22.1) mRNA, variable region, partial cds. |
| 0.191 | 0.026 2586 | musculus sodium channel 2 (mBNaC2) mRNA, complete cds. |
| 0.104 | 0.033 2280 | musculus T cell receptor V alpha mRNA, partial cds. |
| 0.459 | 0.003 1439 | musculus trp-related protein 2 mRNA, partial cds. |
| 0.061 | 0.002 1441 | musculus trp-related protein 5 mRNA, partial cds. |
| 0.054 | 0.004 0474 | istoylated alanine rich protein kinase C substrate (Macs); M60474 Mouse myristoylated alanine-rich inase substrate ( RCKS) mRNA, complete cds |
| 0.378 | 0.017 360 | plastic progression 1 (Npn1); M.musculus (Balb/C) P/LO1 mRNA. |
| 0.153 | 0.000 919 | roblastoma myc-related oncogene 1 (Nmyc1); Mouse N-myc gene. |

| | | | |
|---|---|---|---|
| 0.827 | 0.049 | 819 | ropeptide Y receptor Y1 (Npy1r); D63819 Mouse mRNA for neuropeptide Y-Y1 receptor, complete |
| 0.186 | 0.000 | 0514 | al (Nodal);X70514 M. musculus nodal gene, a TGF-beta-like gene |
| 0.133 | 0.046 | 163 | gin (Nog); |
| 0.238 | 0.029 | 033 | lear protein 220 (Np220); Mouse mRNA for nuclear protein, NP220, complete cds |
| 0.062 | 0.000 | 804 | rnally expressed gene 3 (Peg3); U48804 Mus musculus Zn-finger protein Pw1 gene, complete cds |
| 0.348 | 0.030 | 687 | nylethanolamine-N-methyltransferase (Pnmt); L12687 Mouse phenylethanolamine N-hyltransferase gene, complete cds |
| 0.307 | 0.005 | 279 | sphatidylinositol 3-kinase, catalytic, alpha polypeptide ( Pik3ca); U03279 Mus musculus Balb/c sphatidylinositol 3-kinase 110 kDa subunit mRNA, complete cds |
| 0.233 | 0.046 | 277 | spholipase A2 group VII (platelet-activating factor acetylhydrolase, plasma) (Pla2g7); U34277 Mus culus PAF acetylhydrolase mRNA, complete cds |
| 0.408 | 0.000 | 305 | ssium voltage gated channel, shaker related subfamily, member 1 (Kcna1); Mouse MBK1 mRNA for se brain potassium channel protein-1. |
| 0.958 | 0.038 | 789 | iferation-associated protein 1 (Plfap); M.musculus mRNA for p38-2G4. |
| 0.063 | 0.000 | 594 | iferin related protein (Plfr); Mouse mRNA for proliferin-related protein (PRP). |
| 0.146 | 0.009 | 532 | ein kinase C, beta (Pkcb); Mouse mRNA for protein kinase C beta-II. |
| 0.109 | 0.009 | 242 | ein kinase C, eta (Pkch); D90242 Mouse mRNA for nPKC-eta |
| 0.188 | 0.047 | 577 | ein kinase C, lamda (Pkcl); Mouse mRNA for protein kinase C lambda |
| 0.196 | 0.049 | 935 | ein kinase, cAMP dependent regulatory, type II alpha (Prkar2a); J02935 Mouse cAMP-dependent ein kinase type II regulatory subunit mRNA, 3' end |
| 0.542 | 0.011 | 720 | ein that interacts with C kinase 1 (Pick1); M.musculus mRNA for perinuclear binding protein. |
| 0.374 | 0.013 | 768 | eoglycan 2, bone marrow (Prg2); L46768 Mus musculus major basic protein (MBP-1) gene, complete |
| 0.256 | 0.013 | 133 | eoglycan, secretory granule (Prg); Mouse mRNA for mastocytoma proteoglycan core protein, lycin. |
| 0.904 | 0.022 | 239 | 5B, member RAS oncogene family (Rab5b); X84239 M.musculus mRNA for rab5b protein |
| 0.010 | 0.027 | 247 | -related C3 botulinum substrate 2 (Rac2); M.musculus EN-7 mRNA. |
| 0.115 | 0.034 | 711 | ication factor C, 140 kDa (Recc1); M.musculus mRNA for replication factor C, large subunit. |
| 0.463 | 0.023 | 642 | finger protein (C3HC4 type) 19 (Rnf19)X71642 M.musculus GEG-154 mRNA |
| 0.694 | 0.021 | 5732 | inal vesicle protein 2 (Svp2); Mouse seminal vesicle secretory protein IV (SVS IV) mRNA, 3' end |
| 0.714 | 0.032 | 7790 | m amyloid A pseudogene (Saa-ps); M17790 Mouse SAA4 gene encoding serum amyloid A, exons 3 4 |
| 0.009 | 0.021 | 580 | en in absentia 1B (Siah1b); M.musculus siah-1B protein mRNA. |
| 0.103 | 0.027 | 687 | ium channel, voltage-gated, type I, beta polypeptide: (Scn1b); L48687 Mus musculus voltage-endent Na+ channel beta-1 subunit gene, exons 4-6 |
| 0.328 | 0.002 | 268 | te carrier family 35 (CMP-sialic acid transporter), member 1 (Slc35a1); M.musculus mRNA for CMP-ic acid transporter. |

| | | | |
|---|---|---|---|
| 0.114 | 0.037 | 287 | ulated by retinoic acid gene 8 (Stra8); M.musculus mRNA for Stra8 protein. |
| 0.043 | 0.007 | 749 | interacting factor (Tgif); X89749 M.musculus mRNA for mTGIF protein |
| 0.394 | 0.002 | 6987 | scription factor CP2 ( Tcfcp2); Mouse alpha-globin transcription factor CP2 mRNA sequence |
| 0.177 | 0.034 | 362 | |
| 0.402 | 0.001 | 462 | sforming growth factor beta 1 (Tgfb1); L42462 Mus musculus TGF-1 gene; promoter region and |
| 0.533 | 0.004 | 534 | or necrosis factor receptor superfamily, member 18 (Tnfrsf18); Mus musculus glucocorticoid induced TNFR family related protein precursor, mRNA, complete cds. |
| 0.306 | 0.013 | 581 | uitin-activating enzyme E1, Chr X (Ube1x); ubiquitin-dependent protein degradation |
| 0.438 | 0.006 | 859 | |
| 0.172 | 0.005 | 361 | oncogene (Vav); X64361 M.musculus vav mRNA |
| 0.110 | 0.048 | 01598 | icular inhibitory amino acid transporter (Viaat); |
| 0.008 | 0.019 | 438 | entin (Vim); |
| 0.124 | 0.041 | 434 | |
| 0.495 | 0.0019 | 797 | gless-related MMTV integration site 4 (Wnt4); M89797 Mouse Wnt-4 mRNA, complete cds |
| 0.056 | 0.031 | 496 | 496 Murine H3.1 gene for histone H3.1 |
| 0.567 | 0.010 | 174 | finger protein 30 (Zfp30); Z30174 M.domesticus (C57Bl/6J) mRNA for zinc finger protein 30 |

APPENDIX I known genes: 2-fold up in old CR vs. old Control and unchaged in young CR vs. young Control

| | R 1 | R 2 | R 3 | ont 7 | ont 8 | ont 9 | st | ngCR 16 | ngCR 17 | ngCR 18 | ngCont 19 | ngCont 20 | ngCont 21 | st | notype | ue distribution |
|---|---|---|---|---|---|---|---|---|---|---|---|---|---|---|---|---|
| 602 | 8.75 | 11.48 | 3.04 | 0.00 | 0.00 | 0.00 | 0.003 | 0.00 | 0.00 | 29.61 | 0.00 | 0.00 | 0.00 | .374 | e morphogenetic tein 2 (Bmp2); is mponent of a e-derived extract ical to initiation of ation of cartilage its conversion bone; is cturally related wth facto-beta ransforming vins, and bins. BMP aling is essential development of letogenic and rogenic cranial ral crest. | oblastic cells; or types of -hematopoietic s (these cells uded oblasts, tinocytes, ocytes, kidney helial cells, and or cells of e, muscle, , liver, kidney, ach, colon, state, and ronal tissue) |
| 3463 | 2.96 | 1.91 | 0.92 | 0.00 | 0.00 | 0.00 | 0.031 | 2.38 | 1.43 | 1.49 | 1.08 | 0.62 | 0.00 | .052 | YDROXYACYLSPHINGOSINE 1-A-GALACTOSYLTRANSFERASE CURSOR (EC 2.4.1.45) (UDP-LACTOSE-CERAMIDE LACTOSYLTRANSFERASE) RAMIDE UDP-LACTOSYLTRANSFERASE REBROSIDE SYNTH | |
| 2773 | 1.04 | 0.96 | 1.92 | 0.16 | 0.00 | 0.00 | 0.016 | 1.99 | 2.96 | 1.05 | 0.00 | 0.00 | 1.77 | .155 | HRIN-A3 (EPH-RELATED EPTOR TYROSINE KINASE AND 3) (LERK-3) (EHK1 LIGAND) K1-L) (FRAGMENT). | |

| ID | | | | | | | | | | | | | Description |
|---|---|---|---|---|---|---|---|---|---|---|---|---|---|
| 1172 | 2.83 | 10.69 | 9.99 | 0.00 | 0.00 | *0.000* | 8.70 | 0.00 | 2.72 | 1.52 | 0.00 | *.347* | CYTOKINE RECEPTOR CURSOR (EC 2.7.1.112) ROSINE-PROTEIN KINASE EPTOR FLK-2) (FETAL LIVER ASE 2) (TYROSINE-PROTEIN ASE FLT3). |
| 2049 | 2.43 | 10.05 | 8.49 | 0.00 | 0.00 | *0.040* | 3.04 | 55.00 | 0.00 | 0.00 | 0.00 | *.243* | MEOBOX TEIN HOX-D3 X-4.1) (MH-19). |
| 971 | 3.57 | 30.24 | 5.17 | 0.00 | 0.00 | *0.031* | 1.19 | 0.00 | 2.87 | 0.00 | 18.88 | *.598* | ptor protein plex AP-2, alpha bunit (Ap2a1); gi-plasma brane transport icle; intracellular tein traffic; iates protein ing in the ocytic and late retory pathways uitou |
| 940 | 9.37 | 62.71 | 0.48 | 0.00 | 0.00 | *0.020* | 4.54 | 47.82 | 0.00 | 0.00 | 12.28 | *.445* | aragine thetase (Asns); scription is ced by amino and ohydrate rivation r |
| 0903 | 2.38 | 2.80 | 1.39 | 0.00 | 0.52 | *0.011* | 0.00 | 0.51 | 0.61 | 1.61 | 2.56 | *.007* | mphoid kinase ); a member of tooncogenes; brane- ociated protein sine kinase; ction in B- phocyte specific sduction hway ressed cifically in cells he B-lineage, in e pro-B cells in most pre B mature B cells, not in plasma s |

| 019 | 1.31 | 0.96 | 1.29 | 0.00 | 0.56 | 0.58 | 0.022 | 1.04 | 0.87 | 1.44 | 1.13 | 0.72 | 1.25 | .726 | igin (Bsg); 019 Mouse gene basigin precursor, igin signal ursor roid gland |
|---|---|---|---|---|---|---|---|---|---|---|---|---|---|---|---|
| 991 | 0.78 | 1.33 | 1.43 | 0.34 | 0.58 | 0.37 | 0.025 | 1.12 | 1.84 | 1.91 | 0.00 | 0.88 | 1.83 | .289 | itonin (Calc) uitou |
| 343 | 5.03 | 16.01 | 1.89 | 0.00 | 0.00 | 0.00 | 0.001 | 0.00 | 0.00 | 27.69 | 0.00 | 0.00 | 0.00 | .374 | ium channel beta bunit (Cacnb2); tage-sensitive ium channels are ely expressed plexes which e both trogenic and al transduction ctions. |
| 966 | 2.24 | 2.14 | 1.72 | 0.83 | 1.05 | 0.52 | 0.005 | 0.80 | 1.47 | 0.95 | 0.88 | 0.80 | 2.05 | .725 | onyl reductase 1 uitou r1);a cytosolic ber of the aldo- reductase group nzymes. uitous enzyme abolize a variety ompounds taining carbonyl ups. |

| | | | | | | | | |
|---|---|---|---|---|---|---|---|---|
| 079 | 0.83 | 1.18 | 1.02 | 0.54 | 0.51 | 0.33 | *0.010* | 1.38 | 0.98 | 1.19 | 0.69 | 1.71 | 1.17 | *.994* dermal-neural ex 1 9 (Enc1); an y and highly cific marker of ral induction in ebrates; encodes lch family related tein that is ; ENC- nctions as an n-binding protein t may be ortant in the anization of the n cytoskeleton ing neural fate cification and elopment of the ryogenesis |
| 320 | 8.37 | 14.30 | 8.47 | 0.00 | 0.00 | 0.00 | *0.046* | 0.00 | 0.00 | 7.15 | 0.00 | 0.00 | *.374* structure cific onuclease 1 1); a structure- cific onuclease, |
| 409 | 1.15 | 1.66 | 1.46 | 0.12 | 0.84 | 0.20 | *0.019* | 1.70 | 1.72 | 0.85 | 0.00 | 1.34 | 0.22 | *.148* head box A2 a2); trancription or |
| 023 | 1.55 | 1.31 | 1.38 | 0.79 | 0.31 | 0.61 | *0.006* | 0.37 | 1.69 | 0.96 | 0.00 | 1.08 | 1.04 | *.595* eral transcription or IIH, peptide 1 (62kD unit) (Gtf2h1); |
| 703 | 3.13 | 33.12 | 5.39 | 0.00 | 0.00 | 0.00 | *0.031* | 2.28 | 21.40 | 7.63 | 0.00 | 0.00 | 0.00 | *.141* -Kruppel family member GLI2 2); 222703 M.musculus tinocyte growth factor Fgf-7 r, endoderm- ved tissues, , stomach, ar ll intestine. |

| | | | | | | | | |
|---|---|---|---|---|---|---|---|---|
| 255 | 1.25 | 1.99 | 2.59 | 0.00 | 0.59 | 0.00 | *0.016* | 1.44 0.75 1.26 0.00 1.27 | 0.00.*197*-Kruppel family ber GLI3 musculus mRNA GLI3 protein. |
| 498 | 1.47 | 1.76 | 1.46 | 0.70 | 0.87 | 0.66 | *0.002* | 0.74 1.04 0.96 0.91 1.30 | 1.53.*178* amate cysteine r, embryo se (gamma-amylcysteine thetase), catalytic lc); |
| 498 | 5.92 | 22.45 | 4.96 | 0.00 | 0.00 | 0.00 | *0.039* | 5.05 1.71 28.66 0.00 0.00 | 0.00.*236* amate receptor, tropic, AMPA2 ha 2) (Gria2); |
| 754 | 9.29 | 15.43 | 1.98 | 0.00 | 0.00 | 0.00 | *0.002* | 7.98 18.64 0.00 0.00 0.00 | 0.00.*116* t shock factor 2 f2)M.musculus NA for heat shock scripton factor 2. |
| 0365 | 2.12 | 2.48 | 2.79 | 0.00 | 1.29 | 0.00 | *0.013* | 2.69 0.91 0.37 1.09 0.00 | 0.00.*291* tion plakoglobin (Jup); one of the teins of desmosomal membrane horage site plaques of the helium, and is also acomponent of ues of the adherins junction |
| 239 | 5.76 | 13.54 | 7.04 | 0.00 | 0.00 | 0.00 | *0.022* | 2.55 0.00 26.67 0.00 0.00 | 0.00.*316* usculus mRNA goosecoid eobox. |
| 778 | 1.17 | 17.10 | 8.21 | 0.00 | 0.00 | 13.02 | *0.032* | 9.71 2.14 0.00 0.00 0.00 | 0.00.*251* usculus H2B e. |
| 889 | 0.94 | 1.46 | 1.95 | 0.65 | 0.00 | 0.55 | *0.041* | 1.42 1.73 0.91 0.70 2.19 | 1.06.*950* usculus mRNA wnt-8D protein. |
| 796 | 6.71 | 6.58 | 0.91 | 0.00 | 0.00 | 0.00 | *0.046* | 3.72 13.92 38.64 0.00 0.00 | 0.00.*056* usculus mRNA ologous to S. visiae RAD54. |
| 942 | 4.93 | 4.23 | 1.66 | 0.55 | 0.00 | 1.26 | *0.047* | 4.85 0.74 4.66 0.00 0.68 | 0.44.*088* usculus mRNA nhancer-trap-s 1. |
| 060 | 3.39 | 1.14 | 1.65 | 0.18 | 0.00 | 0.00 | *0.043* | 0.86 2.53 2.91 8.19 0.00 | 0.00.*834* usculus myf-6 e. |

| | | | | | | | | |
|---|---|---|---|---|---|---|---|---|
| 2974 | 2.34 | 1.55 | 1.44 | 0.00 | 0.00 | *0.003* | 1.35 | 1.03 | 2.14 | 0.97 | 0.69 | 0.00.*096* usculus SOX1 e.)PIR:S10950 -determining tein - mouse gment) |
| 3453 | 6.48 | 30.32 | 7.19 | 0.00 | 0.00 | *0.009* | 9.94 | 4.23 | 2.36 | 0.00 | 0.00 | 0.00.*2733453* Mouse somal protein '(rpL32') gene, plete cds |
| 885 | 1.34 | 1.23 | 2.44 | 0.20 | 0.84 | 0.00 | *0.046* | 0.00 | 0.00 | 5.53 | 2.69 | 1.16 | 0.00.*794* tocytoma N-deacetylase/N-otransferase (Mndns): usculus mRNA for glucosaminyl eacetylase / N-sulfotransferase. |
| 461 | 2.63 | 1.67 | 1.27 | 0.40 | 0.00 | 0.00 | *0.015* | 1.26 | 1.84 | 0.81 | 0.00 | 1.19 | 0.00.*144* rine Hox2.2 NA for a eobox protein. |
| 1617 | 1.41 | 1.14 | 1.53 | 0.86 | 0.25 | 0.57 | *0.019* | 1.18 | 1.72 | 1.38 | 0.76 | 0.71 | 0.73.*012* s musculus 5E6 6/Ly-49C) mRNA, plete cds. |
| 2456 | 1.22 | 9.34 | 6.07 | 0.00 | 0.00 | 0.00 | *0.036* | 3.70 | 0.00 | 0.00 | 4.26 | 0.00 | 0.00.*420* s musculus in-2 mRNA, ial cds. |
| 2752 | 1.25 | 1.27 | 0.96 | 0.71 | 0.28 | 0.75 | *0.032* | 1.26 | 1.14 | 1.18 | 0.81 | 0.55 | 1.04.*053* s musculus tocyst unknown tein mRNA, partial |
| 3262 | 0.84 | 1.16 | 1.18 | 0.65 | 0.00 | 0.19 | *0.025* | 1.32 | 1.29 | 1.36 | 1.27 | 0.04 | 0.73.*143* s musculus cea17 e. |
| 2465 | 1.51 | 1.15 | 0.99 | 0.48 | 0.00 | 0.66 | *0.029* | 1.82 | 1.34 | 1.01 | 0.68 | 0.79 | 2.48.*913* s musculus erbB2 NA, partial cds. |
| 737 | 1.13 | 0.87 | 1.16 | 0.00 | 0.76 | 0.00 | *0.041* | 1.26 | 1.33 | 0.00 | 1.41 | 1.27 | 0.80.*557* s musculus ne/threonine-tein kinase 4m (PRP4m) NA, complete cds |

| 889 | 1.50 | 1.60 | 1.40 | 0.55 | 0.83 | 0.51 | *0.002* | 1.02 | 1.14 | 1.01 | 0.99 | 0.47 | 0.88 | *.168* | s musculus SH3-containing protein P3 mRNA, partial |
|---|---|---|---|---|---|---|---|---|---|---|---|---|---|---|---|
| 620 | 1.83 | 9.81 | 3.90 | 0.00 | 0.00 | 0.09 | *0.023* | 1.48 | 0.52 | 0.00 | 8.09 | 0.00 | 14.09 | *.177* | s musculus I/SNF complex 60 subunit (BAF60 |
| 2078 | 0.90 | 1.03 | 1.23 | 0.37 | 0.18 | 0.80 | *0.043* | 1.21 | 1.47 | 1.09 | 0.62 | 1.64 | 0.97 | *.607* | s musculus scription factor 4 (tbx4) mRNA, ial cds. |
| 283 | 2.27 | 0.80 | 1.93 | 0.11 | 0.45 | 0.52 | *0.048* | 1.15 | 0.85 | 0.31 | 1.49 | 1.99 | 3.51 | *.076* | s musculus scription factor 2 (USF2) gene |
| 247 | 1.20 | 13.60 | 8.56 | 0.00 | 0.00 | 0.00 | *0.001* | 2.78 | 19.06 | 0.00 | 0.00 | 0.00 | 30.03 | *.826* | s musculus zinc er protein (kid-1) e, complete cds. |
| 128 | 3.25 | 3.67 | 2.03 | 0.00 | 0.00 | 1.82 | *0.038* | 0.00 | 0.00 | 0.00 | 0.18 | 3.26 | 6.55 | *.144* | assium voltage-gated channel, family H (eag-related), member 2 nh2); Mus musculus ether-a-go-elated protein isoform Merg1a rg1) mRNA, complete cds. |
| 3227 | 1.35 | 1.40 | 1.47 | 0.60 | 1.05 | 0.22 | *0.031* | 0.70 | 0.95 | 0.63 | 0.61 | 1.78 | 1.91 | *.189* | roenkephalin 2 ells k2);a homolog of brain roenkephalin, a rotransmitter |
| 2136 | 2.63 | 30.79 | 0.41 | 0.00 | 0.00 | 0.00 | *0.001* | 0.00 | 51.41 | 43.25 | 0.00 | 0.00 | 0.00 | *.119* | collagen, type IX, alpha ol9a1); a fibrillar collagen, the ely distributed elements of the acellular matrix. |
| 405 | 1.12 | 1.22 | 1.32 | 0.00 | 0.88 | 0.06 | *0.036* | 1.52 | 0.30 | 2.07 | 0.00 | 0.00 | 2.18 | *.558* | collagen, type VI, a 1 (Col6a1); |
| 320 | 1.15 | 1.31 | 1.26 | 0.00 | 0.44 | 0.61 | *0.009* | 1.20 | 1.30 | 1.06 | 0.00 | 0.39 | 0.94 | *.057* | kinje cell protein 4 n 4); |

| | | | | | | | | |
|---|---|---|---|---|---|---|---|---|
| 429 | 4.85 | 13.23 | 5.19 | 0.00 | 0.00 | 0.00 | 0.00 | 0.00 .374 21 homolog (S. pombe) d21); D49429 Mouse P-29 mRNA for PW29, plete cds |
| 071 | 1.10 | 1.20 | 1.12 | 0.73 | 0.26 | 0.70 | 0.047 0.64 | 0.80 | 1.08 | 1.10 .750 -related orphan r, muscle, ptor gamma ey, brain, lung, rc); is, and spleen. |
| 506 | 2.15 | 1.49 | 1.34 | 0.96 | 0.78 | 0.12 | 0.021 0.92 | 1.45 | 0.20 | 1.61 | 1.04 .634 binding motif tein 4 (Rbm4); |
| 921 | 2.76 | 2.75 | 2.49 | 0.31 | 0.90 | 0.00 | 0.044 0.34 | 0.07 | 0.00 | 1.38 | 0.05 .461 0 calcium-binding protein A13 00a13); M.musculus mRNA for 0 calcium-binding protein A13. |
| 262 | 3.53 | 2.20 | 2.52 | 0.33 | 0.22 | 0.17 | 0.001 1.10 | 2.28 | 0.26 | 1.70 | 0.00 .341 solute carrier family 1, member t (Slc1a6); a Purkinje-cell specific neuronal glutamate transporter |
| 542 | 1.58 | 1.23 | 1.42 | 0.85 | 0.00 | 0.00 | 0.003 1.45 | 2.37 | 0.00 | 0.71 | 1.15 .247 ocerebellar ataxia 1 homolog an) (Sca1) M.musculus mRNA ataxin-1. |
| 184 | 1.22 | 8.76 | 8.97 | 0.00 | 0.00 | 0.00 | 0.020 0.57 | 1.61 | 1.68 | 0.00 | 0.00 .360 ell expressing clone j6 (Tj6); usculus J6B7 mRNA for T cell duced protein. |
| 796 | 1.68 | 8.76 | 8.91 | 0.00 | 0.00 | 0.00 | 0.013 3.50 | 2.35 | 2.67 | 0.00 | 0.00 .117 is specific X-ed gene (Tsx); |
| 861 | 2.82 | 1.65 | 2.44 | 0.82 | 0.81 | 0.88 | 0.000 2.27 | 24.48 | 0.00 | 0.00 | 1.46 .626 1 cytotoxic ule-associated -binding protein-1 (Tial1); |
| 4429 | 1.32 | 1.12 | 1.18 | 0.43 | 0.80 | 0.00 | 0.013 1.02 | 0.65 | 0.63 | 1.00 | ptosis |
| 167 | 0.77 | 1.50 | 1.38 | 0.20 | 0.14 | 0.64 | 0.029 1.20 | 0.97 | 0.40 | 0.46 | 2.07 .872 scriptional rmediary factor lpha (Tif1a); |
| 697 | 2.55 | 3.62 | 3.28 | 0.00 | 0.00 | 0.00 | 0.032 1.23 | 1.51 | 1.60 | 0.01 | 0.00 .213 sient receptor tein 1 (Trrp1); |
| | | | | | | | 0.001 2.71 | 0.00 | 0.00 | 0.00 | 2.33 .407 oil factor 2 (spasmolytic protein Tff2); M.musculus spasmolytic peptide (SP) mRNA. |

| | | | | | | | | |
|---|---|---|---|---|---|---|---|---|
| 960 | 1.87 | 1.22 | 0.84 | 0.00 | 0.14 | 0.015 | 1.03 | 0.00 | 1.18 | 3.37 | 3.78 | 0.97.107 sine kinase ptor 1 (Tie1); usculus mRNA TIE receptor sine kinase. |
| 297 | 0.99 | 1.46 | 1.35 | 0.00 | 0.00 | 0.001 | 1.26 | 1.32 | 1.01 | 0.59 | 0.14 | 1.06.100 297 Mus culus chrome B561 yt) mRNA, plete cds |
| 399 | 6.64 | 22.65 | 5.57 | 0.00 | 0.00 | 0.001 | 4.45 | 42.28 | 9.23 | 0.00 | 0.00 | 0.00.099 399 Mus culus Cdk-bitor p57KIP2 2) mRNA, plete cds |
| 788 | 1.60 | 1.19 | 2.04 | 0.00 | 0.00 | 0.003 | 1.25 | 0.92 | 1.93 | 0.35 | 0.00 | 1.08.111 788 Human ative cytochrone c-e synthetase NA, complete cds |
| 818 | 1.30 | 1.21 | 0.93 | 0.79 | 0.52 | 0.043 | 1.07 | 0.68 | 0.51 | 1.45 | 2.13 | 1.88.014 818 Mus culus tuberin C2) mRNA, plete cds |
| 925 | 1.35 | 1.33 | 0.87 | 0.43 | 0.50 | 0.012 | 0.13 | 1.13 | 1.49 | 1.27 | 1.83 | 0.00.871 925 Mus culus scription factor mRNA, complete |
| 085 | 1.43 | 1.51 | 0.76 | 0.00 | 0.47 | 0.020 | 1.40 | 1.24 | 1.56 | 0.00 | 0.00 | 8.39.645 085 Mus culus thiazide-sitive Na-Cl ransporter mRNA, plete cds |
| 673 | 2.43 | 25.66 | 2.46 | 2.34 | 0.00 | 0.028 | 6.97 | 0.00 | 0.00 | 0.00 | 0.00 | 0.00 215.85.460 673 Mus musculus histone (A)-613, histone H2a(B)-613, and one H2b-613 (H2b) genes, plete cds |

| ID | | | | | | | | | | | | | | Description |
|---|---|---|---|---|---|---|---|---|---|---|---|---|---|---|
| 849 | 2.21 | 2.41 | 1.17 | 1.06 | 0.00 | 0.00 | *0.039* | 1.76 | 0.58 | 0.94 | 0.80 | 0.29 | 2.39 | *.928* | 849 Mouse kFGF genomic |
| 998 | 1.75 | 1.67 | 1.29 | 1.03 | 0.65 | 0.36 | *0.022* | 0.83 | 1.38 | 1.51 | 0.24 | 0.00 | 0.97 | *.080* | 998 M.musculus for gamma 2c |
| 438 | 1.25 | 1.54 | 1.20 | 0.00 | 0.00 | 0.00 | *0.000* | 0.80 | 3.02 | 1.36 | 0.15 | 0.00 | 1.56 | *.236* | 438 Mouse MP4 e for a proline-protein |
| 398 | 8.81 | 54.55 | 5.19 | 0.00 | 0.00 | 0.00 | *0.007* | 9.14 | 12.37 | 4.19 | 0.00 | 0.00 | 0.00 | *.051* | 398 Mouse Flt3 NA for tyrosine se receptor of PDGF |
| 091 | 1.09 | 1.23 | 1.06 | 0.54 | 0.00 | 0.67 | *0.027* | 1.00 | 1.19 | 1.05 | 0.41 | 0.00 | 1.00 | *.106* | 091 M.musculus mRNA |
| 719 | 1.51 | 1.33 | 1.41 | 0.00 | 0.00 | 0.13 | *0.000* | 1.25 | 0.84 | 1.19 | 1.16 | 0.00 | 0.27 | *.177* | 719 Mus culus CREB gene cAMP-responsive ent binding tein, exon 2 |
| 904 | 1.21 | 2.04 | 1.39 | 0.00 | 0.96 | 0.00 | *0.039* | 1.97 | 3.00 | 1.04 | 0.00 | 0.07 | 0.82 | *.052* | 904 M.musculus A5T mRNA for T receptor alpha in |
| 850 | 2.50 | 1.83 | 1.79 | 0.00 | 0.00 | 0.00 | *0.001* | 0.00 | 8.14 | 0.52 | 0.00 | 1.48 | 6.28 | *.931* | 850 M. culus mRNA for P kinase-vated protein se 2 |
| 104 | 7.34 | 15.22 | 7.66 | 0.00 | 0.00 | 0.00 | *0.029* | 6.59 | 11.41 | 0.00 | 0.00 | 0.00 | 0.00 | *.175* | 104 M.musculus NA for gli2 gene |
| 677 | 3.74 | 25.02 | 4.42 | 0.00 | 0.00 | 0.00 | *0.008* | 0.00 | 79.97 | 0.00 | 0.00 | 0.00 | 0.00 | *.374* | 677 aguchi sarcoma l (v-yes) ogene homolog s); |
| 509 | 1.18 | 2.10 | 1.25 | 0.46 | 0.00 | 0.72 | *0.037* | 1.18 | 1.23 | 2.33 | 0.72 | 0.00 | 0.82 | *.079* | 509 Mouse NA for PAP ologous protein |

| ID | | | | | | | | | | | | | | Description |
|---|---|---|---|---|---|---|---|---|---|---|---|---|---|---|
| 544 | 0.96 | 1.28 | 1.67 | 0.83 | 0.21 | 0.34 | *0.039* | 0.54 | 1.04 | 1.14 | 1.25 | 0.19 | 1.20 | *.952* use mRNA for ase small unit, complete |
| 801 | 1.99 | 1.90 | 1.93 | 0.00 | 0.00 | 0.00 | *0.000* | 1.41 | 2.04 | 0.59 | 0.00 | 0.00 | 2.64 | *.657* 801 Mouse NA for Emb, plete cds |
| 095 | 1.34 | 1.23 | 1.43 | 0.52 | 0.14 | 0.15 | *0.002* | 1.00 | 2.10 | 1.00 | 0.85 | 1.25 | 0.90 | *.398* 095 Mouse DNA histamine H1 ptor, complete |
| 471 | 5.32 | 27.16 | 8.38 | 0.00 | 0.00 | 0.00 | *0.027* | 2.16 | 27.48 | 17.72 | 0.00 | 0.00 | 0.00 | *.099* 471 House se; Musculus esticus testis NA for gsg3, plete cds |
| 900 | 1.35 | 1.66 | 1.86 | 0.06 | 0.00 | 1.18 | *0.043* | 0.63 | 1.81 | 0.82 | 0.00 | 1.39 | 0.00 | *.351* 900 House se; Musculus esticus male n mRNA for 3, complete cds |
| 146 | 6.21 | 18.86 | 8.67 | 0.00 | 0.16 | 0.00 | *0.000* | 6.27 | 25.66 | 1.84 | 0.00 | 0.00 | 0.08 | *.199* 146 Mouse 9d gene |
| 1090 | 5.84 | 5.50 | 7.16 | 0.00 | 0.00 | 0.00 | *0.000* | 2.92 | 14.39 | 7.89 | 0.00 | 0.00 | 0.00 | *.065* use DNA for odine receptor e-3, exon 2, ial cds. |
| 1642 | 1.28 | 1.60 | 1.43 | 0.25 | 0.00 | 0.00 | *0.000* | 1.73 | 1.46 | 0.94 | 1.06 | 0.00 | 0.31 | *.078* ROTEIN-ACTIVATED INWARD TIFIER POTASSIUM CHANNEL 2 K2) (POTASSIUM CHANNEL, ARDLY RECTIFYING, SUBFAMILY EMBER 6) (KIR3.2). |

| ID | | | | | | | | | | | | | | Description |
|---|---|---|---|---|---|---|---|---|---|---|---|---|---|---|
| 1677 | 3.66 | 4.44 | 0.00 | 0.00 | | 0.000 | 2.77 | 2.79 | 0.93 | 0.00 | 0.00 | 1.07 | .065 | ILORIDE-SENSITIVE SODIUM NNEL ALPHA-SUBUNIT (LUNG CHANNEL ALPHA SUBUNIT) PHA ENAC) (NONVOLTAGE-TED SODIUM CHANNEL 1 ALPHA UNIT) (SCNEA) (ALPHA NACH) AGMENT). |
| 2211 | 1.51 | 1.55 | 1.09 | 0.84 | 0.47 | 0.24 | 0.019 | 1.42 | 0.91 | 1.32 | 0.29 | 0.45 | 1.09 | .104 s musculus ant formin (Fmn) e, partial cds. |
| 2229 | 1.20 | 1.67 | 1.04 | 0.00 | 0.00 | 0.00 | 0.002 | 1.23 | 1.68 | 1.36 | 0.55 | 0.96 | 0.94 | .031 s musculus t10b mRNA, plete cds. |
| 2444 | 2.44 | 1.02 | 0.98 | 0.00 | 0.00 | 0.00 | 0.037 | 1.41 | 1.71 | 2.08 | 0.00 | 1.14 | 0.94 | .060 s musculus Sox4 x4) mRNA, partial |
| 2446 | 9.81 | 28.01 | 8.98 | 0.00 | 0.00 | 0.00 | 0.000 | 9.16 | 15.36 | 0.29 | 0.00 | 0.00 | 0.00 | .182 s musculus Sox12 x12) mRNA, ial cds. |
| 2570 | 1.20 | 1.21 | 1.81 | 0.60 | 0.00 | 0.40 | 0.016 | 0.80 | 2.67 | 3.46 | 0.00 | 0.23 | 1.22 | .105 s musculus Mad olog Smad5 NA, complete |
| 2673 | 1.24 | 1.58 | 1.28 | 0.35 | 0.93 | 0.00 | 0.033 | 1.74 | 0.41 | 0.70 | 1.76 | 1.07 | 0.26 | .900 use hyaluronan thase 3 mRNA, plete cds. |
| 2998 | 0.93 | 1.07 | 1.36 | 0.07 | 0.00 | 0.00 | 0.001 | 1.19 | 1.08 | 1.34 | 0.51 | 0.01 | 1.21 | .153 usculus mRNA dystrobrevin ne m32). |
| 3005 | 1.98 | 1.19 | 0.81 | 0.00 | 0.00 | 0.00 | 0.018 | 0.00 | 2.97 | 1.35 | 3.07 | 5.28 | 0.00 | .487 usculus mRNA phospholipase C ma 1. |
| 3019 | 0.61 | 1.69 | 1.47 | 0.00 | 0.39 | 0.00 | 0.033 | 1.39 | 1.55 | 1.93 | 0.00 | 1.43 | 0.00 | .086 usculus skeletal cle ryanodine ptor gene. |
| 3122 | 1.10 | 1.77 | 1.18 | 0.62 | 0.51 | 0.52 | 0.021 | 0.84 | 1.19 | 1.52 | 1.33 | 0.74 | 0.90 | .515 usculus mRNA beta tectorin |

| | | | | | | | | | |
|---|---|---|---|---|---|---|---|---|---|
| 3226 | 1.13 | 1.26 | 1.06 | 0.59 | 0.30 | 0.64 | *0.006* | 1.02 | 0.98 | 1.05 | 0.47 | 0.79 | 1.15 *.331* usculus htlf e, exon. |
| 3241 | 1.07 | 1.17 | 0.98 | 0.51 | 0.45 | 0.39 | *0.001* | 1.69 | 1.02 | 1.23 | 0.52 | 0.63 | 1.60 *.370* OPAIN PRECURSOR (EC 3.4.22.-) STEINE PROTEASE CPP32) MA PROTEIN) (CASPASE-3 E). |
| 3410 | 1.13 | 1.60 | 1.69 | 0.36 | 0.58 | 0.00 | *0.009* | 1.05 | 1.19 | 1.25 | 0.04 | 0.95 | 0.46 *.065* usculus mRNA semaphorin Hv 88 bp). |
| 3528 | 1.25 | 1.34 | 1.14 | 0.43 | 0.17 | 0.18 | *0.001* | 1.00 | 1.11 | 1.00 | 0.29 | 0.00 | 1.19 *.207* s musculus A-protein (A-myb) e, partial cds. |
| 293 | 8.72 | 10.87 | 2.41 | 0.00 | 0.00 | 0.00 | *0.001* | 0.00 | 2.18 | 0.00 | 8.26 | 2.35 | 0.00 *.335* use skeletal cle sphorylase se, gamma unit mRNA, plete cds |
| 298 | 1.25 | 1.49 | 1.34 | 0.00 | 0.76 | 0.89 | *0.046* | 1.64 | 1.08 | 1.06 | 0.94 | 0.80 | 0.36 *.095* 298 Mouse rine otransferrin NA |
| 060 | 6.51 | 7.40 | 5.77 | 2.15 | 0.00 | 0.00 | *0.002* | 3.72 | 7.47 | 0.00 | 0.00 | 0.00 | 0.00 *.159* 060 Mouse somal protein, e 3A coding for |
| 785 | 1.75 | 0.96 | 1.61 | 0.73 | 0.26 | 0.00 | *0.027* | 2.30 | 1.04 | 1.75 | 0.65 | 1.40 | 0.00 *.138* use mRNA ced by PDGF h some homology -fos. |
| 928 | 2.01 | 3.91 | 3.04 | 0.00 | 1.45 | 0.00 | *0.027* | 5.18 | 0.00 | 0.00 | 1.79 | 0.55 | 0.23 *.654* s musculus erentiation igen (CD22) NA, complete |
| 472 | 1.38 | 1.81 | 1.41 | 0.00 | 0.52 | 0.00 | *0.004* | 1.84 | 0.70 | 1.23 | 1.50 | 0.35 | 0.77 *.458* 472 Mouse Bax a mRNA, plete cds |

| ID | | | | | | | | | | | | | | | Description |
|---|---|---|---|---|---|---|---|---|---|---|---|---|---|---|---|
| 167 | 1.05 | 1.39 | 1.67 | 0.51 | 0.00 | 0.00 | *0.008* | 1.89 | 0.95 | 1.43 | 0.00 | 1.86 | 0.00 | *0.299* | 167 Mouse zinc finger protein mRNA |
| 580 | 2.58 | 18.21 | 9.09 | 0.00 | 0.00 | 0.00 | *0.004* | 7.22 | 42.38 | 12.47 | 0.00 | 0.00 | 0.00 | *0.132* | 580 Mus culus galanin e |
| 567 | 2.83 | 3.57 | 3.79 | 0.00 | 0.10 | 0.03 | *0.000* | 4.39 | 3.25 | 1.24 | 0.14 | 0.76 | 0.20 | *0.052* | 567 Mus culus antigen, B-receptor gene, plete cds |
| 0114 | 1.16 | 1.04 | 0.96 | 0.08 | 0.75 | 0.18 | *0.030* | 1.24 | 1.34 | 1.29 | 0.00 | 0.89 | 1.30 | *0.221* | 0114 Mouse pa-casein mRNA, plete cds |
| 6395 | 1.56 | 1.38 | 1.58 | 0.00 | 0.00 | 0.48 | *0.001* | 1.83 | 1.18 | 1.03 | 0.10 | 0.91 | 0.97 | *0.137* | 6395 Mouse a-fetoprotein P) gene |
| 6762 | 4.79 | 2.65 | 4.76 | 0.00 | 1.37 | 0.00 | *0.013* | 0.00 | 0.72 | 4.12 | 1.28 | 0.00 | 0.00 | *0.425* | 6762 use interleukin 2 ) gene, exon 4 |
| 2740 | 1.19 | 1.33 | 1.36 | 0.79 | 0.43 | 0.15 | *0.012* | 1.21 | 0.99 | 1.46 | 0.00 | 1.01 | 0.34 | *0.077* | 2740 Mouse rotropin beta-unit (TSH-beta) e |
| 3501 | 5.31 | 8.25 | 3.49 | 0.00 | 0.00 | 0.00 | *0.015* | 2.02 | 0.15 | 6.56 | 0.00 | 1.85 | 0.00 | *0.182* | 3501 Mus musculus secreted T protein (P500/TCA3; SIS-epsilon) NA, complete cds |
| 8449 | 1.03 | 0.98 | 1.20 | 0.00 | 0.00 | 0.06 | *0.000* | 1.07 | 1.16 | 0.95 | 1.02 | 0.44 | 1.06 | *0.356* | 8449 Mouse Hox-protein mRNA, nd |
| 9015 | 1.49 | 1.14 | 1.04 | 0.69 | 0.39 | 0.09 | *0.019* | 1.17 | 1.44 | 1.29 | 0.75 | 0.81 | 0.96 | *0.010* | 9015 Mouse somal protein L7 7) gene, plete cds |
| 9395 | 0.76 | 1.38 | 2.00 | 0.00 | 0.00 | 0.00 | *0.018* | 1.63 | 1.09 | 2.66 | 0.08 | 1.08 | 0.92 | *0.119* | 9395 Mouse tidine-5'-ophosphate arboxylase NA, 3' end |

| | | | | | | | | |
|---|---|---|---|---|---|---|---|---|
| 0441 | 1.46 | 1.02 | 1.17 | 0.74 | 0.08 | 0.50 | 0.030 | 1.08 | 1.48 | 0.98 | 0.39 | 1.22 | 0.00 | 1720 0441 Mouse onless potassium nnel gene MK3 |
| 0644 | 1.30 | 1.55 | 1.52 | 0.87 | 0.42 | 0.61 | 0.005 | 1.47 | 1.05 | 1.46 | 0.32 | 0.79 | 0.95 | 052 0644 Mouse ic fibroblast wth factor (Fgfb) NA, complete cds |
| 4094 | 1.09 | 1.27 | 2.18 | 0.00 | 0.46 | 0.00 | 0.022 | 0.45 | 1.09 | 1.97 | 0.00 | 1.12 | 0.91 | 427 4094 Mouse noic acid-onsive protein ) gene, complete |
| 5617 | 5.22 | 6.29 | 1.57 | 0.00 | 0.00 | 0.00 | 0.038 | 3.23 | 6.22 | 0.93 | 0.00 | 1.07 | 0.00 | 1195617 Mus culus mouse t cell protease-4 NA, complete cds |
| 5875 | 3.99 | 3.14 | 3.34 | 0.00 | 0.00 | 0.00 | 0.000 | 0.90 | 3.43 | 5.14 | 0.00 | 1.10 | 0.38 | 105 5875 Mouse C class I T3-d e (H-2-d lotype) |
| 1591 | 1.13 | 0.78 | 1.30 | 0.53 | 0.59 | 0.38 | 0.025 | 1.02 | 0.98 | 1.28 | 0.39 | 1.70 | 1.17 | 991 1591 Murine O neutral opeptidase 24.11 10/NEP) mRNA, ative cds |
| 1243 | 1.23 | 1.00 | 1.00 | 0.00 | 0.00 | 0.59 | 0.014 | 1.22 | 0.34 | 1.65 | 0.00 | 1.25 | 1.41 | 770 1243 Mouse lens r protein MP70 50) gene, plete cds |
| 3128 | 1.27 | 1.33 | 1.20 | 0.89 | 0.00 | 0.00 | 0.032 | 1.00 | 0.77 | 0.78 | 1.00 | 1.32 | 1.48 | 061 3128 Mouse eobox protein X2) mRNA, plete cds |
| 989 | 1.76 | 0.98 | 1.42 | 0.70 | 0.24 | 0.00 | 0.024 | 0.59 | 0.79 | 1.16 | 1.02 | 2.00 | 1.62 | 102 989 Nkx-5.2 = NK-related eobox gene [mice, E11.5 ryos, mRNA Partial, 1483 nt TRACTED 3'UTR) |

| | | | | | | | | | |
|---|---|---|---|---|---|---|---|---|---|
| 662 | 1.03 | 1.38 | 0.83 | 0.00 | 0.21 | 0.35 | *0.009* | 1.49 | 1.29 | 1.35 | 1.41 | 0.67 | 0.97 | *181* | s musculus ofetal antigen NA, partial cds |
| 982 | 2.02 | 1.71 | 1.86 | 0.42 | 0.21 | 0.28 | *0.000* | 2.28 | 2.53 | 0.98 | 0.00 | 1.02 | 0.00 | *054* | 982 Mus culus Balb/c roendothelin-1 e, promoter on |
| 210 | 5.68 | 14.95 | 9.70 | 0.00 | 0.00 | 0.00 | *0.012* | 6.61 | 4.29 | 14.29 | 0.00 | 0.00 | 0.00 | *080* | 210 Mus culus oelastin mRNA, plete cds |
| 932 | 1.42 | 1.13 | 1.28 | 0.86 | 0.16 | 0.48 | *0.024* | 1.40 | 1.30 | 0.87 | 0.00 | 0.80 | 1.32 | *313* | 932 Mus musculus follicle ulating hormone beta subunit H-beta) gene, complete cds |
| 443 | 1.24 | 0.89 | 1.26 | 0.00 | 0.07 | 0.03 | *0.001* | 1.11 | 1.51 | 1.21 | 0.13 | 0.70 | 1.82 | *480* | 443 Mus culus proto- ogene protein c (c-ros) mRNA, plete cds |
| 252 | 0.92 | 1.07 | 1.19 | 0.00 | 0.20 | 0.32 | *0.002* | 1.19 | 1.05 | 1.34 | 0.95 | 1.09 | 0.73 | *114* | 252 Mus culus abotropic amate receptor 8 luR8) mRNA, plete cds |
| 513 | 1.01 | 1.45 | 1.29 | 0.68 | 0.18 | 0.72 | *0.029* | 1.09 | 1.29 | 1.12 | 0.00 | 0.99 | 0.12 | *067* | 513 Mus culus KRAB-zinc er protein 79 79) mRNA, ial cds |
| 005 | 3.41 | 10.25 | 4.71 | 0.00 | 0.00 | 0.00 | *0.043* | 0.00 | 7.73 | 9.70 | 7.06 | 0.00 | 0.00 | *412* | s musculus tbc1 NA, complete cds |
| 245 | 0.89 | 1.28 | 1.19 | 0.00 | 0.00 | 0.00 | *0.001* | 1.21 | 1.16 | 1.11 | 0.00 | 1.24 | 0.00 | *145* | 245 Mus culus fos-related igen-1 (Fra-1) NA, complete cds |

| ID | | | | | | | | | | | | | | | Description |
|---|---|---|---|---|---|---|---|---|---|---|---|---|---|---|---|
| 353 | 1.01 | 1.29 | 1.30 | 0.00 | 0.49 | 0.00 | *0.005* | 1.07 | 0.99 | 1.36 | 0.00 | 1.07 | 0.12 | *.105* | 353 Mus musculus protein sphatase 2A B'alpha3 regulatory unit mRNA, partial cds |
| 189 | 1.11 | 0.90 | 0.86 | 0.20 | 0.00 | 0.65 | *0.030* | 1.40 | 1.23 | 1.29 | 1.10 | 0.83 | 1.74 | *.777* | 189 Mus musculus pancreatic peptide/neuropeptide Y/peptide receptor gene, complete cds |
| 650 | 1.29 | 1.15 | 1.17 | 0.17 | 0.64 | 0.00 | *0.009* | 1.28 | 1.30 | 1.17 | 0.75 | 0.85 | 0.35 | *.020* | 650 Mus musculus neurexophilin xph-2) gene, large exon and 3' of the intron, and partial cds |
| 513 | 0.81 | 1.09 | 1.05 | 0.51 | 0.36 | 0.59 | *0.010* | 1.02 | 1.00 | 1.00 | 1.23 | 0.99 | 1.35 | *.150* | 513 Mus musculus Rho-ociated, coiled-coil forming protein se p160 ROCK-2 mRNA, complete |
| 418 | 0.96 | 1.45 | 1.72 | 0.00 | 0.78 | 0.44 | *0.037* | 2.23 | 1.04 | 1.13 | 1.04 | 0.51 | 0.00 | *.123* | 418 Mus culus Netrin-1 rin-1) mRNA, plete cds |
| 137 | 1.82 | 1.59 | 1.58 | 0.00 | 0.72 | 0.95 | *0.020* | 1.73 | 1.03 | 1.35 | 0.36 | 0.97 | 0.65 | *.057* | 137 Mus culus T2-herin mRNA, ial cds |
| 208 | 1.92 | 19.41 | 5.95 | 0.00 | 0.00 | 0.00 | *0.007* | 8.28 | 13.48 | 38.84 | 0.00 | 0.00 | 0.00 | *.099* | 208 Mus culus neurogenin gn3) gene, plete cds |
| 700 | 5.11 | 3.18 | 3.26 | 0.00 | 0.00 | 0.00 | *0.004* | 5.33 | 1.30 | 4.75 | 0.70 | 0.00 | 0.36 | *.054* | s musculus serine teinase inhibitor 6 I6) mRNA, plete cds. |
| 724 | 8.41 | 5.29 | 5.43 | 0.00 | 2.24 | 0.00 | *0.011* | 1.15 | 1.53 | 0.00 | 0.85 | 0.00 | 0.00 | *.324* | s musculus ative sphoinositide 5-sphatase type II NA, complete |

| ID | | | | | | | | | | | | | Description |
|---|---|---|---|---|---|---|---|---|---|---|---|---|---|
| 755 | 2.04 | 2.40 | 1.68 | 0.82 | 1.17 | 0.10 | *0.023* | 0.83 | 1.18 | 0.00 | 0.82 | 0.71.*110* | senger RNA ment for mouse rferon beta (type oding for the c-inal part. |
| 479 | 1.64 | 1.70 | 1.36 | 0.32 | 0.08 | 1.17 | *0.039* | 1.03 | 0.58 | 1.19 | 0.67 | 0.97 0.00.*317* | use mRNA ment for serum loid A (SAA) 3 tein. |
| 123 | 1.69 | 1.82 | 1.59 | 0.43 | 0.37 | 0.99 | *0.006* | 1.01 | 1.70 | 2.45 | 0.04 | 0.99 0.56.*075* | use mRNA for inal xynucleotidyltransase (TdT). |
| 260 | 1.15 | 1.82 | 2.55 | 0.00 | 0.00 | 0.00 | *0.011* | 3.64 | 1.63 | 0.95 | 1.05 | 0.00 0.21.*130* | use Y mosome RNA script expressed estis (pYMT2/B). |
| 640 | 1.17 | 27.06 | 1.14 | 0.00 | 0.00 | 0.00 | *0.000* | 2.21 | 3.04 | 6.96 | 0.00 | 0.00.*050* 640 | Mouse NF-ene for middle-ecular-mass rofilament protein |
| 115 | 1.83 | 1.63 | 1.23 | 0.00 | 0.00 | 0.17 | *0.001* | 1.15 | 1.02 | 0.98 | 0.15 | 0.24 1.02.*105* | use mRNA for E-herin (= morulin, = L-CAM /80, = Arc-1). |
| 368 | 3.83 | 11.36 | 2.49 | 0.00 | 0.00 | 0.00 | *0.016* | 0.00 | 0.05 | 16.10 | 27.29 | 1.95 0.00.*693* | rine mRNA for c-proto-oncogene. |
| 540 | 1.07 | 1.23 | 1.56 | 0.34 | 0.00 | 0.47 | *0.007* | 1.08 | 1.38 | 1.02 | 0.38 | 0.98 0.65.*078* 540 | Mouse c-abl e exon 1 of type RNA |
| 538 | 7.03 | 5.05 | 0.26 | 0.00 | 0.00 | 0.00 | *0.036* | 0.00 | 1.26 | 14.07 | 26.77 | 0.00 0.74.*702* | rine mRNA for -1.4 protein. |
| 664 | 1.47 | 2.17 | 1.59 | 0.13 | 0.76 | 0.90 | *0.023* | 1.13 | 1.20 | 0.25 | 0.00 | 0.18 1.10.*400* | use mRNA for N-protein (exons 1 - art.). |
| 926 | 1.00 | 1.00 | 1.56 | 0.00 | 0.00 | 0.00 | *0.003* | 1.22 | 1.11 | 1.17 | 1.17 | 0.00 0.00.*117* | use mRNA for eticulin. |

| ID | | | | | | | p-val | | | | | | | code | Description |
|---|---|---|---|---|---|---|---|---|---|---|---|---|---|---|---|
| 972 | 1.63 | 2.07 | 1.66 | 0.55 | 0.66 | 0.85 | *0.003* | 1.99 | 1.04 | 1.95 | 0.79 | 0.00 | 0.96 | *.067* | use mRNA for a-adaptin (C). |
| 830 | 1.42 | 1.63 | 1.21 | 0.56 | 0.00 | 0.00 | *0.005* | 1.12 | 1.07 | 0.87 | 0.93 | 0.23 | 1.82 | *.956* | rine mRNA for roendocrine tein 7B2. |
| 510 | 4.28 | 8.23 | 5.27 | 0.00 | 2.36 | 0.00 | *0.023* | 6.86 | 5.28 | 0.00 | 0.00 | 0.00 | 0.00 | *.123* | use mRNA for 3.3 PRI script. |
| 683 | 4.96 | 35.96 | 6.00 | 0.00 | 0.00 | 0.00 | *0.001* | 1.44 | 32.38 | 0.00 | 0.00 | 0.00 | 0.00 | *.136* | usculus T NA. |
| 991 | 2.51 | 3.70 | 4.67 | 0.00 | 0.00 | 0.00 | *0.004* | 2.85 | 9.53 | 3.06 | 0.00 | 0.00 | 0.00 | *.079* | Mouse NA for homologue he rat T cell erentiation marker |
| 424 | 2.42 | 0.95 | 2.24 | 0.00 | 0.00 | 0.00 | *0.016* | 1.05 | 2.97 | 2.58 | 0.00 | 0.35 | 1.76 | *.134* | Mouse NA for gamma ptin |
| 315 | 1.56 | 5.39 | 4.68 | 0.00 | 0.33 | 0.44 | *0.038* | 5.99 | 1.85 | 1.68 | 0.00 | 0.00 | 0.00 | *.088* | usculus mRNA CAAT-box DNA ing protein unit A (NF-YA) tial). |
| 781 | 0.99 | 1.53 | 1.53 | 0.06 | 0.49 | 0.78 | *0.030* | 1.10 | 1.36 | 1.13 | 0.72 | 1.01 | 0.72 | *.040* | 781 M.musculus 2 gene |
| 044 | 1.26 | 1.03 | 1.66 | 0.71 | 0.40 | 0.27 | *0.019* | 1.10 | 1.23 | 1.59 | 0.97 | 0.47 | 0.79 | *.053* | 044 M.musculus NA for protein C |
| 349 | 2.20 | 1.22 | 2.82 | 0.00 | 0.78 | 0.00 | *0.027* | 6.12 | 2.09 | 1.98 | 0.00 | 0.00 | 0.00 | *.067* | 349 M.musculus NA for transferrin ptor |
| 960 | 1.01 | 56.29 | 4.13 | 0.00 | 0.00 | 0.00 | *0.000* | 6.85 | 17.60 | 0.00 | 0.00 | 0.00 | 0.00 | *.191* | usculus mRNA ribosomal protein |
| 876 | 0.96 | 1.54 | 0.93 | 0.00 | 0.00 | 0.17 | *0.006* | 2.15 | 1.64 | 1.04 | 3.04 | 0.00 | 1.10 | *.823* | 876 Murine 2 mRNA for 2 protein |

| ID | | | | | | | | | | | | | | | Description |
|---|---|---|---|---|---|---|---|---|---|---|---|---|---|---|---|
| 940 | 1.01 | 0.88 | 0.80 | 0.43 | 0.24 | 0.19 | | 1.03 | 1.55 | 1.66 | 0.99 | 1.15 | 1.06 | .160 | use mRNA for a wth factor-cible inmediate y gene (3CH134). |
| 285 | 2.49 | 1.96 | 1.92 | 0.00 | 0.00 | 0.00 | *0.003* | 1.03 | 1.55 | 1.66 | 0.00 | 1.18 | 0.10 | *.108* 285 | M.musculus for HC1 locus |
| 449 | 1.44 | 1.75 | 1.43 | 0.00 | 0.00 | 0.00 | *0.000* | 1.64 | 2.00 | 0.82 | 0.00 | 0.00 | 2.12 | *.558* 449 | M.musculus NA for calcyclin |
| 783 | 4.50 | 3.48 | 4.48 | 0.47 | 0.00 | 1.53 | *0.000* | 1.58 | 1.36 | 0.64 | 0.00 | 0.00 | 0.00 | *.117* | usculus VCAM-1 NA. |
| 061 | 1.34 | 1.51 | 1.45 | 0.74 | 0.41 | 0.56 | *0.003* | 3.31 | 3.70 | 0.00 | 0.98 | 0.29 | 0.65 | *.093* | usculus HCNGP NA. |
| 620 | 4.60 | 22.94 | 3.86 | 0.00 | 0.00 | 0.00 | *0.001* | 1.55 | 1.08 | 1.02 | 0.00 | 0.00 | 0.00 | *.161* | usculus mRNA inhibin beta-B unit. |
| 018 | 1.41 | 1.13 | 1.17 | 0.29 | 0.53 | 0.87 | *0.000* | 6.71 | 34.28 | 0.00 | 0.00 | 0.00 | 2.28 | *.775* 018 | M.musculus NA for Id4 helix-helix protein |
| 295 | 0.99 | 1.24 | 1.01 | 0.00 | 0.24 | 0.65 | *0.024* | 1.27 | 1.39 | 0.72 | 0.85 | 0.75 | 1.06 | *.939* 295 | M.musculus e for anocortin 5 ptor |
| 557 | 1.74 | 2.37 | 1.37 | 0.96 | 0.00 | 0.00 | *0.019* | 1.17 | 0.69 | 1.28 | 0.58 | 1.57 | 0.00 | *.352* | usculus cadL NA. |
| 304 | 1.82 | 1.67 | 0.75 | 0.66 | 0.00 | 0.00 | *0.026* | 0.00 | 1.04 | 3.07 | 1.06 | 0.00 | 0.00 | *.889* 304 | M.musculus (SRP9) al recognition icle subunit NA, 689bp |
| 339 | 1.68 | 1.68 | 1.37 | 0.31 | 0.00 | 0.70 | *0.040* | 0.08 | 1.25 | 1.57 | 1.25 | 1.36 | 0.00 | *.382* | usculus Six1 NA. |
| 320 | 1.32 | 1.81 | 1.76 | 0.73 | 0.00 | 0.39 | *0.003* | 2.01 | 1.98 | 0.00 | 0.29 | 0.19 | 1.30 | *.507* | usculus KIS NA. |
| 577 | 1.23 | 1.01 | 0.81 | 0.48 | 0.28 | 0.75 | *0.009* | 1.15 | 1.58 | 0.85 | 0.51 | 0.33 | 1.70 | *.685* | usculus mRNA K-glypican. |
| 601 | 1.16 | 1.37 | 0.91 | 0.00 | 0.20 | 0.42 | *0.049* | 1.12 | 1.06 | 1.33 | 2.09 | 0.99 | 0.93 | *.101* | usculus PTX3 NA. |
|  |  |  |  |  |  |  | *0.006* | 1.21 | 1.25 | 1.20 | 0.22 | 0.74 | 1.09 |  |  |

| | | | | | | | | |
|---|---|---|---|---|---|---|---|---|
| 932 | 1.54 | 1.19 | 1.07 | 0.66 | 0.34 | 0.38 | 0.010 | 2.12 | 0.93 | 1.88 | 1.12 | 0.64 | 0.33.092 | usculus mRNA ryanodine ptor type 1. |
| 368 | 5.46 | 35.26 | 0.09 | 0.00 | 0.00 | 0.007 | 0.00 | 36.57 | 54.33 | 0.00 | 0.00 | 0.00.131 | usculus putative scription factor. |
| 352 | 1.19 | 1.26 | 1.17 | 0.10 | 0.35 | 0.32 | 0.000 | 1.47 | 1.05 | 1.24 | 0.64 | 0.28 | 0.95.053 | usculus mRNA Bpx protein. |
| 664 | 1.32 | 1.29 | 1.09 | 0.82 | 0.70 | 0.17 | 0.033 | 1.51 | 1.46 | 0.91 | 0.00 | 0.42 | 1.10.103 | 664 M.musculus NA for ubiquitin-jugating enzyme M2 |
| 606 | 1.33 | 1.60 | 1.31 | 0.00 | 0.00 | 0.00 | 0.000 | 1.03 | 1.20 | 2.07 | 0.97 | 0.82 | 0.00.131 | usculus mRNA Ott protein, clone 7. |
| 719 | 1.64 | 1.19 | 1.15 | 0.59 | 0.00 | 0.66 | 0.025 | 1.98 | 0.98 | 1.47 | 0.51 | 0.00 | 1.02.079 | 719 M.musculus ovirus restriction e Fv1 |
| 817 | 1.16 | 1.42 | 1.57 | 0.55 | 0.00 | 0.27 | 0.005 | 1.39 | 1.65 | 0.96 | 1.04 | 0.00 | 0.18.071 | 817 M.musculus NA for aphorin F |
| 581 | 1.13 | 0.64 | 1.18 | 0.10 | 0.00 | 0.14 | 0.007 | 1.09 | 1.15 | 1.36 | 0.91 | 0.00 | 1.65.511 | 581 M.musculus gene encoding ocyte-dervied seven smembrane domain receptor, in B6 |
| 500 | 1.36 | 1.92 | 1.10 | 0.94 | 0.34 | 0.21 | 0.044 | 0.79 | 1.06 | 0.63 | 0.53 | 1.13 | 5.00.379 | use glandular ikrein gene. |
| 848 | 6.67 | 4.44 | 5.83 | 0.00 | 0.00 | 0.03 | 0.001 | 2.48 | 0.00 | 2.96 | 1.25 | 0.75 | 0.00.310 | use int-2 gene. |
| 224 | 0.91 | 1.18 | 1.37 | 0.00 | 0.14 | 0.53 | 0.011 | 1.18 | 1.28 | 0.97 | 0.17 | 1.15 | 1.03.330 | usculus mRNA 5HT1E beta tonin receptor. |
| 103 | 0.95 | 1.40 | 1.05 | 0.24 | 0.19 | 0.28 | 0.003 | 1.07 | 1.16 | 1.18 | 0.54 | 1.08 | 0.61.085 | usculus Mox-1 NA. |
| 143 | 1.19 | 1.38 | 1.28 | 0.15 | 0.67 | 0.54 | 0.007 | 1.20 | 1.71 | 0.93 | 0.01 | 0.16 | 1.07.099 | usculus ALK-6 NA, complete |
| 532 | 1.23 | 1.37 | 1.27 | 0.00 | 0.00 | 0.00 | 0.000 | 1.11 | 1.29 | 0.65 | 1.10 | 0.90 | 0.00.418 | usculus mRNA follistatin. |

| | | | | | | | | | |
|---|---|---|---|---|---|---|---|---|---|
| 166 | 0.95 | 1.35 | 1.34 | 0.00 | 0.26 | 0.002 | 1.71 | 1.51 | 1.05 | 2.29 | 0.00 | 0.56 | .544 | 166 M.musculus lb/c) mRNA for agen IV alpha 3 in |
| 168 | 1.00 | 1.35 | 1.05 | 0.05 | 0.82 | 0.06 | 0.041 | 1.26 | 1.68 | 1.00 | 0.55 | 1.12 | 0.77 | .128 | 168 M.musculus NA for collagen lpha 5 chain |
| 147 | 1.42 | 1.63 | 1.08 | 0.00 | 0.07 | 0.00 | 0.001 | 0.98 | 0.66 | 1.18 | 1.17 | 0.04 | 1.02 | .639 | 147 M.musculus e for cell esion regulator |

What is claimed is:

1. A method of identifiiing an intervention that mimics the effects of caloric restriction in cells, comprising:
    obtaining a biological sample;
    exposing said biological sample to an intervention;
    waiting a specified period of time;
    assessing changes in gene expression levels, levels of RNA, protein, or protein activity levels related to one or more biomarkers of aging; and
    identifying said intervention as one that mimics the effects of caloric restriction if one or more changes in said levels also occurs in caloric restriction.

2. The method of claim 1, wherein said biological sample comprises cells.

3. The method of claim 2, wherein said cells are obtained from a mammal.

4. The method of claim 3, wherein said mammal is a mouse.

5. The method of claim 1, wherein said change in gene expression levels, levels of RNA, protein, or protein activity levels corresponds to a change in gene expression for a gene encoding a chaperone protein.

6. The method of claim 5, wherein said gene encoding a chaperone protein is GRP78.

7. The method of claim 1, wherein said biomarker is apoptosis.

8. The method of claim 1, wherein said biomarker is aging.

9. The method of claim 8, wherein said biomarker of aging is a production of cancer cells.

10. The method of claim 1, wherein said changes in said gene expression level, levels of RNA, protein, or protein activity levels related to one or more biomarkers of aging occur in 6 weeks or less.

11. The method of claim 10, wherein said changes in said gene expression levels, levels of RNA, protein, or protein activity levels related to one or more biomarkers of aging occur in four weeks or less.

12. The method of claim 11, wherein said changes in said gene expression levels, levels of RNA, protein, or protein activity levels related to one or more biomarkers of aging occur in two weeks or less.

13. The method of claim 12, wherein said changes in said gene expression levels, levels of RNA, protein, or protein activity levels related to one or more biomarkers of aging occur in about two days or less.

14. A method according to claim 1 wherein changes in gene expression are evaluated using a gene chip.

15. The method of claim 14, wherein the gene chip contains genes for immune system activation.

16. The method of claim 14, wherein the gene chip contains genes for DNA repair.

17. The method of claim 14, wherein the gene chip contains genes associated with apoptosis.

18. The method of claim 14, wherein the gene chip contains genes for the enteric nervous system.

19. The method of claim 1, wherein said biological sample is a test animal.

20. The method of claim 19 additionally comprising determining changes in said levels in a reference animal having identifying characteristics of a long-term calorie-restricted animal wherein the reference animal has been on a calorie restricted diet for less than about 6 weeks and wherein said changes are used in said identifying said intervention as one that mimics the effects of calorie restriction.

21. The method of claim 20, wherein the reference animal has been on a calorie restricted diet for less than about 4 weeks.

22. The method of claim 20, wherein the reference animal has been on a calorie restricted diet for less than about 2 weeks.

23. The method of claim 19, wherein said test animal is a mouse.

24. The method of claim 19, wherein changes in gene expression are assessed in said test animal.

25. The method of claim 19 which further comprises:
    obtaining a gene expression profile from a calorie-restricted reference animal;
    comparing changes in gene expression for the test animal to the gene expression profile of the calorie-restricted reference animal; and
    identifying said intervention as one that mimics the effects of calorie restriction if the gene expression profile of the test animal is statistically similar to the gene expression profile of the calorie restricted animal.

26. The method of claim 25, wherein the gene expression profile of the test animal is determined to be statistically similar to the gene expression of the calorie restricted animal by one-way ANOVA followed by Fisher's test ($P<0.05$).

* * * * *

UNITED STATES PATENT AND TRADEMARK OFFICE
CERTIFICATE OF CORRECTION

PATENT NO.      : 6,406,853 B1
DATED           : June 18, 2002
INVENTOR(S)     : Spindler It is certified that error appears in the above-identified patent and that said Letters Patent is hereby corrected as shown below:

Column 1,
Lines 4 and 5, delete "U.S. application Ser. No. 09/471,225" and replace with
-- U.S. application Ser. No. 09/471,224 --.

Signed and Sealed this

Twenty-sixth Day of November, 2002

Attest:

Attesting Officer

JAMES E. ROGAN
Director of the United States Patent and Trademark Office